(12) United States Patent
Baric et al.

(10) Patent No.: US 7,618,802 B2
(45) Date of Patent: Nov. 17, 2009

(54) COMPOSITIONS OF CORONAVIRUSES WITH A RECOMBINATION-RESISTANT GENOME

(75) Inventors: Ralph S. Baric, Haw River, NC (US); Rhonda Roberts, Durham, NC (US); Boyd Yount, Hillsborough, NC (US); Kristopher M. Curtis, Frederick, MD (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 336 days.

(21) Appl. No.: 11/334,877

(22) Filed: Jan. 19, 2006

(65) Prior Publication Data

US 2006/0240530 A1    Oct. 26, 2006

Related U.S. Application Data

(63) Continuation-in-part of application No. PCT/US2004/023548, filed on Jul. 21, 2004.

(60) Provisional application No. 60/488,942, filed on Jul. 21, 2003.

(51) Int. Cl.
| | |
|---|---|
| C12N 7/01 | (2006.01) |
| C12N 15/50 | (2006.01) |
| C12N 15/40 | (2006.01) |
| C12N 15/86 | (2006.01) |
| A61K 39/215 | (2006.01) |
| C12N 7/04 | (2006.01) |

(52) U.S. Cl. .............. 435/235.1; 424/221.1; 424/218.1; 536/23.72; 435/320.1; 435/236

(58) Field of Classification Search ........................ None
See application file for complete search history.

(56) References Cited

FOREIGN PATENT DOCUMENTS

WO    WO 99/29872    6/1999

OTHER PUBLICATIONS

Pasternak et al (Journal of General Virology 87:1403-1421, 2006).*
Zuniga et al (Journal of Virology 78:980-994, Jan. 2004).*
Gorbalenya et al (Virus Research 117:17-37, 2006).*
van Marle et al (PNAS 96:12056-12061, 1999).*
Smits et al (Journal of Virology 79:8275, 2005).*
Draker et al (Virus Research 115:56-68, 2006, available online Aug. 30, 2005).*
Genbank locus AY427798, "Breda virus strain Breda 1, complete genome" (Dec. 15, 2005).*
International Search Report for PCT/US04/23548, mailed Oct. 18, 2006.
Marra et al. "The Genome Sequence of the SARS-Associated Coronavirus" *Science* 300:1399-1404 (2003).
Rota et al. "Characterization of a Novel Coronavirus Associated with Severe Acute Respiratory Syndrome" *Science* 300:1394-1399 (2003).
Xu et al. "Small envelope protein E of SARS: cloning, expression, purification, CD determination, and bioinformatics analysis" *Acta Pharmacol ,Sin* 24(6):505-511 (2003).
Agapov et al. "Noncytopathic Sindbis virus RNA vectors for heterologous gene expression" *Proc. Natl. Acad. Sci. USA* 98:12989-12994 (1998).
Almazan et al. "Engineering the largest RNA virus genome as an infectious bacterial artificial chromosome" *PNAS* 97(10):5516-5521 (2000).
Balasuriya et al. "Expression of the Two Major Envelope Proteins of Equine Arteritis Virus as a Heterodimer Is Necessary for Induction of Neutralizing Antibodies in Mice Immunized with Recombinant Venezuelan Equine Encephalitis Virus Replicon Particles" *J. Virol.* 74(22):10623-10630 (2000).
Baudoux et al. "Coronavirus Pseudoparticles Formed with Recombinant M and E Proteins Induce Alpha Interferon Synthesis by Leukocytes" *J. Virol.* 72(11):8636-8643 (1998).
Berglund et al. "Enhancing immune responses using suicidal DNA vaccines" *Nature Biotechnology* 16:562-565 (1998).
Bos et al. "The Production of Recombinant Infectious DI-Particles of a Murine Coronavirus in the Absence of Helper Virus" *Virology* 218:52-60 (1996).
Bredenbeek et al. "Sindbis Virus Expression Vectors: Packaging of RNA Replicons by Using Defective Helper RNAs" *J. Virol.* 67(11):6439-6446 (1993).
Caley et al. "Humoral, Mucosal, and Cellular Immunity in Response to a Human Immunodeficiency Virus Type 1 Immunogen Expressed by a Venezuelan Equine Encephalitis Virus Vaccine Vector" *J. Virol.* 71(4):3031-3038 (1997).
Curtis et al. "A Simple Strategy to Assemble Infectious RNA and DNA Clones" *Adv. Exp. Med. Biol.* 494:475-481 (2001).
Curtis et al. "Coronavirus Derived Vectors for Genetic Analysis and Heterologous Gene Expression" *Recent Res. Devel. Virol.* 4:203-229 (2002).
Curtis et al. "Heterologous Gene Expression from Transmissible Gastroenteritis Virus Replicon Particles" *J. Virol.* 76(3):1422-1434 (2002).
Curtis et al. "Reverse Genetic Analysis of the Transcription Regulatory Sequence of the Coronavirus Transmissible Gastroenteritis Virus" *J. Virol.* 78(11):6061-6066 (2004).
de Haan et al. "Coronavirus Particle Assembly: Primary Structure Requirements of the Membrane Protein" *J. Virol* 72(8):6838-6850 (1998).
DiCiommo et al. "Rapid, High Level Protein Production Using DNA-based Semliki Forest Virus Vectors" *The Journal of Biological Chemistry* 273(29):18060-18066 (1998).
Dollenmaier et al. "Membrane-Associated Respiratory Syncytial Virus F Protein Expressed from a Human Rhinovirus Type 14 Vector Is Immunogenic" *Virology* 281:216-230 (2001).
Dubensky et al. "Sindbis Virus DNA-Based Expression Vectors: Utility for In Vitro and In Vivo Gene Transfer" *J. Virol.* 70(1):508-519 (1996).

(Continued)

*Primary Examiner*—Mary E Mosher
(74) *Attorney, Agent, or Firm*—Myers Bigel Sibley & Sajovec, P.A.

(57) ABSTRACT

The present invention provides a cDNA of a severe acute respiratory syndrome (SARS) coronavirus, recombinant SARS coronavirus vectors, and SARS coronavirus replicon particles. Also provided are methods of making the compositions of this invention and methods of using the compositions as immunogens and/or vaccines and/or to express heterologous nucleic acids.

15 Claims, 2 Drawing Sheets

OTHER PUBLICATIONS

Fischer et al. "Analysis of a Recombinant Mouse Hepatitis Virus Expressing a Foreign Gene Reveals a Novel Aspect of Coronavirus Transcription" *J. Virol.* 71(7):5148-5160 (1997).

Fischer et al. "Analysis of Constructed E Gene Mutants of Mouse Hepatitis Virus Confirms a Pivotal Role for E Protein in Coronavirus Assembly" *J. Virol.* 72(10):7885-7894 (1998).

Fuerst et al. "Eukaryotic transient-expression system based on recombinant vaccinia virus that synthesizes bacteriophage T7 RNA polymerase" *Proc. Natl. Acad. Sci. USA* 83:8122-8126 (1986).

Godeke et al. "Assembly of Spike into Coronavirus Particles Is Mediated by the Carboxy-Terminal Domain of the Spike Protein" *J. Virol.* 74(3):1566-1571 (2000).

Hevey et al. "Marburg Virus Vaccines Based upon Alphavirus Replicons Protect Guinea Pigs and Nonhuman Primates" 251:28-37 (1998).

International Search Report, PCT/US02/12453, Mar. 13, 2003.

Khromykh et al. "Subgenomic Replicons of the Flavivirus Kunjin: Construction and Applications" *Journal of Virology* 71(2):1497-1505 (1997).

Khromykh, A.A. "Replicon-based vectors of positive strand RNA viruses" *Current Opinion in Molecular Therapeutics* 2(5):555-569 (2000).

Liljestrom et al. "A New Generation of Animal Cell Expression Vectors Based On The Semliki Forest Virus Replicon" *Biotechnology* 9:1356-1361 (1991).

Mendez et al. "Molecular Characterization of Transmissible Gastroenteritis Coronavirus Defective Interfering Genomes: Packaging and Heterogeneity" *Virology* 217:495-507 (1996).

Messerle et al. "Cloning and mutagenesis of a herpesvirus genome as an infectious bacterial artificial chromosome" *Proc. Natl. Acad. Sci. USA* 94:14759-14763 (1997).

Meulenberg et al. "Infectious Transcripts from Cloned Genome-Length cDNA of Porcine Reproductive and Respiratory Syndrome Virus" *J. Virol.* 72(1):380-387 (1998).

Ortego et al. "Generation of a Replication-Competent, Propagation-Deficient Virus Vector Based on the Transmissible Gastroenteritis Coronavirus Genome" *J. Virol.* 76(22):11518-11529 (2002).

Percy et al. "A Poliovirus Replicon Containing the Chloramphenicol Acetyltransferase Gene Can Be Used To Study the Replication and Encapsidation of Poliovirus RNA" *J. Virol.* 66(8):5040-5046 (1992).

Porter et al. "Encapsidation of Genetically Engineered Poliovirus Minireplicons Which Express Human Immunodeficiency Virus Type 1 Gag and Pol Proteins upon Infection" *J. Virol.* 67(7):3712-3719 (1993).

Pushko et al. "Replicon-Helper Systems from Attenuated Venezuelan Equine Encephalitis Virus: Expression of Heterologous Genes in Vitro and Immunization against Heterologous Pathogens in Vivo" *Virology* 239:389-401 (1997).

Schutz-Cherry et al. "Influenza (A/HK/156/97) Hemagglutinin Expressed by an Alphavirus Replicon System Protects Chickens against Lethal Infection with Hong Kong-Origin H5N1 Viruses" *Virology* 278:55-59 (2000).

Varnavski et al. "Stable High-Level Expression of Heterologous Genes In Vitro and In Vivo by Noncytopathic DNA-Based Kunjin Virus Replicon Vectors" *J. Virol.* 74(9):4394-4403 (2000).

Vennema et al. "Intracellular Transport of Recombinant Coronavirus Spike Proteins: Implications for Virus Assembly" *J. Virol.* 64(1):339-346 (1990).

Vennema et al. "Nucleocapsid-independent assembly of coronavirus-like particles by co-expression of viral envelope protein genes" *The EMBO Journal* 15(8):2020-2028 (1996).

Yount et al. "Strategy for Systematic Assembly of Large RNA and DNA Genomes: Transmissible Gastroenteritis Virus Model" *J. Virol.* 74(22):10600-10611 (2000).

Yount et al. "Biological consequences of TGEV Gene Rearrangement" 20th Annual American Society for Virology Meeting, Madison, WI (Jul. 21-25, 2001) (Abstract).

Yount et al. "Coronavirus Heterologous Gene Expression Vectors" Sixth Int'l Symposium on Positive Strand RNA viruses, Institute Pasteur, Paris France (May 28-Jun. 2, 2001) (Abstract).

Yount et al. "Reverse genetics with a full-length infectious cDNA of severe acute respiratory syndrome coronavirus" *PNAS* 100(22):12995-13000 (2003).

Yount et al. "Rewiring the severe acute respiratory syndrome coronavirus (SARS-CoV) transcription circuit: Engineering a recombination-resistant genome" *PNAS* 103(33):12546-12551 (2006).

* cited by examiner

A: mRNA encoding ORF3a Leader-Body Junctions

B: leader body junctions in mRNA encoding M glycoprotein

SEQUENCE LISTING

<160> NUMBER OF SEQ ID NOS: 76

<210> SEQ ID NO 1
<211> LENGTH: 29748
<212> TYPE: DNA
<213> ORGANISM: SARS coronavirus

<400> SEQUENCE: 1

```
atattaggtt tttacctacc caggaaaagc caaccaacct cgatctcttg tagatctgtt      60
ctctaaacga actttaaaat ctgtgtagct gtcgctcggc tgcatgccta gtgcacctac     120
gcagtataaa caataataaa ttttactgtc gttgacaaga aacgagtaac tcgtccctct     180
tctgcagact gcttacggtt tcgtccgtgt tgcagtcgat catcagcata cctaggtttc     240
gtccgggtgt gaccgaaagg taagatggag agccttgttc ttggtgtcaa cgagaaaaca     300
cacgtccaac tcagtttgcc tgtccttcag gttagagacg tgctagtgcg tggcttcggg     360
gactctgtgg aagaggccct atcggaggca cgtgaacacc tcaaaaatgg cacttgtggt     420
ctagtagagc tggaaaaagg cgtactgccc cagcttgaac agccctatgt gttcattaaa     480
cgttctgatg ccttaagcac caatcacggc acaaggtcg ttgagctggt tgcagaaatg     540
gacggcattc agtacggtcg tagcggtata acactgggag tactcgtgcc acatgtgggc     600
gaaaccccaa ttgcataccg caatgttctt cttcgtaaga acggtaataa gggagccggt     660
ggtcatagct atggcatcga tctaaagtct tatgacttag gtgacgagct tggcactgat     720
cccattgaag attatgaaca aaactggaac actaagcatg gcagtggtgc actccgtgaa     780
ctcactcgtg agctcaatgg aggtgcagtc actcgctatg tcgacaacaa tttctgtggc     840
ccagatgggt accctcttga ttgcatcaaa gatttctcg cacgcgcggg caagtcaatg     900
tgcactcttt ccgaacaact tgattacatc gagtcgaaga gaggtgtcta ctgctgccgt     960
gaccatgagc atgaaattgc ctggttcact gagcgctctg ataagagcta cgagcaccag    1020
acacccttcg aaattaagag tgccaagaaa tttgacactt caaagggga atgcccaaag    1080
tttgtgtttc ctcttaactc aaaagtcaaa gtcattcaac acgtgttga aagaaaaag    1140
actgagggt tcatggggcg tatacgctct gtgtaccctt tgcatctcc acaggagtgt    1200
aacaatatgc acttgtctac cttgatgaaa tgtaatcatt gcgatgaagt tcatggcag    1260
acgtgcgact ttctgaaagc cacttgtgaa cattgtggca ctgaaaattt agttattgaa    1320
ggacctacta catgtgggta cctacctact aatgctgtag tgaaaatgcc atgtcctgcc    1380
tgtcaagacc cagagattgg acctgagcat agtgttgcag attatcacaa ccactcaaac    1440
```

```
attgaaactc gactccgcaa gggaggtagg actagatgtt ttggaggctg tgtgtttgcc    1500
tatgttggct gctataataa gcgtgcctac tgggttcctc gtgctagtgc tgatattggc    1560
tcaggacata ctggaattac tggtgacaat gtggagacct tgaatgagga tctccttgag    1620
atactgagtc gtgaacgtgt taacattaac attgttggcg atttttcattt gaatgaagag    1680 gttgccatca ttttggcatc tttctctgct tctacaagtg cctttattga cactataaag    1740
agtcttgatt acaagtcttt caaaaccatt gttgagtcct gcggtaacta taaagttacc    1800
aagggaaagc ccgtaaaagg tgcttggaac attggacaac agagatcagt tttaacacca    1860
ctgtgtggtt ttccctcaca ggctgctggt gttatcagat caattttttgc gcgcacactt    1920 gatgcagcaa accactcaat tcctgatttg caaagagcag ctgtcaccat acttgatggt    1980
atttctgaac agtcattacg tcttgtcgac gccatggttt atacttcaga cctgctcacc    2040
aacagtgtca ttattatggc atatgtaact ggtggtcttg tacaacagac ttctcagtgg    2100
ttgtctaatc ttttgggcac tactgttgaa aaactcaggc ctatctttga atggattgag    2160
gcgaaactta gtgcaggagt tgaatttctc aaggatgctt gggagattct caaatttctc    2220
attacaggtg ttttttgacat cgtcaagggt caaatacagg ttgcttcaga taacatcaag    2280
gattgtgtaa aatgcttcat tgatgttgtt aacaaggcac tcgaaatgtg cattgatcaa    2340
gtcactatcg ctggcgcaaa gttgcgatca ctcaacttag gtgaagtctt catcgctcaa    2400
agcaagggac tttaccgtca gtgtatacgt ggcaaggagc agctgcaact actcatgcct    2460
cttaaggcac caaaagaagt aacctttctt gaaggtgatt cacatgacac agtacttacc    2520
tctgaggagg ttgttctcaa gaacggtgaa ctcgaagcac tcgagacgcc cgttgatagc    2580
ttcacaaatg gagctatcgt tggcacacca gtctgtgtaa atggcctcat gctcttagag    2640
attaaggaca agaacaata ctgcgcattg tctcctggtt tactggctac aaacaatgtc    2700
tttcgcttaa aaggggggtgc accaattaaa ggtgtaacct ttggagaaga tactgtttgg    2760
gaagttcaag gttacaagaa tgtgagaatc acatttgagc ttgatgaacg tgttgacaaa    2820
gtgcttaatg aaaagtgctc tgtctacact gttgaatccg gtaccgaagt tactgagttt    2880
gcatgtgttg tagcagaggc tgttgtgaag actttacaac cagtttctga tctccttacc    2940
aacatgggta ttgatcttga tgagtggagt gtagctacat tctacttatt tgatgatgct    3000
ggtgaagaaa acttttcatc acgtatgtat tgttccttttt accctccaga tgaggaagaa    3060
gaggacgatg cagagtgtga ggaagaagaa attgatgaaa cctgtgaaca tgagtacggt    3120
acagaggatg attatcaagg tctccctctg gaatttggtg cctcagctga aacagttcga    3180
gttgaggaag aagaagagga agactggctg gatgatacta ctgagcaatc agagattgag    3240
ccagaaccag aacctacacc tgaagaacca gttaatcagt ttactggtta tttaaaactt    3300
actgacaatg ttgccattaa atgtgttgac atcgttaagg aggcacaaag tgctaatcct    3360
atggtgattg taaatgctgc taacatacac ctgaaacatg gtggtggtgt agcaggtgca    3420
ctcaacaagg caaccaatgg tgccatgcaa aaggagagtg atgattacat taagctaaat    3480
ggccctctta cagtaggagg gtcttgttgtg ctttctggac ataatcttgc taagaagtgt    3540
ctgcatgttg ttggacctaa cctaaatgca ggtgaggaca tccagcttct taaggcagca    3600
tatgaaaatt tcaattcaca ggacatctta cttgcaccat tgttgtcagc aggcatattt    3660
ggtgctaaac cacttcagtc tttacaagtg tgcgtgcaga cggttcgtac acaggtttat    3720
attgcagtca atgacaaagc tctttatgag caggttgtca tggattatct tgataacctg    3780
aagcctagag tggaagcacc taaacaagag gagccaccaa acacagaaga ttccaaaact    3840
```

```
gaggagaaat ctgtcgtaca gaagcctgtc gatgtgaagc caaaaattaa ggcctgcatt    3900
gatgaggtta ccacaacact ggaagaaact aagtttctta ccaataagtt actcttgttt    3960
gctgatatca atggtaagct ttaccatgat tctcagaaca tgcttagagg tgaagatatg    4020
tctttccttg agaaggatgc accttacatg gtaggtgatg ttatcactag tggtgatatc    4080
acttgtgttg taatacccte caaaaaggct ggtggcacta ctgagatgct ctcaagagct    4140
ttgaagaaag tgccagttga tgagtatata accacgtacc ctggacaagg atgtgctggt    4200
tatacacttg aggaagctaa gactgctctt aagaaatgca atctgcatt ttatgtacta     4260
ccttcagaag cacctaatgc taaggaagag attctaggaa ctgtatcctg gaatttgaga    4320
gaaatgcttg ctcatgctga agagacaaga aaattaatgc ctatatgcat ggatgttaga    4380
gccataatgg caaccatcca acgtaagtat aaaggaatta aaattcaaga gggcatcgtt    4440
gactatggtg tccgattctt cttttatact agtaaagagc ctgtagcttc tattattacg    4500
aagctgaact ctctaaatga gccgcttgtc acaatgccaa ttggttatgt gacacatggt    4560
tttaatcttg aagaggctgc gcgctgtatg cgttctctta agctcctgc cgtagtgtca     4620
gtatcatcac cagatgctgt tactacatat aatggatacc tcacttcgtc atcaaagaca    4680
tctgaggagc actttgtaga aacagtttct ttggctggct cttacagaga ttggtcctat    4740
tcaggacagt gtacagagtt aggtgttgaa tttcttaagc gtggtgacaa aattgtgtac    4800
cacactctgg agagccccgt cgagtttcat cttgacggtg aggttctttc acttgacaaa    4860
ctaaagagtc tcttatccct gcgggaggtt aagactataa agtgttcac aactgtggac      4920
aacactaatc tccacacaca gcttgtggat atgtctatga catatggaca gcagtttggt    4980
ccaacatact tggatggtgc tgatgttaca aaaattaaac ctcatgtaaa tcatgagggt    5040
aagactttct ttgtactacc tagtgatgac acactacgta gtgaagcttt cgagtactac    5100
catactcttg atgagagttt tcttggtagg tacatgtctg cttttaaacca cacaaagaaa    5160
tggaaattc ctcaagttgg tggtttaact tcaattaaat gggctgataa caattgttat     5220
ttgtctagtg ttttattagc acttcaacag cttgaagtca aattcaatgc accagcactt    5280
caagaggctt attatagagc ccgtgctggt gatgctgcta cttttgtgc actcatactc     5340
gcttacagta ataaaactgt tggcgagctt ggtgatgtca gagaaactat gacccatctt    5400
ctacagcatg ctaatttgga atctgcaaag cgagttctta atgtggtgtg taaacattgt    5460
ggtcagaaaa ctactacctt aacgggtgta gaagctgtga tgtatatggg tactctatct    5520
tatgataatc ttaagacagg tgtttccatt ccatgtgtgt gtggtcgtga tgctacacaa    5580
tatctagtac aacaagagtc ttcttttgtt atgatgtctg caccacctgc tgagtataaa    5640
ttacagcaag gtacattctt atgtgcgaat gagtacactg gtaactatca gtgtggtcat    5700
tacactcata taactgctaa ggagaccctc tatcgtattg acggagctca ccttacaaag    5760
atgtcagagt acaaaggacc agtgactgat gttttctaca ggaaacatc ttacactaca     5820
accatcaagc ctgtgtcgta taaactcgat ggagttactt acacagagat tgaaccaaaa    5880
ttggatgggt attataaaaa ggataatgct tactatacag agcagcctat agaccttgta    5940
ccaactcaac cattaccaaa tgcgagtttt gataatttca aactcacatg ttctaacaca    6000
aaatttgctg atgatttaaa tcaaatgaca ggcttcacaa agccagcttc acgagagcta    6060
tctgtcacat tcttcccaga cttgaatggc gatgtagtgg ctattgacta tagacactat    6120
tcagcgagtt tcaagaaagg tgctaaatta ctgcataagc caattgtttg gcacattaac    6180
caggctacaa ccaagacaac gttcaaacca aacacttggt gtttacgttg tctttggagt    6240
```

```
acaaagccag tagatacttc aaattcattt gaagttctgg cagtagaaga cacacaagga      6300
atggacaatc ttgcttgtga aagtcaacaa cccacctctg aagaagtagt ggaaaatcct      6360
accatacaga aggaagtcat agagtgtgac gtgaaaacta ccgaagttgt aggcaatgtc      6420
atacttaaac catcagatga aggtgttaaa gtaacacagg agttaggtca tgaggatctt      6480
atggctgctt atgtggaaaa cacaagcatt accattaaga aacctaatga gctttcacta      6540
gccttaggtt taaaaacaat tgccactcat ggtattgctg caattaatag tgttccttgg      6600
agtaaaattt tggcttatgt caaaccattc ttaggacaag cagcaattac aacatcaaat      6660
tgcgctaaga gattagcaca acgtgtgttt aacaattata tgccttatgt gtttacatta      6720
ttgttccaat tgtgtacttt tactaaaagt accaattcta gaattagagc ttcactacct      6780
acaactattg ctaaaaatag tgttaagagt gttgctaaat tatgtttgga tgccggcatt      6840
aattatgtga agtcacccaa attttctaaa ttgttcacaa tcgctatgtg gctattgttg      6900
ttaagtattt gctaggttc tctaatctgt gtaactgctg cttttggtgt actcttatct      6960
aattttggtg ctccttctta ttgtaatggc gttagagaat tgtatcttaa ttcgtctaac      7020
gttactacta tggatttctg tgaaggttct tttccttgca gcatttgttt aagtggatta      7080
gactcccttg attcttatcc agctcttgaa accattcagg tgacgatttc atcgtacaag      7140
ctagacttga caattttagg tctggccgct gagtgggttt tggcatatat gttgttcaca      7200
aaattctttt atttattagg tcttttcagct ataatgcagg tgttctttgg ctattttgct      7260
agtcatttca tcagcaattc ttggctcatg tggtttatca ttagtattgt acaaatggca      7320
cccgtttctg caatggttag gatgtacatc ttctttgctt cttttctacta catatggaag      7380 agctatgttc atatcatgga tggttgcacc tcttcgactt gcatgatgtg ctataagcgc      7440
aatcgtgcca cacgcgttga gtgtacaact attgttaatg gcatgaagag atctttctat      7500
gtctatgcaa atggaggccg tggcttctgc aagactcaca attggaattg tctcaattgt      7560
gacacatttt gcactggtag tacattcatt agtgatgaag ttgctcgtga tttgtcactc      7620
cagtttaaaa gaccaatcaa ccctactgac cagtcatcgt atattgttga tagtgttgct      7680
gtgaaaaatg gcgcgcttca cctctacttt gacaaggctg gtcaaaagac ctatgagaga      7740
catccgctct cccatttgt caatttagac aatttgagag ctaacaacac taaaggttca      7800
ctgcctatta atgtcatagt ttttgatggc aagtccaaat gcgacgagtc tgcttctaag      7860
tctgcttctg tgtactacag tcagctgatg tgccaaccta ttctgttgct tgaccaagtt      7920
cttgtatcag acgttggaga tagtactgaa gtttccgtta agatgtttga tgcttatgtc      7980
gacacccttt cagcaacttt tagtgttcct atggaaaaac ttaaggcact tgttgctaca      8040
gctcacagcg agttagcaaa gggtgtagct ttagatggtg tccttttctac attcgtgtca      8100 gctgcccgac aaggtgttgt tgataccgat gttgacacaa aggatgttat tgaatgtctc      8160
aaactttcac atcactctga cttagaagtg acaggtgaca gttgtaacaa tttcatgctc      8220
acctataata aggttgaaaa catgacgccc agagatcttg gcgcatgtat tgactgtaat      8280
gcaaggcata tcaatgccca agtagcaaaa agtcacaatg tttcactcat ctggaatgta      8340
aaagactaca tgtctcttatc tgaacagctg cgtaaacaaa ttcgtagtgc tgccaagaag      8400
aacaacatac cttttagact aacttgtgct acaactagac aggttgtcaa tgtcataact      8460
actaaaatct cactcaaggg tggtaagatt gttagtactt gttttaaact tatgcttaag      8520
gccacattat tgtgcgttct tgctgcattg gtttgttata tcgttatgcc agtcatacaca      8580 ttgtcaatcc atgatggtta cacaaatgaa atcattggtt acaaagccat tcaggatggt      8640
```

-continued

```
gtcactcgtg acatcatttc tactgatgat tgttttgcaa ataaacatgc tggttttgac    8700
gcatggttta gccagcgtgg cggttcatac aaaaatgaca aaagctgccc tgtagtagct    8760
gctatcatta caagagagat tggtttcata gtgcctggct taccgggtac tgtgctgaga    8820
gcaatcaatg gtgacttctt gcattttcta cctcgtgttt ttagtgctgt tggcaacatt    8880
tgctacacac cttccaaact cattgagtat agtgattttg ctacctctgc ttgcgttctt    8940
gctgctgagt gtacaatttt taaggatgct atgggcaaac ctgtgccata ttgttatgac    9000
actaatttgc tagagggttc tatttcttat agtgagcttc gtccagacac tcgttatgtg    9060
cttatggatg gttccatcat acagtttcct aacacttacc tggagggttc tgttagagta    9120
gtaacaactt ttgatgctga gtactgtaga catggtacat gcgaaaggtc agaagtaggt    9180
atttgcctat ctaccagtgg tagatgggtt cttaataatg agcattacag agctctatca    9240
ggagttttct gtggtgttga tgcgatgaat ctcatagcta acatctttac tcctcttgtg    9300
caacctgtgg gtgctttaga tgtgtctgct tcagtagtgg ctggtggtat tattgccata    9360
ttggtgactt gtgctgccta ctactttatg aaattcagac gtgttttttgg tgagtacaac    9420
catgttgttg ctgctaatgc acttttgttt ttgatgtctt tcactatact ctgtctggta    9480
ccagcttaca gctttctgcc gggagtctac tcagtctttt acttgtactt gacattctat    9540
ttcaccaatg atgtttcatt cttggctcac cttcaatggt ttgccatgtt ttctcctatt    9600
gtgccttttt ggataacagc aatctatgta ttctgtattt ctctgaagca ctgccattgg    9660
ttctttaaca actatcttag gaaaagagtc atgtttaatg gagttacatt tagtaccttc    9720
gaggaggctg ctttgtgtac cttttttgctc aacaaggaaa tgtacctaaa attgcgtagc    9780
gagacactgt tgccacttac acagtataac aggtatcttg ctctatataa caagtacaag    9840
tatttcagtg gagccttaga tactaccagc tatcgtgaag cagcttgctg ccacttagca    9900
aaggctctaa atgactttag caactcaggt gctgatgttc tctaccaacc accacagaca    9960
tcaatcactt ctgctgttct gcagagtggt tttaggaaaa tggcattccc gtcaggcaaa    10020
gttgaagggt gcatggtaca agtaacctgt ggaactacaa ctcttaatgg attgtggttg    10080
gatgacacag tatactgtcc aagacatgtc atttgcacag cagaagacat gcttaatcct    10140
aactatgaag atctgctcat tcgcaaatcc aaccatagct ttcttgttca ggctggcaat    10200
gttcaacttc gtgttattgg ccattctatg caaaattgtc tgcttaggct taaagttgat    10260
acttctaacc ctaagacacc caagtataaa tttgtccgta tccaacctgg tcaaacattt    10320
tcagttctag catgctacaa tggttcacca tctggtgttt atcagtgtgc catgagacct    10380
aatcatacca ttaaaggttc tttccttaat ggatcatgtg gtagtgttgg ttttaacatt    10440
gattatgatt gcgtgtcttt ctgctatatg catcatatgg agcttccaac aggagtacac    10500
gctggtactg acttagaagg taaattctat ggtccatttg ttgacagaca aactgcacag    10560
gctgcaggta cagacacaac cataacatta atgttttgg catggctgta tgctgctgtt    10620
atcaatggtg ataggtggtt tcttaataga ttcaccacta ctttgaatga ctttaacctt    10680
gtggcaatga agtacaacta tgaaccttgg acacaagatc atgttgacat attgggacct    10740
ctttctgctc aaacaggaat tgccgtctta gatatgtgtg ctgctttgaa agagctgctg    10800
cagaatggta tgaatggtcg tactatcctt ggtagcacta ttttagaaga tgagtttaca    10860
ccatttgatg ttgttagaca atgctctggt gttaccttcc aaggtaagtt caagaaaatt    10920
gttaagggca ctcatcattg gatgcttttta actttcttga catcactatt gattcttgtt    10980
caaagtacac agtggtcact gttttttcttt gtttacgaga atgctttctt gccatttact    11040
```

```
cttggtatta tggcaattgc tgcatgtgct atgctgcttg ttaagcataa gcacgcattc    11100
ttgtgcttgt ttctgttacc ttctcttgca acagttgctt actttaatat ggtctacatg    11160
cctgctagct gggtgatgcg tatcatgaca tggcttgaat tggctgacac tagcttgtct    11220
ggttataggc ttaaggattg tgttatgtat gcttcagctt tagttttgct tattctcatg    11280
acagctcgca ctgtttatga tgatgctgct agacgtgttt ggacactgat gaatgtcatt    11340
acacttgttt acaaagtcta ctatggtaat gctttagatc aagctatttc catgtgggcc    11400
ttagttattt ctgtaacctc taactattct ggtgtcgtta cgactatcat gttttagct     11460 agagctatag tgtttgtgtg tgttgagtat tacccattgt tatttattac tggcaacacc    11520
ttacagtgta tcatgcttgt ttattgtttc ttaggctatt gttgctgctg ctactttggc    11580
cttttctgtt tactcaaccg ttacttcagg cttactcttg tgtttatga ctacttggtc     11640 tctacacaag aatttaggta tatgaactcc caggggcttt tgcctcctaa gagtagtatt    11700
gatgctttca agcttaacat taagttgttg ggtattggag gtaaaccatg tatcaaggtt    11760
gctactgtac agtctaaaat gtctgacgta aagtgcacat ctgtggtact gctctcggtt    11820
cttcaacaac ttagagtaga gtcatcttct aaattgtggg cacaatgtgt acaactccac    11880
aatgatattc ttcttgcaaa agacacaact gaagctttcg agaagatggt ttctcttttg    11940
tctgttttgc tatccatgca gggtgctgta gacattaata ggttgtgcga ggaaatgctc    12000
gataaccgtg ctactcttca ggctattgct tcagaattta gttctttacc atcatatgcc    12060
gcttatgcca ctgcccaaga ggcctatgag caggctgtag ctaatggtga ttctgaagtc    12120
gttctcaaaa agttaaagaa atctttgaat gtggctaaat ctgagtttga ccgtgatgct    12180
gccatgcaac gcaagttgga aaagatggca gatcaggcta tgacccaaat gtacaaacag    12240
gcaagatctg aggacaagag ggcaaaagta actagtgcta tgcaaacaat gctcttcact    12300
atgcttagga agcttgataa tgatgcactt aacaacatta tcaacaatgc gcgtgatggt    12360
tgtgttccac tcaacatcat accattgact acagcagcca aactcatggt tgttgtccct    12420
gattatggta cctacaagaa cacttgtgat ggtaacacct ttacatatgc atctgcactc    12480
tgggaaatcc agcaagttgt tgatgcggat agcaagattg ttcaacttag tgaaattaac    12540
atggacaatt caccaaattt ggcttggcct cttattgtta cagctctaag agccaactca    12600
gctgttaaac tacagaataa tgaactgagt ccagtagcac tacgacagat gtcctgtgcg    12660
gctggtacca cacaaacagc ttgtactgat gacaatgcac ttgcctacta taacaattcg    12720
aagggaggta ggtttgtgct ggcattacta tcagaccacc aagatctcaa atgggctaga    12780
ttccctaaga gtgatggtac aggtacaatt tacacagaac tggaaccacc ttgtaggttt    12840
gttacagaca caccaaaagg gcctaaagtg aaatacttgt acttcatcaa aggcttaaac    12900
aacctaaata gaggtatggt gctgggcagt ttagctgcta cagtacgtct tcaggctgga    12960
aatgctacag aagtacctgc caattcaact gtgctttcct tctgtgcttt tgcagtagac    13020
cctgctaaag catataagga ttacctagca agtggaggac aaccaatcac caactgtgtg    13080
aagatgttgt gtacacacac tggtacagga caggcaatta ctgtaacacc agaagctaac    13140
atggaccaag agtcctttgg tggtgcttca tgttgtctgt attgtagatg ccacattgac    13200
catccaaatc ctaaaggatt ctgtgacttg aaaggtaagt acgtccaaat acctaccact    13260
tgtgctaatg acccagtggg ttttacactt agaaacacag tctgtaccgt ctgcggaatg    13320
tggaaaggtt atggctgtag ttgtgaccaa ctccgcgaac ccttgatgca gtctgcggat    13380
gcatcaacgt ttttaaacgg gtttgcggtg taagtgcagc ccgtcttaca ccgtgcggca    13440
```

```
caggcactag tactgatgtc gtctacaggg cttttgatat ttacaacgaa aaagttgctg    13500
gttttgcaaa gttcctaaaa actaattgct gtcgcttcca ggagaaggat gaggaaggca    13560
atttattaga ctcttacttt gtagttaaga ggcatactat gtctaactac caacatgaag    13620
agactattta taacttggtt aaagattgtc cagcggttgc tgtccatgac tttttcaagt    13680
ttagagtaga tggtgacatg gtaccacata tatcacgtca gcgtctaact aaatacacaa    13740
tggctgattt agtctatgct ctacgtcatt ttgatgaggg taattgtgat acattaaaag    13800
aaatactcgt cacatacaat tgctgtgatg atgattattt caataagaag gattggtatg    13860
acttcgtaga gaatcctgac atcttacgcg tatatgctaa cttaggtgag cgtgtacgcc    13920
aatcattatt aaagactgta caattctgcg atgctatgcg tgatgcaggc attgtaggcg    13980
tactgacatt agataatcag gatcttaatg ggaactggta cgatttcggt gatttcgtac    14040
aagtagcacc aggctgcgga gttcctattg tggattcata ttactcattg ctgatgccca    14100
tcctcacttt gactagggca ttggctgctg agtcccatat ggatgctgat ctcgcaaaac    14160
cacttattaa gtgggatctg ctgaaatatg attttacgga agagagactt tgtctcttcg    14220
accgttattt taaatattgg gaccagacat accatcccaa ttgtattaac tgtttggatg    14280
ataggtgtat ccttcattgt gcaaacttta atgtgttatt ttctactgtg tttccaccta    14340
caagttttgg accactagta agaaaaatat ttgtagatgg tgttccttttt gttgtttcaa    14400 ctggatacca ttttcgtgag ttaggagtcg tacataatca ggatgtaaac ttacatagct    14460
cgcgtctcag tttcaaggaa cttttagtgt atgctgctga tccagctatg catgcagctt    14520
ctggcaattt attgctagat aaacgcacta catgctttttc agtagctgca ctaacaaaca    14580
atgttgcttt tcaaactgtc aaacccggta attttaataa agactttttat gactttgctg    14640 tgtctaaagg tttctttaag gaaggaagtt ctgttgaact aaaacacttc ttctttgctc    14700
aggatggcaa cgctgctatc agtgattatg actattatcg ttataatctg ccaacaatgt    14760
gtgatatcag acaactccta ttcgtagttg aagttgttga taaatacttt gattgttacg    14820
atggtggctg tattaatgcc aaccaagtaa tcgttaacaa tctggataaa tcagctggtt    14880
tcccatttaa taaatggggt aaggctagac tttattatga ctcaatgagt tatgaggatc    14940
aagatgcact tttcgcgtat actaagcgta atgtcatccc tactataact caaatgaatc    15000
ttaagtatgc cattagtgca aagaatagag ctcgcaccgt agctggtgtc tctatctgta    15060
gtactatgac aaatagacag tttcatcaga aattattgaa gtcaatagcc gccactagag    15120
gagctactgt ggtaattgga acaagcaagt tttacggtgg ctggcataat atgttaaaaa    15180
ctgtttacag tgatgtagaa actccacacc ttatggggttg ggattatcca aaatgtgaca    15240
gagccatgcc taacatgctt aggataatgg cctctcttgt tcttgctcgc aaacataaca    15300
cttgctgtaa cttatcacac cgtttctaca ggttagctaa cgagtgtgcg caagtattaa    15360
gtgagatggt catgtgtggc ggctcactat atgttaaacc aggtggaaca tcatccggtg    15420
atgctacaac tgcttatgct aatagtgtct ttaacatttg tcaagctgtt acagccaatg    15480
taaatgcact tctttcaact gatggtaata agatagctga caagtatgtc cgcaatctac    15540
aacacaggct ctatgagtgt ctctatagaa atagggatgt tgatcatgaa ttcgtggatg    15600
agttttacgc ttacctgcgt aaacatttct ccatgatgat tctttctgat gatgccgttg    15660
tgtgctataa cagtaactat gcggctcaag gtttagtagc tagcattaag aactttaagg    15720
cagttctttt ttatcaaaac aatgtgttca tgtctgaggc aaaatgttgg actgagactg    15780
accttactaa aggacctcac gaattttgct cacagcatac aatgctagtt aaacaaggag    15840
```

-continued

```
atgattacgt gtacctgcct tacccagatc catcaagaat attaggcgca ggctgttttg    15900
tcgatgatat tgtcaaaaca gatggtacac ttatgattga aaggttcgtg tcactggcta    15960
ttgatgctta cccacttaca aaacatccta atcaggagta tgctgatgtc tttcacttgt    16020
atttacaata cattagaaag ttacatgatg agcttactgg ccacatgttg gacatgtatt    16080
ccgtaatgct aactaatgat aacacctcac ggtactggga acctgagttt tatgaggcta    16140
tgtacacacc acatacagtc ttgcaggctg taggtgcttg tgtattgtgc aattcacaga    16200
cttcacttcg ttgcggtgcc tgtattagga gaccattcct atgttgcaag tgctgctatg    16260
accatgtcat ttcaacatca cacaaattag tgttgtctgt taatccctat gtttgcaatg    16320
ccccaggttg tgatgtcact gatgtgacac aactgtatct aggaggtatg agctattatt    16380
gcaagtcaca taagcctccc attagttttc cattatgtgc taatggtcag gttttttggtt    16440
tatacaaaaa cacatgtgta ggcagtgaca atgtcactga cttcaatgcg atagcaacat    16500
gtgattggac taatgctggc gattacatac ttgccaacac ttgtactgag agactcaagc    16560
ttttcgcagc agaaacgctc aaagccactg aggaaacatt taagctgtca tatggtattg    16620
ctactgtacg cgaagtactc tctgacagag aattgcatct ttcatgggag gttggaaaac    16680
ctagaccacc attgaacaga aactatgtct ttactggtta ccgtgtaact aaaaatagta    16740
aagtacagat tggagagtac acctttgaaa aaggtgacta tggtgatgct gttgtgtaca    16800
gaggtactac gacatacaag ttgaatgttg gtgattactt tgtgttgaca tctcacactg    16860
taatgccact tagtgcacct actctagtgc cacaagagca ctatgtgaga attactggct    16920
tgtacccaac actcaacatc tcagatgagt tttctagcaa tgttgcaaat tatcaaaagg    16980
tcggcatgca aaagtactct acactccaag gaccacctgg tactggtaag agtcatttg    17040
ccatcggact tgctctctat tacccatctg ctcgcatagt gtatacggca tgctctcatg    17100
cagctgttga tgcccctatgt gaaaaggcat taaaatattt gcccatagat aaatgtagta    17160
gaatcatacc tgcgcgtgcg cgcgtagagt gttttgataa attcaaagtg aattcaacac    17220
tagaacagta tgtttttctgc actgtaaatg cattgccaga acaactgctg acattgtag    17280
tctttgatga atctctatg gctactaatt atgacttgag tgttgtcaat gctagacttc    17340
gtgcaaaaca ctacgtctat attggcgatc ctgctcaatt accagcccccc cgcacattgc    17400
tgactaaagg cacactagaa ccagaatatt ttaattcagt gtgcagactt atgaaaacaa    17460
taggtccaga catgttcctt ggaacttgtc gccgttgtcc tgctgaaatt gttgacactg    17520
tgagtgcttt agtttatgac aataagctaa aagcacacaa ggataagtca gctcaatgct    17580
tcaaaatgtt ctacaaaggt gttattacac atgatgttc atctgcaatc aacagacctc    17640
aaataggcgt tgtaagagaa tttcttacac gcaatcctgc ttggagaaaa gctgttttta    17700
tctcaccta taattcacag aacgctgtag cttcaaaaat cttaggattg cctacgcaga    17760
ctgttgattc atcacagggt tctgaatatg actatgtcat attcacacaa actactgaaa    17820
cagcacactc ttgtaatgtc aaccgcttca atgtggctat cacaagggca aaaattggca    17880
ttttgtgcat aatgtctgat agagatcttt atgacaaact gcaatttaca agtctagaaa    17940
taccacgtcg caatgtggct acattacaag cagaaatgt aactggactt tttaaggact    18000
gtagtaagat cattactggt cttcatccta cacaggcacc tacacacctc agcgttgata    18060
taaagttcaa gactgaagga ttatgtgttg acatccagg cataccaaag gacatgacct    18120
accgtagact catctctatg atgggttcca aaatgaatta ccaagtcaat ggttacccta    18180
atatgtttat cacccgcgaa gaagctattc gtcacgttcg tgcgtggatt ggctttgatg    18240
```

```
tagagggctg tcatgcaact agagatgctg tgggtactaa cctacctctc cagctaggat    18300
tttctacagg tgttaactta gtagctgtac cgactggtta tgttgacact gaaaataaca    18360
cagaattcac cagagttaat gcaaaacctc caccaggtga ccagtttaaa catcttatac    18420
cactcatgta taaaggcttg ccctggaatg tagtgcgtat taagatagta caaatgctca    18480
gtgatacact gaaaggattg tcagacagag tcgtgttcgt cctttgggcg catggctttg    18540
agcttacatc aatgaagtac tttgtcaaga ttggacctga aagaacgtgt tgtctgtgtg    18600
acaaacgtgc aacttgcttt tctacttcat cagatactta tgcctgctgg aatcattctg    18660
tgggttttga ctatgtctat aacccattta tgattgatgt tcagcagtgg ggctttacgg    18720
gtaaccttca gagtaaccat gaccaacatt gccaggtaca tggaaatgca catgtggcta    18780
gttgtgatgc tatcatgact agatgtttag cagtccatga gtgctttgtt aagcgcgttg    18840
attggtctgt tgaatacccct attataggag atgaactgag ggttaattct gcttgcagaa    18900
aagtacaaca catggttgtg aagtctgccc tcctggctga taagtttcca gttcttcatg    18960
acattggaaa tccaaaggct atcaagtgtg tgcctcaggc tgaagtagaa tggaagttct    19020
acgatgctca gccatgtagt gacaaagctt acaaaataga ggagctcttc tattcttatg    19080
ctacacatca cgataaattc actgatggtg tttgtttgtt ttggaattgt aacgttgatc    19140
gttacccagc caatgcaatt gtgtgtaggt ttgacacaag agtcttgtca aacttgaact    19200
taccaggctg tgatggtggt agtttgtatg tgaataagca tgcattccac actccagctt    19260
tcgataaaag tgcatttact aatttaaagc aattgccttt cttttactat tctgatagtc    19320
cttgtgagtc tcatggcaaa caagtagtgt cggatattga ttatgttcca ctcaaatctg    19380
ctacgtgtat tacacgatgc aatttaggtg gtgctgtttg cagacaccat gcaaatgagt    19440
accgacagta cttggatgca tataatatga tgatttctgc tggatttagc ctatggattt    19500
acaaacaatt tgatacttat aacctgtgga atacatttac caggttacag agtttagaaa    19560
atgtggctta taatgttgtt aataaaggac actttgatgg acacgccggc gaagcacctg    19620
tttccatcat taataatgct gtttacacaa aggtagatgg tattgatgtg agatctttg    19680 aaaataagac aacacttcct gttaatgttg catttgagct ttgggctaag cgtaacatta    19740
aaccagtgcc agagattaag atactcaata atttgggtgt tgatatcgct gctaatactg    19800
taatctggga ctataaaaga gaagccccag cacatgtatc tacaataggt gtctgcacaa    19860
tgactgacat tgccaagaaa cctactgaga gtgcttgttc ttcacttact gtcttgtttg    19920
atggtagagt ggaaggacag gtagaccttt ttagaaacgc ccgtaatggt gttttaataa    19980
cagaaggttc agtcaaaggt ctaacacctt caaagggacc agcacaagct agcgtcaatg    20040
gagtcacatt aattggagaa tcagtaaaaa cacagtttaa ctactttaag aaagtagacg    20100
gcattattca acagttgcct gaaacctact ttactcagag cagagactta gaggatttta    20160
agcccagatc acaaatggaa actgactttc tcgagctcgc tatggatgaa ttcatacagc    20220
gatataagct cgagggctat gccttcgaac acatcgttta tggagatttc agtcatggac    20280
aacttggcgg tcttcattta atgataggct tagccaagcg ctcacaagat tcaccactta    20340
aattagagga ttttatccct atggacagca cagtgaaaaa ttacttcata acagatgcgc    20400
aaacaggttc atcaaaatgt gtgtgttctg tgattgatct tttacttgat gactttgtcg    20460
agataataaa gtcacaagat tgtcagtgaa tttcaaaagt ggtcaaggtt acaattgact    20520
atgctgagat tcattcatg ctttggtgta aggacggaca tgttgaaacc ttctaccca    20580 aactacaagc aagtcaagcg tggcaaccag gtgttgcgat gcctaacttg tacaagatgc    20640
```

-continued

```
aaagaatgct tcttgaaaag tgtgaccttc agaattatgg tgaaaatgct gttataccaa    20700
aaggaataat gatgaatgtc gcaaagtata ctcaactgtg tcaatactta aatacactta    20760
ctttagctgt accctacaac atgagagtta ttcactttgg tgctggctct gataaaggag    20820
ttgcaccagg tacagctgtg ctcagacaat ggttgccaac tggcacacta cttgtcgatt    20880
cagatcttaa tgacttcgtc tccgacgcag attctacttt aattggagac tgtgcaacag    20940
tacatacggc taataaatgg gaccttatta ttagcgatat gtatgaccct aggaccaaac    21000
atgtgacaaa agagaatgac tctaaagaag ggttttttcac ttatctgtgt ggatttataa    21060
agcaaaaact agccctgggt ggttctatag ctgtaaagat aacagagcat tcttggaatg    21120 ctgacccttta caagcttatg ggccatttct catggtggac agcttttgtt acaaatgtaa    21180
atgcatcatc atcggaagca tttttaattg gggctaacta tcttggcaag ccgaaggaac    21240
aaattgatgg ctataccatg catgctaact acattttctg gaggaacaca atcctatcc    21300 agttgtcttc ctattcactc tttgacatga gcaaatttcc tcttaaatta agaggaactg    21360
ctgtaatgtc tcttaaggag aatcaaatca atgatatgat ttattctctt ctggaaaaag    21420
gtaggcttat cattagagaa acaacagag ttgtggtttc aagtgatatt cttgttaaca    21480
actaaacgaa catgtttatt ttcttattat ttcttactct cactagtggt agtgaccttg    21540
accggtgcac cacttttgat gatgttcaag ctcctaatta cactcaacat acttcatcta    21600 tgagggggt ttactatcct gatgaaattt ttagatcaga cactctttat ttaactcagg    21660
atttatttct tccatttttat tctaatgtta cagggtttca tactattaat catacgtttg    21720
gcaaccctgt catacctttt aaggatggta tttattttgc tgccacagag aaatcaaatg    21780
ttgtccgtgg ttgggttttt ggttctacca tgaacaacaa gtcacagtcg gtgattatta    21840
ttaacaattc tactaatgtt gttatacgag catgtaactt tgaattgtgt gacaacccctt    21900 tctttgctgt ttctaaaccc atgggtacac agacacatac tatgatattc gataatgcat    21960
ttaattgcac tttcgagtac atatctgatg ccttttcgct tgatgtttca gaaaagtcag    22020 gtaatttttaa acacttacga gagtttgtgt ttaaaaataa agatgggttt ctctatgttt    22080
ataagggcta tcaacctata gatgtagttc gtgatctacc ttctggtttt aacactttga    22140
aacctatttt taagttgcct cttggtatta acattacaaa ttttagagcc attcttacag    22200
ccttttcacc tgctcaagac atttgggca cgtcagctgc agcctatttt gttggctatt    22260
taaagccaac tacatttatg ctcaagtatg atgaaaatgg tacaatcaca gatgctgttg    22320
attgttctca aaatccactt gctgaactca atgctctgt taagagcttt gagattgaca    22380
aaggaattta ccagacctct aatttcaggg ttgttccctc aggagatgtt gtgagattcc    22440
ctaatattac aaacttgtgt cctttggag aggtttttaa tgctactaaa ttcccttctg    22500
tctatgcatg ggagagaaaa aaaatttcta attgtgttgc tgattactct gtgctctaca    22560
actcaacatt tttttcaacc tttaagtgct atggcgtttc tgccactaag ttgaatgatc    22620
tttgcttctc caatgtctat gcagattctt ttgtagtcaa gggagatgat gtaagacaaa    22680
tagcgccagg acaaactggt gttattgctg attataatta taaattgcca gatgatttca    22740
tgggttgtgt ccttgcttgg aatactagga acattgatgc tacttcaact ggtaattata    22800
attataaata taggtatctt agacatggca agcttaggcc ctttgagaga gacatatcta    22860
atgtgccttt ctcccctgat ggcaaacctt gcaccccacc tgctcttaat tgttattggc    22920
cattaaatga ttatggttttt tacaccacta ctggcattgg ctaccaacct tacagagttg    22980
tagtactttc ttttgaactt ttaaatgcac cggccacggt ttgtggacca aaattatcca    23040
```

```
ctgaccttat taagaaccag tgtgtcaatt ttaattttaa tggactcact ggtactggtg    23100
tgttaactcc ttcttcaaag agatttcaac catttcaaca atttggccgt gatgtttctg    23160
atttcactga ttccgttcga gatcctaaaa catctgaaat attagacatt tcaccttgct    23220 cttttgggg tgtaagtgta attacacctg aacaaatgc ttcatctgaa gttgctgttc    23280
tatatcaaga tgttaactgc actgatgttt ctacagcaat tcatgcagat caactcacac    23340
cagcttggcg catatattct actggaaaca atgtattcca gactcaagca ggctgtctta    23400
taggagctga gcatgtcgac acttcttatg agtgcgacat tcctattgga gctggcattt    23460
gtgctagtta ccatacagtt tctttattac gtagtactag ccaaaaatct attgtggctt    23520
atactatgtc tttaggtgct gatagttcaa ttgcttactc taataacacc attgctatac    23580
ctactaactt ttcaattagc attactacag aagtaatgcc tgtttctatg ctaaaacct    23640 ccgtagattg taatatgtac atctgcggag attctactga atgtgctaat ttgcttctcc    23700
aatatggtag cttttgcaca caactaaatc gtgcactctc aggtattgct gctgaacagg    23760
atcgcaacac acgtgaagtg ttcgctcaag tcaaacaaat gtacaaaacc caactttga    23820 aatattttgg tggtttaat ttttcacaaa tattacctga ccctctaaag ccaactaaga    23880
ggtcttttat tgaggacttg ctctttaata aggtgacact cgctgatgct ggcttcatga    23940
agcaatatgg cgaatgccta ggtgatatta tgctagaga tctcatttgt gcgcagaagt    24000
tcaatggact tacagtgttg ccacctctgc tcactgatga tatgattgct gcctacacgg    24060 ctgctcagt tagtggtact gccactgctg atggacatt tggtgctggc gctgctcttc    24120
aaataccttt tgctatgcaa atggcatata ggttcaatgg cattggagtt acccaaaatg    24180
ttctctatga gaaccaaaaa caaatcgcca accaatttaa caaggcgatt agtcaaattc    24240
aagaatcact tacaacaaca tcaactgcat tgggcaagct gcaagacgtt gttaaccaga    24300
atgctcaagc attaaacaca cttgttaaac aacttagctc taattttggt gcaatttcaa    24360
gtgtgctaaa tgatatcctt tcgcgacttg ataaagtcga ggcggaggta caaattgaca    24420
ggttaattac aggcagactt caaagccttc aaacctatgt aacacaacaa ctaatcaggg    24480
ctgctgaaat cagggcttct gctaatcttg ctgctactaa aatgtctgag tgtgttcttg    24540
gacaatcaaa aagagttgac ttttgtggaa agggctacca ccttatgtcc ttcccacaag    24600
cagccccgca tggtgttgtc ttcctacatg tcacgtatgt gccatcccag gagaggaact    24660
tcaccacagc gccagcaatt tgtcatgaag gcaaagcata cttccctcgt gaaggtgttt    24720
ttgtgtttaa tggcacttct tggtttatta cacagaggaa cttctttct ccacaaataa    24780 ttactacaga caatacattt gtctcaggaa attgtgatgt cgttattggc atcattaaca    24840
acacagttta tgatcctctg caacctgagc tcgactcatt caaagaagag ctggacaagt    24900
acttcaaaaa tcatacatca ccagatgttg atcttggcga catttcaggc attaacgctt    24960
ctgtcgtcaa cattcaaaaa gaaattgacc gcctcaatga ggtcgctaaa aatttaaatg    25020
aatcactcat tgaccttcaa gaattgggaa atatgagca atatattaaa tggccttggt    25080
atgtttggct cggcttcatt gctggactaa ttgccatcgt catggttaca atcttgcttt    25140
gttgcatgac tagttgttgc agttgcctca gggtgcatg ctcttgtggt tcttgctgca    25200
agtttgatga ggatgactct gagccagttc tcaagggtgt caaattacat tacacataaa    25260
cgaacttatg gatttgttta tgagattttt tactcttgga tcaattactg cacagccagt    25320
aaaaattgac aatgcttctc ctgcaagtac tgttcatgct acagcaacga taccgctaca    25380
agcctcactc cctttcggat ggcttgttat tggcgttgca tttcttgctg ttttcagag    25440
```

```
cgctaccaaa ataattgcgc tcaataaaag atggcagcta gcccctttata agggcttcca   25500 gttcatttgc aatttactgc tgctatttgt taccatctat tcacatcttt tgcttgtcgc   25560
tgcaggtatg gaggcgcaat ttttgtacct ctatgccttg atatattttc tacaatgcat   25620
caacgcatgt agaattatta tgagatgttg gctttgttgg aagtgcaaat ccaagaaccc   25680
attactttat gatgccaact actttgtttg ctggcacaca cataactatg actactgtat   25740
accatataac agtgtcacag atacaattgt cgttactgaa ggtgacggca tttcaacacc   25800
aaaactcaaa gaagactacc aaattggtgg ttattctgag ataggcact caggtgttaa    25860 agactatgtc gttgtacatg gctatttcac cgaagtttac taccagcttg agtctacaca   25920
aattactaca gacactggta ttgaaaatgc tacattcttc atctttaaca agcttgttaa   25980
agacccaccg aatgtgcaaa tacacacaat cgacggctct tcaggagttg ctaatccagc   26040
aatggatcca atttatgatg agccgacgac gactactagc gtgcctttgt aagcacaaga   26100
aagtgagtac gaacttatgt actcattcgt ttcggaagaa acaggtacgt taatagttaa   26160
tagcgtactt ctttttcttg ctttcgtggt attcttgcta gtcacactag ccatccttac   26220
tgcgcttcga ttgtgtgcgt actgctgcaa tattgttaac gtgagtttag taaaaccaac   26280
ggtttacgtc tactcgcgtg ttaaaaatct gaactcttct gaaggagttc ctgatcttct   26340
ggtctaaacg aactaactat tattattatt ctgtttggaa ctttaacatt gcttatcatg   26400
gcagacaacg gtactattac cgttgaggag cttaaacaac tcctggaaca atggaaccta   26460
gtaataggtt tcctattcct agcctggatt atgttactac aatttgccta ttctaatcgg   26520
aacaggtttt tgtacataat aaagcttgtt ttcctctggc tcttgtggcc agtaacactt   26580
gcttgttttg tgcttgctgc tgtctacaga attaattggg tgactggcgg gattgcgatt   26640
gcaatggctt gtattgtagg cttgatgtgg cttagctact tcgttgcttc cttcaggctg   26700
tttgctcgta cccgctcaat gtggtcattc aacccagaaa caaacattct tctcaatgtg   26760
cctctccggg ggacaattgt gaccagaccg ctcatggaaa gtgaacttgt cattggtgct   26820
gtgatcattc gtggtcactt gcgaatggcc ggacaccccc tagggcgctg tgacattaag   26880
gacctgccaa aagagatcac tgtggctaca tcacgaacgc tttcttatta caaattagga   26940
gcgtcgcagc gtgtaggcac tgattcaggt ttttgctgcat acaaccgcta ccgtattgga   27000
aactataaat taaatacaga ccacgccggt agcaacgaca atattgcttt gctagtacag   27060
taagtgacaa cagatgtttc atcttgttga cttccaggtt acaatagcag agatattgat   27120
tatcattatg aggactttca ggattgctat ttggaatctt gacgttataa taagttcaat   27180
agtgagacaa ttatttaagc ctctaactaa gaagaattat tcggagttag atgatgaaga   27240
acctatggag ttagattatc cataaaacga acatgaaaat tattctcttc ctgacattga   27300
ttgtatttac atcttgcgag ctatatcact atcaggagtg tgttagaggt acgactgtac   27360
tactaaaaga accttgccca tcaggaacat acgagggcaa ttcaccattt caccctcttg   27420
ctgacaataa atttgcacta acttgcacta gcacacactt tgcttttgct tgtgctgacg   27480
gtactcgaca tacctatcag ctgcgtgcaa gatcagtttc accaaaactt ttcatcgac    27540 aagaggaggt tcaacaagag ctctactcgc cacttttttct cattgttgct gctctagtat   27600
ttttaatact ttgcttcacc attaagagaa agacagaatg aatgagctca ctttaattga   27660
cttctatttg tgctttttag ccttttctgct attccttgtt ttaataatgc ttattatatt   27720
ttggttttca ctcgaaatcc aggatctaga agaaccttgt accaaagtct aaacgaacat   27780
gaaacttctc attgtttttga cttgtatttc tctatgcagt tgcatatgca ctgtagtaca   27840
```

```
gcgctgtgca tctaataaac ctcatgtgct tgaagatcct tgtaaggtac aacactaggg    27900
gtaatactta tagcactgct tggctttgtg ctctaggaaa ggttttacct tttcatagat    27960
ggcacactat ggttcaaaca tgcacaccta atgttactat caactgtcaa gatccagctg    28020
gtggtgcgct tatagctagg tgttggtacc ttcatgaagg tcaccaaact gctgcattta    28080
gagacgtact tgttgtttta aataaacgaa caaattaaaa tgtctgataa tggaccccaa    28140
tcaaaccaac gtagtgcccc ccgcattaca tttggtggac ccacagattc aactgacaat    28200
aaccagaatg gaggacgcaa tgggcaagg ccaaacagc gccgacccca aggtttaccc     28260
aataatactg cgtcttggtt cacagctctc actcagcatg gcaaggagga acttagattc    28320
cctcgaggcc agggcgttcc aatcaacacc aatagtggtc cagatgacca aattggctac    28380
taccgaagag ctacccgacg agttcgtggt ggtgacggca aaatgaaaga gctcagcccc    28440
agatggtact ctattaccct aggaactggc ccagaagctt cacttcccta cggcgctaac    28500
aaagaaggca tcgtatgggt tgcaactgag ggagccttga atacacccaa agaccacatt    28560
ggcacccgca atcctaataa caatgctgcc accgtgctac aacttcctca aggaacaaca    28620
ttgccaaaag gcttctacgc agagggaagc agaggcggca gtcaagcctc ttctcgctcc    28680
tcatcacgta gtcgcggtaa ttcaagaaat tcaactcctg cagcagtag gggaaattct    28740 cctgctcgaa tggctagcgg aggtggtgaa actgccctcg cgctattgct gctagacaga    28800
ttgaaccagc ttgagagcaa agtttctggt aaaggccaac aacaacaagg ccaaactgtc    28860
actaagaaat ctgctgctga ggcatctaaa aagcctcgcc aaaaacgtac tgccacaaaa    28920
cagtacaacg tcactcaagc atttgggaga cgtggtccag aacaaaccca aggaaatttc    28980
ggggaccaag aacctaatcag acaaggaact gattacaaac attggccgca aattgcacaa    29040
tttgctccaa gtgcctctgc attctttgga atgtcacgca ttggcatgga agtcacacct    29100 tcggaacat ggctgactta tcatggagcc attaaattgg atgacaaaga tccacaattc    29160
aaagacaacg tcatactgct gaacaagcac attgacgcat acaaaacatt cccaccaaca    29220
gagcctaaaa aggacaaaaa gaaaaagact gatgaagctc agcctttgcc gcagagacaa    29280
aagaagcagc ccactgtgac tcttcttcct gcggctgaca tggatgattt ctccagacaa    29340
cttcaaaatt ccatgagtgg agcttctgct gattcaactc aggcataaac actcatgatg    29400
accacacaag gcagatgggc tatgtaaacg ttttcgcaat ccgtttacg atacatagtc    29460 tactcttgtg cagaatgaat tctcgtaact aaacagcaca gtaggttta gttaacttta    29520 atctcacata gcaatcttta atcaatgtgt aacattaggg aggacttgaa agagccacca    29580
cattttcatc gaggccacgc ggagtacgat cgagggtaca gtgaataatg ctagggagag    29640
ctgcctatat ggaagagccc taatgtgtaa aattaatttt agtagtgcta tccccatgtg    29700
attttaatag cttcttagga gaatgacaaa aaaaaaaaa aaaaaaa                  29748
```

<210> SEQ ID NO 2
<211> LENGTH: 29727
<212> TYPE: DNA
<213> ORGANISM: SARS coronavirus
<220> FEATURE:
<221> NAME/KEY: misc_feature
<222> LOCATION: (1)..(29727)
<223> OTHER INFORMATION: SARS Urbani 278741 sequence

<400> SEQUENCE: 2

```
atattaggtt tttacctacc caggaaaagc caaccaacct cgatctcttg tagatctgtt     60
ctctaaacga actttaaaat ctgtgtagct gtcgctcggc tgcatgccta gtgcacctac    120
```

-continued

```
gcagtataaa caataataaa ttttactgtc gttgacaaga aacgagtaac tcgtccctct    180
tctgcagact gcttacggtt tcgtccgtgt tgcagtcgat catcagcata cctaggtttc    240
gtccgggtgt gaccgaaagg taagatggag agccttgttc ttggtgtcaa cgagaaaaca    300
cacgtccaac tcagtttgcc tgtccttcag gttagagacg tgctagtgcg tggcttcggg    360
gactctgtgg aagaggccct atcggaggca cgtgaacacc tcaaaaatgg cacttgtggt    420
ctagtagagc tggaaaaagg cgtactgccc cagcttgaac agccctatgt gttcattaaa    480
cgttctgatg ccttaagcac caatcacggc cacaaggtcg ttgagctggt tgcagaaatg    540
gacggcattc agtacggtcg tagcggtata acactgggag tactcgtgcc acatgtgggc    600
gaaaccccaa ttgcataccg caatgttctt cttcgtaaga acggtaataa gggagccggt    660
ggtcatagct atggcatcga tctaaagtct tatgacttag gtgacgagct tggcactgat    720
cccattgaag attatgaaca aaactggaac actaagcatg gcagtggtgc actccgtgaa    780
ctcactcgtg agctcaatgg aggtgcagtc actcgctatg tcgacaacaa tttctgtggc    840
ccagatgggt accctcttga ttgcatcaaa gattttctcg cacgcgcggg caagtcaatg    900
tgcactcttt ccgaacaact tgattacatc gagtcgaaga gaggtgtcta ctgctgccgt    960
gaccatgagc atgaaattgc ctggttcact gagcgctctg ataagagcta cgagcaccag   1020
acacccttcg aaattaagag tgccaagaaa tttgacactt tcaaggggga atgcccaaag   1080
tttgtgtttc ctcttaactc aaaagtcaaa gtcattcaac cacgtgttga aaagaaaaag   1140
actgagggtt tcatggggcg tatacgctct gtgtaccctg ttgcatctcc acaggagtgt   1200
aacaatatgc acttgtctac cttgatgaaa tgtaatcatt gcgatgaagt ttcatggcag   1260
acgtgcgact ttctgaaagc cacttgtgaa cattgtggca ctgaaaattt agttattgaa   1320
ggacctacta catgtgggta cctacctact aatgctgtag tgaaaatgcc atgtcctgcc   1380
tgtcaagacc cagagattgg acctgagcat agtgttgcag attatcacaa ccactcaaac   1440
attgaaactc gactccgcaa gggaggtagg actagatgtt ttggaggctg tgtgtttgcc   1500
tatgttggct gctataataa gcgtgcctac tgggttcctc gtgctagtgc tgatattggc   1560
tcaggccata ctggcattac tggtgacaat gtggagacct tgaatgagga tctccttgag   1620
atactgagtc gtgaacgtgt taacattaac attgttggcg attttcattt gaatgaagag   1680
gttgccatca ttttggcatc tttctctgct tctacaagtg cctttattga cactataaag   1740
agtcttgatt acaagtcttt caaaaccatt gttgagtcct gcggtaacta taagttacc    1800 aagggaaagc ccgtaaaagg tgcttggaac attggacaac agagatcagt tttaacacca   1860
ctgtgtggtt ttccctcaca ggctgctggt gttatcagat caattttttgc gcgcacactt   1920 gatgcagcaa accactcaat tcctgatttg caaagagcag ctgtcaccat acttgatggt   1980
atttctgaac agtcattacg tcttgtcgac gccatggttt atacttcaga cctgctcacc   2040
aacagtgtca ttattatggc atatgtaact ggtggtcttg tacaacagac ttctcagtgg   2100
ttgtctaatc ttttgggcac tactgttgaa aaactcaggc ctatctttga atggattgag   2160
gcgaaactta gtgcaggagt tgaatttctc aaggatgctt gggagattct caaatttctc   2220
attacaggtg ttttgacat cgtcaagggt caaatacagg ttgcttcaga taacatcaag   2280
gattgtgtaa aatgcttcat tgatgttgtt aacaaggcac tcgaaatgtg cattgatcaa   2340
gtcactatcg ctggcgcaaa gttgcgatca ctcaacttag gtgaagtctt catcgctcaa   2400
agcaagggac tttaccgtca gtgtatacgt ggcaaggagc agctgcaact actcatgcct   2460
cttaaggcac caaaagaagt aaccttttctt gaaggtgatt cacatgacac agtacttacc   2520
```

```
tctgaggagg ttgttctcaa gaacggtgaa ctcgaagcac tcgagacgcc cgttgatagc    2580
ttcacaaatg gagctatcgt tggcacacca gtctgtgtaa atggcctcat gctcttagag    2640
attaaggaca aagaacaata ctgcgcattg tctcctggtt tactggctac aaacaatgtc    2700
tttcgcttaa aggggggtgc accaattaaa ggtgtaacct ttggagaaga tactgtttgg    2760
gaagttcaag gttacaagaa tgtgagaatc acatttgagc ttgatgaacg tgttgacaaa    2820
gtgcttaatg aaaagtgctc tgtctacact gttgaatccg gtaccgaagt tactgagttt    2880
gcatgtgttg tagcagaggc tgttgtgaag actttacaac cagtttctga tctccttacc    2940
aacatgggta ttgatcttga tgagtggagt gtagctacat tctacttatt tgatgatgct    3000
ggtgaagaaa actttttcatc acgtatgtat tgttcctttt accctccaga tgaggaagaa    3060
gaggacgatg cagagtgtga ggaagaagaa attgatgaaa cctgtgaaca tgagtacggt    3120
acagaggatg attatcaagg tctccctctg gaatttggtg cctcagctga aacagttcga    3180
gttgaggaag aagaagagga agactggctg gatgatacta ctgagcaatc agagattgag    3240
ccagaaccag aacctacacc tgaagaacca gttaatcagt ttactggtta tttaaaactt    3300
actgacaatg ttgccattaa atgtgttgac atcgttaagg aggcacaaag tgctaatcct    3360
atggtgattg taaatgctgc taacatacac ctgaaacatg gtggtggtgt agcaggtgca    3420
ctcaacaagg caaccaatgg tgccatgcaa aaggagagtg atgattacat taagctaaat    3480
ggccctctta cagtaggagg gtcttgtttg cttttctgga cataatcttgc taagaagtgt    3540 ctgcatgttg ttggacctaa cctaaatgca ggtgaggaca tccagcttct taaggcagca    3600
tatgaaaatt tcaattcaca ggacatctta cttgcaccat tgttgtcagc aggcatattt    3660
ggtgctaaac cacttcagtc tttacaagtg tgcgtgcaga cggttcgtac acaggtttat    3720
attgcagtca atgacaaagc tctttatgag caggttgtca tggattatct tgataacctg    3780
aagcctagag tggaagcacc taaacaagag gagccaccaa acacagaaga ttccaaaact    3840
gaggagaaat ctgtcgtaca aagcctgtc gatgtgaagc caaaaattaa ggcctgcatt    3900
gatgaggtta ccacaacact ggaagaaact aagtttctta ccaataagtt actcttgttt    3960
gctgatatca atggtaagct ttaccatgat tctcagaaca tgcttagagg tgaagatatg    4020
tctttccttg agaaggatgc accttacatg gtaggtgatg ttatcactag tggtgatatc    4080
acttgtgttg taatacccctc caaaaaggct ggtggcacta ctgagatgct ctcaagagct    4140
ttgaagaaag tgccagttga tgagtatata accacgtacc ctggacaagg atgtgctggt    4200
tatacacttg aggaagctaa gactgctctt aagaaatgca atctgcatt ttatgtacta    4260 ccttcagaag cacctaatgc taaggaagag attctaggaa ctgtatcctg gaatttgaga    4320
gaaatgcttg ctcatgctga agagacaaga aaattaatgc ctatatgcat ggatgttaga    4380
gccataatgg caaccatcca acgtaagtat aaaggaatta aaattcaaga gggcatcgtt    4440
gactatggtg tccgattctt ctttatact agtaaagagc ctgtagcttc tattattacg    4500
aagctgaact ctctaaatga ccgcttgtc acaatgccaa ttggttatgt gacacatggt    4560
tttaatcttg aagaggctgc gcgctgtatg cgttctctta agctcctgc cgtagtgtca    4620 gtatcatcac cagatgctgt tactacatat aatggatacc tcacttcgtc atcaaagaca    4680
tctgaggagc acttttgtaga aacagtttct ttggctggct cttacagaga ttggtcctat    4740
tcaggacagc gtacagagtt aggtgttgaa tttcttaagc gtggtgacaa aattgtgtac    4800
cacactctgg agagcccccgt cgagtttcat cttgacggtg aggttctttc acttgacaaa    4860
ctaaagagtc tcttatcccct gcgggaggtt aagactataa aagtgttcac aactgtggac    4920
```

```
aacactaatc tccacacaca gcttgtggat atgtctatga catatggaca gcagtttggt   4980
ccaacatact tggatggtgc tgatgttaca aaaattaaac ctcatgtaaa tcatgagggt   5040
aagactttct ttgtactacc tagtgatgac acactacgta gtgaagcttt cgagtactac   5100
catactcttg atgagagttt tcttggtagg tacatgtctg ctttaaacca cacaaagaaa   5160
tggaaatttc ctcaagttgg tggtttaact tcaattaaat gggctgataa caattgttat   5220
ttgtctagtg ttttattagc acttcaacag cttgaagtca aattcaatgc accagcactt   5280
caagaggctt attatagagc ccgtgctggt gatgctgcta acttttgtgc actcatactc   5340
gcttacagta ataaaactgt tggcgagctt ggtgatgtca gagaaactat gacccatctt   5400
ctacagcatg ctaatttgga atctgcaaag cgagttctta atgtggtgtg taaacattgt   5460
ggtcagaaaa ctactacctt aacgggtgta aagctgtga tgtatatggg tactctatct   5520
tatgataatc ttaagacagg tgtttccatt ccatgtgtgt gtggtcgtga tgctacacaa   5580
tatctagtac aacaagagtc ttcttttgtt atgatgtctg caccacctgc tgagtataaa   5640
ttacagcaag gtacattctt atgtgcgaat gagtacactg gtaactatca gtgtggtcat   5700
tacactcata taactgctaa ggagaccctc tatcgtattg acggagctca ccttacaaag   5760
atgtcagagt acaaaggacc agtgactgat gttttctaca aggaaacatc ttacactaca   5820
accatcaagc ctgtgtcgta taaactcgat ggagttactt acacagagat tgaaccaaaa   5880
ttggatgggt attataaaaa ggataatgct tactatacag agcagcctat agaccttgta   5940
ccaactcaac cattaccaaa tgcgagtttt gataatttca aactcacatg ttctaacaca   6000
aaatttgctg atgatttaaa tcaaatgaca ggcttcacaa agccagcttc acgagagcta   6060
tctgtcacat tcttcccaga cttgaatggc gatgtagtgg ctattgacta tagacactat   6120
tcagcgagtt tcaagaaagg tgctaaatta ctgcataagc caattgtttg gcacattaac   6180
caggctacaa ccaagacaac gttcaaacca aacacttggt gtttacgttg tctttggagt   6240
acaaagccag tagatacttc aaattcattt gaagttctgg cagtagaaga cacacaagga   6300
atggacaatc ttgcttgtga agtcaacaa cccacctctg aagaagtagt ggaaaatcct   6360
accatacaga aggaagtcat agagtgtgac gtgaaaacta ccgaagttgt aggcaatgtc   6420
atacttaaac catcagatga aggtgttaaa gtaacacaag agttaggtca tgaggatctt   6480
atggctgctt atgtggaaaa cacaagcatt accattaaga aacctaatga gctttcacta   6540
gccttaggtt taaaaacaat tgccactcat ggtattgctg caattaatag tgttccttgg   6600
agtaaaattt tggcttatgt caaaccattc ttaggacaag cagcaattac aacatcaaat   6660
tgcgctaaga gattagcaca acgtgtgttt aacaattata tgccttatgt gtttacatta   6720
ttgttccaat tgtgtacttt tactaaaagt accaattcta gaattagagc ttcactacct   6780
acaactattg ctaaaaatag tgttaagagt gttgctaaat tatgtttgga tgccggcatt   6840
aattatgtga agtcacccaa attttctaaa ttgttcacaa tcgctatgtg ctattgttg   6900
ttaagtattt gcttaggttc tctaatctgt gtaactgctg cttttggtgt actcttatct   6960
aattttggtg ctccttctta ttgtaatggc gttagagaat tgtatcttaa ttcgtctaac   7020
gttactacta tggatttctg tgaaggttct tttccttgca gcatttgttt aagtggatta   7080
gactcccttg attcttatcc agctcttgaa accattcagg tgacgatttc atcgtacaag   7140
ctagacttga caattttagg tctggccgct gagtgggttt tggcatatat gttgttcaca   7200
aaattctttt atttattagg tctttcagct ataatgcagg tgttcttgg ctattttgct   7260
agtcatttca tcagcaattc ttggctcatg tggtttatca ttagtattgt acaaatggca   7320
```

```
cccgtttctg caatggttag gatgtacatc ttctttgctt ctttctacta catatgaaag   7380
agctatgttc atatcatgga tggttgcacc tcttcgactt gcatgatgtg ctataagcgc   7440
aatcgtgcca cacgcgttga gtgtacaact attgttaatg gcatgaagag atctttctat   7500
gtctatgcaa atggaggccg tggcttctgc aagactcaca attggaattg tctcaattgt   7560
gacacatttt gcactggtag tacattcatt agtgatgaag ttgctcgtga tttgtcactc   7620
cagtttaaaa gaccaatcaa ccctactgac cagtcatcgt atattgttga tagtgttgct   7680
gtgaaaaatg gcgcgcttca cctctacttt gacaaggctg gtcaaaagac ctatgagaga   7740
catccgctct cccattttgt caatttagac aatttgagag ctaacaacac taaaggttca   7800
ctgcctatta atgtcatagt ttttgatggc aagtccaaat gcgacgagtc tgcttctaag   7860
tctgcttctg tgtactacag tcagctgatg tgccaaccta ttctgttgct tgaccaagtt   7920
cttgtatcag acgttggaga tagtactgaa gtttccgtta agatgtttga tgcttatgtc   7980
gacaccttt cagcaacttt tagtgttcct atggaaaaac ttaaggcact tgttgctaca   8040
gctcacagcg agttagcaaa gggtgtagct ttagatggtg tccttctac attcgtgtca   8100
gctgcccgac aaggtgttgt tgataccgat gttgacacaa aggatgttat tgaatgtctc   8160
aaactttcac atcactctga cttagaagtg acaggtgaca gttgtaacaa tttcatgctc   8220
acctataata aggttgaaaa catgacgccc agagatcttg gcgcatgtat tgactgtaat   8280
gcaaggcata tcaatgccca agtagcaaaa agtcacaatg tttcactcat ctggaatgta   8340
aaagactaca tgtctttatc tgaacagctg cgtaaacaaa ttcgtagtgc tgccaagaag   8400
aacaacatac cttttagact aacttgtgct acaactagac aggttgtcaa tgtcataact   8460
actaaaatct cactcaaggg tggtaagatt gttagtactt gttttaaact tatgcttaag   8520
gccacattat tgtgcgttct tgctgcattg gtttgttata tcgttatgcc agtacataca   8580
ttgtcaatcc atgatggtta cacaaatgaa atcattggtt acaaagccat tcaggatggt   8640
gtcactcgtg acatcatttc tactgatgat tgttttgcaa ataaacatgc tggttttgac   8700
gcatggttta gccagcgtgg tggttcatac aaaaatgaca aaagctgccc tgtagtagct   8760
gctatcatta aagagagat tggtttcata gtgcctggct taccgggtac tgtgctgaga   8820
gcaatcaatg gtgacttctt gcattttcta cctcgtgttt ttagtgctgt tggcaacatt   8880
tgctacacac cttccaaact cattgagtat agtgattttg ctacctctgc ttgcgttctt   8940
gctgctgagt gtacaatttt taaggatgct atgggcaaac ctgtgccata ttgttatgac   9000
actaatttgc tagagggttc tatttcttat agtgagcttg tccagacac tcgttatgtg   9060
cttatggatg gttccatcat acagtttcct aacacttacc tggagggttc tgttagagta   9120
gtaacaactt ttgatgctga gtactgtaga catggtacat gcgaaaggtc agaagtaggt   9180
atttgcctat ctaccagtgg tagatgggtt cttaataatg agcattacag agctctatca   9240
ggagttttct gtggtgttga tgcgatgaat ctcatagcta acatctttac tcctcttgtg   9300
caacctgtgg gtgctttaga tgtgtctgct tcagtagtgg ctggtggtat tattgccata   9360
ttggtgactt gtgctgccta ctacttatg aaattcagac gtgtttttgg tgagtacaac   9420
catgttgttg ctgctaatgc acttttgttt ttgatgtctt tcactatact ctgtctggta   9480
ccagcttaca gctttctgcc gggagtctac tcagtctttt acttgtactt gacattctat   9540
ttcaccaatg atgtttcatt cttggctcac cttcaatggt tgccatgtt ttctcctatt   9600
gtgccttttt ggataacagc aatctatgta ttctgtattt ctctgaagca ctgccattgg   9660
ttctttaaca actatcttag gaaaagagtc atgtttaatg gagttacatt tagtaccttc   9720
```

```
gaggaggctg cttttgtgtac cttttttgctc aacaaggaaa tgtacctaaa attgcgtagc   9780
gagacactgt tgccacttac acagtataac aggtatcttg ctctatataa caagtacaag   9840
tatttcagtg gagccttaga tactaccagc tatcgtgaag cagcttgctg ccacttagca   9900
aaggctctaa atgactttag caactcaggt gctgatgttc tctaccaacc accacagaca   9960
tcaatcactt ctgctgttct gcagagtggt tttaggaaaa tggcattccc gtcaggcaaa  10020
gttgaagggt gcatggtaca agtaacctgt ggaactacaa ctcttaatgg attgtggttg  10080
gatgacacag tatactgtcc aagacatgtc atttgcacag cagaagacat gcttaatcct  10140
aactatgaag atctgctcat tcgcaaatcc aaccatagct tcttgttca ggctggcaat   10200
gttcaacttc gtgttattgg ccattctatg caaaattgtc tgcttaggct taaagttgat  10260
acttctaacc ctaagacacc caagtataaa tttgtccgta tccaacctgg tcaaacattt  10320
tcagttctag catgctacaa tggttcacca tctggtgttt atcagtgtgc catgagacct  10380
aatcatacca ttaaaggttc tttccttaat ggatcatgtg gtagtgttgg ttttaacatt  10440
gattatgatt gcgtgtcttt ctgctatatg catcatatgg agcttccaac aggagtacac  10500
gctggtactg acttagaagg taaattctat ggtccatttg ttgacagaca aactgcacag  10560
gctgcaggta cagacacaac cataacatta aatgttttgg catggctgta tgctgctgtt  10620
atcaatggtg ataggtggtt tcttaataga ttcaccacta ctttgaatga ctttaacctt  10680
gtggcaatga agtacaacta tgaacctttg acacaagatc atgttgacat attgggacct  10740
cttctgctc aaacaggaat tgccgtctta gatatgtgtg ctgctttgaa agagctgctg   10800
cagaatggta tgaatggtcg tactatcctt ggtagcacta ttttagaaga tgagtttaca  10860
ccatttgatg ttgttagaca atgctctggt gttaccttcc aaggtaagtt caagaaaatt  10920
gttaagggca ctcatcattg gatgctttta actttcttga catcactatt gattcttgtt  10980
caaagtacac agtggtcact gttttctctt gtttacgaga atgctttctt gccatttact  11040
cttggtatta tggcaattgc tgcatgtgct atgctgcttg ttaagcataa gcacgcattc  11100
ttgtgcttgt ttctgttacc ttctcttgca acagttgctt actttaatat ggtctacatg  11160
cctgctagct gggtgatgcg tatcatgaca tggcttgaat tggctgacac tagcttgtct  11220
ggttataggc ttaaggattg tgttatgtat gcttcagctt tagtttttgct tattctcatg  11280
acagctcgca ctgtttatga tgatgctgct agacgtgttt ggacactgat gaatgtcatt  11340
acacttgttt acaaagtcta ctatggtaat gctttagatc aagctatttc catgtgggcc  11400
ttagttattt ctgtaacctc taactattct ggtgtcgtta cgactatcat gttttttagct  11460
agagctatag tgtttgtgtg tgttgagtat tacccattgt tatttattac tggcaacacc  11520
ttacagtgta tcatgcttgt ttattgtttc ttaggctatt gttgctgctg ctactttggc  11580
ctttttctgtt tactcaaccg ttacttcagg cttactcttg gtgtttatga ctacttggtc  11640
tctacacaag aatttaggta tatgaactcc caggggcttt gcctcctaa gagtagtatt   11700
gatgctttca agcttaacat taagttgttg ggtattggag gtaaaccatg tatcaaggtt  11760
gctactgtac agtctaaaat gtctgacgta aagtgcacat ctgtggtact gctctcggtt  11820
cttcaacaac ttagagtaga gtcatcttct aaattgtggg cacaatgtgt acaactccac  11880
aatgatattc ttcttgcaaa agacacaact gaagctttcg agaagatggt ttctcttttg  11940
tctgtttttgc tatccatgca gggtgctgta gacattaata ggttgtgcga ggaaatgctc  12000
gataaccgtg ctactcttca ggctattgct tcagaattta gttctttacc atcatatgcc  12060
gcttatgcca ctgcccagga ggcctatgag caggctgtag ctaatggtga ttctgaagtc  12120
```

```
gttctcaaaa agttaaagaa atctttgaat gtggctaaat ctgagtttga ccgtgatgct    12180
gccatgcaac gcaagttgga aaagatggca gatcaggcta tgacccaaat gtacaaacag    12240
gcaagatctg aggacaagag ggcaaaagta actagtgcta tgcaaacaat gctcttcact    12300
atgcttagga agcttgataa tgatgcactt aacaacatta tcaacaatgc gcgtgatggt    12360
tgtgttccac tcaacatcat accattgact acagcagcca aactcatggt tgttgtccct    12420
gattatggta cctacaagaa cacttgtgat ggtaacacct ttacatatgc atctgcactc    12480
tgggaaatcc agcaagttgt tgatgcggat agcaagattg ttcaacttag tgaaattaac    12540
atggacaatt caccaaattt ggcttggcct cttattgtta cagctctaag agccaactca    12600
gctgttaaac tacagaataa tgaactgagt ccagtagcac tacgacagat gtcctgtgcg    12660
gctggtacca cacaaacagc ttgtactgat gacaatgcac ttgcctacta taacaattcg    12720
aagggaggta ggtttgtgct ggcattacta tcagaccacc aagatctcaa atgggctaga    12780
ttccctaaga gtgatggtac aggtacaatt tacacagaac tggaaccacc ttgtaggttt    12840
gttacagaca caccaaaagg gcctaaagtg aaatacttgt acttcatcaa aggcttaaac    12900
aacctaaata gaggtatggt gctgggcagt ttagctgcta cagtacgtct tcaggctgga    12960
aatgctacag aagtacctgc caattcaact gtgctttcct tctgtgcttt tgcagtagac    13020
cctgctaaag catataagga ttacctagca agtggaggac aaccaatcac caactgtgtg    13080
aagatgttgt gtacacacac tggtacagga caggcaatta ctgtaacacc agaagctaac    13140
atggaccaag agtcctttgg tggtgcttca gtttgtctgt attgtagatg ccacattgac    13200
catccaaatc ctaaaggatt ctgtgacttg aaaggtaagt acgtccaaat acctaccact    13260
tgtgctaatg acccagtggg ttttacactt agaaacacag tctgtaccgt ctgcggaatg    13320
tggaaaggtt atggctgtag ttgtgaccaa ctccgcgaac ccttgatgca gtctgcggat    13380
gcatcaacgt ttttaaacgg gtttgcggtg taagtgcagc ccgtcttaca ccgtgcggca    13440
caggcactag tactgatgtc gtctacaggg cttttgatat ttacaacgaa aaagttgctg    13500
gttttgcaaa gttcctaaaa actaattgct gtcgcttcca ggagaaggat gaggaaggca    13560
atttattaga ctcttacttt gtagttaaga ggcatactat gtctaactac caacatgaag    13620
agactattta aacttggtt aaagattgtc cagcggttgc tgtccatgac ttttcaagt    13680
ttagagtaga tggtgacatg gtaccacata tatcacgtca gcgtctaact aaatacacaa    13740
tggctgattt agtctatgct ctacgtcatt ttgatgaggg taattgtgat acattaaaag    13800
aaatactcgt cacatacaat tgctgtgatg atgattattt caataagaag gattggtatg    13860
acttcgtaga gaatcctgac atcttacgcg tatatgctaa cttaggtgag cgtgtacgcc    13920
aatcattatt aaagactgta caattctgcg atgctatgcg tgatgcaggc attgtaggcg    13980
tactgacatt agataatcag gatcttaatg ggaactggta cgatttcggt gatttcgtac    14040
aagtagcacc aggctgcgga gttcctattg tggattcata ttactcattg ctgatgccca    14100
tcctcactt gactagggca ttggctgctg agtcccatat ggatgctgat ctcgcaaaac    14160
cacttattaa gtgggatttg ctgaaatatg attttacgga agagagactt tgtctcttcg    14220
accgttattt taaatattgg gaccagacat accatcccaa ttgtattaac tgtttggatg    14280
ataggtgtat ccttcattgt gcaaactttta atgtgttatt ttctactgtg tttccaccta    14340
caagttttgg accactagta agaaaaatat tgtagatgg tgttcctttt gttgtttcaa    14400
ctggataccaa ttttcgtgag ttaggagtcg tacataatca ggatgtaaac ttacatagct    14460
cgcgtctcag tttcaaggaa cttttagtgt atgctgctga tccagctatg catgcagctt    14520
```

```
ctggcaattt attgctagat aaacgcacta catgcttttc agtagctgca ctaacaaaca    14580
atgttgcttt tcaaactgtc aaacccggta attttaataa agacttttat gactttgctg    14640
tgtctaaagg tttctttaag gaaggaagtt ctgttgaact aaaacacttc ttctttgctc    14700
aggatggcaa cgctgctatc agtgattatg actattatcg ttataatctg ccaacaatgt    14760
gtgatatcag acaactccta ttcgtagttg aagttgttga taaatacttt gattgttacg    14820
atggtggctg tattaatgcc aaccaagtaa tcgttaacaa tctggataaa tcagctggtt    14880
tcccatttaa taaatggggt aaggctagac tttattatga ctcaatgagt tatgaggatc    14940
aagatgcact tttcgcgtat actaagcgta atgtcatccc tactataact caaatgaatc    15000
ttaagtatgc cattagtgca aagaatagag ctcgcaccgt agctggtgtc tctatctgta    15060
gtactatgac aaatagacag tttcatcaga aattattgaa gtcaatagcc gccactagag    15120
gagctactgt ggtaattgga acaagcaagt tttacggtgg ctggcataat atgttaaaaa    15180
ctgtttacag tgatgtagaa actccacacc ttatgggttg ggattatcca aaatgtgaca    15240
gagccatgcc taacatgctt aggataatgg cctctcttgt tcttgctcgc aaacataaca    15300
cttgctgtaa cttatcacac cgtttctaca ggttagctaa cgagtgtgcg caagtattaa    15360
gtgagatggt catgtgtggc ggctcactat atgttaaacc aggtggaaca tcatccggtg    15420
atgctacaac tgcttatgct aatagtgtct ttaacatttg tcaagctgtt acagccaatg    15480
taaatgcact tctttcaact gatggtaata agatagctga caagtatgtc cgcaatctac    15540
aacacaggct ctatgagtgt ctctatagaa atagggatgt tgatcatgaa ttcgtggatg    15600
agttttacgc ttacctgcgt aaacatttct ccatgatgat tctttctgat gatgccgttg    15660
tgtgctataa cagtaactat gcggctcaag gtttagtagc tagcattaag aactttaagg    15720
cagttcttta ttatcaaaat aatgtgttca tgtctgaggc aaaatgttgg actgagactg    15780
accttactaa aggacctcac gaattttgct cacagcatac aatgctagtt aaacaaggag    15840
atgattacgt gtacctgcct tacccagatc catcaagaat attaggcgca ggctgttttg    15900
tcgatgatat tgtcaaaaca gatggtacac ttatgattga aggttcgtg tcactggcta    15960 ttgatgctta cccacttaca aaacatccta atcaggagta tgctgatgtc tttcacttgt    16020
atttacaata cattagaaag ttacatgatg agcttactgg ccacatgttg gacatgtatt    16080
ccgtaatgct aactaatgat aacacctcac ggtactggga acctgagttt tatgaggcta    16140
tgtacacacc acatcagtc ttgcaggctg taggtgcttg tgtattgtgc aattcacaga    16200
cttcacttcg ttgcggtgcc tgtattagga gaccattcct atgttgcaag tgctgctatg    16260
accatgtcat ttcaacatca cacaaattag tgttgtctgt taatccctat gtttgcaatg    16320
ccccaggttg tgatgtcact gatgtgacac aactgtatct aggaggtatg agctattatt    16380
gcaagtcaca taagcctccc attagttttc cattatgtgc taatggtcag gttttggtt    16440 tatacaaaaa cacatgtgta ggcagtgaca atgtcactga cttcaatgcg atagcaacat    16500
gtgattggac taatgctggc gattacatac ttgccaacac ttgtactgag agactcaagc    16560
ttttcgcagc agaaacgctc aaagccactg aggaaacatt taagctgtca tatggtattg    16620
ctactgtacg cgaagtactc tctgacagag aattgcatct ttcatgggag gttggaaaac    16680
ctagaccacc attgaacaga aactatgtct ttactggtta ccgtgtaact aaaaatagta    16740
aagtacagat tggagagtac acctttgaaa aaggtgacta tggtgatgct gttgtgtaca    16800
gaggtactac gacatacaag ttgaatgttg gtgattactt tgtgttgaca tctcacactg    16860
taatgccact tagtgcacct actctagtgc cacaagagca ctatgtgaga attactggct    16920
```

```
tgtacccaac actcaacatc tcagatgagt tttctagcaa tgttgcaaat tatcaaaagg   16980
tcggcatgca aaagtactct acactccaag gaccacctgg tactggtaag agtcattttg   17040
ccatcggact tgctctctat tacccatctg ctcgcatagt gtatacggca tgctctcatg   17100
cagctgttga tgccctatgt gaaaaggcat taaaatattt gcccatagat aaatgtagta   17160
gaatcatacc tgcgcgtgcg cgcgtagagt gttttgataa attcaaagtg aattcaacac   17220
tagaacagta tgttttctgc actgtaaatg cattgccaga acaactgct gacattgtag    17280 tctttgatga aatctctatg gctactaatt atgacttgag tgttgtcaat gctagacttc   17340
gtgcaaaaca ctacgtctat attggcgatc ctgctcaatt accagccccc cgcacattgc   17400
tgactaaagg cacactagaa ccagaatatt ttaattcagt gtgcagactt atgaaaacaa   17460
taggtccaga catgttcctt ggaacttgtc gccgttgtcc tgctgaaatt gttgacactg   17520
tgagtgcttt agtttatgac aataagctaa aagcacacaa ggataagtca gctcaatgct   17580
tcaaaatgtt ctacaaaggt gttattacac atgatgtttc atctgcaatc aacagacctc   17640
aaataggcgt tgtaagagaa tttcttacac gcaatcctgc ttggagaaaa gctgttttta   17700 tctcaccttta taattcacag aacgctgtag cttcaaaaat cttaggattg cctacgcaga   17760
ctgttgattc atcacagggt tctgaatatg actatgtcat attcacacaa actactgaaa   17820
cagcacactc ttgtaatgtc aaccgcttca atgtggctat cacaagggca aaaattggca   17880
ttttgtgcat aatgtctgat agagatcttt atgacaaact gcaatttaca agtctagaaa   17940
taccacgtcg caatgtggct acattacaag cagaaaatgt aactggactt tttaaggact   18000
gtagtaagat cattactggt cttcatccta cacaggcacc tacacacctc agcgttgata   18060
taaagttcaa gactgaagga ttatgtgttg acataccagg cataccaaag gacatgacct   18120
accgtagact catctctatg atgggtttca aaatgaatta ccaagtcaat ggttacccta   18180
atatgtttat cacccgcgaa gaagctattc gtcacgttcg tgcgtggatt ggctttgatg   18240
tagagggctg tcatgcaact agagatgctg tgggtactaa cctacctctc cagctaggat   18300
tttctacagg tgttaactta gtagctgtac cgactggtta tgttgacact gaaaataaca   18360
cagaattcac cagagttaat gcaaaacctc caccaggtga ccagtttaaa catcttatac   18420
cactcatgta taaggcttg ccctggaatg tagtgcgtat taagatagta caaatgctca   18480
gtgatacact gaaaggattg tcagacagag tcgtgttcgt cctttgggcg catggctttg   18540
agcttacatc aatgaagtac tttgtcaaga ttggacctga agaacgtgt tgtctgtgtg    18600 acaaacgtgc aacttgcttt tctacttcat cagatactta tgcctgctgg aatcattctg   18660
tgggttttga ctatgtctat aacccattta tgattgatgt tcagcagtgg ggctttacgg   18720
gtaaccttca gagtaaccat gaccaacatt gccaggtaca tggaaatgca catgtggcta   18780
gttgtgatgc tatcatgact agatgtttag cagtccatga gtgctttgtt aagcgcgttg   18840
attggtctgt tgaataccct attataggag atgaactgag ggttaattct gcttgcagaa   18900
aagtacaaca catggttgtg aagtctgcat tgcttgctga taagtttcca gttcttcatg   18960
acattggaaa tccaaaggct atcaagtgtg tgcctcaggc tgaagtagaa tggaagttct   19020
acgatgctca gccatgtagt gacaaagctt acaaaataga ggagctcttc tattcttatg   19080
ctacacatca cgataaaattc actgatggtg tttgtttgtt ttggaattgt aacgttgatc   19140
gttacccagc caatgcaatt gtgtgtaggt ttgacacaag agtcttgtca aacttgaact   19200
taccaggctg tgatggtggt agtttgtatg tgaataagca tgcattccac actccagctt   19260
tcgataaaag tgcatttact aatttaaagc aattgccttt ctttactat tctgatagtc    19320
```

```
cttgtgagtc tcatggcaaa caagtagtgt cggatattga ttatgttcca ctcaaatctg   19380
ctacgtgtat tacacgatgc aatttaggtg gtgctgtttg cagacaccat gcaaatgagt   19440
accgacagta cttggatgca tataatatga tgatttctgc tggatttagc ctatggattt   19500
acaaacaatt tgatacttat aacctgtgga atacatttac caggttacag agtttagaaa   19560
atgtggctta taatgttgtt aataaaggac actttgatgg acacgccggc gaagcacctg   19620
tttccatcat taataatgct gtttacacaa aggtagatgg tattgatgtg gagatctttg   19680
aaaataagac aacacttcct gttaatgttg catttgagct ttgggctaag cgtaacatta   19740
aaccagtgcc agagattaag atactcaata atttgggtgt tgatatcgct gctaatactg   19800
taatctggga ctacaaaaga gaagcccag cacatgtatc tacaataggt gtctgcacaa   19860
tgactgacat tgccaagaaa cctactgaga gtgcttgttc ttcacttact gtcttgtttg   19920
atggtagagt ggaaggacag gtagaccttt ttagaaacgc ccgtaatggt gttttaataa   19980
cagaaggttc agtcaaaggt ctaacacctt caaagggacc agcacaagct agcgtcaatg   20040
gagtcacatt aattggagaa tcagtaaaaa cacagtttaa ctactttaag aaagtagacg   20100
gcattattca acagttgcct gaaacctact ttactcagag cagagactta gaggattttg   20160
agcccagatc acaaatggaa actgactttc tcgagctcgc tatggatgaa ttcatacagc   20220
gatataagct cgagggctat gccttcgaac acatcgttta tggagatttc agtcatggac   20280
aacttggcgg tcttcattta atgataggct tagccaagcg ctcacaagat tcaccactta   20340
aattagagga ttttatccct atggacagca cagtgaaaaa ttacttcata acagatgcgc   20400
aaacaggttc atcaaaatgt gtgtgttctg tgattgatct tttacttgat gactttgtcg   20460
agataataaa gtcacaagat ttgtcagtga tttcaaaagt ggtcaaggtt acaattgact   20520
atgctgaaat tcattcatg ctttggtgta aggatggaca tgttgaaacc ttctacccaa   20580
aactacaagc aagtcaagcg tggcaaccag gtgttgcgat gcctaacttg tacaagatgc   20640
aaagaatgct tcttgaaaag tgtgaccttc agaattatgg tgaaaatgct gttataccaa   20700
aaggaataat gatgaatgtc gcaaagtata ctcaactgtg tcaatactta aatacactta   20760
ctttagctgt accctacaac atgagagtta ttcactttgg tgctggctct gataaaggag   20820
ttgcaccagg tacagctgtg ctcagacaat ggttgccaac tggcacacta cttgtcgatt   20880
cagatcttaa tgacttcgtc tccgacgcag attctacttt aattggagac tgtgcaacag   20940
tacatacggc taataaatgg gaccttatta ttagcgatat gtatgaccct aggaccaaac   21000
atgtgacaaa agagaatgac tctaaagaag gttttttcac ttatctgtgt ggatttataa   21060
agcaaaaact agccctgggt ggttctatag ctgtaaagat aacagagcat tcttggaatg   21120 ctgacctta caagctatg ggccatttct catggtggac agcttttgtt acaaatgtaa   21180
atgcatcatc atcggaagca ttttaattg gggctaacta tcttggcaag ccgaaggaac   21240
aaattgatgg ctataccatg catgctaact acatttctg gaggaacaca aatcctatcc   21300
agttgtcttc ctattcactc tttgacatga gcaaatttcc tcttaaatta agaggaactg   21360
ctgtaatgtc tcttaaggag aatcaaatca atgatatgat ttattctctt ctggaaaaag   21420
gtaggcttat cattagagaa aacaacagag ttgtggtttc aagtgatatt cttgttaaca   21480
actaaacgaa catgttatt ttcttattat ttcttactct cactagtggt agtgaccttg   21540
accggtgcac cacttttgat gatgttcaag ctcctaatta cactcaacat acttcatcta   21600
tgaggggggt tactatcct gatgaaattt ttagatcaga cactctttat ttaactcagg   21660
atttatttct tccatttat tctaatgtta cagggtttca tactattaat catacgtttg   21720
```

```
gcaaccctgt cataccttt  aaggatggta tttattttgc tgccacagag aaatcaaatg   21780
ttgtccgtgg ttgggttttt ggttctacca tgaacaacaa gtcacagtcg gtgattatta   21840
ttaacaattc tactaatgtt gttatacgag catgtaactt tgaattgtgt gacaacccttt  21900
tctttgctgt ttctaaaccc atgggtacac agacacatac tatgatattc gataatgcat   21960
ttaattgcac tttcgagtac atatctgatg ccttttcgct tgatgtttca gaaaagtcag   22020
gtaatttta  acacttacga gagtttgtgt ttaaaaataa agatgggttt ctctatgttt   22080
ataagggcta tcaacctata gatgtagttc gtgatctacc ttctggtttt aacactttga   22140
aacctatttt taagttgcct cttggtatta acattacaaa ttttagagcc attcttacag   22200
ccttttcacc tgctcaagac atttgggca  cgtcagctgc agcctatttt gttggctatt   22260
taaagccaac tacattatg  ctcaagtatg atgaaaatgg tacaatcaca gatgctgttg   22320
attgttctca aaatccactt gctgaactca aatgctctgt taagagcttt gagattgaca   22380
aaggaattta ccagacctct aatttcaggg ttgttccctc aggagatgtt gtgagattcc   22440
ctaatattac aaacttgtgt ccttttggag aggttttaa  tgctactaaa ttcccttctg   22500
tctatgcatg ggagagaaaa aaatttcta  attgtgttgc tgattactct gtgctctaca   22560
actcaacatt ttttcaacc  tttaagtgct atggcgtttc tgccactaag ttgaatgatc   22620
tttgcttctc caatgtctat gcagattctt ttgtagtcaa gggagatgat gtaagacaaa   22680
tagcgccagg acaaactggt gttattgctg attataatta taaattgcca gatgatttca   22740
tgggttgtgt ccttgcttgg aatactagga acattgatgc tacttcaact ggtaattata   22800
attataaata taggtatctt agacatggca agcttaggcc ctttgagaga gacatatcta   22860
atgtgccttt ctccctgat  ggcaaaccct gcaccccacc tgctcttaat tgttattggc   22920
cattaaatga ttatggtttt tacaccacta ctggcattgg ctaccaacct tacagagttg   22980
tagtactttc ttttgaactt ttaaatgcac cggccacggt ttgtggacca aaattatcca   23040
ctgaccttat taagaaccag tgtgtcaatt ttaattttaa tggactcact ggtactggtg   23100
tgttaactcc ttcttcaaag agatttcaac catttcaaca atttggccgt gatgtttctg   23160
atttcactga ttccgttcga gatcctaaaa catctgaaat attagacatt tcaccttgct   23220
cttttggggg tgtaagtgta attacacctg gaacaaatgc ttcatctgaa gttgctgttc   23280
tatatcaaga tgttaactgc actgatgttt ctacagcaat tcatgcagat caactcacac   23340
cagcttggcg catatattct actggaaaca atgtattcca gactcaagca ggctgtctta   23400
taggagctga gcatgtcgac acttcttatg agtgcgacat tcctattgga gctggcattt   23460
gtgctagtta ccatacagtt tctttattac gtagtactag ccaaaaatct attgtggctt   23520
atactatgtc tttaggtgct gatagttcaa ttgcttactc taataacacc attgctatac   23580
ctactaactt ttcaattagc attactacag aagtaatgcc tgtttctatg gctaaaacct   23640
ccgtagattg taatatgtac atctgcggag attctactga atgtgctaat ttgcttctcc   23700
aatatggtag cttttgcaca caactaaatc gtgcactctc aggtattgct gctgaacagg   23760
atcgcaacac acgtgaagtg ttcgctcaag tcaaacaaat gtacaaaacc ccaactttga   23820
aatattttgg tggttttaat ttttcacaaa tattacctga ccctctaaag ccaactaaga   23880
ggtcttttat tgaggacttg ctctttaata aggtgacact cgctgatgct ggcttcatga   23940
agcaatatgg cgaatgccta ggtgatatta atgctagaga tctcatttgt gcgcagaagt   24000
tcaatggact tacagtgttg ccacctctgc tcactgatga tatgattgct gcctacactg   24060
ctgctctagt tagtggtact gccactgctg gatggacatt tggtgctggc gctgctcttc   24120
```

```
aaataccttt tgctatgcaa atggcatata ggttcaatgg cattggagtt acccaaaatg    24180
ttctctatga gaaccaaaaa caaatcgcca accaatttaa caaggcgatt agtcaaattc    24240
aagaatcact tacaacaaca tcaactgcat tgggcaagct gcaagacgtt gttaaccaga    24300
atgctcaagc attaaacaca cttgttaaac aacttagctc taattttggt gcaatttcaa    24360
gtgtgctaaa tgatatcctt tcgcgacttg ataaagtcga ggcggaggta caaattgaca    24420
ggttaattac aggcagactt caaagccttc aaacctatgt aacacaacaa ctaatcaggg    24480
ctgctgaaat cagggcttct gctaatcttg ctgctactaa aatgtctgag tgtgttcttg    24540
gacaatcaaa aagagttgac ttttgtggaa agggctacca ccttatgtcc ttcccacaag    24600
cagccccgca tggtgttgtc ttcctacatg tcacgtatgt gccatcccag gagaggaact    24660
tcaccacagc gccagcaatt tgtcatgaag gcaaagcata cttccctcgt gaaggtgttt    24720
ttgtgtttaa tggcacttct tggtttatta cacagaggaa cttcttttct ccacaaataa    24780
ttactacaga caatacattt gtctcaggaa attgtgatgt cgttattggc atcattaaca    24840
acacagttta tgatcctctg caacctgagc tcgactcatt caaagaagag ctggacaagt    24900
acttcaaaaa tcatacatca ccagatgttg atcttggcga catttcaggc attaacgctt    24960
ctgtcgtcaa cattcaaaaa gaaattgacc gcctcaatga ggtcgctaaa aatttaaatg    25020
aatcactcat tgaccttcaa gaattgggaa aatatgagca atatattaaa tggccttggt    25080
atgtttggct cggcttcatt gctggactaa ttgccatcgt catggttaca atcttgcttt    25140
gttgcatgac tagttgttgc agttgcctca agggtgcatg ctcttgtggt tcttgctgca    25200
agtttgatga ggatgactct gagccagttc tcaagggtgt caaattacat tacacataaa    25260
cgaacttatg gatttgttta tgagattttt tactcttgga tcaattactg cacagccagt    25320
aaaaattgac aatgcttctc ctgcaagtac tgttcatgct acagcaacga taccgctaca    25380
agcctcactc ccttttcggat ggcttgttat tggcgttgca tttcttgctg tttttcagag    25440
cgctaccaaa ataattgcgc tcaataaaag atggcagcta gcccttttata agggcttcca    25500 gttcatttgc aatttactgc tgctatttgt taccatctat tcacatcttt tgcttgtcgc    25560
tgcaggtatg gaggcgcaat ttttgtacct ctatgccttg atatattttc tacaatgcat    25620
caacgcatgt agaattatta tgagatgttg gctttgttgg aagtgcaaat ccaagaaccc    25680
attactttat gatgccaact actttgtttg ctggcacaca cataactatg actactgtat    25740
accatataac agtgtcacag atacaattgt cgttactgaa ggtgacggca tttcaacacc    25800
aaaactcaaa gaagactacc aaattggtgg ttattctgag ataggcact caggtgttaa    25860 agactatgtc gttgtacatg gctatttcac cgaagtttac taccagcttg agtctacaca    25920
aattactaca gacactggta ttgaaaatgc tacattcttc atctttaaca gcttgttaa    25980 agacccaccg aatgtgcaaa tacacacaat cgacggctct tcaggagttg ctaatccagc    26040
aatggatcca atttatgatg agccgacgac gactactagc gtgcctttgt aagcacaaga    26100
aagtgagtac gaacttatgt actcattcgt ttcggaagaa acaggtacgt taatagttaa    26160
tagcgtactt cttttctctg ctttcgtggt attcttgcta gtcacactag ccatccttac    26220
tgcgcttcga ttgtgtgcgt actgctgcaa tattgttaac gtgagtttag taaaccaac    26280 ggtttacgtc tactcgcgtg ttaaaaatct gaactcttct gaaggagttc ctgatcttct    26340
ggtctaaacg aactaactat tattattatt ctgtttggaa cttaacatt gcttatcatg    26400 gcagacaacg gtactattac cgttgaggag cttaaacaac tcctggaaca atggaaccta    26460
gtaataggtt tcctattcct agcctggatt atgttactac aatttgccta ttctaatcgg    26520
```

```
aacaggtttt tgtacataat aaagcttgtt ttcctctggc tcttgtggcc agtaacactt   26580
gcttgttttg tgcttgctgc tgtctacaga attaattggg tgactggcgg gattgcgatt   26640
gcaatggctt gtattgtagg cttgatgtgg cttagctact tcgttgcttc cttcaggctg   26700
tttgctcgta cccgctcaat gtggtcattc aacccagaaa caaacattct tctcaatgtg   26760
cctctccggg ggacaattgt gaccagaccg ctcatggaaa gtgaacttgt cattggtgct   26820
gtgatcattc gtggtcactt gcgaatggcc ggacaccccc tagggcgctg tgacattaag   26880
gacctgccaa aagagatcac tgtggctaca tcacgaacgc tttcttatta caaattagga   26940
gcgtcgcagc gtgtaggcac tgattcaggt tttgctgcat acaaccgcta ccgtattgga   27000
aactataaat taaatacaga ccacgccggt agcaacgaca atattgcttt gctagtacag   27060
taagtgacaa cagatgtttc atcttgttga cttccaggtt acaatagcag agatattgat   27120
tatcattatg aggactttca ggattgctat ttggaatctt gacgttataa taagttcaat   27180
agtgagacaa ttatttaagc ctctaactaa gaagaattat tcggagttag atgatgaaga   27240
acctatggag ttagattatc cataaaacga acatgaaaat tattctcttc ctgacattga   27300
ttgtatttac atcttgcgag ctatatcact atcaggagtg tgttagaggt acgactgtac   27360
tactaaaaga accttgccca tcaggaacat acgagggcaa ttcaccattt caccctcttg   27420
ctgacaataa atttgcacta acttgcacta gcacacactt tgcttttgct tgtgctgacg   27480
gtactcgaca tacctatcag ctgcgtgcaa gatcagtttc accaaaactt ttcatcagac   27540
aagaggaggt tcaacaagag ctctactcgc cacttttctt cattgttgct gctctagtat   27600
ttttaatact ttgcttcacc attaagagaa agacagaatg aatgagctca ctttaattga   27660
cttctatttg tgcttttag cctttctgct attccttgtt ttaataatgc ttattatatt   27720
ttggttttca ctcgaaatcc aggatctaga agaaccttgt accaaagtct aaacgaacat   27780
gaaacttctc attgttttga cttgtatttc tctatgcagt tgcatatgca ctgtagtaca   27840
gcgctgtgca tctaataaac ctcatgtgct tgaagatcct tgtaaggtac aacactaggg   27900
gtaatactta tagcactgct tggctttgtg ctctaggaaa ggttttacct tttcatagat   27960
ggcacactat ggttcaaaca tgcacaccta atgttactat caactgtcaa gatccagctg   28020
gtggtgcgct tatagctagg tgttggtacc ttcatgaagg tcaccaaaact gctgcattta   28080 gagacgtact tgttgtttta aataaacgaa caaattaaaa tgtctgataa tggacccccaa   28140 tcaaaccaac gtagtgcccc ccgcattaca tttggtggac ccacagattc aactgacaat   28200
aaccagaatg gaggacgcaa tggggcaagg ccaaaacagc gccgacccca aggtttaccc   28260
aataatactg cgtcttggtt cacagctctc actcagcatg gcaaggagga acttagattc   28320
cctcgaggcc agggcgttcc aatcaacacc aatagtggtc cagatgacca aattggctac   28380
taccgaagag ctacccgacg agttcgtggt ggtgacggca aaatgaaaga gctcagcccc   28440
agatggtact tctattacct aggaactggc ccagaagctt cacttcccta cggcgctaac   28500
aaagaaggca tcgtatgggt tgcaactgag ggagccttga atacacccaa agaccacatt   28560
ggcacccgca atcctaataa caatgctgcc accgtgctac aacttcctca aggaacaaca   28620 tgccaaaag gcttctacgc agagggaagc agaggcggca gtcaagcctc ttctcgctcc   28680
tcatcacgta gtcgcggtaa ttcaagaaat tcaactcctg gcagcagtag gggaaattct   28740
cctgctcgaa tggctagcgg aggtggtgaa actgccctcg cgctattgct gctagacaga   28800
ttgaaccagc ttgagagcaa agtttctggt aaaggccaac aacaacaagg ccaaactgtc   28860
actaagaaat ctgctgctga ggcatctaaa aagcctcgcc aaaaacgtac tgccacaaaa   28920
```

-continued

```
cagtacaacg tcactcaagc atttgggaga cgtggtccag aacaaaccca aggaaatttc  28980
ggggaccaag acctaatcag acaaggaact gattacaaac attggccgca aattgcacaa  29040
tttgctccaa gtgcctctgc attctttgga atgtcacgca ttggcatgga agtcacacct  29100
tcgggaacat ggctgactta tcatggagcc attaaattgg atgacaaaga tccacaattc  29160
aaagacaacg tcatactgct gaacaagcac attgacgcat acaaaacatt cccaccaaca  29220
gagcctaaaa aggacaaaaa gaaaaagact gatgaagctc agcctttgcc gcagagacaa  29280
aagaagcagc ccactgtgac tcttcttcct gcggctgaca tggatgattt ctccagacaa  29340
cttcaaaatt ccatgagtgg agcttctgct gattcaactc aggcataaac actcatgatg  29400
accacacaag gcagatgggc tatgtaaacg ttttcgcaat tccgtttacg atacatagtc  29460
tactcttgtg cagaatgaat tctcgtaact aaacagcaca agtaggttta gttaacttta  29520
atctcacata gcaatcttta atcaatgtgt aacattaggg aggacttgaa agagccacca  29580
cattttcatc gaggccacgc ggagtacgat cgagggtaca gtgaataatg ctagggagag  29640
ctgcctatat ggaagagccc taatgtgtaa aattaatttt agtagtgcta tccccatgtg  29700
attttaatag cttcttagga gaatgac                                      29727
```

<210> SEQ ID NO 3
<211> LENGTH: 29791
<212> TYPE: DNA
<213> ORGANISM: SARS coronavirus

<400> SEQUENCE: 3

```
cgcccttcat taatacgact cactatagat attaggtttt tacctaccca ggaaaagcca     60
accaacctcg atctcttgta gatctgttct ctaaacgaac tttaaaatct gtgtagctgt    120
cgctcggctg catgcctagt gcacctacgc agtataaaca ataataaatt ttactgtcgt    180
tgacaagaaa cgagtaactc gtccctcttc tgcagactgc ttacggtttc gtccgtgttg    240
cagtcgatca tcagcatacc taggtttcgt ccgggtgtga ccgaaaggta agatggagag    300
ccttgttctt ggtgtcaacg agaaaacaca cgtccaactc agtttgcctg tccttcaggt    360
tagagacgtg ctagtgcgtg gcttcgggga ctctgtggaa gaggccctat cggaggcacg    420
tgaacacctc aaaaatggca cttgtggtct agtagagctg gaaaaaggcg tactgcccca    480
gcttgaacag ccctatgtgt tcattaaacg ttctgatgcc ttaagcacca atcacggcca    540
caaggtcgtt gagctggttg cagaaatgga cggcattcag tacggtcgta gcggtataac    600
actgggagta ctcgtgccac atgtgggcga aaccccaatt gcataccgca atgttcttct    660
tcgtaagaac ggtaataagg gagccggtgg tcatagctat ggcatcgatc taaagtctta    720
tgacttaggt gacgagcttg gcactgatcc cattgaagat tatgaacaaa actggaacac    780
taagcatggc agtggtgcac tccgtgaact cactcgtgag ctcaatggag gtgcagtcac    840
tcgctatgtc gacaacaatt tctgtggccc agatgggtac cctcttgatt gcatcaaaga    900
ttttctcgca cgcgcgggca agtcaatgtg cactctttcc gaacaacttg attacatcga    960
gtcgaagaga ggtgtctact gctgccgtga ccatgagcat gaaattgcct ggttcactga   1020
gcgctctgat aagagctacg agcaccagac acccttcgaa attaagagtg ccaagaaatt   1080
tgacactttc aaaggggaat gcccaaagtt tgtgtttcct cttaactcaa aagtcaaagt   1140
cattcaacca cgtgttgaaa agaaaaagac tgagggtttc atggggcgta tacgctctgt   1200
gtaccctgtt gcatctccac aggagtgtaa caatatgcac ttgtctacct tgatgaaatg   1260
taatcattgc gatgaagttt catggcagac gtgcgacttt ctgaaagcca cttgtgaaca   1320
```

```
ttgtggcact gaaaatttag ttattgaagg acctactaca tgtgggtacc tacctactaa   1380
tgctgtagtg aaaatgccat gtcctgcctg tcaagaccca gagattggac ctgagcatag   1440
tgttgcagat tatcacaacc actcaaacat tgaaactcga ctccgcaagg gaggtaggac   1500
tagatgtttt ggaggctgtg tgtttgccta tgttggctgc tataataagc gtgcctactg   1560
ggttcctcgt gctagtgctg atattggctc aggacatact ggaattactg gtgacaatgt   1620
ggagaccttg aatgaggatc tccttgagat actgagtcgt gaacgtgtta acattaacat   1680
tgttggcgat tttcatttga atgaagaggt tgccatcatt ttggcatctt tctctgcttc   1740
tacaagtgcc tttattgaca ctataaagag tcttgattac aagtctttca aaccattgt    1800
tgagtcctgc ggtaactata aagttaccaa gggaaagccc gtaaaaggtg cttggaacat   1860
tggacaacag agatcagttt taacaccact gtgtggtttt ccctcacagg ctgctggtgt   1920
tatcagatca attttgcgc gcacacttga tgcagcaaac cactcaattc ctgatttgca    1980
aagagcagct gtcaccatac ttgatggtat ttctgaacag tcattacgtc ttgtcgacgc   2040
catggtttat acttcagacc tgctcaccaa cagtgtcatt attatggcat atgtaactgg   2100
tggtcttgta caacagactt ctcagtggtt gtctaatctt ttgggcacta ctgttgaaaa   2160
actcaggcct atctttgaat ggattgaggc gaaacttagt gcaggagttg aatttctcaa   2220
ggatgcttgg gagattctca aatttctcat tacaggtgtt tttgacatcg tcaagggtca   2280
aatacaggtt gcttcagata acatcaagga ttgtgtaaaa tgcttcattg atgttgttaa   2340
caaggcactc gaaatgtgca ttgatcaagt cactatcgct ggcgcaaagt tgcgatcact   2400
caacttaggt gaagtcttca tcgctcaaag caagggactt taccgtcagt gtatacgtgg   2460
caaggagcag ctgcaactac tcatgcctct taaggcacca aaagaagtaa ccttcttga    2520
aggtgattca catgacacag tacttacctc tgaggaggtt gttctcaaga acggtgaact   2580
cgaagcactc gagacgcccg ttgatagctt cacaaatgga gctatcgttg cacaccagt    2640
ctgtgtaaat ggcctcatgc tcttagagat taaggacaaa gaacaatact gcgcattgtc   2700
tcctggttta ctggctacaa acaatgtctt tcgcttaaaa gggggtgcac caattaaagg   2760
tgtaaccttt ggagaagata ctgtttggga agttcaaggt tacaagaatg tgagaatcac   2820
atttgagctt gatgaacgtg ttgacaaagt gcttaatgaa aagtgctctg tctacactgt   2880
tgaatccggt accgaagtta ctgagtttgc atgtgttgta gcagaggctg ttgtgaagac   2940
tttacaacca gtttctgatc tccttaccaa catgggtatt gatcttgatg agtggagtgt   3000
agctacattc tacttatttg atgatgctgg tgaagaaaac tttttcatcac gtatgtattg   3060
ttccttttac cctccagatg aggaagaaga ggacgatgca gagtgtgagg aagaagaaat   3120
tgatgaaacc tgtgaacatg agtacggtac agaggatgat tatcaaggtc tccctctgga   3180
atttggtgcc tcagctgaaa cagttcgagt tgaggaagaa aagaggaag actggctgga    3240
tgatactact gagcaatcag agattgagcc agaaccagaa cctacacctg aagaaccagt   3300
taatcagttt actggttatt taaaacttac tgacaatgtt gccattaaat gtgttgacat   3360
cgttaaggag gcacaaagtg ctaatcctat ggtgattgta aatgctgcta acatacacct   3420
gaaacatggt ggtggtgtag caggtgcact caacaaggca accaatggtg ccatgcaaaa   3480
ggagagtgat gattacatta agctaaatgg ccctcttaca gtaggagggt cttgtttgct   3540
ttctggacat aatcttgcta agaagtgtct gcatgttgtt ggacctaacc taaatgcagg   3600
tgaggacatc cagcttctta aggcagcata tgaaaatttc aattcacagg acatcttact   3660
tgcaccattg ttgtcagcag gcatatttgg tgctaaacca cttcagtctt tacaagtgtg   3720
```

```
cgtgcagacg gttcgtacac aggtttatat tgcagtcaat gacaaagctc tttatgagca    3780
ggttgtcatg gattatcttg ataacctgaa gcctagagtg gaagcaccta acaagagga    3840 gccaccaaac acagaagatt ccaaaactga ggagaaatct gtcgtacaga agcctgtcga    3900
tgtgaagcca aaaattaagg cctgcattga tgaggttacc acaacactgg aagaaactaa    3960
gtttcttacc aataagttac tcttgtttgc tgatatcaat ggtaagcttt accatgattc    4020
tcagaacatg cttagaggtg aagatatgtc tttccttgag aaggatgcac cttacatggt    4080
aggtgatgtt atcactagtg gtgatatcac ttgtgttgta ataccctcca aaaaggctgg    4140
tggcactact gagatgctct caagagcttt gaagaaagtg ccagttgatg agtatataac    4200
cacgtaccct ggacaaggat gtgctggtta tacacttgag gaagctaaga ctgctcttaa    4260
gaaatgcaaa tctgcatttt atgtactacc ttcagaagca cctaatgcta aggaagagat    4320
tctaggaact gtatcctgga atttgagaga aatgcttgct catgctgaag agacaagaaa    4380
attaatgcct atatgcatgg atgttagagc cataatggca accatccaac gtaagtataa    4440
aggaattaaa attcaagagg gcatcgttga ctatggtgtc cgattcttct tttatactag    4500
taaagagcct gtagcttcta ttattacgaa gctgaactct ctaaatgagc cgcttgtcac    4560
aatgccaatt ggttatgtga cacatggttt taatcttgaa gaggctgcgc gctgtatgcg    4620
ttctcttaaa gctcctgccg tagtgtcagt atcatcacca gatgctgtta ctacatataa    4680 tggataccctc acttcgtcat caaagacatc tgaggagcac tttgtagaaa cagtttcttt    4740
ggctggctct tacagagatt ggtcctattc aggacagcgt acagagttag gtgttgaatt    4800
tcttaagcgt ggtgacaaaa ttgtgtacca cactctggag agcccgtcg agtttcatct    4860 tgacggtgag gttctttcac ttgacaaact aaagagtctc ttatccctgc gggaggttaa    4920
gactataaaa gtgttcacaa ctgtggacaa cactaatctc cacacacagc ttgtggatat    4980
gtctatgaca tatggacagc agtttggtcc aacatacttg gatggtgctg atgttacaaa    5040 aattaaaccct catgtaaatc atgagggtaa gactttcttt gtactaccta gtgatgacac    5100
actacgtagt gaagctttcg agtactacca tactcttgat gagagttttc ttggtaggta    5160
catgtctgct ttaaaccaca caagaaatg gaaatttcct caagttggtg gtttaacttc    5220
aattaaatgg gctgataaca attgttattt gtctagtgtt ttattagcac ttcaacagct    5280
tgaagtcaaa ttcaatgcac cagcacttca agaggcttat tatagagccc gtgctggtga    5340
tgctgctaac ttttgtgcac tcatactcgc ttacagtaat aaaactgttg gcgagcttgg    5400
tgatgtcaga gaaactatga cccatcttct acagcatgct aatttggaat ctgcaaagcg    5460
agttcttaat gtggtgtgta aacattgtgg tcagaaaact actaccttaa cgggtgtaga    5520
agctgtgatg tatatgggta ctctatctta tgataatctt aagacaggtg tttccattcc    5580
atgtgtgtgt ggtcgtgatg ctacacaata tctagtacaa caagagtctt cttttgttat    5640
gatgtctgca ccacctgctg agtataaatt acagcaaggt acattcttat gtgcgaatga    5700
gtacactggt aactatcagt gtggtcatta cactcatata actgctaagg agaccctcta    5760
tcgtattgac ggagctcacc ttacaaagat gtcagagtac aaaggaccag tgactgatgt    5820
tttctacaag gaaacatctt acactacaac catcaagcct gtgtcgtata aactcgatgg    5880
agttacttac acagagattg aaccaaaatt ggatgggtat tataaaaagg ataatgctta    5940
ctatacagag cagcctatag accttgtacc aactcaacca ttaccaaatg cgagttttga    6000
taatttcaaa ctcacatgtt ctaacacaaa atttgctgat gatttaaatc aaatgacagg    6060
cttcacaaag ccagcttcac gagagctatc tgtcacattc ttcccagact tgaatggcga    6120
```

```
tgtagtggct attgactata gacactattc agcgagtttc aagaaaggtg ctaaattact    6180
gcataagcca attgtttggc acattaacca ggctacaacc aagacaacgt tcaaaccaaa    6240
cacttggtgt ttacgttgtc tttggagtac aaagccagta gatacttcaa attcatttga    6300
agttctggca gtagaagaca cacaaggaat ggacaatctt gcttgtgaaa gtcaacaacc    6360
cacctctgaa gaagtagtgg aaaatcctac catacagaag gaagtcatag agtgtgacgt    6420
gaaaactacc gaagttgtag gcaatgtcat acttaaacca tcagatgaag gtgttaaagt    6480
aacacaggag ttaggtcatg aggatcttat ggctgcttat gtggaaaaca caagcattac    6540
cattaagaaa cctaatgagc tttcactagc cttaggttta aaaacaattg ccactcatgg    6600
tattgctgca attaatagtg ttccttggag taaaattttg gcttatgtca aaccattctt    6660
aggacaagca gcaattacaa catcaaattg cgctaagaga ttagcacaac gtgtgtttaa    6720
caattatatg ccttatgtgt ttacattatt gttccaattg tgtacttttta ctaaaagtac    6780 caattctaga attagagctt cactacctac aactattgct aaaaatagtg ttaagagtgt    6840
tgctaaatta tgtttggatg ccggcattaa ttatgtgaag tcacccaaat tttctaaatt    6900
gttcacaatc gctatgtggc tattgttgtt aagtatttgc ttaggttctc taatctgtgt    6960
aactgctgct tttggtgtac tcttatctaa ttttggtgct ccttcttatt gtaatggcgt    7020
tagagaattg tatcttaatt cgtctaacgt tactactatg gatttctgtg aaggttcttt    7080
tccttgcagc atttgtttaa gtggattaga ctcccttgat tcttatccag ctcttgaaac    7140
cattcaggtg acgatttcat cgtacaagct agacttgaca atttttaggtc tggccgctga    7200 gtgggttttg gcatatatgt tgttcacaaa attcttttat ttattaggtc tttcagctat    7260
aatgcaggtt ttcttttggct attttgctag tcatttcatc agcaattctt ggctcatgtg    7320
gtttatcatt agtattgtac aaatggcacc cgtttctgca atggttagga tgtacatctt    7380
ctttgcttct ttctactaca tatggaagag ctatgttcat atcatggatg gttgcacctc    7440
ttcgacttgc atgatgtgct ataagcgcaa tcgtgccaca cgcgttgagt gtacaactat    7500
tgttaatggc atgaagagat cttcctatgt ctatgcaaat ggaggccgtg gcttctgcaa    7560
gactcacaat tggaattgtc tcaattgtga cacattttgc actggtagta cattcattag    7620
tgatgaagtt gctcgtgatt tgtcactcca gtttaaaaga ccaatcaacc ctactgacca    7680
gtcatcgtat attgttgata gtgttgctgt gaaaaatggc gcgcttcacc tctactttga    7740
caaggctggt caaaagacct atgagagaca tccgctctcc cattttgtca atttagacaa    7800
tttgagagct aacaacacta aaggttcact gcctattaat gtcatagttt ttgatggcaa    7860
gtccaaatgc gacagagtctg cttctaagtc tgcttctgtg tactacagtc agctgatgtg    7920
ccaacctatt ctgttgcttg accaagttct tgtatcagac gttggagata gtactgaagt    7980
ttccgttaag atgtttgatg cttatgtcga caccttttca gcaactttta gtgttcctat    8040
ggaaaaactt aaggcacttg ttgctacagc tcacagcgag ttagcaaagg gtgtagcttt    8100
agatggtgtc ctttctacat tcgtgtcagc tgcccgacaa ggtgttgttg ataccgatgt    8160
tgacacaaag gatgttattg aatgtctcaa actttcacat cactctgact agaagtgac    8220 aggtgacagt tgtaacaatt tcatgctcac ctataataag gttgaaaaca tgacgcccag    8280
agatcttggc gcatgtattg actgtaatgc aaggcatatc aatgcccaag tagcaaaaag    8340
tcacaatgtt tcactcatct ggaatgtaaa agactacatg tctttatctg aacagctgcg    8400
taaacaaatt cgtagtgctg ccaagaagaa caacatacct tttagactaa cttgtgctac    8460
aactagacag gttgtcaatg tcataactac taaaatctca ctcaagggtg gtaagattgt    8520
```

```
tagtacttgt tttaaactta tgcttaaggc cacattattg tgcgttcttg ctgcattggt    8580
ttgttatatc gttatgccag tacatacatt gtcaatccat gatggttaca caaatgaaat    8640
cattggttac aaagccattc aggatggtgt cactcgtgac atcatttcta ctgatgattg    8700
ttttgcaaat aaacatgctg gttttgacgc atggtttagc cagcgtggcg gttcatacaa    8760
aaatgacaaa agctgccctg tagtagctgc tatcattaca agagagattg gtttcatagt    8820
gcctggctta ccgggtactg tgctgagagc aatcaatggt gacttcttgc attttctacc    8880
tcgtgttttt agtgctgttg gcaacatttg ctacacacct tccaaactca ttgagtatag    8940
tgattttgct acctctgctt gcgttcttgc tgctgagtgt acaattttta aggatgctat    9000
gggcaaacct gtgccatatt gttatgacac taatttgcta gagggttcta tttcttatag    9060
tgagcttcgt ccagacactc gttatgtgct tatggatggt tccatcatac agtttcctaa    9120
cacttacctg gagggttctg ttagagtagt aacaactttt gatgctgagt actgtagaca    9180
tggtacatgc gaaaggtcag aagtaggtat ttgcctatct accagtggta gatgggttct    9240
taataatgag cattacagag ctctatcagg agttttctgt ggtgttgatg cgatgaatct    9300
catagctaac atctttactc ctcttgtgca acctgtgggt gctttagatg tgtctgcttc    9360
agtagtggct ggtggtatta ttgccatatt ggtgacttgt gctgcctact actttatgaa    9420
attcagacgt gtttttggtg agtacaacca tgttgttgct gctaatgcac ttttgttttt    9480
gatgtctttc actatactct gtctggtacc agcttacagc tttctgccgg gagtctactc    9540
agtcttttac ttgtacttga cattctattt caccaatgat gtttcattct ggctcacct    9600
tcaatggttt gccatgtttt ctcctattgt gccttttgg ataacagcaa tctatgtatt    9660
ctgtatttct ctgaagcact gccattggtt ctttaacaac tatcttagga aaagagtcat    9720
gtttaatgga gttacattta gtaccttcga ggaggctgct ttgtgtacct ttttgctcaa    9780
caaggaaatg tacctaaaat tgcgtagcga gacactgttg ccacttacac agtataacag    9840
gtatcttgct ctatataaca agtacaagta tttcagtgga gccttagata ctaccagcta    9900
tcgtgaagca gcttgctgcc acttagcaaa ggctctaaat gactttagca actcaggtgc    9960
tgatgttctc taccaaccac cacagacatc aatcacttct gctgttctgc agagtggttt   10020
taggaaaatg gcattcccgt caggcaaagt tgaagggtgc atggtacaag taacctgtgg   10080
aactacaact cttaatggat tgtggttgga tgacacagta tactgtccaa gacatgtcat   10140
ttgcacagca gaagacatgc ttaatcctaa ctatgaagat ctgctcattc gcaaatccaa   10200
ccatagcttt cttgttcagg ctggcaatgt tcaacttcgt gttattggcc attctatgca   10260
aaattgtctg cttaggctta agttgatac ttctaaccct aagacaccca agtataaatt   10320
tgtccgtatc caacctggtc aaacattttc agttctagca tgctacaatg gttccatcc   10380
tggtgtttat cagtgtgcca tgagacctaa tcataccatt aaaggttctt tccttaatgg   10440
atcatgtggt agtgttggtt ttaacattga ttatgattgc gtgtctttct gctatatgca   10500
tcatatggag cttccaacag gagtacacgc tggtactgac ttagaaggta aattctatgg   10560
tccatttgtt gacagacaaa ctgcacaggc tgcaggtaca gacacaacca taacattaaa   10620
tgttttggca tggctgtatg ctgctgttat caatggtgat aggtggtttc ttaatagatt   10680
caccactact ttgaatgact ttaaccttgt ggcaatgaag tacaactatg aacctttgac   10740
acaagatcat gttgacatat gggaccctct ttctgctcaa acaggaattg ccgtcttaga   10800
tatgtgtgct gctttgaaag agctgctgca gaatggtatg aatggtcgta ctatccttgg   10860
tagcactatt ttagaagatg agtttacacc atttgatgtt gttagacaat gctctggtgt   10920
```

```
taccttccaa ggtaagttca agaaaattgt taagggcact catcattgga tgcttttaac    10980
tttcttgaca tcactattga ttcttgttca aagtacacag tggtcactgt ttttctttgt    11040
ttacgagaat gctttcttgc catttactct tggtattatg gcaattgctg catgtgctat    11100
gctgcttgtt aagcataagc acgcattctt gtgcttgttt ctgttacctt ctcttgcaac    11160
agttgcttac tttaatatgg tctacatgcc tgctagctgg gtgatgcgta tcatgacatg    11220
gcttgaattg gctgacacta gcttgtctgg ttataggctt aaggattgtg ttatgtatgc    11280
ttcagcttta gttttgctta ttctcatgac agctcgcact gtttatgatg atgctgctag    11340
acgtgtttgg acactgatga atgtcattac acttgtttac aaagtctact atggtaatgc    11400
tttagatcaa gctatttcca tgtgggcctt agttatttct gtaacctcta actattctgg    11460
tgtcgttacg actatcatgt ttttagctag agctatagtg tttgtgtgtg ttgagtatta    11520
cccattgtta tttattactg gcaacacctt acagtgtatc atgcttgttt attgtttctt    11580
aggctattgt tgctgctgct actttggcct tttctgttta ctcaaccgtt acttcaggct    11640
tactcttggt gtttatgact acttggtctc tacacaagaa tttaggtata tgaactccca    11700
ggggcttttg cctcctaaga gtagtattga tgctttcaag cttaacatta agttgttggg    11760
tattggaggt aaaccatgta tcaaggttgc tactgtacag tctaaaatgt ctgacgtaaa    11820
gtgcacatct gtggtactgc tctcggttct tcaacaactt agagtagagt catcttctaa    11880
attgtgggca caatgtgtac aactccacaa tgatattctt cttgcaaaag acacaactga    11940
agctttcgag aagatggttt ctcttttgtc tgttttgcta tccatgcagg gtgctgtaga    12000
cattaatagg ttgtgcgagg aaatgctcga taaccgtgct actcttcagg ctattgcttc    12060
agaatttagt tctttaccat catatgccgc ttatgccact gcccaagagg cctatgagca    12120
ggctgtagct aatggtgatt ctgaagtcgt tctcaaaaag ttaaagaaat ctttgaatgt    12180
ggctaaatct gagtttgacc gtgatgctgc catgcaacgc aagttggaaa agatggcaga    12240
tcaggctatg acccaaatgt acaaacaggc aagatctgag gacaagaggg caaaagtaac    12300
tagtgctatg caaacaatgc tcttcactat gcttaggaag cttgataatg atgcacttaa    12360
caacattatc aacaatgcgc gtgatggttg tgttccactc aacatcatac cattgactac    12420
agcagccaaa ctcatggttg ttgtccctga ttatggtacc tacaagaaca cttgtgatgg    12480
taacacctt acatatgcat ctgcactctg ggaaatccag caagttgttg atgcggatag    12540
caagattgtt caacttagtg aaattaacat ggacaattca ccaaatttgg cttggcctct    12600
tattgttaca gctctaagag ccaactcagc tgttaaacta cagaataatg aactgagtcc    12660
agtagcacta cgacagatgt cctgtgcggc tggtaccaca caaacagctt gtactgatga    12720
caatgcactt gcctactata caattcgaa gggaggtagg tttgtgctgg cattactatc    12780
agaccaccaa gatctcaaat gggctagatt ccctaagagt gatggtacag gtacaattta    12840
cacagaactg gaaccacctt gtaggtttgt tacagacaca ccaaagggc taaagtgaa    12900
atacttgtac ttcatcaaag gcttaaacaa cctaaataga ggtatggtgc tgggcagttt    12960
agctgctaca gtacgtcttc aggctggaaa tgctacagaa gtacctgcca attcaactgt    13020
gcttcctc tgtgctttg cagtagaccc tgctaaagca tataaggatt acctagcaag    13080
tggaggacaa ccaatcacca actgtgtgaa gatgttgtgt acacacactg gtacaggaca    13140
ggcaattact gtaacaccag aagctaacat ggaccaagag tcctttggtg gtgcttcatg    13200
ttgtctgtat tgtagatgcc acattgacca tccaaatcct aaaggattct gtgacttgaa    13260
aggtaagtac gtccaaatac ctaccacttg tgctaatgac ccagtgggtt ttacacttag    13320
```

```
aaacacagtc tgtaccgtct gcggaatgtg gaaaggttat ggctgtagtt gtgaccaact   13380
ccgcgaaccc ttgatgcagt ctgcggatgc atcaacgttt ttaaacgggt ttgcggtgta   13440
agtgcagccc gtcttacacc gtgcggcaca ggcactagta ctgatgtcgt ctacagggct   13500
tttgatattt acaacgaaaa agttgctggt tttgcaaagt tcctaaaaac taattgctgt   13560
cgcttccagg agaaggatga ggaaggcaat ttattagact cttactttgt agttaagagg   13620
catactatgt ctaactacca acatgaagag actatttata acttggttaa agattgtcca   13680
gcggttgctg tccatgactt tttcaagttt agagtagatg gtgacatggt accacatata   13740
tcacgtcagc gtctaactaa atacacaatg gctgatttag tctatgctct acgtcatttt   13800
gatgagggta attgtgatac attaaaagaa atactcgtca catacaattg ctgtgatgat   13860
gattatttca ataagaagga ttggtatgac ttcgtagaga atcctgacat cttacgcgta   13920
tatgctaact taggtgagcg tgtacgccaa tcattattaa agactgtaca attctgcgat   13980
gctatgcgtg atgcaggcat tgtaggcgta ctgacattag ataatcagga tcttaatggg   14040
aactggtacg atttcggtga tttcgtacaa gtagcaccag gctgcggagt tcctattgtg   14100
gattcatatt actcattgct gatgcccatc ctcactttga ctagggcatt ggctgctgag   14160
tcccatatgg atgctgatct cgcaaaacca cttattaagt gggatctgct gaaatatgat   14220
tttacggaag agagactttg tctcttcgac cgttattta aatattggga ccagacatac   14280
catcccaatt gtattaactg tttggatgat aggtgtatcc ttcattgtgc aaactttaat   14340
gtgttatttt ctactgtgtt tccacctaca agttttggac cactagtaag aaaaatattt   14400
gtagatggtg ttccttttgt tgtttcaact ggataccatt tcgtgagtt aggagtcgta   14460
cataatcagg atgtaaactt acatagctcg cgtctcagtt tcaaggaact tttagtgtat   14520
gctgctgatc cagctatgca tgcagcttct ggcaatttat tgctagataa acgcactaca   14580
tgcttttcag tagctgcact aacaaacaat gttgcttttc aaactgtcaa acccggtaat   14640
tttaataaag acttttatga ctttgctgtg tctaaaggtt tctttaagga aggaagttct   14700
gttgaactaa aacacttctt ctttgctcag gatggcaacg ctgctatcag tgattatgac   14760
tattatcgtt ataatctgcc aacaatgtgt gatatcagac aactcctatt cgtagttgaa   14820
gttgttgata aatactttga ttgttacgat ggtggctgta ttaatgccaa ccaagtaatc   14880
gttaacaatc tggataaatc agctggtttc ccatttaata aatgggggtaa ggctagactt   14940
tattatgact caatgagtta tgaggatcaa gatgcacttt tcgcgtatac taagcgtaat   15000
gtcatcccta ctataactca aatgaatctt aagtatgcca ttagtgcaaa gaatagagct   15060
cgcaccgtag ctggtgtctc tatctgtagt actatgacaa atagacagtt tcatcagaaa   15120
ttattgaagt caatagccgc cactagagga gctactgtgg taattggaac aagcaagttt   15180
tacggtggct ggcataatat gttaaaaact gtttacagtg atgtagaaac tccacacctt   15240
atgggttggg attatccaaa atgtgacaga gccatgccta acatgcttag gataatggcc   15300
tctcttgttc ttgctcgcaa acataacact tgctgtaact tatcacaccg tttctacagg   15360
ttagctaacg agtgtgcgca agtattaagt gagatggtca tgtgtggcgg ctcactatat   15420
gttaaaccag gtggaacatc atccggtgat gctacaactg cttatgctaa tagtgtcttt   15480
aacatttgtc aagctgttac agccaatgta aatgcacttc tttcaactga tggtaataag   15540
atagctgaca agtatgtccg caatctacaa cacaggctct atgagtgtct ctatagaaat   15600
agggatgttg atcatgaatt cgtggatgag ttttacgctt acctgcgtaa acatttctcc   15660
atgatgattc tttctgatga tgccgttgtg tgctataaca gtaactatgc ggctcaaggt   15720
```

-continued

```
ttagtagcta gcattaagaa ctttaaggca gttctttatt atcaaaacaa tgtgttcatg    15780
tctgaggcaa aatgttggac tgagactgac cttactaaag gacctcacga attttgctca    15840
cagcatacaa tgctagttaa acaaggagat gattacgtgt acctgcctta cccagatcca    15900
tcaagaatat taggcgcagg ctgttttgtc gatgatattg tcaaaacaga tggtacactt    15960
atgattgaaa ggttcgtgtc actggctatt gatgcttacc cacttacaaa acatcctaat    16020
caggagtatg ctgatgtctt tcacttgtat ttacaataca ttagaaagtt acatgatgag    16080
cttactggcc acatgttgga catgtattcc gtaatgctaa ctaatgataa cacctcacgg    16140
tactgggaac ctgagtttta tgaggctatg tacacaccac atacagtctt gcaggctgta    16200
ggtgcttgtg tattgtgcaa ttcacagact tcacttcgtt gcggtgcctg tattaggaga    16260
ccattcctat gttgcaagtg ctgctatgac catgtcattt caacatcaca caaattagtg    16320
ttgtctgtta atccctatgt ttgcaatgcc ccaggttgtg atgtcactga tgtgacacaa    16380
ctgtatctag gaggtatgag ctattattgc aagtcacata agcctcccat tagttttcca    16440
ttatgtgcta atggtcaggt ttttggttta tacaaaaaca catgtgtagg cagtgacaat    16500
gtcactgact tcaatgcgat agcaacatgt gattggacta atgctggcga ttacatactt    16560
gccaacactt gtactgagag actcaagctt ttcgcagcag aaacgctcaa agccactgag    16620
gaaacattta agctgtcata tggtattgct actgtacgcg aagtactctc tgacagagaa    16680
ttgcatcttt catgggaggt tggaaaacct agaccaccat gaacagaaa ctatgtcttt     16740 actggttacc gtgtaactaa aaatagtaaa gtacagattg gagagtacac ctttgaaaaa    16800
ggtgactatg gtgatgctgt tgtgtacaga ggtactacga catacaagtt gaatgttggt    16860
gattactttg tgttgacatc tcacactgta atgccactta gtgcacctac tctagtgcca    16920
caagagcact atgtgagaat tactggcttg taccccaacac tcaacatctc agatgagttt    16980
tctagcaatg ttgcaaatta tcaaaaggtc ggcatgcaaa agtactctac actccaagga    17040
ccacctggta ctggtaagag tcattttgcc atcggacttg ctctctatta cccatctgct    17100
cgcatagtgt atacggcatg ctctcatgca gctgttgatg ccctatgtga aaaggcatta    17160
aaatatttgc ccatagataa atgtagtaga atcatacctg cgcgtgcgcg cgtagagtgt    17220
tttgataaat tcaaagtgaa ttcaacacta gaacagtatg ttttctgcac tgtaaatgca    17280
ttgccagaaa caactgctga cattgtagtc tttgatgaaa tctctatggc tactaattat    17340
gacttgagtg ttgtcaatgc tagacttcgt gcaaaacact acgtctatat tggcgatcct    17400
gctcaattac cagccccccg cacattgctg actaaaggca cactagaacc agaatatttt    17460
aattcagtgt gcagacttat gaaaacaata ggtccagaca tgttccttgg aacttgtcgc    17520
cgttgtcctg ctgaaattgt tgacactgtg agtgctttag tttatgacaa taagctaaaa    17580
gcacacaagg ataagtcagc tcaatgcttc aaaatgttct acaaaggtgt tattacacat    17640
gatgtttcat ctgcaatcaa cagacctcaa ataggcgttg taagagaatt tcttacacgc    17700
aatcctgctt ggagaaaagc tgtttttatc tcaccttata attcacagaa cgctgtagct    17760
tcaaaaatct taggattgcc tacgcagact gttgattcat cacagggttc tgaatatgac    17820
tatgtcatat tcacacaaac tactgaaaca gcacactctt gtaatgtcaa ccgcttcaat    17880
gtggctatca aagggcaaa aattggcatt ttgtgcaataa tgtctgatag agatcttttat    17940 gacaaactgc aatttacaag tctagaaata ccacgtcgca atgtggctac attacaagca    18000
gaaaatgtaa ctggactttt taaggactgt agtaagatca ttactggtct tcatcctaca    18060
caggcaccta cacacctcag cgttgatata aagttcaaga ctgaaggatt atgtgttgac    18120
```

```
ataccaggca taccaaagga catgacctac cgtagactca tctctatgat gggtttcaaa  18180
atgaattacc aagtcaatgg ttaccctaat atgtttatca cccgcgaaga agctattcgt  18240
cacgttcgtg cgtggattgg ctttgatgta gagggctgtc atgcaactag agatgctgtg  18300
ggtactaacc tacctctcca gctaggattt tctacaggtg ttaacttagt agctgtaccg  18360
actggttatg ttgacactga aaataacaca gaattcacca gagttaatgc aaaacctcca  18420
ccaggtgacc agtttaaaca tcttatacca ctcatgtata aaggcttgcc ctggaatgta  18480
gtgcgtatta agatagtaca aatgctcagt gatacactga aaggattgtc agacagagtc  18540
gtgttcgtcc tttgggcgca tggctttgag cttacatcaa tgaagtactt tgtcaagatt  18600
ggacctgaaa gaacgtgttg tctgtgtgac aaacgtgcaa cttgcttttc tacttcatca  18660
gatacttatg cctgctggaa tcattctgtg ggttttgact atgtctataa cccatttatg  18720
attgatgttc agcagtgggg ctttacgggt aaccttcaga gtaaccatga ccaacattgc  18780
caggtacatg gaaatgcaca tgtggctagt tgtgatgcta tcatgactag atgtttagca  18840
gtccatgagt gctttgttaa gcgcgttgat tggtctgttg aatacccttat tataggagat  18900
gaactgaggg ttaattctgc ttgcagaaaa gtacaacaca tggttgtgaa gtctgccctc  18960
ctggctgata agtttccagt tcttcatgac attggaaatc caaaggctat caagtgtgtg  19020
cctcaggctg aagtagaatg gaagttctac gatgctcagc catgtagtga caaagcttac  19080
aaaatagagg agctcttcta ttcttatgct acacatcacg ataaattcac tgatggtgtt  19140
tgtttgtttt ggaattgtaa cgttgatcgt tacccagcca atgcaattgt gtgtaggttt  19200
gacacaagag tcttgtcaaa cttgaactta ccaggctgtg atggtggtag tttgtatgtg  19260
aataagcatg cattccacac tccagctttc gataaaagtg catttactaa tttaaagcaa  19320
ttgcctttct tttactattc tgatagtcct tgtgagtctc atggcaaaca agtagtgtcg  19380
gatattgatt atgttccact caaatctgct acgtgtatta cacgatgcaa tttaggtggt  19440
gctgtttgca gacaccatgc aaatgagtac cgacagtact tggatgcata taatatgatg  19500
atttctgctg gatttagcct atggatttac aaacaatttg atacttataa cctgtggaat  19560
acatttacca ggttacagag tttagaaaat gtggcttata atgttgttaa taaaggacac  19620
tttgatggac acgccggcga agcacctgtt tccatcatta taatgctgt ttacacaaag  19680
gtagatggta ttgatgtgga gatctttgaa aataagacaa cacttcctgt taatgttgca  19740
tttgagcttt gggctaagcg taacattaaa ccagtgccag agattaagat actcaataat  19800
ttgggtgttg atatcgctgc taatactgta atctgggact ataaaagaga agccccagca  19860
catgtatcta caataggtgt ctgcacaatg actgacattg ccaagaaacc tactgagagt  19920
gcttgttctt cacttactgt cttgtttgat ggtagagtgg aaggacaggt agacctttttt  19980
agaaacgccc gtaatggtgt tttaataaca gaaggttcag tcaaaggtct aacaccttca  20040
aagggaccag cacaagctag cgtcaatgga gtcacattaa ttggagaatc agtaaaaaca  20100
cagtttaact actttaagaa agtagacggc attattcaac agttgcctga aacctacttt  20160
actcagagca gagacttaga ggattttaag cccagatcac aaatggaaac tgactttctc  20220
gagctcgcta tggatgaatt catacagcga tataagctcg agggctatgc cttcgaacac  20280
atcgtttatg gagatttcag tcatggacaa cttggcggtc ttcatttaat gataggctta  20340
gccaagcgct cacaagatte accacttaaa ttagaggatt ttatccctat ggacagcaca  20400
gtgaaaaatt acttcataac agatgcgcaa acaggttcat caaaatgtgt gtgttctgtg  20460
attgatcttt tacttgatga ctttgtcgag ataataaagt cacaagattt gtcagtgatt  20520
```

```
tcaaaagtgg tcaaggttac aattgactat gctgagattt cattcatgct ttggtgtaag    20580
gacggacatg ttgaaacctt ctacccaaaa ctacaagcaa gtcaagcgtg caaccaggt     20640 gttgcgatgc ctaacttgta caagatgcaa agaatgcttc ttgaaaagtg tgaccttcag    20700
aattatggtg aaaatgctgt tataccaaaa ggaataatga tgaatgtcgc aaagtatact    20760
caactgtgtc aatacttaaa tacacttact ttagctgtac cctacaacat gagagttatt    20820
cactttggtg ctggctctga taaggagtt gcaccaggta cagctgtgct cagacaatgg     20880
ttgccaactg gcacactact tgtcgattca gatcttaatg acttcgtctc cgacgcagat    20940
tctactttaa ttggagactg tgcaacagta catacggcta taaatggga ccttattatt     21000 agcgatatgt atgaccctag gaccaaacat gtgacaaaag agaatgactc taaagaaggg    21060
tttttcactt atctgtgtgg atttataaag caaaaactag ccctgggtgg ttctatagct    21120
gtaaagataa cagagcattc ttggaatgct gaccttaca agcttatggg ccatttctca     21180
tggtggacag cttttgttac aaatgtaaat gcatcatcat cggaagcatt tttaattggg    21240
gctaactatc ttggcaagcc gaaggaacaa attgatggct ataccatgca tgctaactac    21300
attttctgga ggaacacaaa tcctatccag ttgtcttcct attcactctt tgacatgagc    21360
aaatttcctc ttaaattaag aggaactgct gtaatgtctc ttaaggagaa tcaaatcaat    21420
gatatgattt attctcttct ggaaaaaggt aggcttatca ttagagaaaa caacagagtt    21480
gtggtttcaa gtgatattct tgttaacaac taaacgaaca tgtttatttt cttattattt    21540
cttactctca ctagtggtag tgaccttgac cggtgcacca cttttgatga tgttcaagct    21600
cctaattaca ctcaacatac ttcatctatg aggggggttt actatcctga tgaaattttt    21660
agatcagaca ctctttattt aactcaggat ttatttcttc cattttattc taatgttaca    21720
gggtttcata ctattaatca tacgtttggc aaccctgtca taccttttaa ggatggtatt    21780
tattttgctg ccacagagaa atcaaatgtt gtccgtggtt gggttttttgg ttctaccatg    21840 aacaacaagt cacagtcggt gattattatt aacaattcta ctaatgttgt tatacgagca    21900
tgtaactttg aattgtgtga caaccctttc tttgctgttt ctaaacccat gggtacacag    21960
acacatacta tgatattcga taatgcattt aattgcactt tcgagtacat atctgatgcc    22020
ttttcgcttg atgtttcaga aaagtcaggt aattttaaac acttacgaga gtttgtgttt    22080
aaaaataaag atgggtttct ctatgtttat aagggctatc aacctataga gtagttcgt     22140 gatctacctt ctggttttaa cactttgaaa cctattttta agttgcctct tggtattaac    22200
attacaaatt ttagagccat tcttacagcc ttttcacctg ctcaagacat ttggggcacg    22260
tcagctgcag cctatttttgt tggctattta aagccaacta catttatgct caagtatgat    22320
gaaaatggta caatcacaga tgctgttgat tgttctcaaa atccacttgc tgaactcaaa    22380
tgctctgtta agagctttga gattgacaaa ggaatttacc agacctctaa tttcagggtt    22440
gttccctcag gagatgttgt gagattccct aatattacaa acttgtgtcc ttttggagag    22500
gtttttaatg ctactaaatt cccttctgtc tatgcatggg agagaaaaaa aatttctaat    22560
tgtgttgctg attactctgt gctctacaac tcaacatttt tttcaaccttt aagtgctat    22620 ggcgttctg ccactaagtt gaatgatctt tgcttctcca atgtctatgc agattctttt    22680
gtagtcaagg gagatgatgt aagacaaata gcgccaggac aaactggtgt tattgctgat    22740
tataattata aattgccaga tgatttcatg ggttgtgtcc ttgcttggaa tactaggaac    22800
attgatgcta cttcaactgg taattataat tataaaatata ggtatcttag acatggcaag    22860 cttaggcccct ttgagagaga catatctaat gtgcctttct cccctgatgg caaaccttgc    22920
```

```
accccacctg ctcttaattg ttattggcca ttaaatgatt atggttttta caccactact   22980
ggcattggct accaacctta cagagttgta gtactttctt ttgaactttt aaatgcaccg   23040
gccacggttt gtggaccaaa attatccact gaccttatta agaaccagtg tgtcaatttt   23100
aattttaatg gactcactgg tactggtgtg ttaactcctt cttcaaagag atttcaacca   23160
tttcaacaat ttggccgtga tgtttctgat tcactgatt ccgttcgaga tcctaaaaca   23220
tctgaaatat tagacatttc accttgctct tttggggtg taagtgtaat tacacctgga    23280
acaaatgctt catctgaagt tgctgttcta tatcaagatg ttaactgcac tgatgtttct   23340
acagcaattc atgcagatca actcacacca gcttggcgca tatattctac tggaaacaat   23400
gtattccaga ctcaagcagg ctgtcttata ggagctgagc atgtcgacac ttcttatgag   23460
tgcgacattc ctattggagc tggcatttgt gctagttacc atacagtttc tttattacgt   23520
agtactagcc aaaaatctat tgtggcttat actatgtctt taggtgctga tagttcaatt   23580
gcttactcta ataacaccat tgctatacct actaactttt caattagcat tactacagaa   23640
gtaatgcctg tttctatggc taaaacctcc gtagattgta atatgtacat ctgcggagat   23700
tctactgaat gtgctaattt gcttctccaa tatggtagct tttgcacaca actaaatcgt   23760
gcactctcag gtattgctgc tgaacaggat cgcaacacac gtgaagtgtt cgctcaagtc   23820
aaacaaatgt acaaaacccc aactttgaaa tattttggtg gttttaattt ttcacaaata   23880
ttacctgacc ctctaaagcc aactaagagg tctttttattg aggacttgct ctttaataag   23940
gtgacactcg ctgatgctgg cttcatgaag caatatggcg aatgcctagg tgatattaat   24000
gctagagatc tcatttgtgc gcagaagttc aatggactta cagtgttgcc acctctgctc   24060
actgatgata tgattgctgc ctacacggct gctctagtta gtggtactgc cactgctgga   24120
tggacatttg gtgctggcgc tgctcttcaa ataccttttg ctatgcaaat ggcatatagg   24180
ttcaatggca ttgagttac ccaaaatgtt ctctatgaga accaaaaaca aatcgccaac    24240
caatttaaca aggcgattag tcaaattcaa gaatcactta acaacatc aactgcattg     24300 ggcaagctgc aagacgttgt taaccagaat gctcaagcat taaacacact tgttaaacaa   24360
cttagctcta attttggtgc aatttcaagt gtgctaaatg atatccttc gcgacttgat    24420 aaagtcgagg cggaggtaca aattgacagg ttaattacag gcagacttca aagccttcaa   24480
acctatgtaa cacaacaact aatcagggct gctgaaatca gggcttctgc taatcttgct   24540
gctactaaaa tgtctgagtg tgttcttgga caatcaaaaa gagttgactt ttgtggaaag   24600
ggctaccacc ttatgtcctt cccacaagca gccccgcatg gtgttgtctt cctacatgtc   24660
acgtatgtgc catcccagga gaggaacttc accacagcgc cagcaatttg tcatgaaggc   24720
aaagcatact ccctcgtga aggtgttttt tgtgtttaatg gcacttcttg gtttattaca   24780
cagaggaact tcttttctcc acaaataatt actacagaca atacatttgt ctcaggaaat   24840
tgtgatgtcg ttattggcat cattaacaac acagtttatg atcctctgca acctgagctc   24900
gactcattca aagaagagct ggacaagtac ttcaaaaatc atacatcacc agatgttgat   24960
cttggcgaca tttcaggcat taacgcttct gtcgtcaaca ttcaaaaaga aattgaccgc   25020
ctcaatgagg tcgctaaaaa tttaaatgaa tcactcattg accttcaaga attgggaaaa   25080
tatgagcaat atattaaatg gccttggtat gtttggctcg gcttcattgc tggactaatt   25140
gccatcgtca tggttacaat cttgctttgt gcatgacta gttgttgcag ttgcctcaag   25200
ggtgcatgct tgtgtggttc ttgctgcaag tttgatgagg atgactctga gccagttctc   25260
aagggtgtca aattacatta cacataaacg aacttatgga tttgtttatg agattttta    25320
```

```
ctcttggatc aattactgca cagccagtaa aaattgacaa tgcttctcct gcaagtactg   25380
ttcatgctac agcaacgata ccgctacaag cctcactccc tttcggatgg cttgttattg   25440
gcgttgcatt tcttgctgtt tttcagagcg ctaccaaaat aattgcgctc aataaaagat   25500
ggcagctagc cctttataag ggcttccagt tcatttgcaa tttactgctg ctatttgtta   25560
ccatctattc acatcttttg cttgtcgctg caggtatgga ggcgcaattt ttgtacctct   25620
atgccttgat atattttcta caatgcatca acgcatgtag aattattatg agatgttggc   25680
tttgttggaa gtgcaaatcc aagaacccat tactttatga tgccaactac tttgtttgct   25740
ggcacacaca taactatgac tactgtatac catataacag tgtcacagat acaattgtcg   25800
ttactgaagg tgacggcatt tcaacaccaa aactcaaaga agactaccaa attggtggtt   25860
attctgagga taggcactca ggtgttaaag actatgtcgt tgtacatggc tatttcaccg   25920
aagtttacta ccagcttgag tctacacaaa ttactacaga cactggtatt gaaaatgcta   25980
cattcttcat ctttaacaag cttgttaaag acccaccgaa tgtgcaaata cacacaatcg   26040
acggctcttc aggagttgct aatccagcaa tggatccaat ttatgatgag ccgacgacga   26100
ctactagcgt gcctttgtaa gcacaagaaa gtgagtacga acttatgtac tcattcgttt   26160
cggaagaaac aggtacgtta atagttaata gcgtacttct ttttcttgct ttcgtggtat   26220
tcttgctagt cacactagcc atccttactg cgcttcgatt gtgtgcgtac tgctgcaata   26280
ttgttaacgt gagtttagta aaaccaacgg tttacgtcta ctcgcgtgtt aaaaatctga   26340
actcttctga aggagttcct gatcttctgg tctaaacgaa ctaactatta ttattattct   26400
gtttggaact ttaacattgc ttatcatggc agacaacggt actattaccg ttgaggagct   26460
taaacaactc ctggaacaat ggaacctagt aataggtttc ctattcctag cctggattat   26520
gttactacaa tttgcctatt ctaatcggaa caggtttttg tacataataa gcttgttttt   26580
cctctggctc ttgtggccag taacacttgc ttgttttgtg cttgctgctg tctacagaat   26640
taattgggtg actggcggga ttgcgattgc aatggcttgt attgtaggct tgatgtggct   26700
tagctacttc gttgcttcct tcaggctgtt tgctcgtacc cgctcaatgt ggtcattcaa   26760
cccagaaaca aacattcttc tcaatgtgcc tctccggggg acaattgtga ccagaccgct   26820 catgaaagt gaacttgtca ttggtgctgt gatcattcgt ggtcacttgc gaatggccgg   26880
acacccccta gggcgctgtg acattaagga cctgccaaaa gagatcactg tggctacatc   26940
acgaacgctt tcttattaca aattaggagc gtcgcagcgt gtaggcactg attcaggttt   27000
tgctgcatac aaccgctacc gtattggaaa ctataaatta aatacagacc acgccggtag   27060
caacgacaat attgctttgc tagtacagta agtgacaaca gatgtttcat cttgttgact   27120
tccaggttac aatagcagag atattgatta tcattatgag gactttcagg attgctattt   27180
ggaatcttga cgttataata agttcaatag tgagacaatt atttaagcct ctaactaaga   27240
agaattattc ggagttagat gatgaagaac ctatggagtt agattatcca taaaacgaac   27300
atgaaaatta ttctcttcct gacattgatt gtatttacat cttgcgagct atatcactat   27360
caggagtgtg ttagaggtac gactgtacta ctaaaagaac cttgcccatc aggaacatac   27420
gagggcaatt caccatttca ccctcttgct gacaataaat ttgcactaac ttgcactagc   27480
acacactttg cttttgcttg tgctgacggt actcgacata cctatcagct gcgtgcaaga   27540
tcagtttcac caaaactttt catcagacaa gaggaggttc aacaagagct ctactcgcca   27600 cttttttctca ttgttgctgc tctagtattt ttaatacttt gcttcaccat taagagaaag   27660
acagaatgaa tgagctcact ttaattgact tctatttgtg cttttttagcc tttctgctat   27720
```

```
tccttgtttt aataatgctt attatatttt ggttttcact cgaaatccag gatctagaag    27780
aaccttgtac caaagtctaa acgaacatga aacttctcat tgttttgact tgtatttctc    27840
tatgcagttg catatgcact gtagtacagc gctgtgcatc taataaacct catgtgcttg    27900
aagatccttg taaggtacaa cactagrggt aatacttata gcactgcttg gctttgtgct    27960
ctaggaaagg ttttaccttt tcatagatgg cacactatgg ttcaaacatg cacacctaat    28020
gttactatca actgtcaaga tccagctggt ggtgcgctta gctaggtg ttggtacctt     28080
catgaaggtc accaaactgc tgcatttaga gacgtacttg ttgttttaaa taaacgaaca    28140
aattaaaatg tctgataatg accccaatc aaaccaacgt agtgccccc gcattacatt     28200
tggtggaccc acagattcaa ctgacaataa ccagaatgga ggacgcaatg gggcaaggcc    28260
aaaacagcgc cgaccccaag gtttacccaa taatactgcg tcttggttca cagctctcac    28320
tcagcatggc aaggaggaac ttagattccc tcgaggccag ggcgttccaa tcaacaccaa    28380
tagtggtcca gatgaccaaa ttggctacta ccgaagagct acccgacgag ttcgtggtgg    28440
tgacggcaaa atgaaagagc tcagccccag atggtacttc tattacctag gaactggccc    28500
agaagcttca cttccctacg cgctaacaa agaaggcatc gtatgggttg caactgaggg     28560
agccttgaat acacccaaag accacattgg cacccgcaat cctaataaca atgctgccac    28620
cgtgctacaa cttcctcaag gaacaacatt gccaaaaggc ttctacgcag agggaagcag    28680
aggcggcagt caagcctctt ctcgctcctc atcacgtagt cgcggtaatt caagaaattc    28740
aactcctggc agcagtaggg gaaattctcc tgctcgaatg gctagcggag gtggtgaaac    28800
tgccctcgcg ctattgctgc tagacagatt gaaccagctt gagagcaaag tttctggtaa    28860
aggccaacaa caacaaggcc aaactgtcac taagaaatct gctgctgagg catctaaaaa    28920
gcctcgccaa aaacgtactg ccacaaaaca gtacaacgtc actcaagcat tgggagacg     28980
tggtccagaa caaacccaag gaaatttcgg ggaccaagac ctaatcagac aaggaactga    29040
ttacaaacat tggccgcaaa ttgcacaatt tgctccaagt gcctctgcat tctttggaat    29100
gtcacgcatt ggcatggaag tcacaccttc gggaacatgg ctgacttatc atggagccat    29160
taaattggat gacaaagatc cacaattcaa agacaacgtc atactgctga caagcacat     29220
tgacgcatac aaaacattcc caccaacaga gcctaaaaag gacaaaaaga aaagactga    29280
tgaagctcag cctttgccgc agagacaaaa gaagcagccc actgtgactc ttcttcctgc    29340
ggctgacatg gatgatttct ccagacaact tcaaaattcc atgagtggag cttctgctga    29400
ttcaactcag gcataaacac tcatgatgac cacacaaggc agatgggcta tgtaaacgtt    29460
ttcgcaattc cgtttacgat acatagtcta ctcttgtgca gaatgaattc tcgtaactaa    29520
acagcacaag taggtttagt taactttaat ctcacatagc aatctttaat caatgtgtaa    29580
cattagggag gacttgaaag agccaccaca ttttcatcga ggccacgcgg agtacgatcg    29640
agggtacagt gaataatgct agggagagct gcctatatgg aagagcccta atgtgtaaaa    29700
ttaattttag tagtgctatc cccatgtgat tttaatagct tcttaggaga atgacaaaaa    29760
aaaaaaaaaa aaaaagggc gaattctgca g                                    29791

<210> SEQ ID NO 4
<211> LENGTH: 5450
<212> TYPE: DNA
<213> ORGANISM: Artificial
<220> FEATURE:
<223> OTHER INFORMATION: SARS F X1 mutant
```

-continued

```
<400> SEQUENCE: 4
gtgtgctgga attcgccctt cgagtgcccg cggccgcatt gctgcctaca cggctgctct        60
agttagtggt actgccactg ctggatggac atttggtgct ggcgctgctc ttcaaatacc       120
ttttgctatg caaatggcat ataggttcaa tggcattgga gttacccaaa atgttctcta       180
tgagaaccaa aaacaaatcg ccaaccaatt taacaaggcg attagtcaaa ttcaagaatc       240
acttacaaca acatcaactg cattgggcaa gctgcaagac gttgttaacc agaatgctca       300
agcattaaac acacttgtta aacaactag ctctaatttt ggtgcaattt caagtgtgct        360
aaatgatatc ctttcgcgac ttgataaagt cgaggcggag gtacaaattg acaggttaat       420
tacaggcaga cttcaaagcc ttcaaaccta tgtaacacaa caactaatca gggctgctga       480
aatcagggct tctgctaatc ttgctgctac taaaatgtct gagtgtgttc ttggacaatc       540
aaaaagagtt gactttgtg aaagggcta ccaccttatg tccttccac aagcagcccc         600 gcatggtgtt gtcttcctac atgtcacgta tgtgccatcc caggagagga acttcaccac       660
agcgccagca atttgtcatg aaggcaaagc atacttccct cgtgaaggtg ttttgtgtt        720 taatggcact tcttggttta ttacacagag gaacttcttt tctccacaaa taattactac       780
agacaataca tttgtctcag gaaattgtga tgtcgttatt ggcatcatta caacacagt        840 ttatgatcct ctgcaacctg agctcgactc attcaaagaa gagctggaca agtacttcaa       900
aaatcataca tcaccagatg ttgatcttgg cgacatttca ggcattaacg cttctgtcgt       960
caacattcaa aaagaaattg accgcctcaa tgaggtcgct aaaaatttaa atgaatcact      1020
cattgacctt caagaattgg gaaaatatga gcaatatatt aaatggcctt ggtatgtttg      1080
gctcggcttc attgctggac taattgccat cgtcatggtt acaatcttgc tttgttgcat      1140
gactagttgt tgcagttgcc tcaagggtgc atgctcttgt ggttcttgct gcaagtttga      1200
tgaggatgac tctgagccag ttctcaaggg tgtcaaatta cattacacat aaacgaactt      1260
agcaggtggg cgcgccatcg atttaattaa ggaagtgcaa atccaagaac ccattacttt      1320
atgatgccaa ctactttgtt tgctggcaca cacataacta tgactactgt ataccatata      1380
acagtgtcac agatacaatt gtcgttactg aaggtgacgg catttcaaca ccaaaactca      1440
aagaagacta ccaaattggt ggttattctg aggataggca ctcaggtgtt aaagactatg      1500
tcgttgtaca tggctatttc accgaagttt actaccagct tgagtctaca caaattacta      1560
cagacactgg tattgaaaat gctacattct tcatctttaa caagcttgtt aaagacccac      1620
cgaatgtgca aatacacaca atcgacggct cttcaggagt tgctaatcca gcaatggatc      1680
caatttatga tgagccgacg acgactacta gcgtgccttt gtaagcacaa gaaagtgagt      1740
acgaacttat gtactcattc gtttcggaag aaacaggtac gttaatagtt aatagcgtac      1800
ttctttttct tgctttcgtg gtattcttgc tagtcacact agccatcctt actgcgcttc      1860
gattgtgtgc gtactgctgc aatattgtta acgtgagttt agtaaaacca acggtttacg      1920
tctactcgcg tgttaaaaat ctgaactctt ctgaggagt tcctgatctt ctggtctaaa       1980
cgaactaact attattatta ttctgtttgg aactttaaca ttgcttatca tggcagacaa      2040
cggtactatt accgttgagg agcttaaaca actcctggaa caatggaacc tagtaatagg      2100
tttcctattc ctagcctgga ttatgttact acaatttgcc tattctaatc ggaacaggtt      2160
tttgtacata ataaagcttg ttttcctctg gctcttgtgg ccagtaacac ttgcttgttt      2220
tgtgcttgct gctgtctaca gaattaattg ggtgactggc gggattgcga ttgcaatggc      2280
ttgtattgta ggcttgatgt ggcttagcta cttcgttgct tccttcaggc tgtttgctcg      2340
```

```
tacccgctca atgtggtcat tcaacccaga aacaaacatt cttctcaatg tgcctctccg    2400
ggggacaatt gtgaccagac cgctcatgga aagtgaactt gtcattggtg ctgtgatcat    2460
tcgtggtcac ttgcgaatgg ccggacaccc cctagggcgc tgtgacatta aggacctgcc    2520
aaaagagatc actgtggcta catcacgaac gctttcttat tacaaattag gagcgtcgca    2580
gcgtgtaggc actgattcag gttttgctgc atacaaccgc taccgtattg gaaactataa    2640
attaaataca gaccacgccg gtagcaacga caatattgct ttgctagtac agtaagtgac    2700
aacagatgtt tcatcttgtt gacttccagg ttacaatagc agagatattg attatcatta    2760
tgaggacttt caggattgct atttggaatc ttgacgttat aataagttca atagtgagac    2820
aattatttaa gcctctaact aagaagaatt attcggagtt agatgatgaa gaacctatgg    2880
agttagatta tccataaaac gaacatgaaa attattctct tcctgacatt gattgtattt    2940
acatcttgcg agctatatca ctatcaggag tgtgttagag gtacgactgt actactaaaa    3000
gaaccttgcc catcaggaac atacgagggc aattcaccat ttcaccctct tgctgacaat    3060
aaatttgcac taacttgcac tagcacacac tttgcttttg cttgtgctga cggtactcga    3120
catacctatc agctgcgtgc aagatcagtt tcaccaaaac ttttcatcag acaagaggag    3180
gttcaacaag agctctactc gccactttt  ctcattgttg ctgctctagt attttaata    3240 ctttgcttca ccattaagag aaagacagaa tgaatgagct cactttaatt gacttctatt    3300
tgtgcttttt agcctttctg ctattccttg ttttaataat gcttattata ttttggtttt    3360
cactcgaaat ccaggatcta aagaaccctt gtaccaaagt ctaaacgaac atgaaacttc    3420
tcattgtttt gacttgtatt tctctatgca gttgcatatg cactgtagta cagcgctgtg    3480
catctaataa acctcatgtg cttgaagatc cttgtaaggt acaacactag gggtaatact    3540
tatagcactg cttggctttg tgctctagga aaggttttac ctttttcatag atggcacact    3600 atggttcaaa catgcacacc taatgttact atcaactgtc aagatccagc tggtggtgcg    3660
cttatagcta ggtgttggta ccttcatgaa ggtcaccaaa ctgctgcatt tagagacgta    3720
cttgttgttt taaataaacg aacaaattaa aatgtctgat aatggacccc aatcaaacca    3780
acgtagtgcc ccccgcatta catttggtgg acccacagat tcaactgaca ataaccagaa    3840
tggaggacgc aatggggcaa ggccaaaaca gcgccgaccc caaggtttac ccaataatac    3900
tgcgtcttgg ttcacagctc tcactcagca tggcaaggag gaacttagat tccctcgagg    3960
ccagggcgtt ccaatcaaca ccaatagtgg tccagatgac caaattggct actaccgaag    4020
agctacccga cgagttcgtg gtggtgacgg caaaatgaaa gagctcagcc ccagatggta    4080
cttctattac ctaggaactg gcccagaagc ttcacttccc tacggcgcta acaaagaagg    4140
catcgtatgg gttgcaactg agggagcctt gaatacaccc aaagaccaca ttggcacccg    4200
caatcctaat aacaatgctg ccaccgtgct acaacttcct caaggaacaa cattgccaaa    4260
aggcttctac gcagagggaa gcagaggcgg cagtcaagcc tcttctcgct cctcatcacg    4320
tagtcgcggt aattcaagaa attcaactcc tggcagcagt aggggaaatt ctcctgctcg    4380
aatggctagc ggaggtggtg aaactgccct cgcgctattg ctgctagaca gattgaacca    4440
gcttgagagc aaagtttctg gtaaaggcca acaacaacaa ggccaaactg tcactaagaa    4500
atctgctgct gaggcatcta aaaagcctcg ccaaaaacgt actgccacaa aacagtacaa    4560
cgtcactcaa gcatttggga acgtggtcc  agaacaaacc caaggaaatt tcggggacca    4620 agaccta atc agacaaggaa ctgattacaa acattggccg caaattgcac aatttgctcc    4680
aagtgcctct gcattctttg gaatgtcacg cattggcatg gaagtcacac cttcgggaac    4740
```

```
atggctgact tatcatggag ccattaaatt ggatgacaaa gatccacaat tcaaagacaa    4800
cgtcatactg ctgaacaagc acattgacgc atacaaaaca ttcccaccaa cagagcctaa    4860
aaaggacaaa aagaaaaaga ctgatgaagc tcagcctttg ccgcagagac aaaagaagca    4920
gcccactgtg actcttcttc ctgcggctga catggatgat ttctccagac aacttcaaaa    4980
ttccatgagt ggagcttctg ctgattcaac tcaggcataa acactcatga tgaccacaca    5040
aggcagatgg gctatgtaaa cgttttcgca attccgttta cgatacatag tctactcttg    5100
tgcagaatga attctcgtaa ctaaacagca caagtaggtt tagttaactt taatctcaca    5160
tagcaatctt taatcaatgt gtaacattag ggaggacttg aaagagccac cacattttca    5220
tcgaggccac gcggagtacg atcgagggta cagtgaataa tgctagggag agctgcctat    5280
atggaagagc cctaatgtgt aaaattaatt ttagtagtgc tatccccatg tgattttaat    5340
agcttcttag gagaatgaca aaaaaaaaa aaaaaaaaa agggcgaatt ctgcagatat    5400
ccatcacact ggcggccgct cgagcatgca tctagagggc ccaattcgcc               5450
```

<210> SEQ ID NO 5
<211> LENGTH: 5000
<212> TYPE: DNA
<213> ORGANISM: Artificial
<220> FEATURE:
<223> OTHER INFORMATION: SARS F X1X2 mutant

<400> SEQUENCE: 5

```
gtgtgctgga attcgccctt cgagtgcccg cggccgcatt gctgcctaca cggctgctct      60
agttagtggt actgccactg ctggatggac atttggtgct ggcgctgctc ttcaaatacc     120
ttttgctatg caaatggcat ataggttcaa tggcattgga gttacccaaa atgttctcta     180
tgagaaccaa aaacaaatcg ccaaccaatt taacaaggcg attagtcaaa ttcaagaatc     240
acttacaaca catcaactg cattgggcaa gctgcaagac gttgttaacc agaatgctca     300
agcattaaac acacttgtta acaacttag ctctaatttt ggtgcaattt caagtgtgct     360
aaatgatatc ctttcgcgac ttgataaagt cgaggcggag gtacaaattg acaggttaat     420
tacaggcaga cttcaaagcc ttcaaaccta tgtaacacaa caactaatca gggctgctga     480
aatcagggct tctgctaatc ttgctgctac taaaatgtct gagtgtgttc ttggacaatc     540
aaaaagagtt gactttgtg aaagggcta ccaccttatg tccttccac aagcagcccc     600 gcatggtgtt gtcttcctac atgtcacgta tgtgccatcc caggagagga acttcaccac     660
agcgccagca atttgtcatg aaggcaaagc atacttccct cgtgaaggtg ttttttgtgtt     720 taatggcact tcttggttta ttacacagag gaacttcttt tctccacaaa taattactac     780
agacaataca tttgtctcag gaaattgtga tgtcgttatt ggcatcatta acaacacagt     840
ttatgatcct ctgcaacctg agctcgactc attcaaagaa gagctggaca agtacttcaa     900
aaatcataca tcaccagatg ttgatcttgg cgacatttca ggcattaacg cttctgtcgt     960
caacattcaa aaagaaattg accgcctcaa tgaggtcgct aaaaatttaa atgaatcact    1020 cattgaccctt caagaattgg gaaaatatga gcaatatatt aaatggcctt ggtatgtttg    1080
gctcggcttc attgctggac taattgccat cgtcatggtt acaatcttgc tttgttgcat    1140
gactagttgt tgcagttgcc tcaagggtgc atgctcttgt ggttcttgct gcaagtttga    1200
tgaggatgac tctgagccag ttctcaaggg tgtcaaatta cattacacat aaacgaactt    1260
atgtactcat tcgtttcgga agaaacaggt acgttaatag ttaatagcgt acttcttttt    1320
cttgctttcg tggtattctt gctagtcaca ctagccatcc ttactgcgct tcgattgtgt    1380
```

```
gcgtactgct gcaatattgt taacgtgagt ttagtaaaac caacggttta cgtctactcg    1440
cgtgttaaaa atctgaactc ttctgaagga gttcctgatc ttctggtcta aacgaactaa    1500
ctattattat tattctgttt ggaactttaa cattgcttat catggcagac aacggtacta    1560
ttaccgttga ggagcttaaa caactcctgg aacaatggaa cctagtaata ggtttcctat    1620
tcctagcctg gattatgtta ctacaatttg cctattctaa tcggaacagg ttttttgtaca   1680 taataaagct tgttttcctc tggctcttgt ggccagtaac acttgcttgt tttgtgcttg    1740
ctgctgtcta cagaattaat tgggtgactg gcgggattgc gattgcaatg gcttgtattg    1800
taggcttgat gtggcttagc tacttcgttg cttccttcag gctgtttgct cgtacccgct    1860
caatgtggtc attcaaccca gaaacaaaca ttcttctcaa tgtgcctctc cggggggacaa   1920 ttgtgaccag accgctcatg gaaagtgaac ttgtcattgg tgctgtgatc attcgtggtc    1980
acttgcgaat ggccggacac cccctagggc gctgtgacat taaggacctg ccaaaagaga   2040
tcactgtggc tacatcacga acgctttctt attacaaatt aggagcgtcg cagcgtgtag    2100
gcactgattc aggttttgct gcatacaacc gctaccgtat tggaaactat aaattaaata    2160
cagaccacgc cggtagcaac gacaatattg ctttgctagt acagtaagtg acaacagatg    2220
tttcatcttg ttgacttcca ggttacaata gcagagatat tgattatcat tatgaggact    2280
ttcaggattg ctatttggaa tcttgacgtt ataataagtt caatagtgag acaattattt    2340
aagcctctaa ctaagaagaa ttattcggag ttagatgatg aagaacctat ggagttagat    2400
tatccataaa acgaacatga aaattattct cttcctgaca ttgattgtat ttacatcttg    2460
cgagctatat cactatcagg agtgtgttag aggtacgact gtactactaa aagaaccttg    2520
cccatcagga acatacgagg gcaattcacc atttcaccct cttgctgaca ataaatttgc    2580
actaacttgc actagcacac actttgcttt tgcttgtgct gacggtactc gacataccta    2640
tcagctgcgt gcaagatcag tttcaccaaa acttttcatc agacaagagg aggttcaaca    2700
agagctctac tcgccacttt ttctcattgt tgctgctcta gtattttaa tactttgctt     2760 caccattaag agaaagacag aatgaatgag ctcacttttaa ttgacttcta tttgtgcttt   2820
ttagcctttc tgctattcct tgttttaata atgcttatta tattttggtt ttcactcgaa    2880
atccaggatc tagaagaacc ttgtaccaaa gtctaaacga acatgaaact tctcattgtt    2940
ttgacttgta tttctctatg cagttgcata tgcactgtag tacagcgctg tgcatctaat    3000
aaacctcatg tgcttgaaga tccttgtaag gtacaacact aggggtaata cttatagcac    3060
tgcttggctt tgtgctctag gaaaggtttt acctttttcat agatggcaca ctatggttca    3120
aacatgcaca cctaatgtta ctatcaactg tcaagatcca gctggtggtg cgcttatagc    3180
taggtgttgg taccttcatg aaggtcacca aactgctgca tttagagacg tacttgttgt    3240
tttaaataaa cgaacaaatt aaaatgtctg ataatggacc ccaatcaaac caacgtagtg    3300
ccccccgcat tacatttggt ggacccacag attcaactga caataaccag aatggaggac    3360
gcaatggggc aaggccaaaa cagcgccgac cccaaggttt acccaataat actgcgtctt    3420
ggttcacagc tctcactcag catggcaagg aggaacttag attccctcga ggccagggcg    3480
ttccaatcaa caccaatagt ggtccagatg accaaattgg ctactaccga agagctaccc    3540
gacgagttcg tggtggtgac ggcaaaatga aagagctcag cccagatggg tacttctatt    3600
acctaggaac tggcccagaa gcttcacttc cctacggcgc taacaaagaa ggcatcgtat    3660
gggttgcaac tgagggagcc ttgaatacac ccaaagacca cattggcacc cgcaatccta    3720
ataacaatgc tgccaccgtg ctacaacttc ctcaaggaac aacattgcca aaaggcttct    3780
```

-continued

```
acgcagaggg aagcagaggc ggcagtcaag cctcttctcg ctcctcatca cgtagtcgcg   3840
gtaattcaag aaattcaact cctggcagca gtaggggaaa ttctcctgct cgaatggcta   3900
gcggaggtgg tgaaactgcc ctcgcgctat tgctgctaga cagattgaac cagcttgaga   3960
gcaaagtttc tggtaaaggc caacaacaac aaggccaaac tgtcactaag aaatctgctg   4020
ctgaggcatc taaaaagcct cgccaaaaac gtactgccac aaaacagtac aacgtcactc   4080
aagcatttgg gagacgtggt ccagaacaaa cccaaggaaa tttcggggac caagacctaa   4140
tcagacaagg aactgattac aaacattggc cgcaaattgc acaatttgct ccaagtgcct   4200
ctgcattctt tggaatgtca cgcattggca tggaagtcac accttcggga acatggctga   4260
cttatcatgg agccattaaa ttggatgaca aagatccaca attcaaagac aacgtcatac   4320
tgctgaacaa gcacattgac gcatacaaaa cattcccacc aacagagcct aaaaaggaca   4380
aaaagaaaaa gactgatgaa gctcagcctt tgccgcagag acaaaagaag cagcccactg   4440
tgactcttct tcctgcggct gacatggatg atttctccag acaacttcaa aattccatga   4500
gtggagcttc tgctgattca actcaggcat aaacactcat gatgaccaca caaggcagat   4560
gggctatgta aacgttttcg caattccgtt tacgatacat agtctactct tgtgcagaat   4620
gaattctcgt aactaaacag cacaagtagg tttagttaac tttaatctca catagcaatc   4680
tttaatcaat gtgtaacatt agggaggact tgaaagagcc accacatttt catcgaggcc   4740
acgcggagta cgatcgaggg tacagtgaat aatgctaggg agagctgcct atatggaaga   4800
gccctaatgt gtaaaattaa ttttagtagt gctatcccca tgtgatttta atagcttctt   4860
aggagaatga caaaaaaaaa aaaaaaaaaa aaagggcgaa ttctgcagat atccatcaca   4920
ctggcggccg ctcgagcatg catctagagg gcccaattcg ccctatagtg agtcgtatta   4980
caattcactg gccgtcgttt                                               5000
```

<210> SEQ ID NO 6
<211> LENGTH: 5600
<212> TYPE: DNA
<213> ORGANISM: Artificial
<220> FEATURE:
<223> OTHER INFORMATION: SARS F X3 mutant

<400> SEQUENCE: 6

```
gaattcgccc ttcgagtgcc cgcggccgca ttgctgccta cacggctgct ctagttagtg     60
gtactgccac tgctggatgg acatttggtg ctggcgctgc tcttcaaata ccttttgcta    120
tgcaaatggc atataggttc aatggcattg gagttaccca aaatgttctc tatgagaacc    180
aaaaacaaat cgccaaccaa tttaacaagg cgattagtca aattcaagaa tcacttacaa    240
caacatcaac tgcattgggc aagctgcaag acgttgttaa ccagaatgct caagcattaa    300
acacacttgt taaacaactt agctctaatt ttggtgcaat ttcaagtgtg ctaaatgata    360
tcctttcgcg acttgataaa gtcgaggcgg aggtacaaat tgacaggtta attacaggca    420
gacttcaaag ccttcaaacc tatgtaacac aacaactaat cagggctgct gaaatcaggg    480
cttctgctaa tcttgctgct actaaaatgt ctgagtgtgt tcttggacaa tcaaaaagag    540
ttgacttttg tggaaagggc taccacctta tgtccttccc acaagcagcc ccgcatggtg    600
ttgtcttcct acatgtcacg tatgtgccat cccaggagag gaacttcacc acagcgccag    660
caatttgtca tgaaggcaaa gcatacttcc ctcgtgaagg tgtttttgtg tttaatggca    720
cttcttggtt tattacacag aggaacttct tttctccaca aataattact acagacaata    780
catttgtctc aggaaattgt gatgtcgtta ttggcatcat taacaacaca gtttatgatc    840
```

```
ctctgcaacc tgagctcgac tcattcaaag aagagctgga caagtacttc aaaaatcata    900
catcaccaga tgttgatctt ggcgacattt caggcattaa cgcttctgtc gtcaacattc    960
aaaaagaaat tgaccgcctc aatgaggtcg ctaaaaattt aaatgaatca ctcattgacc   1020
ttcaagaatt gggaaaatat gagcaatata ttaaatggcc ttggtatgtt tggctcggct   1080
tcattgctgg actaattgcc atcgtcatgg ttacaatctt gctttgttgc atgactagtt   1140
gttgcagttg cctcaagggt gcatgctctt gtggttcttg ctgcaagttt gatgaggatg   1200
actctgagcc agttctcaag ggtgtcaaat tacattacac ataaacgaac ttatggattt   1260
gtttatgaga tttttttactc ttggatcaat tactgcacag ccagtaaaaa ttgacaatgc   1320
ttctcctgca agtactgttc atgctacagc aacgataccg ctacaagcct cactcccttt   1380
cggatggctt gttattggcg ttgcatttct tgctgttttt cagagcgcta ccaaaataat   1440
tgcgctcaat aaaagatggc agctagccct ttataagggc ttccagttca tttgcaattt   1500
actgctgcta tttgttacca tctattcaca tcttttgctt gtcgctgcag gtatggaggc   1560
gcaattttg tacctctatg ccttgatata ttttctacaa tgcatcaacg catgtagaat   1620
tattatgaga tgttggcttt gttggaagtg caaatccaag aacccattac tttatgatgc   1680
caactacttt gtttgctggc acacacataa ctatgactac tgtataccat ataacagtgt   1740
cacagataca attgtcgtta ctgaaggtga cggcatttca acaccaaaac tcaaagaaga   1800
ctaccaaatt ggtggttatt ctgaggatag gcactcaggt gttaaagact atgtcgttgt   1860
acatggctat ttcaccgaag tttactacca gcttgagtct acacaaatta ctacagacac   1920
tggtattgaa aatgctacat tcttcatctt taacaagctt gttaaagacc accgaatgt   1980
gcaaatacac acaatcgacg gctcttcagg agttgctaat ccagcaatgg atccaattta   2040
tgatgagccg acgacgacta ctagcgtgcc tttgtaagca caagaaagtg agtacgaact   2100
tatgtactca ttcgtttcgg aagaaacagg tacgttaata gttaatagcg tacttctttt   2160
tcttgctttc gtggtattct tgctagtcac actagccatc cttactgcgc ttcgattgtg   2220
tgcgtactgc tgcaatattg ttaacgtgag tttagtaaaa ccaacggttt acgtctactc   2280
gcgtgttaaa aatctgaact cttctgaagg agttcctgat cttctggtct aaacgaacta   2340
actattatta ttattctgtt tggaactttta acattgctta tcatggcaga caacggtact   2400
attaccgttg aggagcttaa acaactcctg gaacaatgga acctagtaat aggtttccta   2460
ttcctagcct ggattatgtt actacaattt gcctattcta atcggaacag gttttttgtac   2520
ataataaagc ttgttttttcct ctggctcttg tggccagtaa cacttgcttg ttttgtgctt   2580
gctgctgtct acagaattaa ttgggtgact ggcgggattg cgattgcaat ggcttgtatt   2640
gtaggcttga tgtggcttag ctacttcgtt gcttccttca ggctgtttgc tcgtacccgc   2700
tcaatgtggt cattcaaccc agaaacaaac attcttctca atgtgcctct ccggggggaca   2760
attgtgacca gaccgctcat ggaaagtgaa cttgtcattg gtgctgtgat cattcgtggt   2820
cacttgcgaa tggccggaca cccctaggg cgctgtgaca ttaaggacct gccaaaagag   2880
atcactgtgt ctacatcacg aacgctttct tattacaaat taggagcgtc gcagcgtgta   2940
ggcactgatt caggttttgc tgcatacaac cgctaccgta ttggaaacta taattaaat   3000
acagaccacg ccggtagcaa cgacaatatt gctttgctag tacagtaagt gacaacagaa   3060
cgaacatgaa aattattctc ttcctgacat tgattgtatt tacatcttgc gagctatatc   3120
actatcagga gtgtgttaga ggtacgactg tactactaaa agaaccttgc ccatcaggaa   3180
catacgaggg caattcacca tttcaccctc ttgctgacaa taaatttgca ctaacttgca   3240
```

```
ctagcacaca ctttgctttt gcttgtgctg acggtactcg acatacctat cagctgcgtg      3300
caagatcagt ttcaccaaaa cttttcatca gacaagagga ggttcaacaa gagctctact      3360
cgccactttt tctcattgtt gctgctctag tattttaat actttgcttc accattaaga       3420
gaaagacaga atgaatgagc tcactttaat tgacttctat ttgtgctttt tagcctttct      3480
gctattcctt gttttaataa tgcttattat attttggttt tcactcgaaa tccaggatct      3540
agaagaacct tgtaccaaag tctaaacgaa catgaaactt ctcattgttt tgacttgtat      3600
ttctctatgc agttgcatat gcactgtagt acagcgctgt gcatctaata aacctcatgt      3660
gcttgaagat ccttgtaagg tacaacacta ggggtaatac ttatagcact gcttggcttt      3720
gtgctctagg aaaggtttta ccttttcata gatggcacac tatggttcaa acatgcacac      3780
ctaatgttac tatcaactgt caagatccag ctggtggtgc gcttatagct aggtgttggt      3840
accttcatga aggtcaccaa actgctgcat ttagagacgt acttgttgtt ttaaataaac      3900
gaacaaatta aaatgtctga taatggaccc caatcaaacc aacgtagtgc cccccgcatt      3960
acatttggtg gacccacaga ttcaactgac aataaccaga atggaggacg caatggggca      4020
aggccaaaac agcgccgacc ccaaggttta cccaataata ctgcgtcttg gttcacagct      4080
ctcactcagc atggcaagga ggaacttaga ttccctcgag gccagggcgt tccaatcaac      4140
accaatagtg gtccagatga ccaaattggc tactaccgaa gagctacccg acgagttcgt      4200
ggtggtgacg gcaaaatgaa agagctcagc cccagatggt acttctatta cctaggaact      4260
ggcccagaag cttcacttcc ctacggcgct aacaaagaag gcatcgtatg ggttgcaact      4320
gagggagcct tgaatacacc caaagaccac attggcaccc gcaatcctaa taacaatgct      4380
gccaccgtgc tacaacttcc tcaaggaaca acattgccaa aaggcttcta cgcagaggga      4440
agcagaggcg gcagtcaagc ctcttctcgc tcctcatcac gtagtcgcgg taattcaaga      4500
aattcaactc ctggcagcag taggggaaat tctcctgctc gaatggctag cggaggtggt      4560
gaaactgccc tcgcgctatt gctgctagac agattgaacc agcttgagag caaagtttct      4620
ggtaaaggcc aacaacaaca aggccaaact gtcactaaga atctgctgc tgaggcatct      4680
aaaaagcctc gccaaaaacg tactgccaca aaacagtaca acgtcactca agcatttggg      4740
agacgtggtc cagaacaaac ccaaggaaat ttcggggacc aagacctaat cagacaagga      4800
actgattaca aacattggcc gcaaattgca caatttgctc caagtgcctc tgcattcttt      4860
ggaatgtcac gcattggcat ggaagtcaca ccttcgggaa catggctgac ttatcatgga      4920
gccattaaat tggatgacaa agatccacaa ttcaaagaca acgtcatact gctgaacaag      4980
cacattgacg catacaaaac attcccacca acagagccta aaaggacaa aaagaaaaag       5040
actgatgaag ctcagcctt gccgcagaga caaaagaagc agcccactgt gactcttctt       5100
cctgcggctg acatggatga tttctccaga caacttcaaa attccatgag tggagcttct      5160
gctgattcaa ctcaggcata aacactcatg atgaccacac aaggcagatg ggctatgtaa      5220
acgttttcgc aattccgttt acgatacata gtctactctt gtgcagaatg aattctcgta      5280
actaaacagc acaagtaggt ttagttaact ttaatctcac atagcaatct ttaatcaatg      5340
tgtaacatta gggaggactt gaaagagcca ccacattttc atcgaggcca cgcggagtac      5400
gatcgagggt acagtgaata atgctaggga gagctgccta tatggaagag ccctaatgtg      5460
taaaattaat tttagtagtg ctatccccat gtgattttaa tagcttctta ggagaatgac      5520
aaaaaaaaaa aaaaaaaaaa aagggcgaat tctgcagata cccatcacac tggcggccgc      5580
tcgagcatgc atctagaggg                                                  5600
```

<210> SEQ ID NO 7
<211> LENGTH: 5450
<212> TYPE: DNA
<213> ORGANISM: Artificial
<220> FEATURE:
<223> OTHER INFORMATION: SARS F X4 mutant

<400> SEQUENCE: 7

| | | | | | |
|---|---|---|---|---|---|
| agtgtgctgg | aattcgccct | tcgagtgccc | gcggccgcat | tgctgcctac | acggctgctc | 60 |
| tagttagtgg | tactgccact | gctggatgga | catttggtgc | tggcgctgct | cttcaaatac | 120 |
| cttttgctat | gcaaatggca | tataggttca | tggcattgg | agttacccaa | aatgttctct | 180 |
| atgagaacca | aaacaaatc | gccaaccaat | ttaacaaggc | gattagtcaa | attcaagaat | 240 |
| cacttacaac | aacatcaact | gcattgggca | agctgcaaga | cgttgttaac | cagaatgctc | 300 |
| aagcattaaa | cacacttgtt | aaacaactta | gctctaattt | tggtgcaatt | tcaagtgtgc | 360 |
| taaatgatat | cctttcgcga | cttgataaag | tcgaggcgga | ggtacaaatt | gacaggttaa | 420 |
| ttacaggcag | acttcaaagc | cttcaaacct | atgtaacaca | acaactaatc | agggctgctg | 480 |
| aaatcagggc | ttctgctaat | cttgctgcta | ctaaaatgtc | tgagtgtgtt | cttggacaat | 540 |
| caaaaagagt | tgacttttgt | ggaaagggct | accaccttat | gtccttccca | caagcagccc | 600 |
| cgcatggtgt | tgtcttccta | catgtcacgt | atgtgccatc | ccaggagagg | aacttcacca | 660 |
| cagcgccagc | aatttgtcat | gaaggcaaag | catacttccc | tcgtgaaggt | gttttgtgt | 720 |
| ttaatggcac | ttcttggttt | attacacaga | ggaacttctt | ttctccacaa | ataattacta | 780 |
| cagacaatac | atttgtctca | ggaaattgtg | atgtcgttat | tggcatcatt | aacaacacag | 840 |
| tttatgatcc | tctgcaacct | gagctcgact | cattcaaaga | agagctggac | aagtacttca | 900 |
| aaaatcatac | atcaccagat | gttgatcttg | gcgacatttc | aggcattaac | gcttctgtcg | 960 |
| tcaacattca | aaaagaaatt | gaccgcctca | atgaggtcgc | taaaaattta | aatgaatcac | 1020 |
| tcattgacct | tcaagaattg | ggaaaatatg | agcaatatat | taaatggcct | tggtatgttt | 1080 |
| ggctcggctt | cattgctgga | ctaattgcca | tcgtcatggt | tacaatcttg | ctttgttgca | 1140 |
| tgactagttg | ttgcagttgc | ctcaagggtg | catgctcttg | tggttcttgc | tgcaagtttg | 1200 |
| atgaggatga | ctctgagcca | gttctcaagg | gtgtcaaatt | acattacaca | taaacgaact | 1260 |
| tatggatttg | tttatgagat | tttttactct | tggatcaatt | actgcacagc | cagtaaaaat | 1320 |
| tgacaatgct | tctcctgcaa | gtactgttca | tgctacagca | acgataccgc | tacaagcctc | 1380 |
| actcccttc | ggatggcttg | ttattggcgt | tgcatttctt | gctgttttc | agagcgctac | 1440 |
| caaaataatt | gcgctcaata | aaagatggca | gctagcccctt | tataagggct | tccagttcat | 1500 |
| ttgcaattta | ctgctgctat | tgttaccat | ctattcacat | cttttgcttg | tcgctgcagg | 1560 |
| tatggaggcg | caatttttgt | acctctatgc | cttgatatat | tttctacaat | gcatcaacgc | 1620 |
| atgtagaatt | attatgagat | gttggctttg | ttggaagtgc | aaatccaaga | acccattact | 1680 |
| ttatgatgcc | aactactttg | tttgctggca | cacacataac | tatgactact | gtataccata | 1740 |
| taacagtgtc | acagatacaa | ttgtcgttac | tgaaggtgac | ggcatttcaa | caccaaaact | 1800 |
| caaagaagac | taccaaattg | gtggttattc | tgaggatagg | cactcaggtg | ttaaagacta | 1860 |
| tgtcgttgta | catggctatt | tcaccgaagt | ttactaccag | cttgagtcta | cacaaattac | 1920 |
| tacagacact | ggtattgaaa | atgctacatt | cttcatcttt | aacaagcttg | ttaaagaccc | 1980 |
| accgaatgtg | caaatacaca | caatcgacgg | ctcttcagga | gttgctaatc | cagcaatgga | 2040 |
| tccaatttat | gatgagccga | cgacgactac | tagcgtgcct | ttgtaagcac | aagaaagtga | 2100 |

```
gtacgaactt atgtactcat tcgtttcgga agaaacaggt acgttaatag ttaatagcgt    2160 acttctttt  cttgctttcg tggtattctt gctagtcaca ctagccatcc ttactgcgct    2220
tcgattgtgt gcgtactgct gcaatattgt taacgtgagt ttagtaaaac caacggttta    2280
cgtctactcg cgtgttaaaa atctgaactc ttctgaagga gttcctgatc ttctggtcta    2340
aacgaactaa ctattattat tattctgttt ggaactttaa cattgcttat catggcagac    2400
aacggtacta ttaccgttga ggagcttaaa caactcctgg aacaatggaa cctagtaata    2460
ggtttcctat tcctagcctg gattatgtta ctacaatttg cctattctaa tcggaacagg    2520
tttttgtaca taataaagct tgttttcctc tggctcttgt ggccagtaac acttgcttgt    2580
tttgtgcttg ctgctgtcta cagaattaat tgggtgactg gcgggattgc gattgcaatg    2640
gcttgtattg taggcttgat gtggcttagc tacttcgttg cttccttcag gctgtttgct    2700
cgtacccgct caatgtggtc attcaaccca gaaacaaaca ttcttctcaa tgtgcctctc    2760
cgggggacaa ttgtgaccag accgctcatg aaagtgaac  ttgtcattgg tgctgtgatc    2820
attcgtggtc acttgcgaat ggccggacac ccctagggc  gctgtgacat taaggacctg    2880
ccaaaagaga tcactgtggc tacatcacga acgctttctt attacaaatt aggagcgtcg    2940
cagcgtgtag gcactgattc aggttttgct gcatacaacc gctaccgtat tggaaactat    3000
aaattaaata cagaccacgc cggtagcaac gacaatattg ctttgctagt acagtaagtg    3060
acaacagatg tttcatcttg ttgacttcca ggttacaata gcagagatat tgattatcat    3120
tatgaggact ttcaggattg ctatttggaa tcttgacgtt ataataagtt caatagtgag    3180
acaattattt aagcctctaa ctaagaagaa ttattcggag ttagatgatg aagaacctat    3240
ggagttagat tatccataaa acgaacatgg caggtgatcg attaattaag agctcacttt    3300
aattgacttc tatttgtgct ttttagcctt tctgctattc cttgttttaa taatgcttat    3360
tatattttgg ttttcactcg aaatccagga tctagaagaa ccttgtacca agtctaaac     3420 gaacatgaaa cttctcattg ttttgacttg tatttctcta tgcagttgca tatgcactgt    3480
agtacagcgc tgtgcatcta ataaacctca tgtgcttgaa gatccttgta aggtacaaca    3540 ctagggggtaa tacttatagc actgcttggc tttgtgctct aggaaaggtt ttacctttc    3600 atagatggca cactatggtt caaacatgca cacctaatgt tactatcaac tgtcaagatc    3660
cagctggtgg tgcgcttata gctaggtgtt ggtaccttca tgaaggtcac caaactgctg    3720
catttagaga cgtacttgtt gttttaaata acgaacaaa  ttaaaatgtc tgataatgga    3780
ccccaatcaa accaacgtag tgcccccgc  attacatttg gtggacccac agattcaact    3840
gacaataacc agaatggagg acgcaatggg gcaaggccaa aacagcgccg accccaaggt    3900
ttacccaata atactgcgtc ttggttcaca gctctcactc agcatggcaa ggaggaactt    3960
agattccctc gaggccaggg cgttccaatc aacaccaata gtggtccaga tgaccaaatt    4020
ggctactacc gaagagctac ccgacgagtt cgtggtggtg acggcaaaat gaaagagctc    4080
agccccagat ggtacttcta ttacctagga actgcccag  aagcttcact tccctacggc    4140
gctaacaaag aaggcatcgt atgggttgca actgagggga ccttgaatac acccaaagac    4200
cacattggca cccgcaatcc taataacaat gctgccaccg tgctacaact tcctcaagga    4260
acaacattgc caaaaggctt ctacgcagag ggaagcagag gcggcagtca agcctcttct    4320
cgctcctcat cacgtagtcg cggtaattca agaaattcaa ctcctggcag cagtagggga    4380
aattctcctg ctcgaatggc tagcggaggt ggtgaaactg ccctcgcgct attgctgcta    4440
gacagattga accagcttga gagcaaagtt tctggtaaag gccaacaaca acaaggccaa    4500
```

-continued

```
actgtcacta agaaatctgc tgctgaggca tctaaaaagc ctcgccaaaa acgtactgcc      4560
acaaaacagt acaacgtcac tcaagcattt gggagacgtg gtccagaaca aacccaagga      4620
aatttcgggg accaagacct aatcagacaa ggaactgatt acaaacattg gccgcaaatt      4680
gcacaatttg ctccaagtgc ctctgcattc tttggaatgt cacgcattgg catggaagtc      4740
acaccttcgg gaacatggct gacttatcat ggagccatta aattggatga caaagatcca      4800
caattcaaag acaacgtcat actgctgaac aagcacattg acgcatacaa acattccca      4860 ccaacagagc ctaaaaagga caaaaagaaa aagactgatg aagctcagcc tttgccgcag      4920
agacaaaaga agcagcccac tgtgactctt cttcctgcgg ctgacatgga tgatttctcc      4980
agacaacttc aaaattccat gagtggagct tctgctgatt caactcaggc ataaacactc      5040
atgatgacca cacaaggcag atgggctatg taaacgtttt cgcaattccg tttacgatac      5100
atagtctact cttgtgcaga atgaattctc gtaactaaac agcacaagta ggtttagtta      5160
actttaatct cacatagcaa tctttaatca atgtgtaaca ttaggaggga cttgaaagag      5220
ccaccacatt ttcatcgagg ccacgcggag tacgatcgag ggtacagtga ataatgctag      5280
ggagagctgc ctatatggaa gagccctaat gtgtaaaatt aattttagta gtgctatccc      5340
catgtgattt taatagcttc ttaggagaat gacaaaaaaa aaaaaaaaa aaaaaagg       5400 cgaattctgc agatatccat cacactggcg gccgctcgag catgcatcta              5450
```

<210> SEQ ID NO 8
<211> LENGTH: 6150
<212> TYPE: DNA
<213> ORGANISM: Artificial
<220> FEATURE:
<223> OTHER INFORMATION: SARS F X4/gfp substitution
<220> FEATURE:
<221> NAME/KEY: misc_feature
<222> LOCATION: (648)..(648)
<223> OTHER INFORMATION: n is a,

```
gatcttggcg acatttcagg cattaacgct tctgtcgtca acattcaaaa agaaattgac      960
cgcctcaatg aggtcgctaa aaatttaaat gaatcactca ttgaccttca agaattggga     1020
aaatatgagc aatatattaa atggccttgg tatgtttggc tcggcttcat tgctggacta     1080
attgccatcg tcatggttac aatcttgctt tgttgcatga ctagttgttg cagttgcctc     1140
aagggtgcat gctcttgtgg ttcttgctgc aagtttgatg aggatgactc tgagccagtt     1200
ctcaagggtg tcaaattaca ttacacataa acgaacttat ggatttgttt atgagatttt     1260
ttactcttgg atcaattact gcacagccag taaaaattga caatgcttct cctgcaagta     1320
ctgttcatgc tacagcaacg ataccgctac aagcctcact cccttttcgga tggcttgtta     1380
ttggcgttgc atttcttgct gttttttcaga gcgctaccaa aataattgcg ctcaataaaa     1440
gatggcagct agcccttat aagggcttcc agttcatttg caatttactg ctgctatttg       1500
ttaccatcta ttcacatctt ttgcttgtcg ctgcaggtat ggaggcgcaa ttttttgtacc     1560
tctatgcctt gatatatttt ctacaatgca tcaacgcatg tagaattatt atgagatgtt     1620
ggctttgttg gaagtgcaaa tccaagaacc cattacttta tgatgccaac tactttgttt     1680
gctggcacac acataactat gactactgta taccatataa cagtgtcaca gatacaattg     1740
tcgttactga aggtgacggc atttcaacac caaaactcaa agaagactac caaattggtg     1800
gttattctga ggataggcac tcaggtgtta aagactatgt cgttgtacat ggctatttca     1860
ccgaagttta ctaccagctt gagtctacac aaattactac agacactggt attgaaaatg     1920
ctacattctt catcttttaac aagcttgtta agacccacc gaatgtgcaa atacacacaa      1980
tcgacggctc ttcaggagtt gctaatccag caatggatcc aatttatgat gagccgacga     2040
cgactactag cgtgcctttg taagcacaag aaagtgagta cgaacttatg tactcattcg     2100
tttcggaaga acaggtacg ttaatagtta atagcgtact tcttttttctt gctttcgtgg      2160
tattcttgct agtcacacta gccatcctta ctgcgcttcg attgtgtgcg tactgctgca     2220
atattgttaa cgtgagttta gtaaaaccaa cggtttacgt ctactcgcgt gttaaaaatc     2280
tgaactcttc tgaaggagtt cctgatcttc tggtctaaac gaactaacta ttattattat     2340
tctgtttgga actttaacat tgcttatcat ggcagacaac ggtactatta ccgttgagga     2400
gcttaaacaa ctcctggaac aatggaacct agtaataggt ttcctattcc tagcctggat     2460
tatgttacta caatttgcct attctaatcg gaacaggttt ttgtacataa taaagcttgt     2520
tttcctctgg ctcttgtggc cagtaacact tgcttgtttt gtgcttgctg ctgtctacag     2580
aattaattgg gtgactggcg ggattgcgat tgcaatggct tgtattgtag gcttgatgtg     2640
gcttagctac ttcgttgctt ccttcaggct gtttgctcgt acccgctcaa tgtggtcatt     2700
caacccagaa acaaacattc ttctcaatgt gcctctccgg gggacaattg tgaccagacc     2760
gctcatggaa agtgaacttg tcattggtgc tgtgatcatt cgtggtcact tgcgaatggc     2820
cggacacccc ctagggcgct gtgacattaa ggacctgcca aaagagatca ctgtggctac     2880
atcacgaacg ctttcttatt acaaattagg agcgtcgcag cgtgtaggca ctgattcagg     2940
ttttgctgca tacaaccgct accgtattgg aaactataaa ttaaatacag accacgccgg     3000
tagcaacgac aatattgctt tgctagtaca gtaagtgaca acagatgttt catcttgttg     3060
acttccaggt tacaatagca gagatattga ttatcattat gaggactttc aggattgcta     3120
tttggaatct tgacgttata ataagttcaa tagtgagaca attatttaag cctctaacta     3180
agaagaatta ttcggagtta gatgatgaag aacctatgga gttagattat ccataaaacg     3240
aacaaattaa aatggtgagc aagggcgagg agctgttcac cggggtggtg cccatcctgg     3300
```

```
tcgagctgga cggcgacgta acggccaca agttcagcgt gtccggcgag ggcgagggcg    3360
atgccaccta cggcaagctg accctgaagt tcatctgcac caccggcaag ctgcccgtgc    3420
cctggcccac cctcgtgacc accctgacct acggcgtgca gtgcttcagc cgctaccccg    3480
accacatgaa gcagcacgac ttcttcaagt ccgccatgcc cgaaggctac gtccaggagc    3540
gcaccatctt cttcaaggac gacggcaact acaagacccg cgccgaggtg aagttcgagg    3600
gcgacaccct ggtgaaccgc atcgagctga agggcatcga cttcaaggag gacggcaaca    3660
tcctggggca caagctggag tacaactaca acagccacaa cgtctatatc atggccgaca    3720
agcagaagaa cggcatcaag gtgaacttca gatccgccaa caatcgag acggcagcg    3780
tgcagctcgc cgaccactac cagcagaaca cccccatcgg cgacggcccc gtgctgctgc    3840
ccgacaacca ctacctgagc acccagtccg ccctgagcaa agaccccaac gagaagcgcg    3900
atcacatggt cctgctggag ttcgtgaccg ccgccgggat cactctcggc atggacgagc    3960
tgtacaagta attaattaag agctcacttt aattgacttc tatttgtgct ttttagcctt    4020
tctgctattc cttgttttaa taatgcttat tatattttgg ttttcactcg aaatccagga    4080
tctagaagaa ccttgtacca aagtctaaac gaacatgaaa cttctcattg ttttgacttg    4140
tatttctcta tgcagttgca tatgcactgt agtacagcgc tgtgcatcta ataaacctca    4200
tgtgcttgaa gatccttgta aggtacaaca ctagggtaa tacttatagc actgcttggc    4260
tttgtgctct aggaaaggtt ttacctttc atagatggca cactatggtt caaacatgca    4320
cacctaatgt tactatcaac tgtcaagatc cagctggtgg tgcgcttata gctaggtgtt    4380
ggtaccttca tgaaggtcac caaactgctg catttagaga cgtacttgtt gttttaaata    4440
aacgaacaaa ttaaaatgtc tgataatgga ccccaatcaa accaacgtag tgcccccgc    4500
attacatttg gtggacccac agattcaact gacaataacc agaatggagg acgcaatggg    4560
gcaaggccaa aacagcgccg accccaaggt ttacccaata atactgcgtc ttggttcaca    4620
gctctcactc agcatggcaa ggaggaactt agattccctc gaggccaggg cgttccaatc    4680
aacaccaata gtggtccaga tgaccaaatt ggctactacc gaagagctac ccgacgagtt    4740
cgtggtggtg acggcaaaat gaaagagctc agccccagat ggtacttcta ttacctagga    4800
actggcccag aagcttcact tccctacggc gctaacaaag aaggcatcgt atgggttgca    4860
actgagggag ccttgaatac acccaaagac cacattggca cccgcaatcc taataacaat    4920
gctgccaccg tgctacaact tcctcaagga acaacattgc caaaaggctt ctacgcagag    4980
ggaagcagag gcggcagtca agcctcttct cgctcctcat cacgtagtcg cggtaattca    5040
agaaattcaa ctcctggcag cagtaggga aattctcctg ctcgaatggc tagcggaggt    5100
ggtgaaactg ccctcgcgct attgctgcta gacagattga accagcttga gagcaaagtt    5160
tctggtaaag gccaacaaca acaaggccaa actgtcacta gaaatctgc tgctgaggca    5220
tctaaaaagc ctcgccaaaa acgtactgcc acaaaacagt acaacgtcac tcaagcattt    5280
gggagacgtg gtccagaaca aacccaagga aatttcgggg accaagacct aatcagacaa    5340
ggaactgatt acaaacattg gccgcaaatt gcacaatttg ctccaagtgc ctctgcattc    5400
tttggaatgt cacgcattgg catggaagtc acaccttcgg gaacatggct gacttatcat    5460
ggagccatta aattggatga caagatcca caattcaaag acaacgtcat actgctgaac    5520
aagcacattg acgcatacaa acattcccca ccaacagagc ctaaaaagga caaaaagaaa    5580
aagactgatg aagctcagcc tttgccgcag agacaaaaga agcagccac tgtgactctt    5640
cttcctgcgg ctgacatgga tgatttctcc agacaacttc aaaattccat gagtggagct    5700
```

```
tctgctgatt caactcaggc ataaacactc atgatgacca cacaaggcag atgggctatg    5760
taaacgtttt cgcaattccg tttacgatac atagtctact cttgtgcaga atgaattctc    5820
gtaactaaac agcacaagta ggtttagtta actttaatct cacatagcaa tctttaatca    5880
atgtgtaaca ttagggagga cttgaaagag ccaccacatt ttcatcgagg ccacgcggag    5940
tacgatcgag ggtacagtga ataatgctag ggagagctgc ctatatggaa gagccctaat    6000
gtgtaaaatt aattttagta gtgctatccc catgtgtattt taatagcttc ttaggagaat    6060
gacaaaaaaa aaaaaaaaaa aaaaaagggc gaattctgca agatatccat cacactggcg    6120
gccgctcgag catgcatcta gagggcccaa                                     6150
```

<210> SEQ ID NO 9
<211> LENGTH: 6370
<212> TYPE: DNA
<213> ORGANISM: Artificial
<220> FEATURE:
<223> OTHER INFORMATION: SARS F X4/luciferase substitution

<400> SEQUENCE: 9

```
tcgagtgccc gcggccgcat tgctgcctac acggctgctc tagttagtgg tactgccact      60
gctggatgga catttggtgc tggcgctgct cttcaaatac cttttgctat gcaaatggca     120
tataggttca atggcattgg agttacccaa aatgttctct atgagaacca aaaacaaatc     180
gccaaccaat ttaacaaggc gattagtcaa attcaagaat cacttacaac aacatcaact     240
gcattgggca agctgcaaga cgttgttaac cagaatgctc aagcattaaa cacacttgtt     300
aaacaactta gctctaattt tggtgcaatt tcaagtgtgc taaatgatat cctttcgcga     360
cttgataaag tcgaggcgga ggtacaaatt gacaggttaa ttacaggcag acttcaaagc     420
cttcaaacct atgtaacaca caactaatc agggctgctg aaatcagggc ttctgctaat     480
cttgctgcta ctaaaatgtc tgagtgtgtt cttggacaat caaaaagagt tgacttttgt     540
ggaaagggct accaccttat gtccttccca caagcagccc cgcatggtgt tgtcttccta     600
catgtcacgt atgtgccatc ccaggagagg aacttcacca cagcgccagc aatttgtcat     660
gaaggcaaag catacttccc tcgtgaaggt gttttttgtgt taatggcac ttcttggtttt     720 attacacaga ggaacttctt ttctccacaa ataattacta cagacaatac atttgtctca     780
ggaaattgtg atgtcgttat ggcatcatt aacaacacag tttatgatcc tctgcaacct     840
gagctcgact cattcaaaga agagctggac aagtacttca aaaatcatac atcaccagat     900
gttgatcttg gcgacatttc aggcattaac gcttctgtcg tcaacattca aaaagaaatt     960
gaccgcctca atgaggtcgc taaaaattta aatgaatcac tcattgacct tcaagaattg    1020
ggaaaatatg agcaatatat taaatggcct tggtatgttt ggctcggctt cattgctgga    1080
ctaattgcca tcgtcatggt tacaatcttg ctttgttgca tgactagttg ttgcagttgc    1140
ctcaagggtg catgctcttg tggttcttgc tgcaagtttg atgaggatga ctctgagcca    1200
gttctcaagg gtgtcaaatt acattacaca taaacgaact tatggatttg tttatgagat    1260
tttttactct tggatcaatt actgcacagc cagtaaaaat tgacaatgct tctcctgcaa    1320
gtactgttca tgctacagca acgataccgc tacaagcctc actcccttc ggatggcttg    1380 ttattggcgt tgcatttctt gctgttttc agagcgctac caaataatt gcgctcaata    1440 aaagatggca gctagcccttt tataagggct tccagttcat ttgcaatttta ctgctgctat    1500 ttgttaccat ctattcacat cttttgcttg tcgctgcagg tatggaggcg caattttgt    1560 acctctatgc cttgatatat tttctacaat gcatcaacgc atgtagaatt attatgagat    1620
```

```
gttggctttg ttggaagtgc aaatccaaga acccattact ttatgatgcc aactactttg    1680
tttgctggca cacacataac tatgactact gtataccata taacagtgtc acagatacaa    1740
ttgtcgttac tgaaggtgac ggcatttcaa caccaaaact caaagaagac taccaaattg    1800
gtggttattc tgaggatagg cactcaggtg ttaaagacta tgtcgttgta catggctatt    1860
tcaccgaagt ttactaccag cttgagtcta cacaaattac tacagacact ggtattgaaa    1920
atgctacatt cttcatcttt aacaagcttg ttaaagaccc accgaatgtg caaatacaca    1980
caatcgacgg ctcttcagga gttgctaatc cagcaatgga tccaatttat gatgagccga    2040
cgacgactac tagcgtgcct ttgtaagcac aagaaagtga gtacgaactt atgtactcat    2100
tcgtttcgga agaaacaggt acgttaatag ttaatagcgt acttcttttt cttgctttcg    2160
tggtattctt gctagtcaca ctagccatcc ttactgcgct tcgattgtgt gcgtactgct    2220
gcaatattgt taacgtgagt ttagtaaaac caacggttta cgtctactcg cgtgttaaaa    2280
atctgaactc ttctgaagga gttcctgatc ttctggtcta aacgaactaa ctattattat    2340
tattctgttt ggaactttaa cattgcttat catggcagac aacggtacta ttaccgttga    2400
ggagcttaaa caactcctgg aacaatggaa cctagtaata ggtttcctat tcctagcctg    2460
gattatgtta ctacaatttg cctattctaa tcggaacagg tttttgtaca taataaagct    2520
tgttttcctc tggctcttgt ggccagtaac acttgcttgt tttgtgcttg ctgctgtcta    2580
cagaattaat tgggtgactg gcgggattgc gattgcaatg gcttgtattg taggcttgat    2640
gtggcttagc tacttcgttg cttccttcag gctgtttgct cgtacccgct caatgtggtc    2700
attcaaccca gaaacaaaca ttcttctcaa tgtgcctctc cggggacaa ttgtgaccag    2760 accgctcatg gaaagtgaac ttgtcattgg tgctgtgatc attcgtggtc acttgcgaat    2820
ggccggacac cccctagggc gctgtgacat taaggacctg ccaaaagaga tcactgtggc    2880
tacatcacga acgctttctt attacaaatt aggagcgtcg cagcgtgtag gcactgattc    2940
aggttttgct gcatacaacc gctaccgtat tggaaactat aaattaaata cagaccacgc    3000
cggtagcaac gacaatattg ctttgctagt acagtaagtg acaacagatg tttcatcttg    3060
ttgacttcca ggttacaata gcagagatat tgattatcat tatgaggact ttcaggattg    3120
ctatttggaa tcttgacgtt ataataagtt caatagtgag acaattattt aagcctctaa    3180
ctaagaagaa ttattcggag ttagatgatg aagaacctat ggagttagat tatccataaa    3240
acgaacaaat taaatggcct tccaaggtgt acgaccccga gcaacgcaaa cgcatgatca    3300
ctgggcctca gtggtgggct cgctgcaagc aaatgaacgt gctggactcc ttcatcaact    3360
actatgattc cgagaagcac gccgagaacg ccgtgatttt tctgcatggt aacgctgcct    3420
ccagctacct gtggaggcac gtcgtgcctc acatcgagcc cgtggctaga tgcatcatcc    3480
ctgatctgat cggaatgggt aagtccggca agagcgggaa tggctcatat cgcctcctgg    3540
atcactacaa gtacctcacc gcttggttcg agctgctgaa ccttccaaag aaaatcatct    3600
ttgtgggcca cgactggggg gcttgtctgg cctttcacta ctcctacgag caccaagaca    3660
agatcaaggc catcgtccat gctgagagtg tcgtggacgt gatcgagtcc tgggacgagt    3720
ggcctgacat cgaggaggat atcgccctga tcaagagcga agagggcgag aaaatggtgc    3780
ttgagaataa cttcttcgtc gagaccatgc tcccaagcaa gatcatgcgg aaactggagc    3840
ctgaggagtt cgctgcctac ctggagccat caaggagaa gggcgaggtt agacggccta    3900
ccctctcctg gcctcgcgag atccctctcg ttaagggagg caagcccgac gtcgtccaga    3960
ttgtccgcaa ctacaacgcc taccttcggg ccagcgacga tctgcctaag atgttcatcg    4020
```

```
agtccgaccc tgggttcttt tccaacgcta ttgtcgaggg agctaagaag ttccctaaca    4080
ccgagttcgt gaaggtgaag ggcctccact tcagccagga ggacgctcca gatgaaatgg    4140
gtaagtacat caagagcttc gtggagcgcg tgctgaagaa cgagcagtaa ttaattaaga    4200
gctcacttta attgacttct atttgtgctt tttagccttt ctgctattcc ttgttttaat    4260
aatgcttatt atattttggt tttcactcga aatccaggat ctagaagaac cttgtaccaa    4320
agtctaaacg aacatgaaac ttctcattgt tttgacttgt atttctctat gcagttgcat    4380
atgcactgta gtacagcgct gtgcatctaa taaacctcat gtgcttgaag atccttgtaa    4440
ggtacaacac taggggtaat acttatagca ctgcttggct ttgtgctcta ggaaaggttt    4500
tacctttcca tagatggcac actatggttc aaacatgcac acctaatgtt actatcaact    4560
gtcaagatcc agctggtggt gcgcttatag ctaggtgttg gtaccttcat gaaggtcacc    4620
aaactgctgc atttagagac gtacttgttg ttttaaataa acgaacaaat taaaatgtct    4680
gataatggac cccaatcaaa ccaacgtagt gccccccgca ttacatttgg tggacccaca    4740
gattcaactg acaataacca gaatggagga cgcaatgggg caaggccaaa acagcgccga    4800
ccccaaggtt tacccaataa tactgcgtct tggttcacag ctctcactca gcatggcaag    4860
gaggaactta gattccctcg aggccagggc gttccaatca acaccaatag tggtccagat    4920
gaccaaattg gctactaccg aagagctacc cgacgagttc gtggtggtga cggcaaaatg    4980
aaagagctca gccccagatg gtacttctat tacctaggaa ctggcccaga agcttcactt    5040
ccctacggcg ctaacaaaga aggcatcgta tgggttgcaa ctgagggagc cttgaataca    5100
cccaaagacc acattggcac ccgcaatcct aataacaatg ctgccaccgt gctacaactt    5160
cctcaaggaa caacattgcc aaaaggcttc tacgcagagg gaagcagagg cggcagtcaa    5220
gcctcttctc gctcctcatc acgtagtcgc ggtaattcaa gaaattcaac tcctggcagc    5280
agtaggggaa attctcctgc tcgaatggct agcggaggtg gtgaaactgc cctcgcgcta    5340
ttgctgctag acagattgaa ccagcttgag agcaaagttt ctggtaaagg ccaacaacaa    5400
caaggccaaa ctgtcactaa gaaatctgct gctgaggcat ctaaaaagcc tcgccaaaaa    5460
cgtactgcca caaaacagta caacgtcact caagcatttg ggagacgtgg tccagaacaa    5520
acccaaggaa atttcgggga ccaagaccta atcagacaag gaactgatta caaacattgg    5580
ccgcaaattg cacaatttgc tccaagtgcc tctgcattct ttggaatgtc acgcattggc    5640
atggaagtca caccttcggg aacatggctg acttatcatg gagccattaa attggatgac    5700
aaagatccac aattcaaaga caacgtcata ctgctgaaca gcacattga cgcatacaaa    5760
acattcccac caacagagcc taaaaaggac aaaaagaaaa agactgatga agctcagcct    5820
ttgccgcaga gacaaaagaa gcagcccact gtgactcttc ttcctgcggc tgacatggat    5880
gatttctcca gacaacttca aaattccatg agtggagctt ctgctgattc aactcaggca    5940
taaacactca tgatgaccac acaaggcaga tgggctatga aacgttttc gcaattccgt    6000
ttacgataca tagtctactc ttgtgcagaa tgaattctcg taactaaaca gcacaagtag    6060
gtttagttaa ctttaatctc acatagcaat ctttaatcaa tgtgtaacat tagggaggac    6120
ttgaaagagc caccacattt tcatcgaggc cacgcggagt acgatcgagg gtacagtgaa    6180
taatgctagg gagagctgcc tatatggaag agccctaatg tgtaaaatta attttagtag    6240
tgctatcccc atgtgatttt aatagcttct taggagaatg acaaaaaaaa aaaaaaaaa    6300
aaaaaagggc gaattctgca gatatccatc acactggcgg ccgctcgagc atgcatctag    6360
agggcccaat                                                            6370
```

```
<210> SEQ ID NO 10
<211> LENGTH: 11
<212> TYPE: DNA
<213> ORGANISM: SARS coronavirus

<400> SEQUENCE: 10
gccataatgg c                                                                11

<210> SEQ ID NO 11
<211> LENGTH: 11
<212> TYPE: DNA
<213> ORGANISM: SARS coronavirus

<400> SEQUENCE: 11
gccagcgtgg c                                                                11

<210> SEQ ID NO 12
<211> LENGTH: 11
<212> TYPE: DNA
<213> ORGANISM: SARS coronavirus

<400> SEQUENCE: 12
gcccaagagg c                                                                11

<210> SEQ ID NO 13
<211> LENGTH: 11
<212> TYPE: DNA
<213> ORGANISM: SARS coronavirus

<400> SEQUENCE: 13
gccctcctgg c                                                                11

<210> SEQ ID NO 14
<211> LENGTH: 11
<212> TYPE: DNA
<213> ORGANISM: SARS coronavirus

<400> SEQUENCE: 14
gcctacacgg c                                                                11

<210> SEQ ID NO 15
<211> LENGTH: 15
<212> TYPE: DNA
<213> ORGANISM: SARS coronavirus

<400> SEQUENCE: 15
ttggcgttgc aggtg                                                            15

<210> SEQ ID NO 16
<211> LENGTH: 15
<212> TYPE: DNA
<213> ORGANISM: SARS coronavirus

<400> SEQUENCE: 16
cacctgcgtt attgg                                                            15

<210> SEQ ID NO 17
<211> LENGTH: 15
<212> TYPE: DNA
<213> ORGANISM: SARS coronavirus

<400> SEQUENCE: 17
atgaaaatgc aggtg                                                            15
```

```
<210> SEQ ID NO 18
<211> LENGTH: 15
<212> TYPE: DNA
<213> ORGANISM: SARS coronavirus

<400> SEQUENCE: 18
cacctgcgaa catga                                                    15

<210> SEQ ID NO 19
<211> LENGTH: 15
<212> TYPE: DNA
<213> ORGANISM: SARS coronavirus

<400> SEQUENCE: 19
gacgagttgc aggtg                                                    15

<210> SEQ ID NO 20
<211> LENGTH: 15
<212> TYPE: DNA
<213> ORGANISM: SARS coronavirus

<400> SEQUENCE: 20
cacctgcacc cgacg                                                    15

<210> SEQ ID NO 21
<211> LENGTH: 15
<212> TYPE: DNA
<213> ORGANISM: Artificial
<220> FEATURE:
<223> OTHER INFORMATION: AarI restriction site
<220> FEATURE:
<221> NAME/KEY: misc_feature
<222> LOCATION: (8)..(15)
<223> OTHER INFORMATION: n is a, c, g, or t

<400> SEQUENCE: 21
cacctgcnnn nnnnn                                                    15

<210> SEQ ID NO 22
<211> LENGTH: 45
<212> TYPE: DNA
<213> ORGANISM: Artificial
<220> FEATURE:
<223> OTHER INFORMATION: Synthetic oligonucleotide primer

<400> SEQUENCE: 22
tactaatacg actcactata gatattaggt ttttacctac ccagg                   45

<210> SEQ ID NO 23
<211> LENGTH: 20
<212> TYPE: DNA
<213> ORGANISM: Artificial
<220> FEATURE:
<223> OTHER INFORMATION: Synthetic oligonucleotide primer

<400> SEQUENCE: 23
acaccatagt caacgatgcc                                               20

<210> SEQ ID NO 24
<211> LENGTH: 23
<212> TYPE: DNA
<213> ORGANISM: Artificial
<220> FEATURE:
<223> OTHER INFORMATION: Synthetic oligonucleotide primer
```

```
<400> SEQUENCE: 24
gcctatatgc atggatgtta gat                                           23

<210> SEQ ID NO 25
<211> LENGTH: 23
<212> TYPE: DNA
<213> ORGANISM: Artificial
<220> FEATURE:
<223> OTHER INFORMATION: Synthetic oligonucleotide primer

<400> SEQUENCE: 25
tgaaccgcca cgctggctaa acc                                           23

<210> SEQ ID NO 26
<211> LENGTH: 21
<212> TYPE: DNA
<213> ORGANISM: Artificial
<220> FEATURE:
<223> OTHER INFORMATION: Synthetic oligonucleotide primer

<400> SEQUENCE: 26
agccagcgtg gcggttcata c                                             21

<210> SEQ ID NO 27
<211> LENGTH: 24
<212> TYPE: DNA
<213> ORGANISM: Artificial
<220> FEATURE:
<223> OTHER INFORMATION: Synthetic oligonucletotide primer

<400> SEQUENCE: 27
aggcctcttg ggcagtggca taag                                          24

<210> SEQ ID NO 28
<211> LENGTH: 22
<212> TYPE: DNA
<213> ORGANISM: Artificial
<220> FEATURE:
<223> OTHER INFORMATION: Synthetic oligonucleotide primer

<400> SEQUENCE: 28
actgcccaag atgcctatga gc                                            22

<210> SEQ ID NO 29
<211> LENGTH: 26
<212> TYPE: DNA
<213> ORGANISM: Artificial
<220> FEATURE:
<223> OTHER INFORMATION: Synthetic oligonucleotide primer

<400> SEQUENCE: 29
cagccaggag ggcagacttc acaacc                                        26

<210> SEQ ID NO 30
<211> LENGTH: 29
<212> TYPE: DNA
<213> ORGANISM: Artificial
<220> FEATURE:
<223> OTHER INFORMATION: Synthetic oligonucleotide primer

<400> SEQUENCE: 30
gtctgccctc ctggctgata agtttccag                                     29
```

```
<210> SEQ ID NO 31
<211> LENGTH: 22
<212> TYPE: DNA
<213> ORGANISM: Artificial
<220> FEATURE:
<223> OTHER INFORMATION: Synthetic oligonucleotide primer

<400> SEQUENCE: 31
gagcagccgt gtaggcagca at                                              22

<210> SEQ ID NO 32
<211> LENGTH: 22
<212> TYPE: DNA
<213> ORGANISM: Artificial
<220> FEATURE:
<223> OTHER INFORMATION: Synthetic oligonucleotide primer

<400> SEQUENCE: 32
attgctgcct acacggctgc tc                                              22

<210> SEQ ID NO 33
<211> LENGTH: 39
<212> TYPE: DNA
<213> ORGANISM: Artificial
<220> FEATURE:
<223> OTHER INFORMATION: Synthetic oligonucleotide primer

<400> SEQUENCE: 33
tttttttttt tttttttttt tgtcattctc ctaagaagc                            39

<210> SEQ ID NO 34
<211> LENGTH: 56
<212> TYPE: DNA
<213> ORGANISM: Artificial
<220> FEATURE:
<223> OTHER INFORMATION: Synthetic oligonucleotide primer
<220> FEATURE:
<221> NAME/KEY: misc_feature
<222> LOCATION: (1)..(2)
<223> OTHER INFORMATION: n is a, c, g, or t

<400> SEQUENCE: 34
nnggcctcga tggccattta ggtgacacta tagatgtctg ataatggacc ccaatc         56

<210> SEQ ID NO 35
<211> LENGTH: 50
<212> TYPE: DNA
<213> ORGANISM: Artificial
<220> FEATURE:
<223> OTHER INFORMATION: Synthetic oligonucleotide primer
<220> FEATURE:
<221> NAME/KEY: misc_feature
<222> LOCATION: (1)..(3)
<223> OTHER INFORMATION: n is a, c, g, or t

<400> SEQUENCE: 35
nnnttttttt tttttttttt ttttttttta tgcctgagtt gaatcagcag                50

<210> SEQ ID NO 36
<211> LENGTH: 39
<212> TYPE: DNA
<213> ORGANISM: Artificial
<220> FEATURE:
<223> OTHER INFORMATION: Synthetic oligonucleotide primer

<400> SEQUENCE: 36
tttttttttt tttttttttt tgtcattctc ctaagaagc                            39
```

-continued

<210> SEQ ID NO 37
<211> LENGTH: 20
<212> TYPE: DNA
<213> ORGANISM: Artificial
<220> FEATURE:
<223> OTHER INFORMATION: Synthetic oligonucleotide primer

<400> SEQUENCE: 37
aaagccaacc aacctcgatc 20

<210> SEQ ID NO 38
<211> LENGTH: 11
<212> TYPE: DNA
<213> ORGANISM: Artificial
<220> FEATURE:
<223> OTHER INFORMATION: BglI recognition sequence
<220> FEATURE:
<221> NAME/KEY: misc_feature
<222> LOCATION: (4)..(8)
<223> OTHER INFORMATION: n is a, c, g, or t

<400> SEQUENCE: 38
gccnnnnngg c 11

<210> SEQ ID NO 39
<211> LENGTH: 15
<212> TYPE: DNA
<213> ORGANISM: Artificial
<220> FEATURE:
<223> OTHER INFORMATION: AarI recognition sequence
<220> FEATURE:
<221> NAME/KEY: misc_feature
<222> LOCATION: (8)..(15)
<223> OTHER INFORMATION: n is a, c, g, or t

<400> SEQUENCE: 39
cacctgcnnn nnnnn 15

<210> SEQ ID NO 40
<211> LENGTH: 13
<212> TYPE: DNA
<213> ORGANISM: SARS coronavirus

<400> SEQUENCE: 40
cagtgtcaca gat 13

<210> SEQ ID NO 41
<211> LENGTH: 13
<212> TYPE: DNA
<213> ORGANISM: Artificial
<220> FEATURE:
<223> OTHER INFORMATION: Mutant ORF3b premature stop stop sequence

<400> SEQUENCE: 41
cagtgtgaca gat 13

<210> SEQ ID NO 42
<211> LENGTH: 27
<212> TYPE: DNA
<213> ORGANISM: Artificial
<220> FEATURE:
<223> OTHER INFORMATION: Synthetic oligonucleotide primer

<400> SEQUENCE: 42
gctgtgacat taaggacctg ccaaaag 27

```
<210> SEQ ID NO 43
<211> LENGTH: 42
<212> TYPE: DNA
<213> ORGANISM: Artificial
<220> FEATURE:
<223> OTHER INFORMATION: Synthetic oligonucleotide primer

<400> SEQUENCE: 43
aggtgcacct gcagccattt taatttatcc ggtttatgga ta                            42

<210> SEQ ID NO 44
<211> LENGTH: 42
<212> TYPE: DNA
<213> ORGANISM: Artificial
<220> FEATURE:
<223> OTHER INFORMATION: Synthetic oligonucleotide primer

<400> SEQUENCE: 44
aggtgcacct gcagccattt taatttatcc gttttatgga ta                            42

<210> SEQ ID NO 45
<211> LENGTH: 27
<212> TYPE: DNA
<213> ORGANISM: Artificial
<220> FEATURE:
<223> OTHER INFORMATION: Synthetic oligonucleotide primer

<400> SEQUENCE: 45
ggtgcacctg caaataaatg gcttcca                                             27

<210> SEQ ID NO 46
<211> LENGTH: 30
<212> TYPE: DNA
<213> ORGANISM: Artificial
<220> FEATURE:
<223> OTHER INFORMATION: Synthetic oligonucleotide primer

<400> SEQUENCE: 46
taaagtgagc tcttaattaa ttactgctcg                                          30

<210> SEQ ID NO 47
<211> LENGTH: 17
<212> TYPE: DNA
<213> ORGANISM: Artificial
<220> FEATURE:
<223> OTHER INFORMATION: Synthetic oligonucleotide primer

<400> SEQUENCE: 47
caggaaacag ctatgac                                                        17

<210> SEQ ID NO 48
<211> LENGTH: 31
<212> TYPE: DNA
<213> ORGANISM: Artificial
<220> FEATURE:
<223> OTHER INFORMATION: Synthetic oligonucleotide primer

<400> SEQUENCE: 48
aaaatccggt tagagaacag atctacaaga g                                        31

<210> SEQ ID NO 49
<211> LENGTH: 31
<212> TYPE: DNA
<213> ORGANISM: Artificial
<220> FEATURE:
<223> OTHER INFORMATION: Synthetic oligonucleotide primer
```

<400> SEQUENCE: 49
ctaaccggat tttaaaatct gtgtagctgt c    31

<210> SEQ ID NO 50
<211> LENGTH: 21
<212> TYPE: DNA
<213> ORGANISM: Artificial
<220> FEATURE:
<223> OTHER INFORMATION: Synthetic oligonucleotide primer

<400> SEQUENCE: 50
atagggctgt tcaagctggg g    21

<210> SEQ ID NO 51
<211> LENGTH: 20
<212> TYPE: DNA
<213> ORGANISM: Artificial
<220> FEATURE:
<223> OTHER INFORMATION: Synthetic oligonucleotide primer

<400> SEQUENCE: 51
tgctggctct gataaaggag    20

<210> SEQ ID NO 52
<211> LENGTH: 43
<212> TYPE: DNA
<213> ORGANISM: Artificial
<220> FEATURE:
<223> OTHER INFORMATION: Synthetic oligonucleotide primer
<220> FEATURE:
<221> NAME/KEY: misc_feature
<222> LOCATION: (1)..(3)
<223> OTHER INFORMATION: n is a, c, g, or t

<400> SEQUENCE: 52
nnncacctgc acatatccgg ttagttgtta acaagaatat cac    43

<210> SEQ ID NO 53
<211> LENGTH: 48
<212> TYPE: DNA
<213> ORGANISM: Artificial
<220> FEATURE:
<223> OTHER INFORMATION: Synthetic oligonucleotide primer
<220> FEATURE:
<221> NAME/KEY: misc_feature
<222> LOCATION: (1)..(3)
<223> OTHER INFORMATION: n is a, c, g, or t

<400> SEQUENCE: 53
nnncacctgc aaccggatat gtttatttc ttattatttc ttactctc    48

<210> SEQ ID NO 54
<211> LENGTH: 21
<212> TYPE: DNA
<213> ORGANISM: Artificial
<220> FEATURE:
<223> OTHER INFORMATION: Synthetic oligonucleotide primer

<400> SEQUENCE: 54
catcaagcga aaaggcatca g    21

<210> SEQ ID NO 55
<211> LENGTH: 20
<212> TYPE: DNA
<213> ORGANISM: Artificial
<220> FEATURE:
<223> OTHER INFORMATION: Synthetic oligonucleotide primer

```
<400> SEQUENCE: 55
tgatcctctg caacctgagc                                                      20

<210> SEQ ID NO 56
<211> LENGTH: 40
<212> TYPE: DNA
<213> ORGANISM: Artificial
<220> FEATURE:
<223> OTHER INFORMATION: Synthetic oligonucleotide primer
<220> FEATURE:
<221> NAME/KEY: misc_feature
<222> LOCATION: (1)..(3)
<223> OTHER INFORMATION: n is a, c, g, or t

<400> SEQUENCE: 56
nnncacctgc ataaatccgg actcactttc ttgtgcttac                                40

<210> SEQ ID NO 57
<211> LENGTH: 39
<212> TYPE: DNA
<213> ORGANISM: Artificial
<220> FEATURE:
<223> OTHER INFORMATION: Synthetic oligonucleotide primer
<220> FEATURE:
<221> NAME/KEY: misc_feature
<222> LOCATION: (1)..(3)
<223> OTHER INFORMATION: n is a, c, g, or t

<400> SEQUENCE: 57
nnncacctgc gtccggattt atgtactcat tcgtttcgg                                 39

<210> SEQ ID NO 58
<211> LENGTH: 45
<212> TYPE: DNA
<213> ORGANISM: Artificial
<220> FEATURE:
<223> OTHER INFORMATION: Synthetic oligonucleotide primer
<220> FEATURE:
<221> NAME/KEY: misc_feature
<222> LOCATION: (1)..(3)
<223> OTHER INFORMATION: n is a, c, g, or t

<400> SEQUENCE: 58
nnncacctgc aatagttaat ccggttagac cagaagatca ggaac                          45

<210> SEQ ID NO 59
<211> LENGTH: 39
<212> TYPE: DNA
<213> ORGANISM: Artificial
<220> FEATURE:
<223> OTHER INFORMATION: Synthetic oligonucleotide primer
<220> FEATURE:
<221> NAME/KEY: misc_feature
<222> LOCATION: (1)..(3)
<223> OTHER INFORMATION: n is a, c, g, or t

<400> SEQUENCE: 59
nnncacctgc ggattaacta ttattattat tctgtttgg                                 39

<210> SEQ ID NO 60
<211> LENGTH: 21
<212> TYPE: DNA
<213> ORGANISM: Artificial
<220> FEATURE:
<223> OTHER INFORMATION: Synthetic oligonucleotide primer

<400> SEQUENCE: 60
taccaacacc tagctataag c                                                    21
```

<210> SEQ ID NO 61
<211> LENGTH: 63
<212> TYPE: DNA
<213> ORGANISM: Artificial
<220> FEATURE:
<223> OTHER INFORMATION: Synthetic oligonucleotide primer

<400> SEQUENCE: 61
gctgcattta gagacgtact tgttgtttta ataaccgga taaattaaaa tgtctgataa    60
tgg    63

<210> SEQ ID NO 62
<211> LENGTH: 31
<212> TYPE: DNA
<213> ORGANISM: Artificial
<220> FEATURE:
<223> OTHER INFORMATION: Synthetic oligonucleotide primer

<400> SEQUENCE: 62
ttaattaatt atgcctgagt tgaatcagca g    31

<210> SEQ ID NO 63
<211> LENGTH: 29
<212> TYPE: DNA
<213> ORGANISM: Artificial
<220> FEATURE:
<223> OTHER INFORMATION: Synthetic oligonucleotide primer

<400> SEQUENCE: 63
cgtctcatgt gtaatgtaat ttgacaccc    29

<210> SEQ ID NO 64
<211> LENGTH: 48
<212> TYPE: DNA
<213> ORGANISM: Artificial
<220> FEATURE:
<223> OTHER INFORMATION: Synthetic oligonucleotide primer

<400> SEQUENCE: 64
cgtctcacac ataaccggat ttatggattt gtttatgaga ttttttac    48

<210> SEQ ID NO 65
<211> LENGTH: 20
<212> TYPE: DNA
<213> ORGANISM: Artificial
<220> FEATURE:
<223> OTHER INFORMATION: Synthetic oligonucleotide primer

<400> SEQUENCE: 65
gtgcttgctg ttgtctacag    20

<210> SEQ ID NO 66
<211> LENGTH: 33
<212> TYPE: DNA
<213> ORGANISM: Artificial
<220> FEATURE:
<223> OTHER INFORMATION: Synthetic oligonucleotide primer

<400> SEQUENCE: 66
cgtctccgtc cgggatgtag ccacagtgat ctc    33

<210> SEQ ID NO 67
<211> LENGTH: 34
<212> TYPE: DNA
<213> ORGANISM: Artificial

-continued

```
<220> FEATURE:
<223> OTHER INFORMATION: Synthetic oligonucleotide primer

<400> SEQUENCE: 67
cgtctccgga cgctttctta ttacaaatta ggag                                    34

<210> SEQ ID NO 68
<211> LENGTH: 40
<212> TYPE: DNA
<213> ORGANISM: Artificial
<220> FEATURE:
<223> OTHER INFORMATION: Synthetic oligonucleotide primer

<400> SEQUENCE: 68
cgtctctcat atccggttta tggataatct aactccatag                              40

<210> SEQ ID NO 69
<211> LENGTH: 31
<212> TYPE: DNA
<213> ORGANISM: Artificial
<220> FEATURE:
<223> OTHER INFORMATION: Synthetic oligonucleotide primer

<400> SEQUENCE: 69
cgtctcatat gaaaattatt ctcttcctga c                                       31

<210> SEQ ID NO 70
<211> LENGTH: 22
<212> TYPE: DNA
<213> ORGANISM: Artificial
<220> FEATURE:
<223> OTHER INFORMATION: Synthetic oligonucleotide primer

<400> SEQUENCE: 70
ggactttcag gattgctatt tg                                                 22

<210> SEQ ID NO 71
<211> LENGTH: 33
<212> TYPE: DNA
<213> ORGANISM: Artificial
<220> FEATURE:
<223> OTHER INFORMATION: Synthetic oligonucleotide primer

<400> SEQUENCE: 71
cgtctcatcc ggttagactt tggtacaagg ttc                                     33

<210> SEQ ID NO 72
<211> LENGTH: 35
<212> TYPE: DNA
<213> ORGANISM: Artificial
<220> FEATURE:
<223> OTHER INFORMATION: Synthetic oligonucleotide primer

<400> SEQUENCE: 72
cgtctcccgg atatgaaact tctcattgtt ttgac                                   35

<210> SEQ ID NO 73
<211> LENGTH: 39
<212> TYPE: DNA
<213> ORGANISM: Artificial
<220> FEATURE:
<223> OTHER INFORMATION: Synthetic oligonucleotide primer
<220> FEATURE:
<221> NAME/KEY: misc_feature
<222> LOCATION: (1)..(3)
<223> OTHER INFORMATION: n is a, c, g, or t
```

-continued

```
<400> SEQUENCE: 73
nnnttaatta attaatttgt tcgtttattt aaaacaaca                              39

<210> SEQ ID NO 74
<211> LENGTH: 56
<212> TYPE: DNA
<213> ORGANISM: Artificial
<220> FEATURE:
<223> OTHER INFORMATION: Synthetic oligonucleotide primer
<220> FEATURE:
<221> NAME/KEY: misc_feature
<222> LOCATION: (1)..(2)
<223> OTHER INFORMATION: n is a, c, g, or t

<400> SEQUENCE: 74
nnggcctcga tggccattta ggtgacacta tagatgtctg ataatggacc ccaatc           56

<210> SEQ ID NO 75
<211> LENGTH: 50
<212> TYPE: DNA
<213> ORGANISM: Artificial
<220> FEATURE:
<223> OTHER INFORMATION: Synthetic oligonucleotide primer
<220> FEATURE:
<221> NAME/KEY: misc_feature
<222> LOCATION: (1)..(3)
<223> OTHER INFORMATION: n is a, c, g, or t

<400> SEQUENCE: 75 nnntttttt tttttttttt tttttttta tgcctgagtt gaatcagcag                    50

<210> SEQ ID NO 76
<211> LENGTH: 28
<212> TYPE: DNA
<213> ORGANISM: Artificial
<220> FEATURE:
<223> OTHER INFORMATION: Synthetic oligonucleotide probe
<220> FEATURE:
<221> NAME/KEY: misc_feature
<222> LOCATION: (19)..(20)
<223> OTHER INFORMATION: biotinylation
<220> FEATURE:
<221> NAME/KEY: misc_feature
<222> LOCATION: (24)..(24)
<223> OTHER INFORMATION: biotinylation
<220> FEATURE:
<221> NAME/KEY: misc_feature
<222> LOCATION: (26)..(26)
<223> OTHER INFORMATION: biotinylation
<220> FEATURE:
<221> NAME/KEY: misc_feature
<222> LOCATION: (28)..(28)
<223> OTHER INFORMATION: biotinylation

<400> SEQUENCE: 76
cttgactgcc gcctctgctt ccctctgc                                          28
```

US 7,618,802 B2

COMPOSITIONS OF CORONAVIRUSES WITH A RECOMBINATION-RESISTANT GENOME

STATEMENT OF PRIORITY

This application is a continuation-in-part application claiming priority to PCT Application Serial No. PCT/US2004/023548, filed Jul. 21, 2004, which was published in English on Apr. 21, 2005 as PCT Publication No. WO 2005/035712 and which claims the benefit of U.S. provisional application No. 60/488,942, filed Jul. 21, 2003, the entire contents of each of which are incorporated by reference herein.

STATEMENT OF FEDERAL SUPPORT

This invention was supported by government funding under grant numbers AI23946 and GM 63228 from the National Institute of Health, Allergy and Infectious Diseases. The United States Government has certain rights to this invention.

FIELD OF THE INVENTION

The present invention relates to compositions of infectious cDNA of the severe acute respiratory syndrome (SARS) coronavirus, recombinant SARS coronavirus vectors, SARS coronavirus replicon particles, methods of making the compositions of this invention and methods of using the compositions as immunogens and/or vaccines and/or to express heterologous nucleic acids.

BACKGROUND OF THE INVENTION

Severe acute respiratory syndrome is a life-threatening respiratory disease that probably originated in Guangdong Province, China in the fall of 2002 [1, 2]. The agent responsible for the disease spread rapidly [3,4]. A novel coronavirus (SARS-CoV), isolated from febrile and dying patients, is the etiologic agent responsible for the disease [5-8]. SARS-CoV infection is associated with overall case fatality rates thought to approach ~14-15%, with selected populations being at increased risk (>50% in the elderly). SARS-CoV has infected over 8,000 individuals worldwide and caused over 800 deaths, before aggressive infection control measures successfully contained the scope of the outbreak. Despite intensive efforts, no effective antiviral treatments against SARS have been described.

Coronaviruses, members of the order Nidovirus, contain the largest single-stranded, positive-polarity RNA genome in nature and are divided into three main serogroups; group I: transmissible gastroenteritis virus (TGEV) and human coronavirus 229E (HCV-229E), group II: mouse hepatitis virus (MHV) and bovine coronavirus (BoCV), and group III: infectious bronchitis virus (IBV). Sequence analyses suggest that SARS-CoV represents the prototype strain of group IV [6, 8-10]. The SARS-CoV genomic RNA is ~29,700 base pairs in length and has several large open reading frames (ORFs) encoded in subgenomic and full-length mRNAs [8-10]. The subgenomic mRNAs are arranged in the form of a nested set from the 3 proximal end, and leader RNA sequences, encoded at the 5' end of the genome, are joined to body sequences at a highly conserved consensus sequence (CS) located just upstream of each of the ORFs. The exact SARS CS sequence has been reported as either CUAAAC or AAACGAAC by different laboratories [8,9]. The SARS-CoV genome length RNA is likely packaged by a 50-kDa-nucleocapsid protein (N) [8]. As with other coronaviruses, the virion contains several viral structural proteins including the ~140 kDa spike glycoprotein (S), a 23 kDa membrane glycoprotein (M) and a ~10 kDa protein (E).

The coronavirus gene 1, or replicase gene, comprises two-thirds of the genome. MHV contains two overlapping open reading frames, ORF1a and ORF1b, which are connected by a ribosomal frameshift structure. In MHV, three proteinases, papain-like proteinases 1 and 2 (PLP-1, PLP-2) [11-13] and 3C-like proteinase (3CLpro) [14], are expressed as part of the replicase gene polyprotein and mediate cleavage of the polyproteins into at least 15 mature proteins. Continuous protein processing is crucial for ongoing virus transcription so MHV replication is sensitive to protease inhibitors that prevent replicase processing [11]. Additional functions have been predicted for proteins processed from the replicase polyprotein, including an RNA-dependent RNA polymerase (pol), an RNA helicase (hel) and a capping enzymatic activity [6, 15, 16]. The SARS virus replicase gene is similarly organized except that the SARS virus replicase has been predicted to encode only the PLP-2 equivalent and the 3CLpro proteases [6, 7].

The present invention provides a full length cDNA of the SARS coronavirus, from which transcripts are produced that replicate and/or are infectious in vitro or in vivo, multiplication-defective replicon vector particles produced from the cDNA and methods of making and using these compositions as immunogens, vaccines and/or nucleic acid delivery vectors.

SUMMARY OF THE INVENTION

Figure 1:
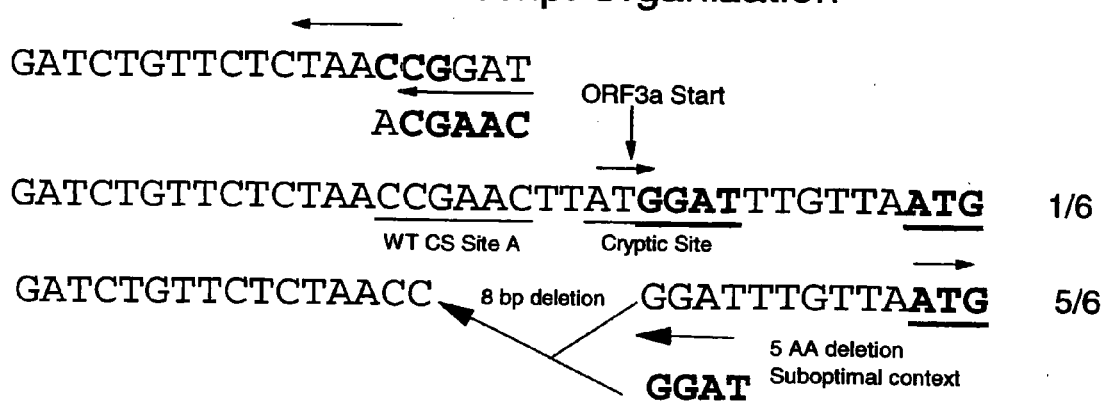
FIGS. 1A-B. Leader body TRS junctions in wild type and chimeric recombinant viruses. Leader-containing cDNAs were isolated, subcloned and sequenced as described. The expected leader body junctions were noted for icSARS-CoV (SEQ ID NO:77) and icSARS-CoV CRG (SEQ ID NOS:78 and 79), using the body TRS CS junctions ACGAAG and CCGGAT. Leader containing transcripts were analyzed for M, and ORF3a-encoding mRNAs. Panel A: Leader-body junctions in ORF3a-encoding mRNAs. Panel B: Leader-containing junctions in ORF M-encoding mRNAs.
Figure 1:
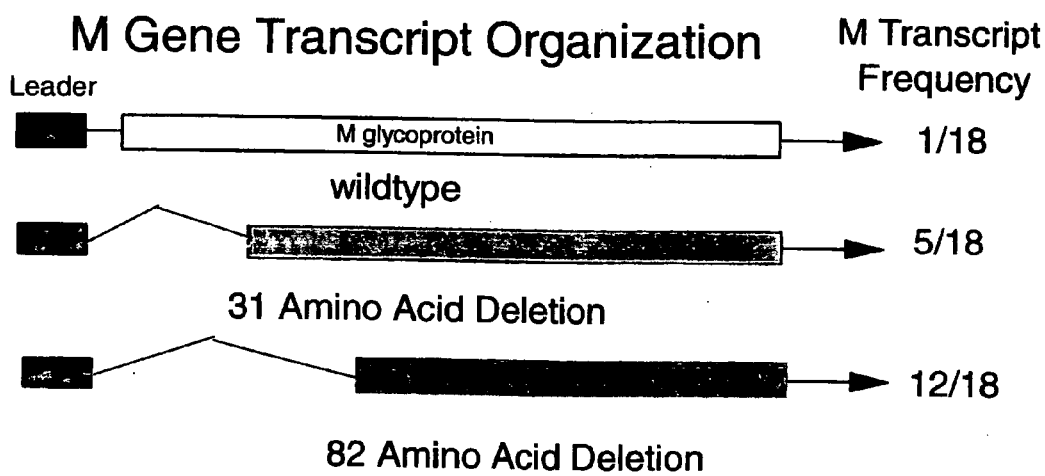
Figure 2:
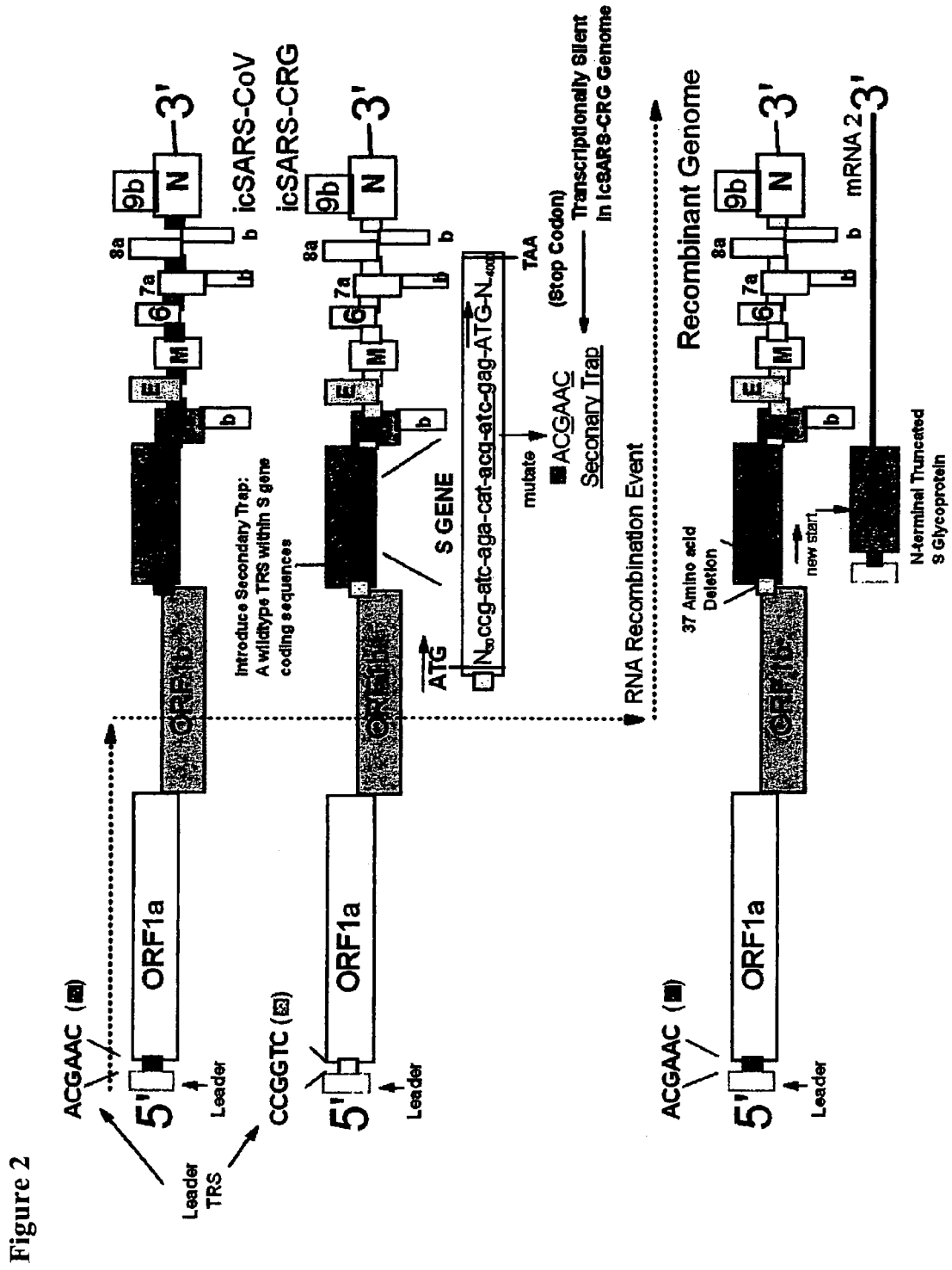
FIG. 2. Mechanism of secondary genetic trap. In the recombinant virus, there is miscommunication between the leader TRS CS and the body TRS CS. In this example, subgenomic transcripts of the essential S gene are directed to initiate within the S gene, resulting in N terminal truncations in the S glycoprotein product. Similar mutations can be introduced in the essential M and N structural protein genes.

The present invention provides a cDNA of the SARS coronavirus, from which transcripts are produced that replicate and/or are infectious in vitro or in vivo. Two examples of a nucleic acid sequence encoding a cDNA of this invention are provided in the attached Sequence Listing as SEQ ID NO:1 and SEQ ID NO:3. As this invention encompasses all such cDNAs of all SARS coronavirus isolates, in one embodiment, the present invention provides an isolated nucleic acid comprising, consisting of and/or consisting essentially of, a nucleotide sequence selected from the group consisting of: a) SEQ ID NO:1 or SEQ ID NO:3 or a fragment of at least 25 contiguous nucleotides of SEQ ID NO:1 or SEQ ID NO:3; b) a nucleotide sequence that is functionally equivalent to the nucleotide sequence of SEQ ID NO:1 or SEQ ID NO:3 but comprises different codons encoding the same amino acid sequences; c) a nucleotide sequence having at least 70% homology to the nucleotide sequence of SEQ ID NO:1 or SEQ ID NO:3; d) a nucleotide sequence having at least 95% homology to the nucleotide sequence of SEQ ID NO:1 or SEQ ID NO:3; e) a nucleotide sequence that hybridizes to the complement of SEQ ID NO:1 or SEQ ID NO:3 under stringent conditions; and f) a nucleotide sequence having complete complementarity to the nucleotide sequence of (a)-(e) above.

Further provided herein is a cDNA of a SARS coronavirus, wherein all or part of a nucleotide sequence of the cDNA is deleted and wherein the nucleotide sequence is selected from the group consisting of a nucleotide sequence encoding ORF1, ORF2, ORF3a, ORF3b, ORF4, ORF5, ORF6, ORF7a/b, ORF8a/b, ORF9a, ORF9b and any other ORF of a SARS coronavirus now known or later identified, and any combination thereof.

The present invention further provides a cDNA of a SARS coronavirus, comprising a mutation in a nucleotide sequence of the cDNA, selected from the group consisting of a nucleotide sequence encoding ORF1, ORF2, ORF3a, ORF3b, ORF4, ORF5, ORF6, ORF7a/b, ORF8a/b, ORF9a, ORF9b, ORF 10, ORF 13, ORF 14, any other ORF of a SARS coronavirus now known or later identified, and any combination thereof, wherein the mutation results in a nonfunctional gene product.

In an additional embodiment, the present invention provides a cDNA of a SARS coronavirus, wherein the order of nucleotide sequences of the cDNA encoding replicase, accessory ORFs and/or structural proteins S, E, M and N is rearranged in comparison to the order in wild type SARS coronavirus.

Additionally provided herein is a cDNA of a SARS coronavirus, wherein one or more of the nucleotide sequences encoding replicase, accessory ORFS and/or structural proteins S, E, M and N is present two or more times.

The present invention further provides a cDNA of a SARS coronavirus, comprising an attenuating mutation in a consensus sequence of the nucleotide sequence of the cDNA, selected from the group consisting of a leader consensus sequence, an S (ORF2) consensus sequence, an ORF3a consensus sequence, an E consensus sequence, an M consensus sequence, an ORF6 consensus sequence, an ORF7 consensus sequence, an ORF8 consensus sequence, an N consensus sequence, and any combination thereof.

In one embodiment provided herein, the present invention provides a cDNA of a SARS coronavirus comprising a 29 bp insertion in ORF8a/b.

Also provided herein is a cDNA of a SARS coronavirus, wherein all or part of a nucleotide sequence of the cDNA is deleted and wherein the nucleotide sequence is selected from the group consisting of a nucleotide sequence encoding ORF1, ORF2, ORF3a, ORF3b, ORF4, ORF5, ORF6, ORF7a/b, ORF8a/b, ORF9a, ORF9b, or any other ORF of a SARS coronavirus now known or later identified, and any combination thereof and furthermore, wherein the order of nucleotide sequences of the cDNA encoding replication, accessory ORFs and/or structural proteins S, E, M and N is rearranged in comparison to the order in wild type SARS coronavirus. In this embodiment, the cDNA can further comprise an attenuating mutation in a consensus sequence of a nucleotide sequence of the cDNA, selected from the group consisting of a leader consensus sequence, an S consensus sequence, an ORF3a consensus sequence, an E consensus sequence, an M consensus sequence, an ORF6 consensus sequence, an ORF7 consensus sequence, an ORF8 consensus sequence, an N consensus sequence, and any combination thereof.

The present invention also provides a SARS coronavirus replicon RNA comprising a coronavirus packaging signal and a heterologous RNA sequence, wherein the replicon RNA lacks a sequence encoding at least one coronavirus structural protein.

Furthermore, the present invention provides an infectious, multiplication-defective, coronavirus particle, comprising a SARS coronavirus replicon RNA, wherein the replicon RNA comprises a coronavirus packaging signal and a heterologous RNA sequence, and wherein the replicon RNA lacks a sequence encoding at least one coronavirus structural protein.

Additionally provided is a population of infectious, multiplication defective, coronavirus particles, wherein each particle comprises a SARS coronavirus replicon RNA, and wherein the replicon RNA comprises a SARS coronavirus packaging signal and a heterologous RNA sequence, and wherein the replicon RNA lacks a sequence encoding at least one coronavirus structural protein, wherein the population contains no detectable replication-competent coronavirus particles as determined by passage on coronavirus permissive cells in culture.

The present invention further provides a method of introducing a heterologous RNA into a subject, comprising administering to the subject an effective amount of the particles or populations and/or compositions of this invention.

Also provided herein is a method of inducing an immune response and/or treating and/or preventing a SARS coronavirus infection in a subject, comprising administering to the subject an effective amount of the viruses, vectors, particles or populations and/or compositions of this invention.

In further embodiments, the present invention provides a helper cell for producing an infectious, multiplication-defective, coronavirus particle, comprising: (a) a SARS coronavirus replicon RNA comprising a coronavirus packaging signal and a heterologous RNA sequence, wherein said replicon RNA lacks a sequence encoding at least one coronavirus structural protein; and/or (b) at least one separate helper RNA encoding the at least one coronavirus structural protein absent from the replicon RNA, said helper RNA lacking a coronavirus packaging signal; wherein the combined expression of the replicon RNA and the helper RNA produces an infectious, multiplication-defective coronavirus particle. Thus, the present invention includes the embodiment of a helper cell comprising a helper RNA encoding at least one coronavirus structural protein and the embodiment of a helper cell comprising a SARS coronavirus replicon RNA comprising a coronavirus packaging signal and a heterologous RNA sequence, wherein said replicon RNA lacks a sequence encoding at least one coronavirus structural protein.

The present invention additionally provides a method of making infectious, multiplication-defective, coronavirus particles, comprising: a) providing the helper cell of this invention; and b) producing coronavirus particles in the helper cell.

The foregoing and other objects and aspects of the present invention are explained in detail in the specification set forth below.

DETAILED DESCRIPTION OF THE INVENTION

As used herein, "a" or "an" or "the" can mean one or more than one. For example, "a" cell can mean one cell or a plurality of cells.

Also as used herein, "and/or" refers to and encompasses any and all possible combinations of one or more of the associated listed items, as well as the lack of combinations when interpreted in the alternative ("or").

Furthermore, the term "about," as used herein when referring to a measurable value such as an amount of a compound or agent of this invention, dose, time, temperature, and the like, is meant to encompass variations of ±20%, ±10%, ±5%, ±1%, ±0.5%, or even ±0.1% of the specified amount.

As used herein, the transitional phrase "consisting essentially of" means that the scope of a claim is to be interpreted to encompass the specified materials or steps recited in the claim, "and those that do not materially affect the basic and novel characteristic(s)" of the claimed invention. See, In re Herz, 537 F.2d 549, 551-52, 190 USPQ 461, 463 (CCPA 1976) (emphasis in the original); see also MPEP § 2111.03.

"Nidovirus" as used herein refers to viruses within the order Nidovirales, including the families Coronaviridae and Arteriviridae. All viruses within the order Nidovirales share the unique feature of synthesizing a nested set of multiple subgenomic mRNAs. See M. Lai and K. Holmes, Coronaviridae: The Viruses and Their Replication, in Fields Virology, pg 1163, (4$^{th}$ Ed. 2001). Particular examples of Coronaviridae include, but are not limited to, toroviruses and coronaviruses.

"Coronavirus" as used herein refers to a genus in the family Coronaviridae, which family is in turn classified within the order Nidovirales. The coronaviruses are large, enveloped, positive-stranded RNA viruses. They have the largest genomes of all RNA viruses and replicate by a unique mechanism that results in a high frequency of recombination. The coronaviruses include antigenic groups I, II, and III. While the present invention is described primarily with respect to SARS coronavirus, the invention may be carried out with any coronavirus, such as transmissible gastroenteritis virus (TGEV), human respiratory coronavirus, porcine respiratory coronavirus, canine coronavirus, feline enteric coronavirus, feline infectious peritonitis virus, rabbit coronavirus, murine hepatitis virus, sialodacryoadenitis virus, porcine hemagglutinating encephalomyelitis virus, bovine coronavirus, avian infectious bronchitis virus, and turkey coronavirus, as well as chimeras of any of the foregoing. See generally M. Lai and K. Holmes, "Coronaviridae: The Viruses and Their Replication," in Fields *Virology*, (4$^{th}$ Ed. 2001).

A "nidovirus permissive cell" or "coronavirus permissive cell" as used herein can be any cell in which a coronavirus can at least replicate, including both naturally occurring and recombinant cells. In some embodiments the permissive cell is also one that the nidovirus or coronavirus can infect. The permissive cell can be one that has been modified by recombinant means to produce a cell surface receptor for the nidovirus or coronavirus.

A "heterologous RNA" as described herein can encode any protein, peptide, antisense sequence, ribozyme, etc., to be administered to a subject of this invention for any purpose. For example, the heterologous RNA can encode, and be expressed in the subject to produce, a protein or peptide. The protein or peptide may, for example, be an antigen or immunogen in embodiments where it is desired to produce antibodies in an animal subject, which antibodies can be collected and used for diagnostic and/or therapeutic purposes, or where it is desired to elicit an immune response to the protein or peptide in a subject.

A "structural protein" as used herein refers to a protein required for production of coronavirus particles of this invention, such as those encoded by the S, E, M and N genes, as well as any other structural proteins now known or later identified in the coronavirus and in particular in the SARS virus genome. In embodiments of this invention wherein the replicon RNA and/or helper RNAs lack a nucleotide sequence encoding a structural protein, the nucleotide sequence can be wholly or partly deleted, or the sequence can be present but in a mutated form, so that the net effect is that the replicon RNA and/or the helper RNA is effectively incapable of producing the necessary structural protein in functional form. Thus, for example, in an embodiment that recites a replicon RNA or helper RNA that "lacks a sequence encoding at least one coronavirus structural protein," it is meant that the nucleotide sequence encoding the at least one coronavirus structural protein is deleted completely or in part from the replicon RNA or helper RNA or it is meant that the nucleotide sequence encoding the at least one coronavirus structural protein is present on the replicon RNA or helper RNA but in a form (e.g., mutated or otherwise altered) that cannot be expressed to produce a functional protein.

"Multiplication-defective" or "replication-defective" as used herein means that the replicon RNA contained within viral particles produced according to the present invention does not itself contain sufficient genetic information to allow for the production of new infectious viral particles.

As noted above, the present invention is based on the discovery of a full-length cDNA of the SARS coronavirus. As used herein, a "cDNA of a SARS coronavirus" or "infectious cDNA of a SARS coronavirus" is a nucleic acid molecule comprising the nucleotide sequence of a SARS coronavirus, from which RNA transcripts are produced that replicate and/or are infectious in vitro or in vivo. A SARS coronavirus cDNA of this invention can encode the sequence of any SARS coronavirus isolate now known or later identified. The genomic sequences of some of the known SARS coronavirus isolates are set forth in Genbank and assigned Accession numbers AY278741 (SEQ ID NO:2, provided herein), AY274119, AY278554 and AY278554 and the entire contents of each of these sequences are incorporated by reference herein in their entireties as embodiments of this invention. (See also Rota et al. (2003) *Science* 300:1394; Marra et al. (2003) *Science* 300:1399; the entire contents of each of which are incorporated by reference herein for the teachings of the identification and characterization of the genomic sequence of a SARS coronavirus).

Two examples of a nucleic acid sequence encoding a cDNA of this invention are provided in the attached Sequence Listing as SEQ ID NO:1 and SEQ ID NO:3. As this invention encompasses all such cDNAs of all SARS coronavirus isolates, in one embodiment, the present invention provides an isolated nucleic acid comprising, consisting of and/or consisting essentially of, a nucleotide sequence selected from the group consisting of: a) SEQ ID NO:1 and/or SEQ ID NO:3 or a fragment of at least 25 contiguous nucleotide sequences of SEQ ID NO:1 and/or SEQ ID NO:3; b) a nucleotide sequence that is functionally equivalent to the nucleotide sequence of SEQ ID NO:1 and/or SEQ ID NO:3 but comprises different codons encoding the same amino acid sequences; c) a nucleotide sequence having at least 70% homology to the nucleotide sequence of SEQ ID NO:1 and/or SEQ ID NO:3; d) a nucleotide sequence having at least 95% homology to the nucleotide sequence of SEQ ID NO:1 and/or SEQ ID NO:3; e) a nucleotide sequence that hybridizes to the complement of SEQ ID NO:1 and/or SEQ ID NO:3 under stringent conditions; and f) a nucleotide sequence having complementarity (e.g., partial or complete) to any of the nucleotide sequences of (a)-(e) above.

The present invention further provides nucleic acid molecules comprising, consisting of and/or consisting essentially of, a fragment of at least 25, 50, 100, 200, 300, 400, 500, 600, 700, 800, 900, 950 or 1000, 2000, 3000, 4000, 5000, 6000, 7000, 8000, 9000, 10,000, 15,000, 20,000, 25,000, 26,000, 27,000, 28,000, 29,000, 29,500, etc. contiguous nucleotides (including any values within this range not specifically recited herein, e.g., 56 nucleotides or 6345 nucleotides) of the nucleotide sequence of SEQ ID NO:1, or a complement thereof. A fragment of this invention can be a fragment that hybridizes to a sequence that is unique to the cDNA of this invention. The production, identification and characterization of such fragments for desired properties as described herein is carried out according to protocols well known in the art.

An "isolated" nucleic acid molecule is one that is chemically synthesized (e.g., derived from reverse transcription) or is separated from other nucleic acid molecules that are present in the natural source of the nucleic acid molecule. Preferably, an "isolated" nucleic acid molecule is free of sequences (preferably protein encoding sequences) that naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kB, 4 kB, 3 kB, 2 kB, 1 kB, 0.5 kB or 0.1 kB of nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material, or culture medium when produced by recombinant techniques, or substantially free of chemical precursors or other chemicals when chemically synthesized. (e.g., as described in Sambrook et al., eds., Molecular Cloning: A Laboratory Manual, 2nd ed., Cold Spring Harbor Laboratory, Cold Spring Harbor Laboratory Press, Cold Spring Harbor, N.Y., 1989).

In another embodiment of this invention, an isolated nucleic acid molecule of the invention comprises a nucleic acid molecule that is a complement of the nucleotide sequence of SEQ ID NO:1 or a fragment thereof. A nucleic acid molecule which is complementary to a given nucleotide sequence is one which is sufficiently complementary to the given nucleotide sequence that it can hybridize to the given nucleotide sequence under conditions described herein, thereby forming a stable duplex.

The invention further encompasses nucleic acid molecules that differ from the nucleotide sequence of SEQ ID NO:1 due to degeneracy of the genetic code and thus encode the same proteins as those encoded by the nucleotide sequence of SEQ ID NO:1.

In particular embodiments, a nucleic acid of this invention has at least about 50%, 60%, 70%, 75%, 80%, 85%, 90%, 95%, 98% or more nucleic acid sequence homology with the sequences specifically disclosed herein. The term "homology" as used herein refers to a degree of similarity between two or more sequences. There can be partial homology or complete homology (i.e., identity). A partially homologous sequence that at least partially inhibits an identical sequence from hybridizing to a target nucleic acid is referred to using the functional term "substantially homologous." The inhibition of hybridization to the target sequence can be examined using a hybridization assay (Southern or northern blot, solution hybridization and the like) under conditions of low stringency. A substantially homologous sequence or hybridization probe will compete for and inhibit the binding of a completely homologous sequence to the target sequence under conditions of low stringency. This is not to say that conditions of low stringency are such that non-specific binding is permitted; low stringency conditions require that the binding of two sequences to one another be a specific (i.e., selective) interaction. The absence of non-specific binding can be tested by the use of a second target sequence, which lacks even a partial degree of complementarity (e.g. less than about 30% identity). In the absence of non-specific binding, the probe will not hybridize to the second non-complementary target sequence.

Alternatively stated, in particular embodiments, nucleic acids encoding a cDNA of a SARS coronavirus that hybridize under the conditions described herein to the complement of the sequences specifically disclosed herein can also be used according to the present invention. The term "hybridization" as used herein refers to any process by which a first strand of nucleic acid binds with a second strand of nucleic acid through base pairing.

The term "stringent" as used here refers to hybridization conditions that are commonly understood in the art to define the commodities of the hybridization procedure. High stringency hybridization conditions that will permit homologous nucleotide sequences to hybridize to a nucleotide sequence as given herein are well known in the art. As one example, hybridization of such sequences to the nucleic acid molecules disclosed herein can be carried out in 25% formamide, 5×SSC, 5×Denhardt's solution and 5% dextran sulfate at 42° C., with wash conditions of 25% formamide, 5×SSC and 0.1% SDS at 42° C., to allow hybridization of sequences of about 60% homology. Another example includes hybridization conditions of 6×SSC, 0.1% SDS at about 45° C., followed by wash conditions of 0.2×SSC, 0.1% SDS at 50-65° C. Another example of stringent conditions is represented by a wash stringency of 0.3 M NaCl, 0.03M sodium citrate, 0.1% SDS at 60-70° C. using a standard hybridization assay (see SAMBROOK et al., EDS., MOLECULAR CLONING: A LABORATORY MANUAL 2d ed. (Cold Spring Harbor, N.Y. 1989, the entire contents of which are incorporated by reference herein).

As is known in the art, a number of different programs can be used to identify whether a nucleic acid or amino acid has sequence identity or similarity to a known sequence. Sequence identity or similarity may be determined using standard techniques known in the art, including, but not limited to, the local sequence identity algorithm of Smith & Waterman, *Adv. Appl. Math.* 2, 482 (1981), by the sequence identity alignment algorithm of Needleman & Wunsch, *J. Mol. Biol.* 48,443 (1970), by the search for similarity method of Pearson & Lipman, *Proc. Natl. Acad. Sci. USA* 85,2444 (1988), by computerized implementations of these algorithms (GAP, BESTFIT, FASTA, and TFASTA in the Wisconsin Genetics Software Package, Genetics Computer Group, 575 Science Drive, Madison, Wis.), the Best Fit sequence program described by Devereux et al., *Nucl. Acid Res.* 12, 387-395 (1984), preferably using the default settings, or by inspection.

An example of a useful algorithm is PILEUP. PILEUP creates a multiple sequence alignment from a group of related sequences using progressive, pairwise alignments. It can also plot a tree showing the clustering relationships used to create the alignment. PILEUP uses a simplification of the progressive alignment method of Feng & Doolittle, *J. Mol. Evol.* 35, 351-360 (1987); the method is similar to that described by Higgins & Sharp, *CABIOS* 5, 151-153 (1989).

Another example of a useful algorithm is the BLAST algorithm, described in Altschul et al., *J. Mol. Biol.* 215, 403-410, (1990) and Karlin et al., *Proc. Natl. Acad. Sci. USA* 90, 5873-5787 (1993). A particularly useful BLAST program is the WU-BLAST-2 program that was obtained from Altschul et al., *Methods in Enzymology,* 266, 460-480 (1996). WU-BLAST-2 uses several search parameters, which are preferably set to the default values. The parameters are dynamic values and are established by the program itself depending upon the composition of the particular sequence and composition of the particular database against which the sequence of interest is being searched; however, the values may be adjusted to increase sensitivity. An additional useful algorithm is gapped BLAST as reported by Altschul et al. *Nucleic Acids Res.* 25, 3389-3402.

The CLUSTAL program can also be used to determine sequence similarity. This algorithm is described by Higgins et al. (1988) *Gene* 73:237; Higgins et al. (1989) *CABIOS* 5:151-153; Corpet et al. (1988) *Nucleic Acids Res.* 16: 10881-90; Huang et al. (1992) *CABIOS* 8: 155-65; and Pearson et al. (1994) *Meth. Mol. Biol.* 24: 307-331.

The alignment may include the introduction of gaps in the sequences to be aligned. In addition, for sequences that contain either more or fewer nucleotides than the nucleic acids disclosed herein, it is understood that in one embodiment, the percentage of sequence identity will be determined based on the number of identical nucleotides in relation to the total number of nucleotide bases. Thus, for example, sequence identity of sequences shorter than a sequence specifically disclosed herein will be determined using the number of nucleotide bases in the shorter sequence, in one embodiment. In percent identity calculations, relative weight is not assigned to various manifestations of sequence variation, such as, insertions, deletions, substitutions, etc.

In certain embodiments of this invention, the nucleic acid of this invention can comprise a promoter that directs the production of an RNA transcript from the cDNA. This promoter can be active in vitro or in vivo to produce an RNA transcript from the SARS coronavirus cDNA that can replicate and/or is infectious. Non-limiting examples of the promoter of this invention include a T7 promoter, a SP6 promoter a T3 promoter, a CMV promoter, a MoMLV promoter, a metallothionein promoter, a glucocorticoid promoter, a SV40 promoter, a CaMV 35S promoter, a nopaline synthetase promoter, and any other promoter that directs RNA transcription in vitro or in a cell.

Also provided herein is an RNA and a SARS coronavirus particle produced by the cDNA of this invention and a SARS coronavirus particle comprising the RNA produced from the cDNA of this invention. Further provided herein is a vector comprising the cDNA or RNA of this invention and a cell comprising the vector of this invention.

The present invention further provides a cDNA of a SARS coronavirus, wherein all or part of a nucleotide sequence of the cDNA is deleted and wherein the nucleotide sequence is selected from the group consisting of a nucleotide sequence encoding ORF1, ORF2, ORF3a, ORF3b, ORF4, ORF5, ORF6, ORF7a/b, ORF8a/b, ORF9a, ORF9b, any other ORF of a SARS coronavirus now known or later identified, and any combination thereof. It is also intended that the ORF sequence of this invention can be intact but altered to have the same effect as a total or partial deletion. Methods of deleting all or part of an ORF and/or altering an ORF of a cDNA of a SARS coronavirus of this invention and testing the resulting genotype and phenotype are set forth in the Examples and such methods are also routine to one of ordinary skill in the art. Examples of deletion mutants of this invention are provides in the Sequence Listing provided herein as SEQ ID NOs:4-9. These are sequences of subclone F having deletions in ORFX1 (SEQ ID NO:4), ORFX1 and X2 (SEQ ID NO:5), ORFX3 (SEQ ID NO:6), ORFX4 (SEQ ID NO:7) ORFX4 substituted with green fluorescent protein (GFP) (SEQ ID NO:8) and ORFX4 substituted with luciferase (SEQ ID NO:9).

Further provided herein is a cDNA of a SARS coronavirus, comprising a mutation in a nucleotide sequence selected from the group consisting of a nucleotide sequence encoding ORF1, ORF2, ORF3a, ORF3b, ORF4, ORF5, ORF6, ORF7a/b, ORF8a/b, ORF9a, ORF9b, ORF 10, ORF 13, ORF 14, any other ORF of a SARS coronavirus, and any combination thereof, wherein the mutation results in a nonfunctional gene product. Methods of producing the various mutants of this invention and testing the resulting genotype and phenotype are set forth in the Examples provided herein and such methods are also routine to one of ordinary skill in the art.

In additional embodiments, the present invention provides a cDNA of a SARS coronavirus, wherein the order of nucleotide sequences encoding replicase, accessory ORFs and/or structural proteins S, E, M and N is rearranged in comparison to the order in wild type SARS coronavirus. In addition, or alternatively, one or more of the nucleotide sequences encoding replicase, accessory ORFS and/or structural proteins S, E, M and N can be present two or more times on the cDNA. Nonlimiting examples of these embodiments include cDNAs wherein the order of nucleotide sequences encoding structural proteins is: a) 5' S, N, E and M 3', b) 5' N, S, E and M 3', c) 5' E, M, S and N 3', d) 5' E, M, N and S 3', e) 5' S, N, E, M, N 3'. These examples are provided to show the order of the nucleotide sequences encoding the structural proteins S, E, M and N, relative to one another, with respect to the 5' and 3' ends of the cDNA molecule. However, these examples are not intended to be limiting in any way with respect to the positioning of the replicase, accessory ORFs and/or any other coding sequences present in the cDNA sequence. Thus, for example, the replicase, accessory ORFs and/or other coding sequences present in the cDNA sequence can be positioned anywhere (e.g., before, after, in multiple repeats before and/or after) relative to the each of the coding sequences of the S, E, M and N proteins. Furthermore, any of the coding sequences of the structural proteins, replicase, accessory ORFs and/or other coding sequences can be modified by mutation and/or deletion in this embodiment.

The present invention also provides a cDNA of a SARS coronavirus, comprising an attenuating mutation in a consensus sequence, ACGAAC, which can be, but is not limited to, a leader consensus sequence, an S (ORF2) consensus sequence, an ORF3a consensus sequence, an E consensus sequence, an M consensus sequence, an ORF6 consensus sequence, an ORF7 consensus sequence, an ORF8 consensus sequence, an N consensus sequence, and any combination thereof. The mutations of this invention can also include any mutation in any combination of the six consensus nucleotides and the surrounding flanking nucleotides (+/−50 nucleotides) that function as regulatory junctions to direct transcription of full length and subgenomic mRNAs. Two nonlimiting examples of mutations in the consensus sequence include "ACGAAC" to "ACCAAC" and "ACGAAC" to AGGAAG." Other examples of mutations of this invention are provided in Tables 1 and 2.

Further provided herein is a cDNA of a SARS coronavirus comprising a 29 bp insertion in ORF8a/b, or any other modification or alteration that reproduces a full length ORF8 protein sequence. In some embodiments, the full length ORF8 protein sequence provides an attenuating phenotype to the SARS coronavirus.

In additional embodiments, the present invention provides a cDNA of a SARS coronavirus wherein all or part of a nucleotide sequence of the cDNA is deleted and wherein the nucleotide sequence is selected from the group consisting of a nucleotide sequence encoding ORF1, ORF2, ORF3a, ORF3b ORF4, ORF5, ORF6, ORF7a/b, ORF8a/b, ORF9a, ORF9b, any other ORF of a SARS coronavirus now known or later identified, and any combination thereof and furthermore, wherein the order of nucleotide sequences of the cDNA encoding replication, accessory ORFs and/or structural proteins S, E, M and N is rearranged in comparison to the order in wild type SARS coronavirus. In some variations of this embodiment, it is also contemplated that the cDNA can further comprise an attenuating mutation in a consensus sequence of a nucleotide sequence of the cDNA selected from the group consisting of a leader consensus sequence, an S consensus sequence, an ORF3a consensus sequence, an E consensus sequence, an M consensus sequence, an ORF6 consensus sequence, an ORF7 consensus sequence, an ORF8 consensus sequence, an N consensus sequence and any combination thereof.

Furthermore, in additional embodiments, the present invention provides a SARS coronavirus replicon RNA comprising a coronavirus (e.g., SARS) packaging signal and a heterologous RNA sequence, wherein the replicon RNA lacks a sequence encoding at least one coronavirus structural protein.

Further provided herein is a DNA encoding a replicon RNA of this invention. In certain embodiments, the DNA can comprise a promoter to direct the transcription of the RNA, either in vitro or within a cell.

The present invention additionally provides an infectious, multiplication-defective, coronavirus particle, comprising a SARS coronavirus replicon RNA, wherein the replicon RNA comprises a coronavirus (e.g., SARS) packaging signal and a heterologous RNA sequence, and wherein the replicon RNA lacks a sequence encoding at least one coronavirus structural protein.

In some embodiments, the replicon RNA of this invention can comprise a nucleic acid sequence encoding at least one coronavirus structural protein, provided the replicon RNA does not comprise nucleic acid sequences functionally encoding all of the coronavirus structural proteins. In other embodiments, the replicon RNA can comprise a promoter. In yet other embodiments, the replicon RNA may or may not comprise a nucleic acid sequence encoding a replicase protein. It is also contemplated that the replicon RNA can lack a coronavirus packaging signal under circumstances wherein the replicon RNA is packaged into coronavirus particles nonspecifically or under conditions wherein it is contacted with a coronavirus structural protein comprising a nucleic acid binding site that facilitates packaging of the replicon RNA in the absence of a coronavirus packaging signal.

It is also an embodiment of this invention wherein the nucleic acid of the replicon RNA encodes, and/or the particle itself comprises, a coronavirus structural protein that is produced from nucleic acid of a coronavirus that can be, but is not limited to, SARS coronavirus, human respiratory coronavirus, mouse hepatitis virus, porcine transmissible gastroenteritis virus, porcine respiratory coronavirus, canine coronavirus, feline enteric coronavirus, feline infectious peritonitis virus, rabbit coronavirus, murine hepatitis virus, sialodacryoadenitis virus, porcine hemagglutinating encephalomyelitis virus, bovine coronavirus, avian infectious bronchitis virus, turkey coronavirus and/or any other coronavirus now known or later identified, as well as any combination thereof, thereby resulting in chimeric coronavirus particles.

In embodiments wherein one or more of the structural proteins are from different coronaviruses in a particle and/or one or more structural proteins are encoded by the nucleic acid of the replicon RNA, the coronavirus structural protein encoded by the nucleic acid of the replicon RNA can be S, E, M, N or combinations thereof.

The coronavirus packaging signal of this invention can be a packaging signal of any coronavirus now known or later identified. For example, the packaging signal can be from a coronavirus that can be, but is not limited to, SARS coronavirus, human respiratory coronavirus, mouse hepatitis virus, porcine transmissible gastroenteritis virus, porcine respiratory coronavirus, canine coronavirus, feline enteric coronavirus, feline infectious peritonitis virus, rabbit coronavirus, murine hepatitis virus, sialodacryoadenitis virus, porcine hemagglutinating encephalomyelitis virus, bovine coronavirus, avian infectious bronchitis virus, turkey coronavirus.

Further provided herein is a population of infectious, multiplication defective, coronavirus particles, wherein each particle comprises a SARS coronavirus replicon RNA, and wherein the replicon RNA comprises a coronavirus (e.g., SARS) packaging signal and a heterologous RNA sequence, and wherein the replicon RNA lacks a sequence encoding at least one coronavirus structural protein, wherein the population contains no detectable replication-competent coronavirus particles as determined by passage on coronavirus permissive cells in culture. Methods of detecting replication competent particles by passage on cell culture are standard in the art. These assays can also be carried out by passage of the replicon particles of this invention on cells constitutively expressing nucleic acid encoding the missing coronavirus structural protein(s), with the expected result of obtaining replication competent coronavirus particles.

It is also contemplated that the replicon RNA and/or replicon particles of this invention can comprise coronavirus RNA and/or structural proteins that comprise any or all of the gene order rearrangements, deletions and/or mutations described herein that can be present in the SARS coronavirus cDNA of this invention.

Another aspect of the present invention is a renetworked or rewired nidovirus genome and/or replicon RNA that results in a genetic trap for wild type viruses should recombination occur, e.g., when the genome or replicon RNA is contacted with wild type virus. Thus, in one embodiment, the present invention provides an isolated nucleic acid comprising, consisting essentially of and/or consisting of a nucleotide sequence encoding a Nidovirus genome or replicon RNA, wherein the genome or replicon RNA comprises, consists essentially of and/or consists of one or more of the same mutations in a consensus sequence (CS) present in a transcription regulatory sequence (TRS) of a leader sequence and in the TRS located upstream of each of the structural genes and further wherein wild type CS sequences are present in the CS of the TRS for the group specific ORFs 3a/b, ORF4, ORF5, ORF6, ORF7a/b, ORF8a/b and ORF9a/b. This remodeled genome or replicon RNA can be considered to be partially remodeled (e.g., PRG). Other mutations in the genome or replicon RNA may or may not be present, provided such other mutants do not affect the genetic trap function of the rewired (e.g., mutated) CSs.

Further provided herein is an isolated nucleic acid comprising, consisting essentially of and/or consisting of a nucleotide sequence encoding a Nidovirus genome or replicon RNA, wherein the genome or replicon RNA comprises, consists essentially of and/or consists of one or more of the same mutations in a consensus sequence (CS) present in a transcription regulatory sequence (TRS) of a leader sequence and in the TRS located upstream of each of the structural genes and further comprising one or more of the same mutations in the CS of the TRS located upstream of open reading frame (ORF) 3a/3b, ORF 4, ORF 5, ORF6, ORF 7a/7b, ORF 8a/b and ORF 9a/b and downstream of the leader RNA. This remodeled genome or replicon RNA can be considered to be completely remodeled (e.g., CRG). Other mutations in the genome or replicon RNA may or may not be present, provided such other mutants do not affect the genetic trap function of the rewired (e.g., mutated) CSs.

The isolated nucleic acids described herein can be from a Nidovirus that is a severe acute respiratory syndrome (SARS) coronavirus having the CS of ACGAAC. In this embodiment, the mutation can be a single mutation in the CS sites (e.g., ACGGAC, etc.), two mutations in the CS sites (e.g., ACGGAT, CCGGAC, CCGAAT, etc.), three mutations in the CS sites (e.g., CCGGAT, CCGCGC, CGCAAC, etc.), four mutations in the CS sites (e.g., CCCGAT, AGCGAT, etc.), five mutations in the CS sites (CGCGAT, CCCGTT, etc.) and six mutations in the CS sites (CGCGTT, TGCGGT, etc.). It is contemplated in this invention and applicants are in possession of the embodiment wherein the CS sequence is mutated according to any one of $4^6$ possible combinations of sequence variations, which combinations can be readily calculated and identified according to methods standard in the art. Factors governing site selection for mutation are based on 1) a unique sequence element that is not repeated elsewhere in the genome and 2) a mutant CS that functions as a regulatory start site when coupled with compensating changes at the leader CS site. Thus, the mutation(s) can be any possible combination of changes in the body CSs and in the leader CS and a particular mutation or combination of mutations is not critical as long as the same mutations are present in the body CSs as in the leader CS. In other words, the actual mutant CS sequence is not critical, the major factor being that CS sites must allow for communication via efficient base-pairing for discontinuous transcription of subgenomic RNAs, thus the same mutation(s) is present in the leader CS as in the body CS(s).

In further embodiments, the Nidovirus of this invention can be a group I coronavirus having the CS of CUAAAC and the mutation can be a single mutation (e.g., GUAAAC, etc.), two mutations (e.g., GCAAAC, etc.), three mutations (e.g., CGAAAG, etc.), four mutations (e.g., GCTAAAG, etc.), five mutations (e.g., GCTTAG. etc.) and/or six mutations (GCTTGG, etc.). It is contemplated as part of this invention and applicants are in possession of a total of $4^6$ possible combinations of sequence variation in the CS of this invention, as could be identified and produced according to standard methods. Factors to consider in selecting mutations include whether the mutation(s) are unique and able to interact with an identical leader CS site to drive expression of subgenomic mRNAs.

The Nidovirus of this invention can also be a group II coronavirus having the CS of TCTAAAC and the mutation can be a single mutation (e.g., CCTAAAC, etc.), two mutations (e.g., CCGAAAC, etc.), three mutations (e.g., CGTAAAG, etc.), four mutations (e.g., CCGAAGG, etc.), five mutations (e.g., CGTCCGC, etc), six mutations (e.g., CGGATTG, etc) and/or seven mutations (e.g., CGGCCTG, etc). It is contemplated as part of this invention and applicants are in possession of a total of $4^7$ possible combinations of sequence variation in the CS of this invention, as could be identified and produced according to standard methods. As noted herein for other nidoviruses, the principle requirements for mutation selection are that the sequence not be located elsewhere in the genome and that it function to regulate subgenomic transcription when paired with a leader TRS of like sequence.

In yet further embodiments, the Nidovirus of this invention can be a group III coronavirus having the CS of CUUAACAA and the mutation can be a single mutation (e.g., CUUAAGAA, etc.) two mutations (e.g., GUUAAGAA, etc.) three mutations (GUUGAGAA, etc.), four mutations (e.g., GUUTTCAG, five mutations (e.g., CAAGGCAA, TCCAAGAT, etc.), six mutations (e.g., GUUCCTTC, etc.), seven mutations (e.g., GCCTAGCG, etc.) and/or eight mutations (e.g., GCCTGGCT, etc.). It is contemplated as part of this invention and applicants are in possession of a total of $4^8$ possible combinations of sequence variation in the CS of this invention, as could be identified and produced according to standard methods.

The present invention further provides an embodiment wherein the Nidovirus is a torovirus having a CS regulatory sequence of UUUAGA and the mutation is a single mutation (e.g., GUUAGA, etc.) two mutations (e.g., GUUGGA, etc.), three mutations (e.g., GUUGCA, etc.), four mutations (e.g., GCUCCA, etc.) five mutations (e.g. GCCACT, etc.) and/or six mutations (e.g., GCCTCT, etc.). It is contemplated as part of this invention and applicants are in possession of a total of $4^6$ possible combinations of sequence variation in the CS of this invention, as could be identified and produced according to standard methods. As noted herein for other nidoviruses, the exact mutation(s) are dependent upon the uniqueness of this sequence in the different Torovirus genome CS regions coupled with its ability to regulate subgenomic transcription via a matching mutation in the leader CS region.

The nidovirus of this invention can also be an arterivirus having a CS of UCNUUAACC, U(A/G)(U/A)AACC, or UUAACC and the mutation can be a single mutation (e.g., CUAACC. etc.) two mutations (e.g., CCAACC, etc.), three mutations (e.g., CCAAGC, etc.) four mutations (e.g., CCAGGC, etc.) five mutations (e.g., CCAGGT, etc.) and/or six mutations (e.g., GGTTAG, etc.), including a cluster of mutations in a six nucleotide segment of these CSs. It is contemplated as part of this invention and applicants are in possession of a total of $4^9$ possible combinations of potential mutant CS sites available for use in this invention. The mutated CS sequence should be unique to that particular arterivirus and able to interact with the identically mutated leader CS site located at the 5' end of the genome.

The present invention further provides the isolated nucleic acids described herein having all of the body and leader CS sites reengineered by mutation (e.g., CRG), wherein the nucleic acid further comprises a secondary CS trap that is preferentially recognized in RNA recombinant viruses. These secondary CS trap sites are engineered wild type CSs located within a structural protein gene that lead to expression of one or more subgenomic mRNAs that do not encode a full length structural protein when present in a recombinant virus.

Thus, a CRG genome or replicon RNA of this invention can further comprise, consist essentially of and/or consist of a wild type CS engineered within one or more structural protein genes. As one example, the genome or replicon RNA can be of a SARS coronavirus having a wild type CS sequence of ACGAAC. In addition to mutations in the body CSs and leader CS, additional mutations would be introduced into the N, M, E and/or S gene(s) in any combination to provide an artificial CS having the same nucleotide sequence as the wild type CS, ACGAAC. This artificial CS is introduced into the structural gene sequence as described herein in Example 6.

Thus, in one embodiment, the present invention provides an isolated nucleic acid comprising, consisting essentially of and/or consisting of a nucleotide sequence encoding a Nidovirus genome or replicon RNA, wherein the genome or replicon RNA comprises, consists essentially of and/or consists of one or more of the same mutations in a consensus sequence (CS) present in a transcription regulatory sequence (TRS) of a leader sequence and in the TRS located upstream of each of the structural genes and further comprising one or more of the same mutations in the CS of the TRS located upstream of open reading frame (ORF) 3a/3b, ORF 4, ORF 5, ORF6, ORF 7a/7b, ORF 8a/b and ORF 9a/b and downstream of the leader RNA and further comprising one or more than one artificial CS having the nucleotide sequence of the wild type CS of the nidovirus, in one or more of the structural protein genes (e.g., N, M, E and/or S).

Additionally provided is an isolated nucleic acid comprising, consisting essentially of and/or consisting of a nucleotide sequence encoding a Nidovirus genome or replicon RNA, wherein the genome or replicon RNA comprises, consists essentially of and/or consists of one or more of the same mutations in a consensus sequence (CS) present in a transcription regulatory sequence (TRS) of a leader sequence and in the TRS located upstream of each of the structural genes S, E, M and N and further wherein wild type CS sequences are present in the CS of the TRS for the group specific ORFs 3a/b, ORF4, ORF5, ORF6, ORF7a/b, ORF8a/b and ORF9a/b and further comprising one or more than one artificial CS having the nucleotide sequence of the wild type CS of the nidovirus, in one or more of the structural protein genes (e.g., N, M, E and/or S).

The present invention further provides a nidovirus particle as well as a population of nidovirus particles comprising any of the nucleic acids of this invention The nidovirus and/or nidovirus particle of this invention can be a coronavirus, a torovirus, an arterivirus and chimeras thereof, as are known in the art.

A coronavirus of this invention can be, but is not limited to, transmissible gastroenteritis virus (TGEV), human respiratory coronavirus, human coronavirus, porcine respiratory coronavirus, porcine epidemic diarrhea virus, respiratory bovine virus, canine coronavirus, bat SARS-CoV, human coronavirus NL63, human coronavirus HKU1, human coronavirus OC43, human coronavirus 229E, feline enteric coronavirus, bat coronaviruses, feline infectious peritonitis virus, rabbit coronavirus, murine hepatitis virus, sialodacryoadenitis virus, porcine hemagglutinating encephalomyelitis virus, bovine coronavirus, avian infectious bronchitis virus, turkey coronavirus, and a chimera of any combination of these viruses.

An arterivirus of this invention can be but is not limited to, equine arteritis virus, lactate dehydrogenase-elevating virus, simian hemorrhagic fever virus, porcine reproductive and respiratory disease virus, human arteriviruses, and chimeras of any combination of these viruses containing, e.g., replicase protein genes from one arterivirus fused with structural ORFs and group specific ORFs of other arteriviruses. A torovirus of this invention can include, but is not limited to, bovine torovirus, equine torovirus, human torovirus, porcine torovirus and a chimera of any combination of these viruses.

An example of a chimera of any combination of these nidoviruses is a chimeric virus comprising replicase protein genes from one nidovirus fused with structural ORFs and group specific ORFs of other nidoviruses Additionally provided herein is a composition comprising the nucleic acids, nidovirus particles and/or population of nidovirus particles as described herein and a pharmaceutically acceptable carrier.

In further embodiments, the present invention provides a method of eliciting an immune response in a subject, comprising administering to, delivering to, and/or introducing into the subject an effective amount of the nucleic acids, viruses, particles, compositions and/or populations of this invention.

Also provided herein is a method of treating and/or preventing a Nidovirus infection in a subject, comprising administering/delivering/introducing into to the subject an effective amount of the nucleic acids, viruses, particles, compositions and/or populations of this invention.

Methods are also provided herein for producing a nidovirus particle comprising a replicon RNA or a nucleic acid comprising a nucleotide sequence encoding a Nidovirus genome, wherein the genome or replicon RNA comprises one or more of the same mutations in a consensus sequence (CS) present in a transcription regulatory sequence (TRS) of a leader sequence and in the TRS located upstream of each of the structural genes S, E, M and N and further comprising a wild type CS sequence in a TRS for ORFs 3a/b, ORF6, ORF7a/b and ORF8a/b, comprising introducing the replicon RNA or nucleic acid into a nidovirus-permissive cell under conditions whereby nidovirus particles are produced.

Further provided herein is a method of producing a nidovirus particle comprising a replicon RNA or a nucleic acid comprising a nucleotide sequence encoding a Nidovirus genome, wherein the replicon RNA or genome comprises one or more of the same mutations in a consensus sequence (CS) present in a transcription regulatory sequence (TRS) of a leader sequence and in the TRS located upstream of each of the structural genes S, E, M and N and further comprising one or more of the same mutations in the CS of the TRS located upstream of open reading frame (ORF) 3a/3b, ORF6, ORF 7a/7b, ORF 8a/b and ORF 9a/b, comprising introducing the nucleic acid or replicon RNA into a nidovirus-permissive cell under conditions whereby nidovirus particles are produced.

In addition, the present invention provides a method of producing a nidovirus particle comprising a replicon RNA or a nucleic acid comprising a nucleotide sequence encoding a Nidovirus genome, wherein the replicon RNA or genome comprises one or more of the same mutations in a consensus sequence (CS) present in a transcription regulatory sequence (TRS) of a leader sequence and in the TRS located upstream of each of the structural protein genes and further comprising one or more of the same mutations in the CS of the TRS located upstream of open reading frame (ORF) 3a/3b, ORF6, ORF 7a/7b, ORF 8a/b and ORF 9a/b and further comprising one or more than one artificial CS having the nucleotide sequence of the wild type CS of the nidovirus in one or more of the structural protein genes, comprising introducing the nucleic acid or replicon RNA into a nidovirus-permissive cell under conditions whereby nidovirus particles are produced.

Methods are also provided herein for producing a nidovirus particle comprising a replicon RNA or a nucleic acid comprising a nucleotide sequence encoding a Nidovirus genome, wherein the genome or replicon RNA comprises one or more of the same mutations in a consensus sequence (CS) present in a transcription regulatory sequence (TRS) of a leader sequence and in the TRS located upstream of each of the structural protein genes (e.g., S, E, M and/or N) and further comprising a wild type CS sequence in a TRS for ORFs 3a/b, ORF6, ORF7a/b and ORF8a/b and further comprising one or more than one artificial CS having the nucleotide sequence of the wild type CS of the nidovirus in one or more of the structural protein genes (e.g., S, E, M and/or N), comprising introducing the replicon RNA or nucleic acid into a nidovirus-permissive cell under conditions whereby nidovirus particles are produced.

In methods wherein nidovirus particles are made that comprise a replicon RNA of this invention, a "nidovirus-permissive cell" is a cell that contains transcripts encoding the structural proteins that are not encoded for on the replicon RNA, as described herein. For example, a replicon RNA comprising a remodeled TRS CS site in the leader region and in the N gene can be packaged by transfection into cells containing transcripts encoding the remaining structural proteins, S, E and M.

The present invention further provides nidovirus particles produced by the methods described herein.

Also provided herein is a method of producing a nidovirus genome or replicon RNA comprising reengineered CS sequences for the purpose of preventing recombination repair of a live attenuated or replicon viral construct and/or preventing repair of attenuating alleles and/or for stabilizing attenuating mutations, comprising producing the nucleic acids of this invention. Additionally provided herein is a method of preventing recombination repair or repair of attenuating alleles of a live attenuated or replicon construct to be used in a therapeutic and/or immunological method comprising producing the nucleic acids of this invention. Thus, the present invention provides therapeutic and immunological compositions that are engineered to prevent recombination repair or repair of attenuating alleles if the nucleic acids of the compositions are contacted with wild type virus under conditions whereby recombination can occur. Further provides are therapeutic and immunological compositions that are engineered to stabilize attenuating mutations in the nucleic acid therein.

The nucleic acids, viruses, vectors, particles and populations are intended for use as therapeutic agents and immunological reagents, for example, as antigens, immunogens, vaccines, and/or nucleic acid delivery vehicles. Thus, in various embodiments, the present invention provides a composition comprising the nucleic acid, virus, vector, particle, and/or population of this invention in a pharmaceutically acceptable carrier. The compositions described herein can be formulated for use as reagents (e.g., to produce antibodies) and/or for administration in a pharmaceutical carrier in accordance with known techniques. See, e.g., Remington, *The Science And Practice of Pharmacy* (latest edition). In the manufacture of a pharmaceutical composition according to embodiments of the present invention, the composition of this invention is typically admixed with, inter alia, a pharmaceutically acceptable carrier. By "pharmaceutically acceptable carrier" is meant a carrier that is compatible with other ingredients in the pharmaceutical composition and that is not harmful or deleterious to the subject. The carrier may be a solid or a liquid, or both, and is preferably formulated with the composition of this invention as a unit-dose formulation. The pharmaceutical compositions are prepared by any of the well-known techniques of pharmacy including, but not limited to, admixing the components, optionally including one or more accessory ingredients. Exemplary pharmaceutically acceptable carriers include, but are not limited to, sterile pyrogen-free water and sterile pyrogen-free physiological saline solution. Such carriers can further include protein (e.g., serum albumin) and sugar (sucrose, sorbitol, glucose, etc.)

The pharmaceutical compositions of this invention include those suitable for oral, rectal, topical, inhalation (e.g., via an aerosol) buccal (e.g., sub-lingual), vaginal, parenteral (e.g., subcutaneous, intramuscular, intradermal, intraarticular, intrapleural, intraperitoneal, intracerebral, intraarterial, or intravenous), topical (i.e., both skin and mucosal surfaces, including airway surfaces) and transdermal administration. The compositions herein may also be administered via a skin scarification method, or transdermally via a patch or liquid. The compositions may be delivered subdermally in the form of a biodegradable material that releases the compositions over a period of time. The most suitable route in any given case will depend, as is well known in the art, on such factors as the species, age, gender and overall condition of the subject, the nature and severity of the condition being treated and/or on the nature of the particular composition (i.e., dosage, formulation) that is being administered.

Subjects to whom the viruses, vectors, particles, populations and/or other compositions of this invention can be administered according to the methods described herein can be any subject, generally vertebrates, for which the particles, populations and/or compositions are infectious, including but not limited to, birds and mammals such as pigs, mice, cows, and humans.

As used herein, an "effective amount" refers to an amount of a compound or composition that is sufficient to produce a desired effect, which can be a therapeutic, prophylactic and/or beneficial effect.

Thus, the present invention provides a method of inducing an immune response in a subject, comprising administering to the subject an effective amount of a virus, vector, particle, population and/or composition of this invention.

The present invention also provides a method of treating and/or preventing a SARS coronavirus infection in a subject, comprising administering to the subject an effective amount of a virus, vector, particle, population and/or composition of this invention.

Also as used herein, the terms "treat," "treating" and "treatment" include any type of mechanism, action or activity that results in a change in the medical status of a subject, including an improvement in the condition of the subject (e.g., change or improvement in one or more symptoms and/or clinical parameters), delay in the progression of the condition, prevention or delay of the onset of a disease or illness, etc.

One example of an effective amount is from about $10^4$ to about $10^{10}$, preferably $10^5$ to $10^9$, and in particular $10^6$ to $10^8$ infectious units (IU, as measured by indirect immunofluorescence assay), or virus particles, per dose, which can be administered to a subject, depending upon the age, species and/or condition of the subject being treated.

In some embodiments of the present invention, the compositions can be administered with an adjuvant. As used herein, "adjuvant" describes a substance, which can be any immunomodulating substance capable of being combined with the polypeptide or nucleic acid vaccine to enhance, improve or otherwise modulate an immune response in a subject without deleterious effect on the subject.

Non-limiting examples of adjuvants that can be used in the vaccine of the present invention include the RIBI adjuvant system (Ribi Inc., Hamilton, Mont.), alum, mineral gels such as aluminum hydroxide gel, oil-in-water emulsions, water-in-oil emulsions such as, e.g., Freund's complete and incomplete adjuvants, Block copolymer (CytRx, Atlanta Ga.), QS-21 (Cambridge Biotech Inc., Cambridge Mass.), SAF-M (Chiron, Emeryville Calif.), AMPHIGEN™ adjuvant, saponin, Quil A or other saponin fraction, monophosphoryl lipid A, and Avridine lipid-amine adjuvant. Non-limiting examples of oil-in-water emulsions useful in the vaccine of the invention include modified SEAM62 and SEAM 1/2 formulations. Modified SEAM62 is an oil-in-water emulsion containing 5% (v/v) squalene (Sigma), 1% (v/v) SPAN™ 85 detergent (ICI Surfactants), 0.7% (v/v) TWEEN™ 80 detergent (ICI Surfactants), 2.5% (v/v) ethanol, 200 pg/ml Quil A, 100 μg/ml cholesterol, and 0.5% (v/v) lecithin. Modified SEAM 1/2 is an oil-in-water emulsion comprising 5% (v/v) squalene, 1% (v/v) SPAN 85 detergent, 0.7% (v/v) Tween 80 detergent, 2.5% (v/v) ethanol, 100 μg/ml Quil A, and 50 μg/ml cholesterol. Other immunomodulatory agents that can be included in the vaccine include, e.g., one or more interleukins, interferons, or other known cytokines.

SARS coronavirus vectors also provide a system for the incorporation and expression of one or more heterologous nucleic acids, as coronaviruses contain a polycistronic genome organization and synthesize multiple subgenomic-length mRNAs (Enjuanes and van der Zeijst (1995) In: S. G. Siddell (ed.), The Coronaviridae. Plenum Press, New York, N.Y., p. 337-376).

In certain embodiments, the present invention describes the assembly of recombinant transmissible virus and replicons that express heterologous nucleic acids, which can be used to deliver such nucleic acids and/or make vaccines/immunogenic compositions against homologous and heterologous pathogens (Agapov et al. (1998) Proc. Natl. Acad. Sci. USA 95:12989-12994; Balasuriya et al. (2000) J. Virol. 74:10623-10630; Berglund et al. (1998) Nat. Biotechnol. 16:562-565; Bredenbeek et al. (1993) J. Virol. 67:6439-6446; DiCiommo and Bremner (1998) J. Biol. Chem. 273:18060-18066; Dollenmaier et al. (2001) Virology 281:216-230; Dubensky et al. (1996) J. Virol. 70:508-519; Hevey et al. (1998) Virology 251:28-37; Johanning et al. (1995) Nucleic Acids Res. 23:1495-1501; Khromykh (2000) Curr. Opin. Mol. Ther. 2:555-569; Khromykh and Westaway (1997) J. Virol. 71:1497-1505; Liljestrom and Garoff (1991) Bio/Technology 9:1356-1361; Percy et al. (1992) J. Virol. 66:5040-5046; Porter, et al. (1993) J. Virol. 67:3712-3719; Pushko et al. (2000) Vaccine 19:142-153; Schultz-Cherry et al (2000) Virology 278:55-59; Varnavski and Khromykh (1999) Virology 255:366-375; Varnavski et al. (2000) J. Virol. 74:4394-4403).

The use of replicons as a vaccine delivery system offers a number of important advantages over the use of live, attenuated virus vaccines, which are capable of independent spread and recombination with wild-type virus populations. Replicon vectors are an inherently safer alternative to the use of live, attenuated virus vaccines due to the lack of progeny virus production. In addition, high-level expression of heterologous nucleic acids can result in the use of a relatively low dose of virus replicon particles (VRPs) for vaccination and immune induction. Moreover, gene order rearranged and/or otherwise attenuated replicon particles will be inherently more stable and less pathogenic than attenuated wild-type strains.

Thus, the present invention also provides a method of introducing a heterologous RNA into a subject, comprising administering to the subject an effective amount of the particles and/or the populations and/or compositions of this invention comprising these particles or populations. The heterologous RNA can encode any protein or peptide or antisense sequence or ribozyme and can be administered to impart any type of effect (e.g., immunological or therapeutic, etc.).

The production of virus replicon particles is well known in the art for a variety of virus systems, including coronaviruses (see, e.g., Curtis et al. (2002) J. Virol. 76:1422-1434; PCT Publication No. WO 02/086068, the entire contents of each of which are incorporated by reference herein). The present invention can also be implemented in any of a variety of ways, including by techniques, compositions and formulations known in the art (see, e.g., U.S. Pat. No. 6,593,311 to Baric et al.; U.S. Pat. No. 6,156,558 to Johnston et al.; and U.S. Pat. No. 5,639,650 to Johnston et al.; U.S. Pat. No. 6,342,372 to Dubensky et al.) modified in light of the teachings set forth herein. Applicants specifically intend that the disclosures of all United States patent references and patent publications cited herein be incorporated herein by reference in their entirety.

The synthesis of large RNA transcripts (~27 to 29 kb) in vitro is problematic, and the electroporation of such large RNA constructs, even in the presence of enhancing N transcripts, has also proven difficult, resulting in a 1% transfection efficiency. Therefore, transfecting cells with helper packaging constructs and subsequently passing the coronavirus VRPs in the presence of VEE-(E) VRPs can address this issue. In this way, VRPs can be amplified and high concentrations may amplify replicon titers for future applications. In addition, the use of a DNA launch platform, such as with a cytomegalovirus promoter, may be used to overcome any problems associated with an RNA launch system.

The strategy presented herein for the assembly of SARS replicon constructs was based on a similar strategy for the construction of TGEV cDNA, employing six cDNA subclones that span the entire length of the SARS genome (see Yount et al. J. Virol. 74:10600-10611 (2000)). Each fragment is flanked by restriction sites that leave unique interconnecting junctions of 3 or 4 nt in length. These sticky ends are not complementary to most other sticky ends generated with the same enzyme at other sites in the DNA, allowing for the systematic assembly of SARS cDNAs by in vitro ligation.

The infectious, replication defective, coronavirus particles can be prepared according to the methods disclosed herein in combination with techniques known to those skilled in the art. As one example, the method can comprise a) introducing into a coronavirus-permissive cell 1) a SARS coronavirus replicon RNA comprising a coronavirus packaging signal and a heterologous RNA, a first helper RNA encoding at least one coronavirus structural protein and a second (and possibly third, fourth, etc.) helper RNA encoding at least one coronavirus structural protein that is different from that encoded by the first helper RNA; b) producing the coronavirus particles in the cell; and c) optionally collecting the particles from the cell. The step of introducing the replicon RNA and helper RNA(s) into the coronavirus-permissive cell can be carried out according to any suitable means known to those skilled in the art. For example, uptake of the RNA into the cell can be achieved by any suitable means, such as for example, by treating the cells with DEAE-dextran, treating the cells with "LIPOFECTIN™," and/or by electroporation, with electroporation being the currently preferred means. These techniques are well known in the art. See e.g., U.S. Pat. No. 5,185,440 to Davis et al., and PCT Publication No. WO 92/10578 to Bioption AB, the disclosures of which are incorporated herein by reference in their entirety. Alternatively, a DNA encoding the replicon RNA and/or a DNA encoding the helper RNA(s) can be introduced into the cell according to known methods and the DNA can be transcribed into RNA within the cell.

The present invention also provides methods for producing SARS coronavirus replicon particles, as well as helper RNAs and helper cells employed in the production. Thus, in further embodiments, the present invention provides a helper cell for producing an infectious, multiplication-defective, coronavirus particle, comprising: (a) a SARS coronavirus replicon RNA comprising a SARS coronavirus packaging signal and a heterologous RNA sequence, wherein said replicon RNA further lacks a sequence encoding at least one coronavirus structural protein; and (b) at least one separate helper RNA encoding the at least one structural protein absent from the replicon RNA, said helper RNA lacking a coronavirus packaging signal; wherein the combined expression of the replicon RNA and the helper RNA produces an infectious, multiplication-defective coronavirus particle.

As noted above, the replicon RNA can further comprise a sequence encoding at least one of the coronavirus structural proteins, provided that the replicon RNA does not comprise nucleic acid encoding all of the coronavirus structural proteins.

In the helper cells of this invention, the helper RNA can comprise a nucleic acid sequence encoding a coronavirus structural protein that can be E, M, N, S, or any combination thereof, provided that the helper RNA does not comprise nucleic acid encoding all of the coronavirus structural proteins. The nucleic acid encoding the coronavirus structural protein can be from a coronavirus that can be SARS coronavirus, human respiratory coronavirus, mouse hepatitis virus, porcine transmissible gastroenteritis virus, porcine respiratory coronavirus, canine coronavirus, feline enteric coronavirus, feline infectious peritonitis virus, rabbit coronavirus, murine hepatitis virus, sialodacryoadenitis virus, porcine hemagglutinating encephalomyelitis virus, bovine coronavirus, avian infectious bronchitis virus, turkey coronavirus and/or any other coronavirus now known or later identified, as well as combinations thereof, thereby resulting in chimeric coronavirus particles.

Furthermore, the helper RNA can comprise nucleic acid of any other non-coronavirus, including, but not limited to, vaccinia virus, alphavirus, flavivirus, vesicular stomatitis virus, poxvirus, adenovirus, herpesvirus, paramyxovirus, parvovirus, papovavirus, adeno-associated virus, and retrovirus. The helper RNA can also be a vector of non-viral origin that provides nucleic acid encoding the coronavirus structural protein(s) not present on the replicon RNA in the helper cell.

In certain embodiments, the replicon RNA and/or the helper RNA contains at least one attenuating gene order rearrangement among the 3A, 3B, HP, S, E, M and N genes. Helper or replicon RNAs (and their corresponding DNAs) that contain two or more genes optionally but preferably include a gene order rearrangement to attenuate (e.g., reduce the virulence) as compared to a corresponding wild-type virus that does not contain such a gene order rearrangement (i.e., comparing a virus with all of the necessary genes and the order rearrangement with a wild-type virus). Depending upon the number of genes within the helper or replicon RNA, it may contain two, three, or four or more gene order rearrangements. The wild-type gene order, from 5' to 3', is: S, 3A, 3B, E, M, N, and HP. For example, modified orders for the replicon RNA, when the helper RNA(s) contains the E gene, may include: S, 3B, M, N, HP and 3A; 3A, 3B, M, N, HP and S; S, 3A, 3B, N, Hp, and M; etc. In other embodiments, the E gene may be provided alone on the replicon RNA, and the helper RNA(s) may contain the genes described above in the orders given above. Modified orders for the replicon RNA, when the helper RNA(s) contains the M and N (in natural or reverse order) genes, may include: 3A, 3B, E, S and HP; S, E, 3A, 3B, and HP; S, 3A, 3B, E, and HP; S, E, HP, 3A, and 3B, etc. In other embodiments, the replicon RNA may contain the M and N genes (in natural or reverse orders), and the remaining genes may be provided on the helper RNA(s) in orders such as given above. In still other embodiments, where the helper RNA(s) contains the S gene, the replicon RNA may contain the remaining genes in the order 3B 3A, E, M, N, and HP; 3A, 3B, E, N, M, and HP; 3B, 3A, E, N, M, and HP; etc. Again, the replicon RNA may contain the S gene, and the helper RNA(s) may contain the remaining genes in the orders given above. The 3A, 3B, and HP genes are nonessential and some or all may be deleted, or they may be included in an alternate order to serve as attenuating mutations. The genes may be divided among multiple helper RNAs, some or all of which contain gene order rearrangements. The foregoing examples are merely illustrative, and numerous additional variations will be readily apparent to those skilled in the art.

In other embodiments, an attenuating mutation can be introduced by deleting one or more of the nonessential genes 3A, 3B, and HP.

In additional embodiments of the helper cells of this invention, the helper RNA(s) and/or the replicon RNA can comprise a promoter.

Additionally provided herein as an embodiment of this invention is a DNA encoding a helper RNA of this invention and a helper cell comprising said helper RNA-encoding DNA, as well as a DNA encoding a replicon RNA of this invention and a helper cell comprising said replicon-encoding DNA. The DNA can be present in the cell transiently or in a stably transformed state. The DNAs of this invention can further comprise a promoter to direct the transcription of the helper RNA and the replicon RNA, respectively, in the helper cell.

A further embodiment of this invention is a method of making infectious, multiplication-defective, coronavirus particles, comprising: a) providing the helper cells of this invention: and b) producing coronavirus particles in the helper cell. Optionally, the particles can be collected from the cells.

In certain embodiments, the helper cell can be provided by introducing the replicon RNA and/or the helper RNA into the helper cell by electroporation. However, the replicon RNA and/or helper RNA, as well as their respective DNAs can be introduced into the helper cell according to any methods known in the art for introducing nucleic acid into a cell. The nucleic acids can be present in the helper cell transiently or as stable transformants.

The present invention additionally provides infectious coronavirus particles produced by the methods of this invention.

The step of producing the infectious viral particles in the helper cells can also be carried out using conventional techniques. See e.g., U.S. Pat. No. 5,185,440 to Davis et al., PCT Publication No. WO 92/10578 to Bioption AB, and U.S. Pat. No. 4,650,764 to Temin et al. (although Temin et al. relates to retroviruses rather than coronaviruses). The infectious viral particles may be produced by standard cell culture growth techniques.

The step of collecting the infectious coronavirus particles can also be carried out using conventional techniques. For example, the infectious particles can be collected by cell lysis, or collection of the supernatant of the cell culture, as is known in the art. See e.g., U.S. Pat. No. 5,185,440 to Davis et al., PCT Publication No. WO 92/10578 to Bioption AB, and U.S. Pat. No. 4,650,764 to Temin et al. (although Temin et al. relates to retroviruses rather than coronaviruses). Other suitable techniques will be known to those skilled in the art. Optionally, the collected infectious coronavirus particles can be purified if desired. Suitable purification techniques are well known to those skilled in the art.

In some embodiments, VEE replicon vectors can be used to express coronavirus structural genes in producing combination vaccines. Dendritic cells, which are professional antigen-presenting cells and potent inducers of T-cell responses to viral antigens, are preferred targets of VEE and VEE replicon particle infection, while SARS coronavirus targets the mucosal surfaces of the respiratory and gastrointestinal tract. As the VEE and SARS replicon RNAs synergistically interact, two-vector vaccine systems are feasible that may result in increased immunogenicity when compared with either vector alone. Combination prime-boost vaccines (e.g., DNA immunization and vaccinia virus vectors) have dramatically enhanced the immune response (notably cellular responses) against target papillomavirus and lentivirus antigens compared to single-immunization regimens (Chen et al. (2000) *Vaccine* 18:2015-2022; Gonzalo et al. (1999) *Vaccine* 17:887-892; Hanke et al. (1998) *Vaccine* 16:439-445; Pancholi et al. (2000) *J. Infect. Dis.* 182:18-27). Using different recombinant viral vectors (influenza and vaccinia) to prime and boost may also synergistically enhance the immune response, sometimes by an order of magnitude or more (Gonzalo, et al. (1999) *Vaccine* 17:887-892). Thus, the present invention also provides methods of combining different recombinant viral vectors (e.g., VEE and SARS) in prime boost protocols.

The examples, which follow, are set forth to illustrate the present invention, and are not to be construed as limiting thereof. In the following examples, mM means milli molar, µg means microgram, µl means milliliter, µl means microliter, V means volt, µF means microfarad, cm means centimeter, h means hour, ORF means open reading frame, GFP means green fluorescent protein, PBS means phosphate-buffered saline, M means molar, means second, nt means nucleotide, and min means minute.

EXAMPLES

Example 1

Production of Full-Length Infectious cDNA of SARS Coronavirus

Virus and Cells. The Urbani, Tor-2 and Tor-7 Canadian strains of SARS-CoV were propagated on VeroE6 cells in Eagle's MEM supplemented with 10% fetal calf serum and kanamycin (0.25 µg/ml) and gentamycin (0.05 µg/ml) at 37° C. in a humidified $CO_2$ incubator (Tor isolates were kindly provided by H. Feldmann). For virus growth, cultures of VeroE6 cells were infected at a multiplicity of infection (MOI) of 5 for 1 hr and samples were titered by plaque assay. At 1 hr postinfection, some cultures were treated with the cysteine protease inhibitor E64-d ({2S, 3S}-trans-epoxysuccinyl-L-leucylamido-3-methylbutane ethyl ester) at a concentration of 500 µg/ml. Virus plaques were visualized by neutral red staining at 2 days postinfection.

Strategy for Cloning the SARS-CoV cDNAs. Reverse transcription was performed using Superscript II™, oligodeoxynucleotide primers and intracellular RNA from SARS infected cultures [17, 18]. The cDNA was denatured for 2 min at 94° C. and amplified by PCR with Expand Long TAQ polymerase (Boehringer Mannheim Biochemical) for 25 cycles at 94° C. for 30 sec, 58° C. for 25-30 sec and 68° C. for 1-7 min. The amplicons were cloned into Topo II TA (Invitrogen) (SARS subclones D-F) or in pSMART vectors (Lucigen) (SARS subclones A-C). All cDNAs were assembled as consensus sequences based on independent sequence analysis of 4-7 sibling clones and the reported Urbani sequence [8]. The following primers were used in the isolation of the SARS A subclone (forward: tactaatacgactcactatagatattag-gtttttacctacccagg-1, SEQ ID NO:22; reverse: acaccatagtcaac-gatgcc-4452, SEQ ID NO:23), SARS B subclone (forward: gcctatatgcatggatgttagat-4359, SEQ ID NO:24; reverse: tgaaccgccacgctggctaaacc-8727), SEQ ID NO:25, SARS C subclone (forward: agccagcgtggcggttcatac-8710, SEQ ID NO:26; reverse: aggcctcttgggcagtggcataag-12,085, SEQ ID NO:27), SARS D subclone (forward: actgcccaagatgcctat-gagc-12,070, SEQ ID NO:28; reverse: cagccaggagggcagact-tcacaacc-18,939, SEQ ID NO:29), SARS E subclone (forward: gtctgccctcctggctgataagtttccag-18,923, SEQ ID NO:30; reverse: gagcagccgtgtaggcagcaat-24066, SEQ ID NO:31) and SARS F subclone (forward: attgctgcctacacggctgctc-24,045, SEQ ID NO:32; reverse: (ttt)$_7$gtcattctcctaagaagc-29,710, SEQ ID NO:33).

To repair sibling clones, primer pairs were designed that contained a Class IIS restriction enzyme (e.g., AarI). Using high fidelity PCR, the consensus portions of different sibling clones were amplified, digested with AarI and ligated into plasmid. The AarI junctions were designed to seamlessly link consensus fragments, resulting in the production of a full-length cDNA [17]. Using an automated ABI DNA sequencer, 2-3 candidate DNAs were sequenced to identify the consensus clone.

Systematic Assembly of a Full-Length SARS-CoV cDNA. The SARS A through F inserts were restricted, separated through 0.8% agarose gels, visualized with a Darkreader Lightbox (Claire Chemical), excised, and purified using the Qiaex II DNA purification kit. The SARS A+B, C+D and E+F subclones were ligated overnight and isolated [17, 18]. The SARS AB+CD+EF cDNAs were ligated overnight at 4° C., phenol/chloroform extracted and precipitated under isopropyl alcohol. Full-length transcripts were generated in vitro as described by the manufacturer (Ambion, mMessage mMachine) with certain modifications [17]. For SARS N transcripts, 1 µg of plasmid DNA encoding the N gene (primer: 5'-nnggcctcgatggccatttaggtgacactatagatgtctgataatggacccc-aatc-3'; SEQ ID NO:34 and reverse primer 5-nnnttttttttttttttttttttttttttatgcctgagttcaatcagcag-3; SEQ ID NO:35) was transcribed by SP6 RNA polymerase with a 2:1 ratio of cap analog to GTP.

Transfection of Full-Length Transcripts. RNA transcripts were added to 800 µl of the BHK cell suspension (8.0×10$^6$) in an electroporation cuvette and three electrical pulses of 850 V at 25 µF were given with a Gene Pulser II electroporator (BioRad) [17, 18]. The transfected BHK cells were seeded with 1.0-2.0×10$^6$ uninfected Vero E6 cells in a 75 cm$^2$ flask and incubated at 37° C. for 2 days. Virus progeny were then passaged in Vero E6 cells at ~30 hr intervals and purified by plaque assay.

Detection of Marker Mutations Inserted in icSARS-CoV. Intracellular RNA was isolated from either wild type or icSARS-CoV infected cells at 24 hrs postinfection. After RT-PCR, a 1668 nt amplicon (nt position 1007-2675) was obtained, spanning the Bgl1 site at position 1572 that had been ablated in the icSARS-CoV component clones, but not wild type SARS-CoV. Other PCR products included a 799 nt amplicon spanning the SARS-CoV B/C junction (nt position 8381-9180), a 544 nt amplicon (nt position 11,721-12,265) spanning the SARS-CoV C/D junction, a 652 nt amplicon spanning the SARS-CoV D/E junction, and a 1594 nt amplicon (nt position 23,665-25,259) spanning the SARS-CoV E/F junction. The 1594 nt SARS E/F junction-containing amplicon was subcloned and sequenced.

RT-PCR of Leader-containing Transcripts. Leader containing amplicons were obtained from wild type and icSARS-CoV infected cells using primers at the 3' end of the genome (5'-tttttttttttttttttttttgtcattctcctaagaagc-3'; SEQ ID NO:36)) and in the SARS leader RNA sequence (5'-aaagccaaccaacctc-gatc-3'; SEQ ID NO:37)). Leader-containing amplicons were excised from gels, subcloned into TopoII vectors and sequenced using appropriate primers.

Assembly of Coronavirus Full Length cDNAs. Rapid response and control of exigent emerging pathogens requires an approach to rapidly generate full-length infectious cDNAs that afford genetic control over the genome. Full-length infectious cDNAs were isolated for TGEV, HCoV-229E, IBV and MHV strain A59 [17-21]. The approach described herein has been to isolate a panel of cDNAs spanning the entire coronavirus genome, which can be systematically and directionally assembled into a genome-length cDNA by in vitro ligation [17, 18].

Patterned after the strategy devised for TGEV [18], the SARS genome was cloned by RT-PCR as six contiguous subclones linked by unique Bgl I restriction endonuclease sites. Bgl I is a class IIS restriction endonuclease that cleaves the symmetrical sequence GCCNNNN↓NGGC (SEQ ID NO:38), but leaves 64 different asymmetrical ends. Consequently, pairs of contiguous subclones encoded junctions that allow unidirectional assembly of intermediates into a full-length cDNA. Two Bgl I junctions were derived from sites encoded within the SARS-CoV genome at positions nt 4373 (A/B junction) and nt 12,065 (C/D junction) [8-10]. A third Bgl I site at position nt 1557 was removed and new Bgl I sites were inserted by the introduction of silent mutations into the SARS-CoV sequence at positions nt 8700 (B/C junction), nt 18,916 (D/E junction) and at nt 24,040 (E/F junction). These mutations are shown in the Sequence Listing as SEQ ID NOs:10-14. SARS-CoV sequence toxicity was circumvented by disruption of toxic domains and the use of stable cloning vectors [17]. The resulting cDNAs include SARS A (nt 1-4436), SARS B (nt 4344-8712), SARS C (nt 8695-12,070), SARS D (nt 12,055-18,924), SARS E (nt 18,907-24,051) and SARS F (nt 24,030-29,736) subclones. The SARS A subclone contains a T7 promoter and the SARS F subclone terminates in 21 Ts, allowing for in vitro transcription of capped, poly-adenylated transcripts.

Numerous mutations were noted in each of the four to seven sibling subclones encoding a given SARS cDNA. To rapidly assemble a consensus clone, the "No See'm" approach was used with another group of class IIS restriction endonucleases that cut at asymmetric sites and leave asymmetric ends. These enzymes cut strand specific and allow the seamless ligation of cDNAs with the loss of the restriction site used to join two component clones [17]. As illustrated with the SARS F sibling clones, primer pairs were designed that contained terminal Aar I (CACCTGCNNN↓NNNN, SEQ ID NO:39) sites that flanked each of the various consensus portions of different sibling clones. In some instances (amplicons 3 and 2 in sibling clones 1 and 4, respectively), primers were also designed to repair specific mutations located near the ends of a given amplicon. The combination of high fidelity PCR, oligonucleotide primer repair and the seamless ligation of sequence fragments [17], rapidly generated Urbani consensus cDNAs for each of the SARS A, B, C, D, E and F subclones. Silent changes retained in the full length construct included an A to G change at nt position 6460, a T to C change at nt position 14,178, a T to C change at nt position 15,740, a C to T change at nt position 19,814, an A to G change at nt position 20,528 and a T to C change at nt position 20,555. These mutations are shown in the Sequence Listing as SEQ ID NOs:15-21.

Rescue of Molecularly Cloned SARS-CoV. To build full length SARS-CoV cDNAs, individual subclones were digested with the appropriate restriction enzymes, ligated together in vitro and used as template for in vitro transcription with the T7 RNA polymerase. Since N transcripts enhance RNA transfection efficiencies of TGEV and MHV [17,22], and are essential for IBV transcript infectivity [20], SARS-CoV full-length transcripts were either electroporated into cells alone or mixed with SARS-CoV N transcripts. Within 48 hrs post transfection, SARS-CoV infected cells were detected by fluorescent antibody staining. Infectious virus (icSARS-CoV) titers approached $1.0 \times 10^6$ PFU/ml at 48 hrs postinfection in the mixed transcript transfected cultures. Recombinant viruses were also detected in cultures transfected with genome-length SARS transcripts alone, but titers were reduced. As described with MHV [17], SARS N transcripts may enhance infectivity of SARS full-length transcripts, but are not essential. The molecular cloned viruses were plaque purified in VeroE6 cells and produced similar sized plaques as wild type SARS Urbani.

icSARS CoV Marker Mutations. Rescued icSARS-CoV, but not wild type SARS-CoV should contain several Bgl I sites that were engineered as junctions between the SARS B/C, D/E and E/F subclones and lack the Bgl I site at nt position 1557. Intracellular RNA was isolated from infected cultures, RT-PCR amplified using primer pairs flanking these various sites and subjected to restriction fragment length polymorphism (RFLP) analysis with Bgl I. Clearly, icSARS-CoV contained the marker mutations inserted within and between the component clones. To confirm these findings, selected amplicons were cloned and sequenced, demonstrating that the icSARS-CoV originated from transcripts derived from the full-length cDNA construct.

Phenotype of Rescued icSARS-CoV. Cultures of cells were infected with an MOI of 5. In untreated cultures, intracellular RNA and virus titers were determined as described herein. At 1 hr, cultures were treated with E64-d at a concentration of 500 µg/ml and virus titers determined by plaque assay in VeroE6 cells.

The recombinant icSARS CoV isolate replicated as efficiently as wild type Urbani, but less efficiently than the Canadian isolates, Tor-2 and Tor-7 SARS-CoV. These data demonstrate that the introduced alterations were not debilitating to virus growth in culture as both replicated to titers of about $10^7$ within ~24-48 hrs postinfection. To further characterize the transcription strategy of SARS-CoV, intracellular RNA was isolated from Urbani wild type and icSARS-CoV-infected cultures. Following RT-PCR amplification of leader containing amplicons, sequence analysis indicated that wild type and icSARS-CoV subgenomic transcripts originated at identical CS sites, defined by the core sequence ACGAAC, as illustrated by leader-containing transcripts encoding X1, E, M, X3 and X4. SARS S and N encoding transcripts initiated subgenomic transcription at similar CS sites. This sequence represents a truncation of the AAACGAAC CS site that had been predicted by Rota et al., 2003 and is different from the group I, II and III coronavirus CS sequences, CUAAAC (TGEV), UCTAAAC (MHV), and CUUAACAA (IBV), respectively. Although previous studies had suggested that the SARS E protein and ORF X3 might be expressed from polycistronic mRNA, these findings indicate that independent transcripts are initiated at the core CS sequence ACGAAC noted at nt positions 26,109 for E transcripts and 26,913 for ORF X3 transcripts, respectively.

In vitro inhibition of SARS-CoV Replication. Given the high virulence of SARS-CoV infection in humans, antiviral drugs will be required to reduce the scope and severity of disease. In MHV, the cysteine proteinase inhibitor E64-d blocks replicase polyprotein processing and thereby inhibits viral RNA synthesis and virus growth [11]. To determine if icSARS-CoV was susceptible to the inhibitory effects of E64-d, growth analysis was performed in the presence and absence of 500 µg/ml of drug. In the absence of E64-d, wild type and icSARS-CoV grew to equivalent titers of ~$1.0 \times 10^7$ PFU/ml after 24-48 hrs postinfection. Treatment of cells with a single dose of E64-d at 1 hr pi resulted in almost complete elimination of viral CPE and viral antigen expression and a significant ~3-4 log reduction in virus yield for both wild type SARS-CoV and icSARS-CoV at 24 and 48 hrs postinfection.

Example 2

Development of SARS Virus Single Hit Replicon Vector Vaccines

SARS Replicon Particle Assembly. Viral replicon particles are single hit vectors that are incapable of spreading beyond the site of initial infection and are novel vaccine candidates for human and animal diseases. The SARS single hit replicon particles will be produced in the helper cells as described herein. Specifically, the SARS E, M, S and/or N structural proteins will be produced in helper cells from helper RNA or DNA, e.g., VEE VRPs, noncytotoxic Sindbis virus replicons, BAC or vaccinia vectors, CMV eukaryotic expression plasmids, etc., using standard protocols in order to provide SARS coronavirus structural proteins in trans for assembly of coronavirus replicon particles in helper cells. The SARS E, M, S and/or N coding sequences will be deleted from the replicon RNA and one or more heterologous coding sequences will be inserted into the replicon RNA. The replicon RNA will be packaged into coronavirus particles in the helper cells. Populations of the particles produced in the helper cells as described herein can be tested for the ability to maintain only a single round of infection by passage on coronavirus-permissive cells.

Cell Preparation: VERO E6 Cells Expressing SARS E protein or M glycoprotein. Sindbis noncytotoxic replicon vectors (pSinRep) induce persistent infections in VERO and BHK cells, and constitutively express resistance to puromycin and a foreign gene of interest. these vectors have been used to constitutively express human CEA receptors in BHK cells, converting these cells to susceptible hosts for the MHV host range mutant V51. SARS E and M coding sequences will be inserted into pSinRep or CMV expression vectors, VERO E6 cells will be transfected and selected with puromycin (or G-418 for CMV vectors) for clones that stably express high concentrations of selected SARS structural proteins. The SARS E protein and M glycoprotein will also be expressed from VEE VRPs, and inoculated into mice for the production of monospecific antisera against each of these proteins. VEE VRPs have been used to produce high titer antiserum against Norovirus antigens, as well as the TGEV M and N proteins. Using flow cytometry and polyspecific antisera directed against the SARS E protein and M glycoprotein, enrichment for cells expressing high or low levels of the desired protein will be carried out. As VERO E6 cells are susceptible hosts for SARS replication, these cells will allow for additional rounds of infection with SARS VRPs with subsequent packaging and release of progeny VRPs.

SARS Vector Replicon Design: First, a determination will be carried out regarding whether any of the group specific ORFs (X1-X5) can be deleted and replaced with either luciferase or GFP. Specifically, the focus will be on ORFs X1, X4 and X5 because of their position in the genome and the possibility that they encode luxury functions that are not essential for replication in vitro. The overall goal is to identify a group specific ORF that can be deleted and replaced with an indicator gene that allows for easy visualization of replication and gene expression. Such mutants will also be of value for drug screening. Essential points in these experiments are to leave the CS and surrounding flanking sequences intact, so that foreign gene expression is maximized. A second issue is that foreign genes may encode noncanonical CS sites that are transcriptionally active. To circumvent this problem, noncanonical "TAAACGAAC" CS sites in GFP or luciferase will be altered at the $3^{rd}$ codon to prevent spurious expression of cryptic subgenomic RNAs. Growth curves will be performed to determine if rescued viruses replicate at equivalent levels with wild type SARS coronavirus and cultures will be examined for GFP or luciferase expression. The most viable of the ORFX1-X3 constructs will be used for future studies.

SARS replicon genomes will be assembled by systematically deleting the E and/or M genes using the No See'm Strategy described in Yount et al. (2002). These constructs will be built within a backbone that encodes the luciferase gene as described above. In the case of M, the M ORF will be deleted and GFP or luciferase will be inserted, leaving the M CS site intact. In the latter two instances, this approach will allow for coordinated and equivalent levels of expression of upstream genes, while inserting a heterologous foreign nucleic acid for easy quantitation of VRP titers.

SARS replicon constructs will be assembled as described, except that Not 1 sites will be encrypted at the 5' end of Clone A and 3' end of Clone F. Following assembly, the DNA will be restricted with Not 1 and inserted into BAC vectors. This allows for BAC propagation in bacteria and circumvents tedious reconstructions of SARS replicon constructs. The stability of these BAC vectors will be evaluated by serial passage and sequence analysis.

Stable VRP Single Hit Expression Vectors. Successful development of stable single hit SARS replicon vectors will be demonstrated by standard approaches. To titer VRP stocks, quantitative methods have been developed that rely on serial dilution and counting cells expressing nucleic acid encoding GFP or viral and heterologous antigens by fluorescent antibody staining in a number of randomly chosen but defined ($\mu m^2$) fields. Titers are estimated by counting the number of fluorescent cells in a known area, statistically determining the mean and then adjusting for total area of the plate. Alternatively, viral VRP stocks can be quantified by endpoint PCR or quantitative PCR, potentially compromised by an unknown particle/PFU ratio. It is expected that the SARS M glycoprotein and E protein will be essential for assembly and release, based upon experience with TGEV. However, it has been suggested that SARS is more closely akin to the group II coronaviruses like MHV, so it is also possible that SARS E protein may be nonessential for packaging and release.

A number of VRP phenotypes will be analyzed. The SARS VRPs lacking E protein should be single hit vectors in VERO E6 cells, but should serially passage in VERO E6 cells expressing E in trans. Similarly, SARS VRPs lacking M glycoprotein should be packaged and released from VERO E6 cells expressing M, but not E. SARS VRP protein expression will be determined by Western Blot assays, to determine if E or M excision alters expression levels of other SARS structural and nonstructural ORFs as compared with wild type. This will be accomplished with antiserum generated from the VEE VRPs inoculated into mice. GFP or luciferase expression will be measured by fluorescence and Western Blot assays, using commercially available antibodies and screens. The ability of different packaging cell lines (e.g., alphavirus vectored, CMV vectored) to support the production of high titered SARS VRPs will be compared. RNA recombination is always a concern with a vectored packaging cell lines, so progeny VRPs will be isolated and passaged several fold in a packaging cell line and passaged onto control cells lacking the appropriate structural protein in trans.

SARS-CoV Recombinant Protein Assays. Venezuelan equine encephalitis virus (VEE) is a member of the alphavirus genus of the family Togaviridae. The virus consists of an icosahedral nucleocapsid composed of 240 copies of the capsid protein (C) surrounded by an envelope containing spikes formed from two glycoproteins, E1 and E2. The VEE genome is a positive sense single stranded RNA of 11.5 kb, which replicates through a minus strand intermediate. A subgenomic 26S mRNA, transcribed from the 26S promoter resident internally on the minus strand, encodes the structural proteins and is synthesized at ~10× molar excess relative to genome. Four nonstructural replicase proteins (nsp1-4) mediate all transcription steps, which occur in the cell cytoplasm, and virus budding is at the plasma membrane.

The VEE genome, when introduced into a cell, can be viewed as a highly efficient machine for the production of large amounts of its own structural proteins through the transcription of a subgenomic mRNA encoding these proteins. If a nucleic acid of interest is substituted for the structural protein genes, then the VEE replicative machine expresses high levels of that gene product. In the VEE replicon vaccine vectors, an immunizing gene is substituted for the structural protein genes. Upon electroporation of replicon RNA into cells, the VEE replication machinery produces high levels of the subgenomic mRNA and vectored gene product. However, as the structural protein genes are not present in the replicon RNA, no new virus particles are released. One can package the replicon into "replicon particles" by supplying the structural proteins in trans from helper RNAs. The replicase proteins encoded on the replicon RNA provide the machinery for replicating the helper RNAs, while the structural proteins encoded by the helpers encapsidate and envelope the replicon RNA. Only the replicon RNA is packaged into VEE replicon particles (VRP), because only the replicon RNA contains the cis-acting packaging signal. When VRPs infect another cell, either in culture or in vivo, the replicon RNA synthesizes high levels of the gene product, but no new replicon particles are formed due the absence of the structural protein genes. Therefore, these vectors are not cell to cell transmitted.

Alphavirus Vectored Expression of Recombinant SARS-CoV Proteins. The SARS S, E, N, M, and the group specific ORFs were cloned into VEE and packaged into VRPs. Following infection with VRP-S and VRP-N, cultures were radiolabeled with $^{35}$S-Met from 12-16 hrs post infection, resulting in the expression of a SARS 46 kDa N protein and a ~177/205 kDa S glycoprotein. VRP-E and VRP-M also expressed appropriately sized products using these conditions. Various VRP-group specific ORFs have also been inoculated into mice and cells. These data suggest 1) VRP immunization induced significant antibodies to authentic S protein expressed from three different SARS isolates or with the rescued molecularly cloned icSARS-CoV (Similar results have been obtained with VRP-E, VRP-M and VRP-N antiserum), 2) patient serum was reactive with the S protein expressed by the VRPs and by icSARS-CoV, and 3) SARS ORF3a is immunogenic and detected by convalescent patient serum. The SARS-S gene, designed to produce either membrane-bound or secreted forms, is also available and antiserum against the group specific ORFs is being raised in mice. SARS-CoV PRNT$_{90}$ titers were ~1:905 with VRP-S vs. <1:80 with VRP-HA (flu HA).

VEE replicon particles (VRPs) expressing the SARS S protein have been constructed and antigen derived from cells infected with these vectors was initially evaluated as a target for EIA assays. Vero cells were infected with VRP-SARS(S) at a MOI of 6.0 for 15 hours and the cells were lysed with 0.5% NP-40. The optimal antigen concentration was found to be a 1:300 dilution. Using this assay, the human convalescent serum was shown to have an endpoint (the last dilution with an O.D. reading≧0.200) anti-SARS virus IgG titer of 1:3200, while serum from two uninfected control individuals had titers of <1:200. Sera from mice that received a primary inoculation of VRP-SARS(S) in the rear footpads, followed by a boost at week 5 post primary inoculation, were evaluated at two weeks post boost and ranged from 1:1600 to 1:6400 (ave.=3300, n=12), while control animals that received VRP expressing the influenza virus A/PR/8 HA gene had titers of 1:100-1:200 (ave=150, n=2). Similar assays were developed for other SARS structural protein, providing a unique panel of reagents to measure immune responses following SARS-CoV infection in rodents.

To perform CTL assays and other immunologic experiments, the SARS S and N proteins were inserted into vaccinia virus vectors.

Example 3

Deletion of SARS Virus Group Specific ORFs

The SARS virus genome encodes several group specific ORFs at the 3' end of the genome including ORFs 3a/b (X1, X2), 6 (X3), 7a/b (X4), 8a/b (X5) and 9b. By analogy with other coronaviruses, it is believed that one or more of these group specific ORFs encode luxury functions that do not specifically contribute to virus replication in vitro but disable virus pathogenesis in vivo. This invention includes the systematic and combined deletion or knocking out of expression of these various ORFs and rescue of the molecularly cloned viruses containing these genetic lesions. All recombinant viruses are obtained following transfection in Vero cells similar to those certified for cultivation and production of human virus vaccines.

Protocols are carried out wherein the group specific nucleic acid sequences designated ORFs 3a/b, 6, 7a/b, 8 and 9a are deleted. Initially, each of the ORFs is systematically deleted, either by deletion of individual ORFs (ORF3a-X1, ORF6-X3, ORF7a, ORF7b, ORF8a, ORF8b), entire TRS cistrons (e.g., ORF3a/b; ORF7a/b-X4; ORF8a/b-X5), or by mutations that specifically ablate ATG start codons and introduce premature stop codons in an overlapping gene (ORF3b-X2, ORF9b). For deletions, a particular gene and its corresponding CS site (when appropriate) is excised, and the flanking upstream and downstream ORFs seamlessly stitched together. For example, two amplicons are isolated using primer pairs that are designed to contain external Bsa1 sites that are lost but leave complementary four nucleotide asymmetric sites that direct seamless ligation of the SARS CoV ORF 6 and ORF 8 CS sites, simultaneously deleting the entire ORF 7a/b sequence. The ATG start is knocked out and a premature stop is inserted into ORF3a (X1) and ORF6 (X3) because virus phenotypes are not confounded by changes in transcription.

SARS-CoV from civet cats and human patients early in the epidemic contained a 29 bp insertion in ORF8a/b that resulted in a single ORF 8 protein. As it has been suggested that this deletion may have enhanced SARS-CoV pathogenicity in humans and perhaps transmission, the Civet cat full length ORF8 by fusing ORF8a and 8b will be reconstructed by insertion of the 29 bp sequence identified in this virus, with the expectation that the addition of a full-length civet cat ORF8 will attenuate pathogenesis.

In mRNA3 transcripts encoding ORF 3a, ORF 3b is encoded as an overlapping out of frame 124 amino acid ORF that cannot be deleted without removing a significant portion of ORF 3a. If both ORFs encode luxury functions in vitro, recombinant viruses lacking each ORF will be rescued separately. While deletion of ORF 3a is straightforward, ORF 3b also contains ten in frame ATG start codons, thus selective mutagenesis of ORF3b start codons will only N-terminally truncate ORF X3b (if internal ATGs translate efficiently). Consequently, premature ORF3b stop codons will be introduced into the sequence: "$^{25735}$CAGTGTCACAGAT" (SEQ ID NO:40) to "CAGTGTGACAGAT" (SEQ ID NO:41). This alteration introduces a stop codon that truncates ORF3b after 24 amino acids, but doesn't change the protein sequence of ORF3a. A global approach is to combine this termination codon with additional mutations that destroy the ORF3b ATG start codon at residues 1 and 2, but leave the ORF 3a amino acid sequence intact. Changes will be introduced into the SARS CoV F subclone, which will be re-sequenced and then reassembled into full-length cDNAs. A similar strategy will be used to knockout ORF9b in mRNA9, which also encodes the N protein (ORF9a). Following in vitro transcription, full-length transcripts will be mixed with N transcripts (to enhance infectivity), introduced into cells by electroporation. Rescued viruses will be quantified by plaque assay.

Deletion of SARS-CoV Group Specific Genes. The SARS-CoV ORF3a (X1), ORF 6 (X3) and ORF 7a/b (X4) domains have been deleted and recombinant viruses have been isolated that replicated in Vero cells. Moreover, ORF7a/b has been replaced with luciferase under control of the 7a/b TRS and is expressed in icSARS-CoVΔX4 infected cells. Following transfection, leader containing transcripts were identified, and ORF3a/ORF6/ORF 7a/b deletions were confirmed by RT-PCR and sequencing. Passage of progeny virions revealed abundant viral protein expression in icSARS-CoV, icSARS-CoV ΔX3 and ΔX4-infected cultures, although protein expression in icSARS-CoV ΔX1 infected cultures was less robust. At this time it is not possible to determine if this reflected a lower initial transfection efficiency or lower rates of virus replication. The SARS-CoV X1 and X3 ORFs encode interferon antagonist genes. It seems likely that virus growth might be boosted in certain cell types by providing IFN antagonist genes in trans, should the ΔX1 molecularly cloned variant be highly attenuated in replication. Based on findings with other highly pathogenic viruses, the deletion of IFN antagonists should attenuate virus replication and pathogenesis in vitro. More importantly, the data demonstrate the feasibility of using 1) the SARS-CoV cDNA reverse genetics to modify the SARS-CoV genome, 2) that several group specific genes of SARS-CoV encode luxury functions for in vitro growth (ORF3a, ORF3b, ORF6 and ORF7a and ORF7b) and 3) it can be determined if deletion of SARS-CoV IFN antagonist genes and group specific genes attenuate pathogenesis in vivo in the mouse, ferret and eventually primate model for SARS-CoV pathogenesis. Deletion of ORF3a/b (X1 and X2 protein) also results in the rescue of viable progeny viruses, supporting the notion that deletion of multiple accessory (group specific) ORFs still allow for the recovery of robust viruses. All deletion mutants tested replicate to titers in excess of $10^7$ PFU/ml in 32 hrs. We have also produced a SARS-CoV isolate expressing GFP from the ORF7a/b location. Recombinant viruses encoding either the Luciferase or GFP indicator molecules provide a rapid screen for identifying compounds that block SARS-CoV replication and gene expression. Reduced expression of either luciferase or GFP in the presence of drug allows for rapid identification of compounds with antiviral activity.

SARS-CoV Minimal Genome Recombinants/Multiple Accessory Gene Knockouts. In addition to deleting each of the group specific ORFs, the nonessential ORFs can be deleted in combination. The goal is to produce a minimal SARS genome lacking as many of the group specific ORFs as possible (SARS Δ3a/b,6,7a/b,8a/b), while retaining adequate levels of virus replication in vitro. In the case of MHV, deletion of group specific ORFs significantly attenuated MHV pathogenesis in mice and recombinants lacking combinations of group specific genes were generally more attenuated than isolates lacking a single group specific ORF, but not always. No experiments were conducted to determine if mutant-infected animals were protected against wild type challenge.

All TGEV and MHV group specific ORFs were nonessential for in vitro replication and at least ORF3a (X1), ORF3a/3b (X1/X2), ORF6 (X3) and ORF7a/b (X4) are nonessential for SARS-CoV replication. Thus, most, if not all, of the SARS virus group specific ORFs are believed to be capable of being deleted, resulting in a minimal genome that should be attenuated in vivo. Following mutagenesis of the SARS F subclone, assembly of the cDNAs and electroporation of transcripts, recombinants will be rescued from transfected cultures.

Other attenuating mutations. Mutations can be inserted virtually anywhere in the SARS-CoV genome including the replicase, the replicase ribosome frame shifting site, 5' and 3' transcriptional regulatory sequences, and alterations in the SARS-CoV structural genes as examples.

Characterization of Rescued Viruses. Rescued viruses will be harvested between 24 to 36 hrs post transfection and plaque purified prior to isolating low passage stocks in Vero E6 cells. During production of the recombinant virus stocks, passage numbers will be kept to a minimum so that potential $2^{nd}$ site compensatory changes that restore virus replication and fitness do not have time to evolve and severely complicate an accurate interpretation of the effects of particular changes on SARS replication fitness.

Genotype Analysis. Plaque purified molecularly cloned viruses will be inoculated into Vero E6 cells and intracellular RNA isolated using Trizol reagents. Using RT-PCR and primer-pairs that flank the various group specific ORFs, the presence or absence of group specific ORFs will be determined in recombinant viruses by size analysis of PCR product and by sequence analysis of amplicons. The S gene through the 3' end of the genome will also be cloned and sequenced to identify potential $2^{nd}$ site alterations that may have evolved in response to group specific gene deletion. As the gene order has been restructured by deleting various group specific ORFs, it is possible that these rearrangements may restructure TRS networks and the function of individual CS sites involved in the synthesis of a particular subgenomic transcript (most likely a gene upstream or downstream of the deleted ORF). To determine if subgenomic RNA synthesis originated from the appropriate CS sites, leader containing amplicons that flank the various group specific ORF deletions will be RT-PCR cloned and sequenced.

Phenotype Analysis. There are no precise in vitro correlates to in vivo SARS pathogenesis, so a variety of phenotypic characteristics will be measured to provide a global view of rescued-virus fitness in cell culture. Virus growth will be evaluated in culture, as well as plaque morphology. Rescued molecularly cloned viruses will be analyzed for SARS protein expression by immunoprecipitation or Western blots using antiserum from mice inoculated with alphavirus VRPs encoding the various SARS virus structural and group specific ORFs. By immunoblot, the expression of the structural and various group specific nonstructural proteins that are produced following gene deletion will be measured. Northern Blot analysis will be used to identify the viral mRNAs and determine if selected gene deletion(s) alter the molar ratio of the upstream and downstream viral mRNAs. In selected instances, cultures will be radiolabeled with $^3$H-uridine and the labeling kinetics of viral mRNAs and replicative forms RNAs analyzed. These experiments will also determine 1) deletion effects on RNA expression patterns, and 2) deletion effects on relative molar ratios of mRNA. These experiments will also determine if full length and subgenomic length replicative form RNAs are present in SARS virus infected cells, as shown with other group I and II coronaviruses.

Stability of Rescued Virus with Passage: Compensatory Evolution. TGEV deletion and gene rearranged viruses have been shown to rapidly evolve $2^{nd}$ site compensatory changes that restore virus growth fitness in vitro. It is believed that the $2^{nd}$ site changes will subtly alter coronavirus gene networks and protein-protein interactions to restore virus growth in vitro, yet enhance attenuation in animal models by subtly changing the affinity of these highly orchestrated interactions that influence replication in the human host. To test this hypothesis, the most debilitated rescued viruses that have deletions in one or more group specific ORFs will be tested. Recombinant viruses will be inoculated onto Vero E6 cells and progeny viruses passaged into fresh cultures at 24 hrs intervals. After 15-20 passages, progeny virus will be plaque purified and compared to wild type virus by growth curves and gene expression patterns. The corresponding SARS E and F genome fragments will be cloned and sequenced. Consensus SARS E and F subclones will be assembled into the full length cDNA to identify the exact $2^{nd}$ site mutations that restore replication fitness. In the case of multiple alterations, the mutation that confers the strongest fitness recovery phenotype will be tracked. Although replicase mutations may also restore growth, preliminary data suggests that most of the compensatory changes will cluster at the 3' end of the genome.

Rewiring the Coronavirus Genome. Mutation in the SARS Transcription Regulatory Sequence Attenuates Replication and Recombination. Live virus vaccine development provides an approach for identifying virulence alleles and pathogenic determinants, providing a template our understanding viral pathogenesis. Live viruses that lack several of the SARS-CoV group specific ORFs have been rescued, and are being tested for whether such viruses are attenuated.

The coronavirus TRS includes the highly conserved CS and flanking sequences, which regulate the efficiency of coronavirus transcription. It is believed that 1) mutations in the leader and body CS will attenuate SARS-CoV gene expression, and 2) SARS-CoV CS regulatory networks can be rewired, making these rescued viruses highly resistant to RNA recombination repair at the 3' end of the genome. The goal is to develop viruses that have significantly different TRS regulatory networks that upon recombination create incompatibility networks that disrupt expression of subgenomic mRNAs. These "rewired" SARS-CoV will be highly resistant to recombination repair from wild type viruses and other coronaviruses. These experiments will enhance the feasibility of safe SARS-CoV attenuated seed stocks for killed vaccines and serve as a model for engineering recombination resistant viruses.

Leader/body CS Compensatory Mutations. Previous studies with arteriviruses and TGEV indicated that mutations in the leader CS globally suppress transcription of all subgenomic mRNAs, unless the corresponding mutations are also duplicated into the body CS. Rewiring the Nidovirus transcription regulatory network provides a novel approach to selectively attenuate gene expression of certain genes while maintaining efficient expression of other genes. The current hypothesis is that the actual CS sequence is not so critical, the major factor being that CS sites must allow for communication via efficient base-pairing for discontinuous transcription of subgenomic RNAs. It is believed that double and triple compensatory mutations in the leader/body CS will allow for viable viruses with robust gene expression, but be highly resistant to recombination repair.

Selected mutations (CS mutations 1 and 2) will be inserted into the 5' leader CS and body CS of the N structural gene (Tables 1 and 2), in essence producing SARS-CoV single hit replicon RNAs as described herein. N CS sites are targeted initially, as N subgenomic transcripts are closest to the 3' end of the genome and expressed most abundantly, providing a reliable signal for detection. N transcript expression from single hit TGEV replicons has been detected under similar conditions. The CS mutational spectra were chosen as: 1) the sequence is unique in the SARS-CoV genome and 2) it differs from CS sites present in other group I-III coronaviruses. Cultures will be transfected with recombinant virus RNA genomes and subgenomic transcription will be measured by quantitative RT-PCR using primers in the leader sequence and the body sequence of several structural genes, including N and genomic RNA. It is expected that robust N transcript expression will be demonstrated, with little if any expression of other subgenomic mRNAs. It may prove necessary to test other potential leader/body CS sequences that effectively optimize subgenomic expression of N, but not the other SARS-CoV transcripts. This will be tested empirically should the initial mutations prove unsatisfactory for driving mRNA expression (as determined by the relative ratio of genome to mRNA expression).

Using the most robust CS sites identified in the initial experiment, the remainder of the SARS-CoV CS sites will be converted to the new consensus sequence. Recombinant viruses (csSARS-CoV) will be assembled and transcripts electroporated into cells. Such viruses will be viable in culture and should express normal ratios of mRNA, RF RNA and protein.

At 24-36 hrs post transfection, rescued viruses will be plaque purified and stocks grown in Vero E6 cells as previously described. Virus passage will be minimized to prevent the emergence of $2^{nd}$ site compensatory changes that restore virus growth fitness in culture. If recombinant viruses grow inefficiently, virus will be passaged 15-20× and mutants with increased growth kinetics and gene expression patterns will be identified by comparison with wild type (e.g., growth curves, structural protein expression, and northern blots). Given that reversion to wild type sequence in the leader/body CS sites is unlikely because of the requirement for multiple mutations (~18-27 changes in total genome CS sites), revertants will likely contain compensatory changes that reside in replicase proteins that interact with SARS-CoV TRS sites or in the flanking TRS sites that regulate discontinuous transcription (less likely as several would be required). These will be identified by sequence analysis followed by reintroduction of specific mutations into the full length cDNA construct.

Genotype Analysis. Plaque purified molecularly cloned viruses will be inoculated onto Vero E6 cells and intracellular RNA isolated using Trizol reagents. Using RT-PCR and primer-pairs that flank selected leader and body TRS mutations, amplicons will be sequenced to confirm that rescued viruses contain the expected alterations. Using RT-PCR, leader-containing amplicons representing each of the downstream transcripts that are synthesized during infection will also be cloned and sequenced. However, it is possible that altered CS mutants might initiate subgenomic transcripts from noncanonical sites. Any such aberrant leader-containing amplicons will be identified by sequencing. Depending upon the level of expression, the aberrant CS sequence in newly emerged TRS sites will be mutated to knock out indiscriminant subgenomic transcription.

Phenotype Analysis. Virus growth will be evaluated in culture and by plaque morphology. Rescued molecularly cloned viruses will be analyzed for SARS protein expression by Western Blot using antiserum from mice inoculated with alphavirus replicon particles encoding the various SARS structural and selected group specific ORFs. The ratios of structural proteins that are expressed in the rescued viruses will be determined by Western blot. Northern blot analysis will be used to identify the viral mRNAs and determine if selected TRS mutations alter the molar ratio of the upstream and downstream subgenomic viral mRNAs or the emergence of additional transcripts originating from newly recognized body CS sites. In selected instances, cultures will be radiolabeled with ³H-uridine and the labeling kinetics of viral mRNAs and replicative form RNAs will be analyzed.

New CS sites will be demonstrated to be stable in the SARS-CoV genome and allow for efficient gene expression and virus growth. The stability of selected mutants will be determined by serial passage in Vero E6 cells with particular focus on: 1) stability of leader/body CS sites and the evolution of group specific gene expression, and 2) mechanisms of fitness recovery. Putative compensatory mutations that restore virus replication fitness will be reintroduced into the full-length construct to prove causality between particular alterations, growth recovery and enhanced gene expression.

RNA Recombination with wild type SARS-CoV. Several approaches will be used to test whether "re-networked" SARS-CoV can recombine efficiently with wild type SARS-CoV. In one approach, select wild type CS sites will be introduced back into the SARS-CoV re-networked genome. For example, the M CS site will be altered back to "ACGAAC" and a determination will be made regarding whether viable recombinant viruses can be isolated. As the M glycoprotein is essential for growth, this is a strong selective screen for viability. It is anticipated that such viruses will grow poorly and require passage for selection of compensatory changes that reestablish growth. Such changes would likely evolve within the CS site, given only 1 or 2 mutations might be required to restore functionality of the body CS. In a second approach, a theoretical single crossover recombinant virus that contains the "mutated" leader CS will be coupled with all 3' end CS sites derived from the wild type virus. Reflecting what would happen if a recombination event occurred in the replicase of a "re-networked" virus and wild type virus, it will be determined if the engineered leader CS site will communicate and drive subgenomic transcripts from a wild type 3 end genome. It is anticipated that such viruses would be heavily impaired and that subgenomic transcription might occur from noncanonical sites. Subgenomic transcription will be measured by quantitative RT-PCR using primer sets in the leader sequence and in various structural genes. Transfected cultures and supernatants will be passaged (15-20×) to allow for the emergence of revertants that will be analyzed as described herein. Reversion, if it occurs, would likely occur through the emergence of one or more mutations in the leader CS. In a third approach, as in the second approach, a similar experiment will be performed, but in this instance, the 3' end of the re-networked SARS-CoV genome will be replaced with the 3' end of MHV (S through N). In one construct, the 3'-most ~500 nucleotides of the SARS-CoV genome that might contain cis-acting sequences needed for replication will be maintained and in a second construct, the entire SARS-CoV N gene and CS site will be included. In essence, a potential double recombinant genome will be generated that might occur between another group II coronavirus and SARS-CoV. Such viruses are not anticipated to be viable because of communication problems between the SARS-CoV replicase and the leader/body CS sites and potential encapsidation sequence problems associated with an MHV N protein (construct 1). In the second construct, the N protein will be derived from SARS-CoV but it must communicate with the MHV M, E and S proteins to mediate assembly of infectious virus, which is not likely.

Other rewiring approaches to prevent recombination repair of live attenuated viruses: Other approaches to produce recombination resistant viruses include: 1) repositioning the SARS-CoV encapsidation sequence to different locations in the genome, 2) rewiring the replicase protein cleavage sites to a different recognition sequence, 3) reorganizing the SARS-CoV gene order and 4) any other methods that establish genome incompatibilities following recombination with any other circulating human strain.

Example 4

SARS Virus Gene Order Rearrangement

Because N gene rearrangements are well tolerated in the group I and II coronavirus genomes, in initial studies, the N gene position will be moved to new sites immediately downstream (SARS SNEM) and upstream of S (SARS NSEM). Second generation constructs will include rearrangement of ORF7 or 8, the N gene upstream of S (SARS 7/8NSEM6) and an E protein/M glycoprotein reposition upstream of S as well (SARS EMSN). The SARS S glycoprotein will also be repositioned to the 3' proximal location (SARS EMNS). The putative IFN antagonist genes encoded in ORF3a and ORF6 will also be repositioned, potentially altering levels of gene expression and activity. Depending upon the outcome of these experiments, more radical rearrangements may be performed in which multiple genes are repositioned to multiple sites. Care will be taken to maintain tight genetic juxtaposition and the appropriate TRS control such that rearranged genes will use their normal CS site for expression of subgenomic mRNAs. After introducing these rearrangements into the SARS F subclone, sequence analysis will be used to identify the consensus cDNA used in the assembly of full length SARS cDNAs. Molecularly cloned viruses will be rescued as described. Any number of rearranged SARS-CoV genomes can be built using the molecular clone or any other method to alter the 3' end of the SARS-CoV genome. Gene order rearranged viruses should be significantly resistant to recombination repair.

Phenotype and Genotype Analysis of Rescued Viruses. Rescued viruses will be isolated between 24-36 hrs post transfection, plaque purified and stocks grown in Vero E6 cells as previously described. Virus passage will be minimized to prevent the emergence of mutations that restore growth fitness in culture.

Genotype Analysis. Plaque purified molecularly cloned viruses will be inoculated into Vero E6 cells and intracellular RNA isolated using Trizol reagents. Using RT-PCR and primer-pairs that flank the newly rearranged genes, the presence of the mutant gene order in rescued viruses will be demonstrated. The amplicons will be sequenced to confirm the expected gene rearrangements. As rearrangements may alter expression of flanking genes, leader-containing amplicons will be RT-PCR cloned and sequenced to determine if subgenomic RNA synthesis has originated from appropriate CS sites.

Phenotype Analysis. Virus growth will be evaluated in culture and by plaque morphology. Rescued molecularly cloned viruses will be analyzed for SARS protein production by Western Blot using antiserum from mice inoculated with VRPs encoding the various SARS virus structural proteins and group specific ORFs. By Western Blot or immunoprecipitation with ³⁵S-methionine labeled cell extracts, the expression of the structural and various group specific non-structural proteins that are expressed following gene rearrangement will be measured. Northern Blot analysis will be used to identify the viral mRNAs and determine if selected gene rearrangements alter the molar ratio of the upstream and downstream viral mRNAs. In selected instances, cultures will be radiolabeled with ³H-Uridine and the kinetics of viral mRNA and replicative forms (RF) RNA synthesis will be analyzed. These experiments will allow for the determination of 1) whether full length and subgenomic length RF RNAs are present in SARS-CoV infected cells, 2) effects of reorganization on RNA expression, and 3) reorganization effects on relative molar ratios of mRNA and RF RNA.

Stability and Recombination Repair. Compensatory Evolution. Recombinants will be inoculated into Vero E6 cells and progeny viruses passaged into fresh cultures at 24 hrs postinfection. After 15-20 passages, growth curves and plaque size will be compared to wild type virus. Then, consensus SARS E and F subclones that contain mutations of interest will be reintroduced back into the full length cDNA to identify $2^{nd}$ site mutations that restore replication fitness in the rearranged viruses.

RNA Recombination Repair: Gene order rearranged viruses are expected to be highly stable and several fold more resistant to RNA recombination repair by wild type viruses. Using SARS NSEM and SARS wild type as an example, it is noted that most recombination events originating from SARS NSEM to SARS wild type will result in an N gene deletion, a lethal event which reduces the recombination frequency by one-half. In contrast, recombination events originating from SARS wild type to SARS NSEM will predominantly lead to recombinant genomes containing two copies of N, which at least in the case of TGEV reduces replication fitness by about 1 log of titer. Only recombination events occurring within the pol genes of both viruses will reconstruct wild type virus, hardly a significant problem as it would only add to the wild type virus burden already present. Consequently, it is expected that gene order rearrangements will attenuate RNA recombination repair to give wild type genomes. In the absence of wild type virus, it is highly unlikely that RNA recombination can restore the gene order of SARS NSEM. This is because several recombination events are necessary, including duplication of the N gene at the 3' end of the genome (a double recombination event), followed by deletion of N from the upstream position.

To test this hypothesis, two approaches will be used. In the first approach, cultures of cells will be coinfected with selected gene order rearranged viruses (SARS SNEM) and SARS wild type virus containing a deletion in the S CS and N-terminal S protein sequence and a GFP indicator. This genome should replicate but result in noninfectious virus particles lacking S. Rescue of the genome can occur by recombination or by phenotypic mixing of S glycoprotein provided by SARS SNEM in trans. The basic approach is to transfect with SARS ΔS and then infect with SARS SNEM at a MOI of 2 and passage progeny 3× (at high MOI<SARS ΔS should passage if S provided in trans). Using quantitative RT-PCR and primer pairs spanning the N/adjacent gene (SARS SNEM would be N/ORF3a; SARS wild type would be ORF8/N), virions will be harvested from supernatants at each passage, concentrated through gradients, and titered by plaque assay and quantitative RT-PCR using primer sets that detect SARS SNEM, SARS wild type and SARS SNEMN recombinant viruses. Green plaques (3×) can also be plaque-purified and the genotype of recombinant viruses characterized. In the second approach, a SARS 2N virus (the progeny of a wild type x SNEM recombination event) is constructed, which is expected to be replication impaired as compared to wild type.

Example 5

Remodeling SARS-CoV Genome Regulatory Networks Obstructs RNA Recombination

Live virus vaccines are a crucial intervention strategy documented to improve the overall health of communities because they have induced long-term immune responses that protect against a variety of highly pathogenic human and animal pathogens over the past century. Concerns regarding reversion to virulence by mutation and recombination, coupled with the associated challenges in commercially developing these vaccines, have diminished the appeal of using live virus vaccines in human and animal populations. The dichotomy between the well known protective efficacy and costs and risks of developing live virus vaccines has been recognized as one of the grand challenges in global health by the National Foundation for Infectious Diseases, calling for the development of new methods to stabilize and prevent reversion or recombination repair of attenuating alleles in live virus vaccines.

SARS-CoV was recognized as a highly pathogenic respiratory human pathogen that emerged suddenly and subsequently spread worldwide during the first few months of 2003. By the end of the outbreak, over 8,000 people had been infected, resulting in some 800 deaths worldwide. Demonstration of zoonotic forms of the SARS-CoV, both in farm animals and in bat populations, dictate a need for continued surveillance and the development of efficacious vaccines and therapeutics targeted to prevent reemergence and spread of this important human pathogen. SARS-CoV is an excellent model system for coronavirus vaccine development as this pathogen replicates efficiently in a variety of animal models, it is highly pathogenic in its normal host, the genome is well characterized, a reverse genetic system exists to manipulate the genome (49), and other important coronaviruses have been identified that cause significant diseases in human and in animal populations.

The SARS-CoV virion contains a single-stranded positive polarity 29,700 nucleotide RNA genome bound by the nucleocapsid protein, N. The capsid is surrounded by a lipid bilayer containing at least four structural proteins, designated S, ORF3a, M and E. The SARS-CoV genome contains nine open reading frames (ORFs), the first of which encodes the viral replicase proteins required for subgenomic and genome length RNA synthesis. ORFs 2-8 are encoded in eight subgenomic mRNAs synthesized as a nested set of 3' co-terminal molecules in which the leader RNA sequences, encoded at the 5' end of the genome, are joined to body sequences at distinct transcription regulatory sequences (TRS) which contains a highly conserved consensus sequence (CS), ACGAAC in SARS-CoV and ACTAAAC in other group II coronaviruses, respectively. Based on studies with other coronaviruses, SARS-CoV likely uses transcription attenuation to synthesize both full length and subgenomic length negative strand RNAs containing antileader sequences, which then function as the templates for the synthesis of like-sized mRNAs (44, 47, 48). It has been well established that alterations in body TRS sequences attenuate expression of individual subgenomic mRNAs while alterations in the leader TRS globally impact the synthesis of all subgenomic mRNAs. Interspaced among the SARS-CoV structural genes are the accessory or group specific genes, ORF3a/b, ORF6, ORF7a/b, ORF8a/b and ORF9b, which are not conserved in other coronaviruses and whose function in replication and pathogenesis are generally unknown. Group specific ORFs encoded in the SARS-CoV, mouse hepatitis virus (MHV), feline infectious peritonitis virus (FIPV) and transmissible gastroenteritis virus (TGEV) genome often encode luxury functions for replication in vitro, but may attenuate virulence in vivo (22, 46, 51). The exact functions of the SARS-CoV group specific ORFs are unclear in replication and pathogenesis. Importantly, coronaviruses undergo RNA recombination events at high frequency, presumably because of the large size of the genome, the presence of transcriptionally active full length and subgenomic length templates and a transcription strategy that requires disassociation/reassociation with template strands.

In the present invention, the SARS-CoV transcription network has been globally remodeled by engineering a novel six nucleotide TRS domain that is not present in the genome of SARS-CoV or any other known coronavirus. Studies described herein demonstrate that the recombinant virus, icSARS-CRG, replicates efficiently in cell culture and expressed normal levels of the expected complement of subgenomic mRNAs that encoded both structural and nonstructural proteins. A second recombinant virus, icSARS-PRG, containing a new TRS network that regulated expression of the genome length RNA as well as the subgenomic RNAs encoding essential structural proteins, but not the group specific ORFs 3a/b, ORF6, ORF7a/b and ORF8a/b, also replicated efficiently, demonstrating that the group specific ORFs were not essential for in vitro and in vivo replication. In contrast, chimeras containing a mixture of natural and rewired TRS networks that influenced essential gene expression were lethal. This is the first example of successfully designing new regulatory circuits into the genome of a mammalian virus. These studies serve as a paradigm for designing unique networks of interacting alleles that function as lethal genetic traps following RNA recombination with wild type viruses.

Viruses and Cells. The Urbani and icSARS strains of SARS-CoV (AY278741), icSARS-CoV Luc, icSARS-CoV Luc1, icSARS-CoV Luc-2 and the icSARS-CRG and PRG recombinant viruses were propagated on VeroE6 cells in Eagle's MEM supplemented with 10% fetal calf serum, kanamycin (0.25 µg/ml) and gentamycin (0.05 µg/ml) at 37° C. in a humidified $CO_2$ incubator. For virus growth, cultures of VeroE6 cells were infected at a multiplicity of infection (MOI) of 0.1 PFU for 1 hr, the monolayer washed 2× with 2 mls of PBS and overlaid with complete MEM. Virus samples were harvested at different times post infection and titered by plaque assay in 60 $mm^2$ dishes. Plaques were visualized by neutral red staining and counted at 48 hrs. All virus work was performed in a biological safety cabinet in a biosafety level 3 laboratory containing redundant exhaust fans. Personnel were double-gloved and dressed in TYVEK suits with full hoods and face shields. Powered air purifying respirators (PAPR) with high efficiency particulate air (HEPA) and organic vapor filters were used to provide positive pressure environment within the hoods.

Construction of Renilla Luciferase encoding SARS-CoV Recombinant Clones. Plasmid DNAs were amplified in One Shot® Top 10 chemically competent cells (Invitrogen) and purified with the QIAPREP miniprep kit (Qiagen Inc., Valencia, Calif.). All restriction enzymes were purchased from New England BioLabs (NEB, Beverly, Mass.) and used according to manufacture's instructions. DNA fragments were isolated from 1.0% agarose gels with the QIAQUICK gel extraction kit (Qiagen Inc.). All DNA was visualized using DARKREADER technology (Clare Chemical Research, Denver, Colo.) to prevent UV-induced damage that potentially could affect efficacy of assembly at later stages, such as transcription. The six subgenomic cDNA clones (A to F) that include the entire ic SARS genome when combined were isolated using known molecular techniques. ORF 7a/b is located within cDNA F, nucleotides 27273-27772. The Renilla luciferase gene was inserted to replace ORF 7a/b.

Mutations were introduced to the TRS site by utilizing the 'no see'm' strategy. Three primer sets were designed to amplify three cDNA fragments. A forward primer (Ppum3: 5'-GCTGTGACATTAAGGACCTGCCAAAAG-3'; SEQ ID NO:42) extending from the PpumI site was used concurrently with a reverse primer (3MUT3: 5'-AGGTGCACCTGCAGC-CATTTTAATTTATCCGGTTTATGGATA-3'; SEQ ID NO:43 or 2MUT3: 5'-AGGTGCACCTGCAGCCATTT-TAATTTATCCGTTTTATGGATA-3'; SEQ ID NO:44) ending at the ORF 7a/b TRS site, which included the appropriate TRS mutations and the outside cutter restriction site for AarI (Fermentas). This resulted in Amplicon 1 (TRS2), by PCR, with three mutations (CCGGAT) in the TRS site and Amplicon 2 (TRS1), with two mutations (ACGGAT) in the TRS site. The third amplicon was created using a forward primer (3MUT5: 5'-GGTGCACCTGCAAATAAATGGCTTCCA-3': SEQ ID NO:45) that overlapped with the previously mentioned AarI site designed into AMP1 and AMP2. The reverse primer (PacI3: 5'-TAAAGTGAGCTCTTAATTAATTACT-GCTCG-3'; SEQ ID NO:46) ended at the downstream PacI site. This created, by PCR techniques, Amplicon 3 (AMP3). Each amplicon was digested with the appropriate restriction enzyme cocktail: AMP1 and AMP2-PpumI/AarI and AMP3-AarI/PacI. AMP1 and AMP2 were separately ligated to AMP3 for a 1.34 kb cDNA fragment that was subsequently cloned into pTOPO PCR-XL plasmid (Invitrogen). The ic SARS wild type luciferase (icSARS wt-Luc) construct and the new mutated clones were digested with PpuMI and PacI and the 7.91 kb band of the icSARS wt-Luc and the 1.34 kb band of the mutated clones were gel purified and ligated overnight at 4° C. in the presence of 1% T4 DNA Ligase (NEB). Clones with the correct mutations were verified by DNA sequencing with an automated sequencer (UNC-CH Genome Analysis Facility).

Construction of SARS Plasmids Containing Mutated Leader and Intergenic Sequences. To create a leader with the consensus sequence CCGGAT, the SARS A plasmid was PCR amplified with primer set M13R3 (CAGGAAACAGC-TATGAC; SEQ ID NO:47) and MuL1-(AAAATCCGGTTA-GAGAACAGATCTACAAGAG; SEQ ID NO:48) or MuL1+ (CTAACCGGATTTTAAAATCTGTGTAGCTGTC; SEQ ID NO:49) and SARS 453– (ATAGGGCTGT-TCAAGCTGGGG; SEQ ID NO:50). The resulting fragments were combined in an overlapping PCR reaction to create an approximately 620 bp product that was subsequently cloned and sequenced. A plasmid containing the appropriate changes was digested with restriction enzymes MluI and AvrII and this fragment was used to replace the same fragment from the SARS A plasmid. Further sequencing of this plasmid confirmed that it was identical to the SARS A plasmid except for the altered leader. To mutate the spike (S) gene TRS, the SARS E fragment was PCR amplified with either primer set SARS #37 (TGCTGGCTCTGATAAAG-GAG; SEQ ID NO:51) and MuSgene– (NNNCACCTGCA-CATATCCGGTTAGTTGTTAACAAGAATATCAC; SEQ ID NO:52) or MuSgene+ (NNNCACCTGCAACCGGATAT-GTTTATTTTCTTATTATTTCTTACTCTC; SEQ ID NO:53) and #10AgeI– (CATCAAGCGAAAAGGCATCAG; SEQ ID NO:54). These fragments were digested with restriction enzyme AarI, ligated and subcloned. A consensus clone with the desired changes, was digested with BsmBI and AgeI, and used to replace the corresponding fragment in the SARS E plasmid. Next, the SARS F plasmid was PCR amplified with the following sets of primers: SARS #44 (TGATCCTCTG-CAACCTGAGC (SEQ ID NO:55) and MuEgene– (NNNC-ACCTGCATAAATCCGGACTCACTTTCTTGTGCTTAC; SEQ ID NO:56); MuEgene+ (NNNCACCTGCGTCCGG-ATTTATGTACTCATTCGTTTCGG; SEQ ID NO:57) and MuMgene– (NNNCACCTGCAATAGTTAATCCGGTTA-GACCAGAAGATCAGGAAC; SEQ ID NO:58); and MuMgene+(NNNCACCTGCGGATTAACTATTATTAT-TATTCTGTTTGG; SEQ ID NO:59) and 28033– (TACCAA-CACCTAGCTATAAGC; SEQ ID NO:60). The three fragments were digested with the restriction enzyme AarI, directionally ligated and subcloned. A clone, containing the new consensus sequence CCGGAT for the E and M genes, was digested with SwaI and NdeI and this fragment was inserted into the SARS F plasmid that had been identically digested. The resulting plasmid was designated FmuEand M. The SARS N gene TRS was mutated by PCR amplifying the F plasmid with primers MuNgene1 (GCTGCATTTA-GAGACGTACTTGTTGTTTTAAATAACCG-GATAAATTAAAATG TCTGATAATGG; SEQ ID NO:61) and SARS 3' Ng (TTAATTAATTATGCCTGAGTTGAAT-CAGCAG; SEQ ID NO:62). The product was digested with BsmBI and used to replace the corresponding section in plasmid FmuEand M, this new plasmid was called FmuE/M/N. Altering the ORF 3a TRS consisted of amplifying plasmid FmuE/M/N with the following primer sets; SARS #44 and SARSX1– (CGTCTCATGTGTAATGTAATTTGACACCC; SEQ ID NO:63) or SARSX1+ (CGTCTCACACATAACCG-GATTTATGGATTTGTTTATGAGATTTTTTAC; SEQ ID NO:64) and 28033–, and then joining the two fragments using the restriction endonuclease BsmBI. This product was used to replace the SwaI-NdeI portion of FmuE/M/N. Primer sets SARS #47 (GTGCTTGCTGTTGTCTACAG; SEQ ID NO:65) and SARSX3– (CGTCTCCGTCCG-GGATG-TAGCCACAGTGATCTC; SEQ ID NO:66), SARSX3+ (CGTCTCCGGACGCTTTCTT-ATTACAAATTAGGAG; SEQ ID NO:67) and SARSX4– (CGTCTCTCATATCCG-GTTTATGGATAATCTAACTCCATAG; SEQ ID NO:68), and SARSX4+ (CGTCTCATATGAAAATTATTCTCTTC-CTGAC; SEQ ID NO:69) and 28033– were used to generate three PCR fragments that were digested with BsmBI, ligated with T4 DNA ligase and subcloned. A clone containing only the required changes was digested with AvrII and inserted into plasmid FmuE/M/N/X1 that had also been digested with AvrII. Finally, primer set SARS #48 (GGACTTTCAGGAT-TGCTATTTG; SEQ ID NO:70) and SARSX5– (CGTCT-CATCCGGTTAGACTTTGGTACAAGGTTC; SEQ ID NO:71) and set SARSX5+(CGTCTCCCGGATAT-GAAACTTCTCATTGTTTTGAC; SEQ ID NO:72) and SARS3'X5 (NNNTTAATTAATTAATTTGTTCGTT-TATTTAAAACAACA; SEQ ID NO:73) created PCR products that were similarly joined using BsmBI and T4 DNA ligase. This product was introduced into plasmid FmuE/M/N/X1/X3/X4 using the NdeI-BstEII restriction sites. This plasmid, named FmuE/M/N/Xorfs, was sequenced to verify all mutations.

Assembly of Full Length cDNAs. The SARS A through F inserts were digested, separated through 0.8% agarose gels, visualized with a DARKREADER lightbox (Claire Chemical), excised and purified using the QIAEX II DNA purification kit. The SARS A+B, C+D and E+F fragments were ligated overnight, and the products isolated (17, 49). The SARS AB+CD+EF fragments were ligated overnight at 4° C., phenol/chloroform extracted and precipitated under isopropyl alcohol. Full-length transcripts were generated in vitro as described by the manufacturer (Ambion, MMESSAGE MMACHINE) with certain modifications. To produce full length capped SARS N gene transcripts, 1 μg of plasmid DNA encoding the SARS N gene was PCR amplified using forward primer (5'-nnggcctcgatggccatttaggtgacac-tatagatgtctgataatggacccccaatc-3'; SEQ ID NO:74) and reverse primer (5'-nnnttttttttttttttttttttttttttttttttatgcctgattgaatcagcag-3'; SEQ ID NO:75) and the amplicons purified from gels. Full length, polyadenylated N gene transcripts were transcribed by SP6 RNA polymerase with a 2:1 ratio of cap analog to GTP (Ambion, Austin, Tex.), mixed with full length transcripts and electroporated into cells.

Transfection of Full-Length Transcripts. RNA transcripts were added to 800 μl of the Vero E6 cell suspension ($8.0 \times 10^6$) in an electroporation cuvette and four electrical pulses of 450 V at 50 μF were given with a GENE PULSER II electroporator (BioRad) similar to protocols previously described (17, 49). The presence of full length cDNAs and transcripts was verified by separation on agarose gels and visualization by UV light. The transfected Vero cells were seeded in a 75 $cm^2$ flask and incubated at 37° C. for 2 days. Viruses were plaque purified in Vero E6 cells and stock grown in 75 $cm^2$ flasks.

Northern Blot Analysis. Cultures of Vero E6 cells were inoculated with the wild type SARS-CoV Urbani strain and various recombinant viruses at a MOI of 1.0 and incubated for 1 hr at 37° C. At 12 hrs post infection, intracellular RNA was isolated using RiboPure™ reagents as directed by the manufacturer (Ambion, Austin, Tex.). The mRNA was isolated using Qiagen's Oliogtex® (mRNA spin-Column reagents according to the manufacturer's direction (Qiagen, Valencia, Calif.). The mRNA was treated with glyoxal and separated on agarose gels using NorthernMax®-Gly according to the manufacturer's directions (Ambion, Austin, Tx). The RNA was transferred to BRIGHTSTAR-PLUS membrane (Ambion) for 4-5 hrs and the RNA cross-linked to the membrane by UV light. The blot was prehybridized and probed with an N gene-specific oligodeoxynucleotide probe (5'-CTTGACTGC-CGCCTCTGCT$^b$T$^b$CCCT$^b$CT$^b$GC$^b$-3'; SEQ ID NO:76), where biotinylated nucleotides are designated with a superscript $^b$. Blots were hybridized overnight and washed with low and high stringency buffers as recommended by the manufacturer. Filters were incubated with streptavidin-AP, washed, and then incubated with chemiluminescence substrate CDP-STAR. The blots were overlaid with film and developed.

Western Blot Analysis. Twelve hours post infection, Urbani, icSARS-CoV, icSARS-CoV Luc, icSARS-CoV Luc-1, icSARS-CoV Luc2, icSARS-CRG or icSARS PRG virus infected cells were washed in 1×PBS, lysed in buffer containing 20 mM Tris-HCl, pH 7.6, 150 mM NaCl, 0.5% deoxycholine, 1% nonidet-p-40, 0.1% sodium dodecyl sulphate (SDS), and post nuclear supernatants were added to an equal volume of 5 mM EDTA/0.9% SDS, resulting in a final SDS concentration of 0.5%. Samples were then heat inactivated for 30 minutes at 90° C. in the BL3 facility prior to removal. In a BL2 facility, samples were again heat inactivated for 30 minutes at 90° C. before use. Equivalent sample volumes were loaded onto 4 to 20% Criterion gradient gels (BioRad) and transferred to PVDF membrane (BioRad). For detecting SARS-CoV antigens, lots were probed with polyclonal mouse antisera directed against Venezuelan equine encephalitis virus replicon particles (VRPs) that expressed the SARS-CoV ORF3a (VRP-ORF3a), S (VRP-S) or N (VRP-N) proteins diluted 1:200 and developed using ECL chemiluminescence reagents (Amersham Biosciences). Renilla luciferase expression was verified using antibodies purchased from commercial vendors.

TRS Function in SARS-CoV Transcription. Previous studies using TGEV as a model have established that high fidelity complementary base-pair communication between sequences encoded within the body TRS and the leader TRS encoded in the genome is absolutely essential for efficient expression of coronavirus subgenomic RNAs. As a first step toward remodeling the SARS-CoV TRS network, the nonessential ORF7a/b domain was replaced with the Renilla luciferase gene under the control of the ORF7a/b TRS motif (icSARS-CoV Luc). Double (icSARS-CoV Luc1) and triple (icSARS-CoV Luc2) mutations were then engineered in that should disrupt the ORF7a/b TRS communication network in the genome, ablating efficient mRNA 7 subgenomic transcription. Although the wild type SARS-CoV TRS is ACGAAC, the double mutant (TRS1-ACGGAT) and triple mutant (TRS2-CCGGAT) TRS sequences were unique with the latter not being encoded elsewhere in the Urbani genome and not used as a regulatory sequence in any known coronavirus. Recombinant cDNA genomes were assembled as previously described and recombinant viruses isolated by plaque purification. RT-PCR RFLP and sequence analysis demonstrated the appropriate ΔORF7a/b and luciferase replacement. Recombinant viruses encoding the luciferase gene replicated as efficiently as wild type virus, achieving titers greater than $10^7$ PFU/ml within 20 hrs post infection, consistent with previous reports that demonstrated that ORF7a/b deletion did not significantly reduce virus replication in vitro or in vivo. In Vero cells, a progressive increase in Renilla luciferase expression was noted over the course of infection that peaked at 4-5 logs above background in icSARS-CoV Luc infected cultures. Under identical conditions, icSARS-CoV Luc-1 and icSARS-CoV Luc-2 displayed significant 90-95% reductions in global levels of luciferase protein expression, respectively over the course of infection. Western blot analysis confirmed the significant reduction in Renilla luciferase expression, but not N protein expression following infection of Vero cells. Further, Northern blot analyses clearly demonstrated that the TRS-1 and TRS-2 motifs significantly ablated expression of subgenomic mRNA 7 encoding luciferase.

Rewiring Coronavirus TRS Transcription Networks. Having demonstrated that the remodeled TRS-2 motif significantly attenuates communication with leader TRS elements and results in significant reductions in subgenomic mRNA synthesis, all of the SARS-CoV TRS elements were changed to the TRS-2 signature (icSARS-CoV CRG). A second mutant was engineered that contained the novel TRS-2 regulatory network, effectively establishing efficient communication between the leader sequence and the four essential structural genes, S, E, M and N (icSARS-PRG). However, this second regulatory network retained the wild type TRS sites that normally regulate expression of the group specific genes ORF3a/b, ORF6, ORF7a/b and ORF8a/b. The inefficient communication between the leader TRS-2 site and wild type TRS sites located just upstream of the group specific genes should significantly attenuate expression of the group specific genes. Recombinant viruses encoding the new TRS-2 and chimeric networks were readily isolated and plaque purified. Recombinant viruses icSARS-CRG and icSARS-PRG both replicated efficiently in Vero cells, approaching titers of mid $10^7$ PFU/ml within 20 hrs post infection, equivalent to wild type viruses. Northern blot analyses revealed appropriately sized subgenomic mRNAs in icSARS-CRG infected cells, typical of wild type SARS-CoV infection. Importantly, subgenomic RNA profiles in icSARS-PRG infected cells displayed the expected set of subgenomic mRNAs encoding the structural genes (mRNA 2, 4, 5 and 9) that were driven from networked TRS-2 sites, but reduced and/or mis-sized subgenomic mRNAs driven from the wild type TRS sites regulating expression of the group specific ORFs. For example, expression of mRNA 3 is reduced by about 50%, while mRNAs 6 and 8 are mis-sized and mRNA 7 is apparently not expressed. Western blot analyses confirmed abundant levels of expression of the structural proteins S and N in all recombinant and wild type viruses, abundant expression of ORF3a in wild type and icSARS-CRG, but little if any expression of ORF3a in icSARS-PRG infected cultures. Analysis of leader-body TRS junctions in wild type and icSARS-CRG revealed usage of the appropriate wild type or mutant TRS sites. In icSARS-PRG, leader-body TRS-2 sites drove expression of subgenomic mRNAs encoding the structural proteins demonstrating efficient communication between networked leader/body TRS sites. The wild type TRS site ACGAAC was rarely used for initiating expression of the group specific ORF encoding subgenomic RNAs. When this was the case, the body TRS sequence was preserved in mRNA consistent with the transcription attenuation model for Nidovirus mRNA synthesis. Most often, upstream and downstream noncanonical TRS sites were typically activated; most likely because they displayed increased homology with TRS-2. Aberrant leader-body junction sites oftentimes result in mRNAs that encode deletions in a group specific ORF or potentially silence group specific ORF expression because new upstream ATG start codons and small ORFs are encoded in the mRNA that are likely recognized and translated by host translational machinery, interfering with efficient translation and expression of the group specific ORF. The data demonstrate that deletion or efficient expression of the group specific ORFs is not essential for SARS-CoV replication in vitro.

Remodeled TRS Networks Encode Lethal Genetic Traps Following RNA Recombination with Wild type Viruses. A series of wild type and chimeric recombinant viruses were engineered as described herein. In the first example, wild type or TRS-2 networks were preserved to efficiently express mRNA 2 encoding the S glycoprotein, but encode the heterologous TRS site for driving expression of the other structural genes (icSARS-Rec1; icSARS-Rec2). In another case, only the N gene TRS site was misaligned with the leader TRS site (icSARS-Rec3).

Full length cDNAs were constructed for wild type icSARS-CoV, icSARS-CRG and the three chimeric recombinant viruses and full length transcripts were electroporated in Vero cells. One-fifth of the electroporated cells were overlaid onto confluent monolayers, allowed to attach for 3 hrs and overlaid with agarose for plaque assay to determine the number of infectious centers. The remaining cells were maintained in complete medium and virus samples and RNA harvested at different times post-electroporation. Approximately $10^3$ infectious centers were detected for icSARS-CoV and icSARS-CRG, but no infectious centers were detected from icSARS-Rec1-3 transfected cultures. Moreover, infectious virus was readily detected, which increased to greater than $10^7$ PFU/ml after about 72 hrs in icSARS-CoV and icSARS-CRG, but no virus was detected in cSARS-Rec 1-3 transfected cultures.

Using RT-PCR, leader-containing transcripts were detected in all wild type and icSARS-CRG transfected cultures at 24 and 48 hrs. These leader-containing transcripts originated at the appropriately networked combination of leader/body TRS sites. In contrast, only low levels of subgenomic mRNA transcripts were detected in icSARS-Rec1-3 transfected cultures at 24 hrs that had mostly disappeared by 48 hrs post-electroporation. Sequence analysis revealed that most leader-containing RNAs originated from noncanonical TRS sites located upstream or more often, downstream of the appropriate start location (FIG. 1A). In many cases, the non-canonical site usage results in large lethal deletions in critical structural genes like M (FIG. 1B) that prevent the production of infectious progeny.

Animal studies. Mice and ferrets are inoculated with 1.0× $10^6$ plaque forming units (PFU) of icSARS-CRG and icSARS-PRG. A variety of immune responses (e.g., innate, mucosal, humoral, cellular) are measured according to standard protocols well known in the art at different times postinfection.

Example 6

Secondary Genetic Traps

A TRS consensus sequence (which is the wild type sequence and not a mutation) is engineered into a nidovirus genome or replicon RNA upstream or downstream from the normal TRS consensus sequence (e.g., of an essential structural protein gene such as S, M and/or N) site. This is done by identifying locations that are "CS-like, e.g., that naturally have 3-5 nucleotides of a six nucleotide CS and that fall just upstream or downstream of the wild type CS. The primary nucleotide sequence is modified at the "CS-like" site to be as close to the wild type CS as possible without altering the amino acid sequence of the protein. This modified CS site functions as a site for subgenomic transcription in recombinant virus progeny after recombination with wild type virus. In a resulting recombinant genome, expression of wild type genes is driven from these engineered start sites, resulting in N-terminal truncated proteins and/or out-of-frame ORFs.

In one embodiment, the sequence of the CRG or PRG genome S, M and N genes is analyzed and six nucleotide domains with close homology to the wild type TRS sequence, ACGAAC, are identified and characterized. Close sequence motifs within about 50, 75, 100, 150, 200, 250, 300, 350, 400, 450 or 500 nucleotides (upstream or downstream) of the normal mRNA CS initiation site are identified and those that can be mutated to near exact (5/6 or 6/6) duplicates of the wild type TRS sequence, ACGAAC, are introduced within one or more of the essential gene coding sequences, simultaneously maintaining the normal protein sequence. Following recombination events in which the wild type TRS site is joined to the body of a CRG genome, the secondary trap becomes activated as a preferred site for subgenomic mRNA synthesis. Secondary traps can be introduced in the S, M or N proteins to introduce N-terminal or C-terminal deletions or to introduce out-of-frame ATG starts as the translated product of the subgenomic mRNA. All result in poor expression and/or deleted protein products. Using the sequence of the virus genes, the rewired TRS CS sites and the wild type TRS CS sites, different secondary traps can be introduced into any nidovirus rewired genome of this invention.

In a particular example, the CS of a SARS coronavirus is ACGAAC. Locations nearby this sequence in a structural protein gene (e.g., S, E, M, N) of a rewired genome or a replicon RNA comprising a structural protein gene would be identified that have 4 or 5 of the 6 nucleotides of this CS (e.g., AGGAAG). This site would be changed using standard procedures from AGGAAG to ACGAAC. This site would then be preferentially used when a wild type leader TRS is present in a recombinant virus genome. In an example where the secondary trap is introduced into the S gene, the S protein is truncated by 37 amino acids and a new ATG start site is used to produce a smaller S glycoprotein. The truncated protein functions poorly, resulting in a lethal phenotype.

The foregoing examples are illustrative of the present invention, and are not to be construed as limiting thereof. The invention is described by the following claims, with equivalents of the claims to be included therein.

All publications, patent applications, patents and other references cited herein are incorporated by reference in their entireties for the teachings relevant to the sentence and/or paragraph in which the reference is presented.

REFERENCES

1. Tsang et al. (2003). *N Engl J Med* 348:1977-1985.
2. Lee et al. (2003). *N Engl J Med* 348:1986-1994.
3. Peiris et al. (2003) *Lancet* 361: 1767-1772.
4. Poutanen et al. (2003). *N Engl J. Med.* 348: 1995-2005.
5. Peiris et al. (2003) *Lancet* 361: 1319-1325.
6. Ksiazek et al. (2003) *N Engl J Med* 348: 1953-1966.
7. Drosten et al. (2003) *N Engl J Med* 348: 1967-1976.
8. Rota et al. (2003) *Science* 300:1394-1398.
9. Marra et al. (2003) *Science* 300: 1399-1404.
10. Ruan et al. (2003) *Lancet* 361: 1779-1785.
11. Kim et al. (1995). *Virology* 208:1-8.
12. Kanjanahaluethai et al. (2003) *J Virol* 77: 7376-7382.
13. Gorbalenya et al. (1991) *FEBS Lett* 288: 201-205.
14. Lu et al. (1998) *J Virol* 72: 2265-71.
15. von Grotthuss et al. (2003). *Cell* 113: 701-702.
16. Zeibuhr et al. (2000) *J Gen Virol* 81: 853-879.
17. Yount et al. (2002) *J Virol* 76: 11065-11078.
18. Yount et al. (2000) *J. Virol.* 74: 10600-10611.
19. Almazon et al. (2000) *Proc Natl Acad Sci USA* 97: 5516-5521.
20. Casais et al. (2001) *J Virol* 75:12359-12369.
21. Thiel et al. (2001). *J Gen Virol* 82: 1273-81.
22. Curtis et al. (2002) *J Virol* 76:1422-1434.
23. Pensaert and de Bouck. (1978) *Arch Virol* 58: 243-247.
24. Pensaert et al. (1986). *Vet Q* 8: 257-261.
25. Duarte et al. *Virology* 198: 486-476.
26. Baric et al. (1997) *J Virol* 71:1946-1955.
27. Baric et al. (1999) *J Virol.* 73:638-649.
28. Fischer et al. (1998) *J Virol* 71: 7885-7894.
29. de Haan et al. (2002) *Virology* 296:177-189.
30. Sola et al. (2002). *J Virol* 77: 4357-4369.
31. Ortega et al. (2002). *J Virol* 76: 11518-11529.
32. Enjuanes & van der Zeijst (1995). In: *The Coronaviridae*; S G Siddell. ed, p. 337-376.
33. Ladman et al. (2002). *Avian Dis* 46: 938-44.
34. Saif (1999). *Adv Vet Med* 41: 429-46.
35. van Nieuwstadt et al. (1989) *Vet Res.* 125: 58-60.
36. Crouch et al. (2000) *Vaccine* 19:189-196.
37. Park et al. (1998) *Am J Vet Res* 59:1002-8.
38. Rottier (1999) *Vet Microbiol* 69:117-25.
39. Vennema et al. (1997) *J Virol* 64:1407-1409.
40. Wang et al. (2002) *Avian Dis,* 46: 831-838.
41. Baron et al. (1997) *J Gen Virol.* 80:2031-2039.
42. Fouchier et al. (2003) *Nature* 423: 240.
43). Komatsu et al. (1986) *Exp Neurol* 91: 23-29.
44. Baric and Yount. (2000) *J Virol* 74:4039-46.
45. de Haan et al. (2002) *Virology* 296:177-89.
46. Haijema et al. (2004) *J. Virol.* 78: 3863-3871.
47. Sawicki and Sawicki. (1990) *J Virol* 64:1050-6.
48. Schaad and Baric. (1994) *J Virol* 68:8169-79.
49. Yount et al. (2003)) *Proc Natl Acad Sci USA* 100: 12995-13000.

TABLE 1

SARS Consensus Sequences

| TRS SITE | WT SEQUENCE | CS MUTANT #1 | CS MUTANT #2 |
|---|---|---|---|
| Leader CS | TAAACGAAC | TAAACGgtC | TAAcCGgtC |
| S CS | TAAACGAAC | TAAACGgtC | TAAcCGgtC |
| ORF3a | TAAACGAAC | TAAACGgtC | TAAcCGgtC |
| E CS | AGTACGAAC | AGTACGgtC | AGTcCGgtC |
| M CS | TAAACGAAC | TAAACGgtC | TAAcCGgtC |
| ORF6 CS | ATCACGAAC | ATCACGgtC | ATCcCGgtC |
| ORF7 CS | AAAACGAAC | AAAACGgtC | AAAcCGgtC |
| ORF8 CS | TAAACGAAC | TAAACGgtC | TAAcCGgtC |
| N CS | TAAACGAAC | TAAACGgtC | TAAcCGgtC |

TABLE 2

SARS Consensus Sequences

| TRS SITE | WT SEQUENCE | CS MUTANT #1 | CS MUTANT #2 |
|---|---|---|---|
| Leader CS | TAAACGAAC | TAAACGgAt | TAAcCGgAt |
| S CS | TAAACGAAC | TAAACGgAt | TAAcCGgAt |
| ORF3a | TAAACGAAC | TAAACGgAt | TAAcCGgAt |
| E CS | AGTACGAAC | AGTACGgAt | AGTcCGgAt |
| M CS | TAAACGAAC | TAAACGgAt | TAAcCGgAt |

TABLE 2-continued

SARS Consensus Sequences

| TRS SITE | WT SEQUENCE | CS MUTANT #1 | CS MUTANT #2 |
|---|---|---|---|
| ORF6 CS | ATCACGAAC | ATCACGgAt | ATCcCGgAt |
| ORF7 CS | AAAACGAAC | AAAACGgAt | AAAcCGgAt |
| ORF8 CS | TAAACGAAC | TAAACGgAt | TAAcCGgAt |
| N CS | TAAACGAAC | TAAACGgAt | TAAcCGgAt |

* the functional CS is an ACGAAC

What is claimed is:

1. An isolated nucleic acid comprising a nucleotide sequence encoding a nidovirus genome or replicon RNA, wherein the genome or replicon RNA comprises one or more of the same mutations in a consensus sequence (CS) present in a transcription regulatory sequence (TRS) of a leader sequence and in the TRS located upstream of each essential structural gene and further comprising a wild type CS in a TRS for each group specific open reading frame (ORF).

2. An isolated nucleic acid comprising a nucleotide sequence encoding a nidovirus genome or replicon RNA, wherein the genome or replicon RNA comprises one or more of the same mutations in a consensus sequence (CS) present in a transcription regulatory sequence (TRS) of a leader sequence and in the TRS located upstream of each essential structural gene and further comprising one or more of the same mutations in the CS of the TRS located upstream of one or more group specific open reading frame (ORF).

3. The nucleic acid of claim 1, wherein the nidovirus is a severe acute respiratory syndrome (SARS) coronavirus having the wild type CS of ACGAAC, and the group specific open reading frames are ORF 3a/b, ORF6, ORF7a/b, and ORF 8a/b.

4. The nucleic acid of claim 2, wherein the nidovirus is a severe acute respiratory syndrome (SARS) coronavirus having the wild type CS of ACGAAC, and the group specific open reading frames are ORFs 3a/b, Orff, ORF7a/b, and ORF 8a/b.

5. The nucleic acid of claim 3, wherein the mutation is selected from the group consisting of ACGGAC, ACGGAT, ACGGAT, CCGGAC, CCGAAT, CCGGAT, CCGCGC, CGCAAC, CCCGAT, AGCGAT, CGCGAT, CCCGTT, CGCGTT and TGCGGT.

6. The nucleic acid of claim 4, wherein the mutation is selected from the group consisting of ACGGAC, ACGGAT, ACGGAT, CCGGAC, CCGAAT, CCGGAT, CCGCGC, CGCAAC, CCCGAT, AGCGAT, CGCGAT, CCCGTT, CGCGTT and TGCGGT.

7. The nucleic acid of claim 1, wherein the Nidovirus is a group I coronavirus having the CS of CUAAAC and wherein the mutation is selected from the group consisting of GUAAAC, GCAAAC, CGAAAG, GCTAAAG, GCTTAG and GCTTGG.

8. The nucleic acid of claim 1, wherein the Nidovirus is a group II coronavirus having the CS of TCTAAAC and wherein the mutation is selected from CCTAAC, CGAAAC, CGTAAAG, CCGAAGG, CGTCCGC, CGGATTG and GGCCTG.

9. The nucleic acid of claim 1, wherein the Nidovirus is a group III coronavirus having the CS of CUUAACAA and wherein the mutation is selected from the group consisting of CUUAAGAA, GUUAAGAA, GUUGAGAA, GUUTTCAG, CAAGGCAA, TCCAAGAT, GUUCCTTC, GCCTAGCG and GCCTGGCT.

10. The nucleic acid of claim 1, wherein the Nidovirus is a torovirus having a CS of UUUAGA and wherein the mutation is selected from the group consisting of GUUAGA, GUUGGA, GUUGCA, GCUCCA, GCCACT and GCCTCT.

11. The nucleic acid of claim 1, wherein the Nidovirus is an arterivirus having a CS of UUAACC and wherein the mutation is selected from the group consisting of CUAACC, CCAACC, CCAAGC, CCAGGC, CCAGGT and GGTTAG.

12. A nidovirus particle comprising the nucleic acid of claim 1.

13. A nidovirus particle comprising the nucleic acid of claim 2.

14. A composition comprising a population of the nidovirus particles of claim 12 and a pharmaceutically acceptable carrier.

15. A composition comprising a population of the nidovirus particles of claim 13 and a pharmaceutically acceptable carrier.

* * * * *

UNITED STATES PATENT AND TRADEMARK OFFICE
CERTIFICATE OF CORRECTION

PATENT NO. : 7,618,802 B2 Page 1 of 1
APPLICATION NO. : 11/334877
DATED : November 17, 2009
INVENTOR(S) : Baric et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 638 days.

Signed and Sealed this

Twenty-sixth Day of October, 2010

David J. Kappos
*Director of the United States Patent and Trademark Office*